US010487093B2

(12) United States Patent
Cooper et al.

(10) Patent No.: US 10,487,093 B2
(45) Date of Patent: Nov. 26, 2019

(54) HETEROCYCLIC COMPOUNDS, IN PARTICULAR 2-OXO-4,4,5,5,6,6,7,7-OCTAHYDROBENZOXAZOLE DERIVATIVES, AND THEIR USE AS ANTIBACTERIAL COMPOUNDS

(71) Applicant: Redx Pharma PLC, Alderley Edge (GB)

(72) Inventors: Ian Cooper, Alderley Edge (GB); Amanda Lyons, Alderley Edge (GB); David Orr, Alderley Edge (GB); James Kirkham, Alderley Edge (GB); Kevin Blades, Alderley Edge (GB)

(73) Assignee: Redx Pharma PLC, Alderley Edge (GB)

( * ) Notice: Subject to any disclaimer, the term of this patent is extended or adjusted under 35 U.S.C. 154(b) by 0 days.

(21) Appl. No.: 16/074,904

(22) PCT Filed: Feb. 8, 2017

(86) PCT No.: PCT/GB2017/050318

§ 371 (c)(1),
(2) Date: Aug. 2, 2018

(87) PCT Pub. No.: WO2017/137744

PCT Pub. Date: Aug. 17, 2017

(65) Prior Publication Data

US 2019/0055266 A1 Feb. 21, 2019

(30) Foreign Application Priority Data

Feb. 8, 2016 (GB) .................................... 1602241
Sep. 28, 2016 (GB) .................................... 1616460

(51) Int. Cl.

| | |
|---|---|
| ***A61K 31/423*** | (2006.01) |
| ***A61K 31/428*** | (2006.01) |
| ***A61K 31/536*** | (2006.01) |
| ***A61K 31/5415*** | (2006.01) |
| ***C07D 519/00*** | (2006.01) |
| ***C07D 498/04*** | (2006.01) |
| ***A61P 31/04*** | (2006.01) |
| ***C07D 263/58*** | (2006.01) |
| ***A61K 31/5383*** | (2006.01) |

(52) U.S. Cl.
CPC .......... *C07D 519/00* (2013.01); *A61K 31/423* (2013.01); *A61K 31/5383* (2013.01); *A61P 31/04* (2018.01); *C07D 263/58* (2013.01); *C07D 498/04* (2013.01)

(58) Field of Classification Search
CPC .. A61K 31/423; A61K 31/428; A61K 31/536; A61K 31/5415; C07D 519/00; C07D 498/04; A61P 31/04
USPC .......... 514/375, 367, 230.5, 224.2; 548/221, 548/159, 165; 544/92, 50
See application file for complete search history.

(56) References Cited

U.S. PATENT DOCUMENTS

2007/0037781 A1* 2/2007 Konetzki ............ A61K 31/538 514/171

FOREIGN PATENT DOCUMENTS

| | | | |
|---|---|---|---|
| WO | WO-2008/126024 | A2 | 10/2008 |
| WO | WO-2008/126034 | A2 | 10/2008 |
| WO | WO-2009/104159 | A1 | 8/2009 |
| WO | WO-2013/021363 | A1 | 2/2013 |
| WO | WO-2013/068948 | A1 | 5/2013 |
| WO | WO-2013/080156 | A1 | 6/2013 |

OTHER PUBLICATIONS

Hameed et al., "Novel N-Linked Aminipiperidine-Based Gyrase Inhibitors with Improved hERG and in Vivo Efficacy Against Mycobacterium Tuberculosis," Journal of Medicinal Chemistry, 57(11):4889-4905 (2014).
International Search Report and Written Opinion for International Application No. PCT/GB2017/050318 dated May 9, 2017.
Reck et al., "Novel N-Linked Aminopiperidine Inhibitors of Bacterial Topoisomerase Type II: Broad-Spectrum Antibacterial Agents with Reduced hERG Activity," Journal of Medicinal Chemistry, 54(22):7834-7847 (2011).

* cited by examiner

*Primary Examiner* — Matthew P Coughlin
*Assistant Examiner* — Sagar Patel
(74) *Attorney, Agent, or Firm* — Foley Hoag LLP

(57) ABSTRACT

This invention relates to antibacterial drug compounds containing a bicyclic core, typically a bicycle in which one of the rings is an oxazolidinone. It also relates to pharmaceutical formulations of antibacterial drug compounds. It also relates to uses of the compounds in treating bacterial infections and in methods of treating bacterial infections.

20 Claims, No Drawings

HETEROCYCLIC COMPOUNDS, IN PARTICULAR 2-OXO-4,4,5,5,6,6,7,7-OCTAHYDROBENZOXAZOLE DERIVATIVES, AND THEIR USE AS ANTIBACTERIAL COMPOUNDS

RELATED APPLICATIONS

This application is a § 371 national stage application based on Patent Cooperation Treaty Application serial number PCT/GB2017/050318, filed Feb. 8, 2017; which claims the benefit of priority to United Kingdom Patent Application No. GB 1602241.0, filed Feb. 8, 2016, and United Kingdom Patent Application No. GB 1616460.0, filed Sep. 28, 2016.

This invention relates to antibacterial drug compounds containing a bicyclic core, typically a bicycle in which one of the rings is an oxazolidinone. It also relates to pharmaceutical formulations of antibacterial drug compounds. It also relates to uses of the compounds in treating bacterial infections and in methods of treating bacterial infections. The invention is also directed to antibacterial drug compounds which are capable of treating bacterial infections which are currently hard to treat with existing drug compounds. Such infections are frequently referred to as resistant strains.

The increasing occurrence of bacterial resistance to antibiotics is viewed by many as being one of the most serious threats to human health. Multidrug resistance has become common among some pathogens, for example *Staphylococcus aureus, Streptococcus pneumoniae, Clostridium difficile* and *Pseudomonas aeruginosa*. Of these, *Staphylococcus aureus*, a Gram-positive bacterium, is a major concern due to its potency and its capacity to adapt to environmental conditions. Methicillin-resistant *Staphylococcus aureus* (MRSA) is probably the most well-known group of resistant strains and has reached pandemic proportions. Of particular concern is the increasing incidence of 'community acquired' infections, i.e. those occurring in subjects with no prior hospital exposure.

While less widespread, antibiotic resistant Gram-negative strains, such as either *Escherichia coli* NDM-1 (New Delhi metallo-β-lactamase 1) or *Klebsiella pneumoniae* NDM-1, are also very difficult to treat. Frequently only expensive antibiotics such as vancomycin and colistin are effective against these strains.

The fluoroquinolone antibacterial family are synthetic broad-spectrum antibiotics. They were originally introduced to treat Gram-negative bacterial infections, but are also used for the treatment of Gram-positive strains. One problem with existing fluoroquinolones can be the negative side effects that may sometimes occur as a result of their use. In general, the common side-effects are mild to moderate but, on occasion, more serious adverse effects occur. Some of the serious side effects that occur, and which occur more commonly with fluoroquinolones than with other antibiotic drug classes, include central nervous system (CNS) toxicity and cardiotoxicity. In cases of acute overdose there may be renal failure and seizure. In addition, an increasing number of strains of MRSA are also resistant to fluoroquinolone antibiotics, in addition to β-lactam antibiotics such as methicillin.

Gonorrhoea is a human sexually-transmitted infection (STI) caused by the Gram-negative bacterium *Neisseria gonorrhoeae*, a species of the genus *Neisseria* that also includes the pathogen *N. meningitidis*, which is one of the aetiological agents of meningitis. Untreated infection can result in a range of clinical complications including urethritis, dysuria, epididymitis, pelvic inflammatory disease, cervicitis, endometritis and even infertility and ectopic pregnancy. In rare cases, gonorrhoea can also spread to the blood to cause disseminated gonococcal infection that can manifest as arthritis, endocarditis or meningitis. Human immunodeficiency virus (HIV) is more readily-transmitted in individuals co-infected with gonorrhoea. Throughout the twentieth and twenty-first centuries gonorrhoea has been treated with a range of antibiotics. The sulphonamides were the first antibiotics used for the treatment of gonorrhoea, followed by penicillin, tetracycline and spectinomycin. In each case the development of resistance to these drugs by *N. gonorrhoeae* led to their use being discontinued. The fluoroquinolone antibiotics ciprofloxacin and ofloxacin were also historically recommended for the treatment of gonorrhoea. However, by 2007, fluoroquinolone resistance rates had reached 15% of gonococcal isolates and their use was abandoned. Current treatment recommendations comprise the cephalosporin antibiotics cefixime or ceftriaxone in combination with azithromycin or doxycycline. Resistance to cefixime and ceftriaxone has emerged in recent years. The CDC estimates that approximately 246,000 of the 820,000 gonococcal infections per year in the United States are drug-resistant (Antibiotic Resistance Threats in the United States, 2013, Centers for Disease Control and Prevention).

Another disease in which the development of resistance and multidrug resistance is of particular concern is tuberculosis (TB). From the $17^{th}$ century to the early-$20^{th}$ century TB was one of the most common causes of death. The development of effective treatments and vaccinations during the mid-$20^{th}$ century led to a sharp reduction in the number of deaths arising from the disease. TB is usually caused by *Mycobacterium tuberculosis*. Mycobacteria are aerobic bacteria and, as a result, tuberculosis infections most often develop in the lungs (pulmonary tuberculosis), although this is not always the case. Mycobacteria lack an outer cell membrane and as such they are often classified as Gram-positive bacteria, although they are in many ways atypical. They have a unique cell wall which provides protection against harsh conditions (e.g. acidic, oxidative) but also provides natural protection against many antibiotics. Other antibiotics, such as beta-lactams, are inactive against TB due to the intrinsic lack of activity of the compounds in the mycobacteria. Thus, a drug molecule may have excellent activity against other bacterial strains but no activity against wild-type TB. A number of TB-specific antibiotics have been developed, such as isoniazid, rifampicin, pyrazinamide and ethambutol and these are typically used in combination. Unfortunately, there is now increasing incidence of multi-drug-resistant TB (MDR-TB). MDR-TB is the term typically used to refer to TB that has developed resistance to isoniazid and rifampicin. MDR-TB can also be resistant to fluoroquinolones and also to the so-called 'second-line' injectable anti-TB drugs: kanamycin, capreomycin and amikacin. Where a strain of TB is resistant to isoniazid and rifampicin as well as one fluoroquinolone and one of the injectable anti-TB drugs, it is known as extensively drug resistant (XDR-TB). MDR-TB and XDR-TB are often found in those who have been previously treated for TB, but these forms of TB are just as infectious as wild-type TB and the incidence of MDR-TB and XDR-TB around the world is increasing.

According to a 2013 World Health Organisation report, infections arising from XDR-TB had at that time been identified in 84 different countries. There have even been some reports of strains of TB which were resistant to all drugs tested against them (so-called 'totally drug resistant tuberculosis', TDR-TB). The 'second-line' anti-TB drugs and other antibiotics typically used to treat resistant infections can have unfavourable side effects.

Bacterial resistance is also becoming a problem in the treatment of animals. Antibiotics find widespread use in industrial farming, e.g. to prevent mastitis in dairy cattle, where they are often used prophylactically. Such widespread prophylactic use has led to the build-up of resistance in certain bacterial strains that are particularly relevant to animal health.

In spite of the numerous different antibiotics known in the art for a variety of different infections, there continues to be a need for antibiotics that can provide an effective treatment in a reliable manner. In addition, there remains a need for antibiotic drugs that can avoid or reduce the side-effects associated with known antibiotics.

It is an aim of certain embodiments of this invention to provide new antibiotics. In particular, it is an aim of certain embodiments of this invention to provide antibiotics that are active against resistant strains of Gram-positive and/or Gram-negative bacteria. It is an aim of certain embodiments of this invention to provide compounds that have activity that is comparable to those of existing antibiotics, and ideally which is better. It is an aim of certain embodiments of this invention to provide such activity against wild-type strains at the same time as providing activity against one or more resistant strains.

It is an aim of certain embodiments of this invention to provide compounds that exhibit a smaller decrease in activity against resistant strains compared to wild-type strains than prior art compounds do. It may be that certain compounds of the invention are less active than prior art compounds but there is a benefit associated with having a more consistent activity against a range of strains.

It is an aim of certain embodiments of this invention to provide antibiotics that exhibit reduced cytotoxicity relative to prior art compounds and existing therapies.

It is an aim of certain embodiments of this invention to provide treatment of bacterial infections that is effective in a selective manner at a chosen site of interest. Another aim of certain embodiments of this invention is to provide antibiotics having a convenient pharmacokinetic profile and a suitable duration of action following dosing. A further aim of certain embodiments of this invention is to provide antibiotics in which the metabolised fragment or fragments of the drug after absorption are GRAS (Generally Regarded As Safe).

Certain embodiments of the present invention satisfy some or all of the above aims.

Compounds of the Invention

In a first aspect, the invention provides a compound of formula (I), or a pharmaceutically acceptable salt or N-oxide thereof:

(I)

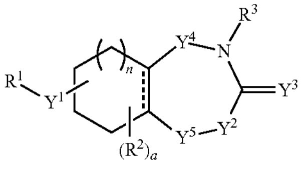

wherein 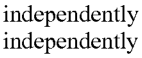 is a double bond or a single bond;

$Y^1$ is independently selected from $NR^4$, O and S;

$Y^2$ is independently selected from O and S;

$Y^3$ is independently selected from O and S;

$Y^4$ is $(CH_2)_m$;

$Y^5$ is $(CH_2)_p$;

$R^1$ is independently selected from $-L^1-Ar^1-Ar^2$ and

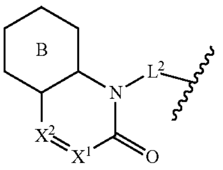

;

$Ar^1$ and $Ar^2$ are each independently selected from a phenyl or monocyclic heteroaryl group;

$-L^1-$ is $-C_1-C_3$-alkylene-;

$X^1$ is independently selected from N and $CR^5$ and $X^2$ is independently selected from N and $CR^6$; or $X^1$ and $X^2$ together form a 5-membered heteroaryl ring;

$-L^2-$ is $-C_2-C_3$-alkylene-;

Ring B is independently selected from: phenyl, monocyclic 6-membered heteroaryl and pyridinone, optionally substituted with a single $-Y^6-R^7$ group; wherein $Y^6$ is absent or is independently selected from $NR^8$, O and S; where Ring B is a pyridinone ring, the nitrogen of the Ring B pyridinone may be attached to the proximal end of a $-C_1-C_3$-alkylene- group that is attached at its distal end to the group $-L^2-$ $R^2$ is independently at each occurrence selected from: halo, nitro, cyano, $NR^9R^{10}$, $NR^9S(O)_2R^9$, $NR^9CONR^9R^9$, $NR^9C(O)R^9$, $NR^9CO_2R^9$, $OR^9$, $SR^9$, $SOR^9$, $SO_3R^9$, $SO_2R^9$, $SO_2NR^9R^9$, $CO_2R^9$, $C(O)R^9$, $CONR^9R^9$, $C_1-C_4$-alkyl, $C_2-C_4$-alkenyl, $C_2-C_4$-alkynyl, $C_1-C_4$-haloalkyl and $O-C_1-C_4$-haloalkyl;

$R^3$ is a bicyclic carbocyclic or heterocyclic ring system in which at least one of the two rings is aryl or heteroaryl;

or $R^3$ is $-L^3$-phenyl; wherein $-L^3-$ is selected from $-CR^{11}=CR^{11}-$ and $-C_4$-cycloalkyl-;

$R^4$ is independently selected from: H, $C_1-C_4$-alkyl, $C(O)-C_1-C_4$-alkyl, and $C_1-C_3$-alkylene-$R^{12}$;

wherein $R^{12}$ is independently selected from phenyl or monocyclic heteroaryl;

or wherein $R^4$ and either $-L^1-$ or $-L^2-$ and the nitrogen to which they are attached together form a 4- to 7-membered heterocycloalkyl ring;

$R^5$ and $R^6$ are each independently selected from H, halo, cyano, $C_1-C_4$-alkyl and $O-C_1-C_4$-alkyl;

$R^7$ is independently selected from: H, $C_1-C_4$-alkyl, $C_2-C_4$-alkenyl, $C_2-C_4$-alkynyl, $C_1-C_4$-haloalkyl, $C_3-C_8$-cycloalkyl, $_{4-7}$-heterocycloalkyl, phenyl, monocyclic heteroaryl and $C_1-C_3$-alkylene-$R^{7a}$; wherein $R^{7a}$ is independently selected from $C_3-C_8$-cycloalkyl, $_{4-7}$-heterocycloalkyl, phenyl and monocyclic heteroaryl;

$R^8$ is independently selected from: H and $C_1-C_4$-alkyl;

or $R^7$ and $R^8$ together with the nitrogen to which they are attached form a 4- to 7-membered heterocycloalkyl ring;

$R^9$ is independently at each occurrence selected from: H and $C_1-C_4$-alkyl;

$R^{10}$ is independently selected from: H, $C_1-C_4$-alkyl, $C_1-C_4$-haloalkyl, $S(O)_2-C_1-C_4$-alkyl and $C(O)-C_1-C_4$-alkyl;

$R^{11}$ is independently at each occurrence selected from H and $C_1-C_4$-alkyl;

a is an integer from 0 to 4;

n is an integer selected from 0, 1 and 2;

m and p are each an integer selected from: 0 and 1;

wherein any of the aforementioned alkyl, alkylene, alkenyl, alkynyl, haloalkyl, cycloalkyl, carbocyclic, heterocyclic, heterocycloalkyl, aryl, phenyl and heteroaryl groups is optionally substituted, where chemically possible, by 1 to 5 substituents which are each independently at each occurrence selected from the group consisting of: oxo, $=NR^a$, $=NOR^a$, halo, nitro, cyano, $NR^aR^a$, $NR^aS(O)_2R^a$, $NR^aC(O)R^a$, $NR^aCONR^aR^a$, $NR^aCO_2R^a$, $OR^a$, $SR^a$, $SOR^a$, $SO_3R^a$, $SO_2R^a$, $SO_2NR^aR^a$, $CO_2R^a$, $C(O)R^a$, $CONR^aR^a$, $CR^aR^aNR^aR^a$, $CR^aR^aOR^a$, $C_1$-$C_4$-alkyl, $C_2$-$C_4$-alkenyl, $C_2$-$C_4$-alkynyl, $C_1$-$C_4$-haloalkyl and O—$C_1$-$C_4$-haloalkyl; wherein $R^a$ is independently at each occurrence selected from H, $C_1$-$C_4$-alkyl.

For the absence of doubt, where ring B is substituted with a single —$Y^6$—$R^7$ group it may also be substituted with further substituents as described above, i.e. further substituents selected from selected from oxo, $=NR^a$, $=NOR^a$, halo, nitro, cyano, $NR^aR^a$, $NR^aS(O)_2R^a$, $NR^aC(O)R^a$, $NR^aCONR^aR^a$, $NR^aCO_2R^a$, $OR^a$; $SR^a$, $SOR^a$, $SO_3R^a$, $SO_2R^a$, $SO_2NR^aR^a$, $CO_2R^a$, $C(O)R^a$, $CONR^aR^a$, $CR^aR^aNR^aR^a$, $CR^aR^aOR^a$, $C_1$-$C_4$-alkyl, $C_2$-$C_4$-alkenyl, $C_2$-$C_4$-alkynyl and $C_1$-$C_4$-haloalkyl.

In certain embodiments, the compound of formula (I) is a compound of formula (II):

(II)

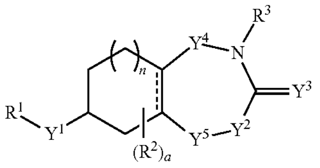

wherein $\overline{\text{-----}}$ , $R^1$, $R^2$, $R^3$, $Y^1$, $Y^2$, $Y^3$, $Y^4$, $Y^5$, n and a are as defined above for formula (I).

In certain embodiments, the compound of formula (I) is a compound of formula (III):

(III)

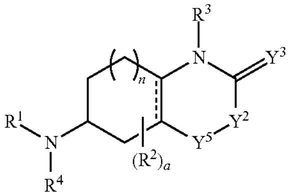

wherein $\overline{\text{-----}}$ , $R^1$, $R^2$, $R^3$, $R^4$, $Y^2$, $Y^3$, $Y^5$, n and a are as defined above for formula (I).

In certain embodiments, the compound of formula (I) is a compound of formula (IV):

(IV)

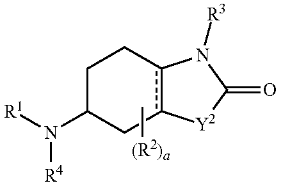

wherein $\overline{\text{-----}}$ , $R^1$, $R^2$, $R^3$, $R^4$, $Y^2$ and a are as defined above for formula (I).

In certain embodiments, the compound of formula (I) is a compound of formula (V):

(V)

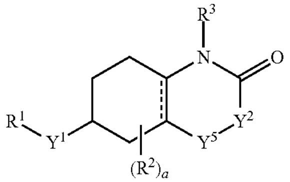

wherein $\overline{\text{-----}}$ , $R^1$, $R^2$, $R^3$, $Y^1$, $Y^2$, $Y^5$ and a are as defined above for formula (I).

In certain embodiments, the compound of formula (I) is a compound of formula (VI):

(VI)

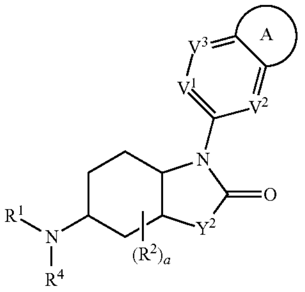

wherein $R^1$, $R^2$, $R^4$ and a are as defined above for formula (I) and wherein $Y^2$ is independently selected from O and S; $V^1$, $V^2$ and $V^3$ are each independently selected from: N and $CR^{13}$; with the proviso that no more than two of $V^1$, $V^2$ and $V^3$ are N; and wherein the ring A is a substituted or unsubstituted 5- or 6-membered saturated cycloalkyl or heterocycloalkyl ring; and $R^{13}$ is independently at each occurrence selected from H, halo, nitro, cyano, $NR^aR^a$, $NR^aS(O)_2R^a$, $NR^aC(O)R^a$, $NR^aCONR^aR^a$, $NR^aCO_2R^a$, $OR^a$; $SR^a$, $SOR^a$, $SO_3R^a$, $SO_2R^a$, $SO_2NR^aR^a$, $CO_2R^a$, $C(O)R^a$, $CONR^aR^a$, $CR^aR^aNR^aR^a$, $CR^aR^aOR^a$, $C_1$-$C_4$-alkyl, $C_2$-$C_4$-alkenyl, $C_2$-$C_4$-alkynyl and $C_1$-$C_4$-haloalkyl.

In certain embodiments, the compound of formula (I) is a compound of formula (VII):

(VII)

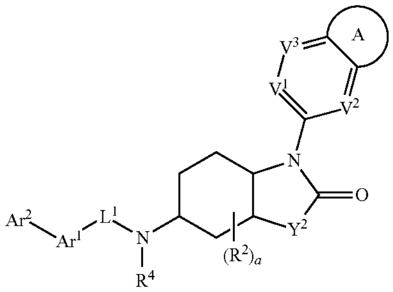

wherein $Ar^1$, $Ar^2$, $R^2$, $R^4$, $L^1$, $Y^2$ and a are as defined above for formula (I) and wherein $V^1$, $V^2$ and $V^3$ and ring A are as described above for formula (VI).

In certain embodiments, the compound of formula (I) is a compound of formula (VIII):

(VIII)

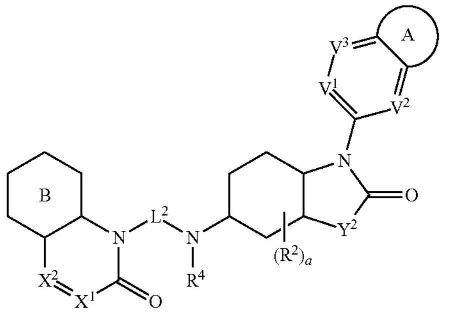

wherein $R^2$, $R^4$, $L^2$, $Y^2$, $X^1$, $X^2$ Ring B and a are as defined above for formula (I) and wherein $V^1$, $V^2$ and $V^3$ and ring A are as described above for formula (VI).

In certain embodiments, the compound of formula (I) is a compound of formula (IX):

(IX)

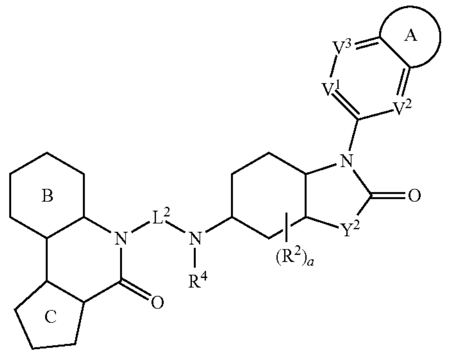

wherein $R^2$, $R^4$, $L^2$, $Y^2$, Ring B and a are as defined above for formula (I) and wherein $V^1$, $V^2$ and $V^3$ and ring A are as described above for formula (VI) and wherein ring C is a 5-membered heteroaryl ring.

In certain embodiments, the compound of formula (I) is a compound of formula (X):

(X)

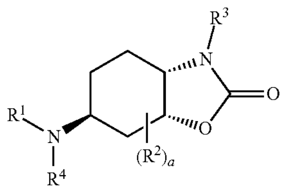

wherein $R^1$, $R^2$, $R^3$, $R^4$ and a are as defined above for formula (I). For the absence of doubt the hashed and solid wedges in formula (X) are intended to depict the relative stereochemistry of the indicated bonds and not the absolute stereochemistry, i.e. the compound may be in the form of a single enantiomer or in the form of a racemate. In certain embodiments, the compound is in a substantially enantiomerically pure form (i.e. greater than 95%) and has the absolute stereochemistry depicted in formula (X). In certain embodiments, the compound is in a substantially enantiomerically pure form (i.e. greater than 95%) and has the absolute stereochemistry the opposite to that depicted in formula (X).

In certain embodiments, the compound of formula (I) is a compound of formula (XI):

(XI)

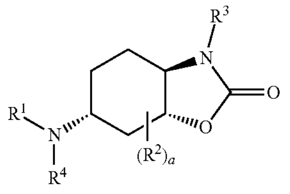

wherein $R^1$, $R^2$, $R^3$, $R^4$ and a are as defined above for formula (I). For the absence of doubt the hashed and solid wedges in formula (XI) are intended to depict the relative stereochemistry of the indicated bonds and not the absolute stereochemistry, i.e. the compound may be in the form of a single enantiomer or in the form of a racemate. In certain embodiments, the compound is in a substantially enantiomerically pure form (i.e. greater than 95%) and has the absolute stereochemistry depicted in formula (XI). In certain embodiments, the compound is in a substantially enantiomerically pure form (i.e. greater than 95%) and has the absolute stereochemistry the opposite to that depicted in formula (XI).

In certain embodiments, the compound of formula (I) is a compound of formula (XII):

(XII)

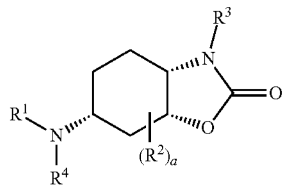

wherein $R^1$, $R^2$, $R^3$, $R^4$ and a are as defined above for formula (I). For the absence of doubt the hashed and solid wedges in formula (XII) are intended to depict the relative stereochemistry of the indicated bonds and not the absolute stereochemistry, i.e. the compound may be in the form of a single enantiomer or in the form of a racemate. In certain embodiments, the compound is in a substantially enantiomerically pure form (i.e. greater than 95%) and has the absolute stereochemistry depicted in formula (XII). In certain embodiments, the compound is in a substantially enantiomerically pure form (i.e. greater than 95%) and has the absolute stereochemistry the opposite to that depicted in formula (XII).

In certain embodiments, the compound of formula (I) is a compound of formula (XIII):

(XIII)

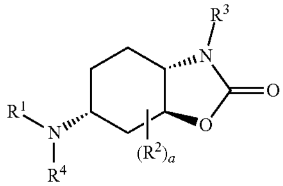

wherein $R^1$, $R^2$, $R^3$, $R^4$ and a are as defined above for formula (I). For the absence of doubt the hashed and solid wedges in formula (XIII) are intended to depict the relative stereochemistry of the indicated bonds and not the absolute stereochemistry, i.e. the compound may be in the form of a single enantiomer or in the form of a racemate. In certain embodiments, the compound is in a substantially enantiomerically pure form (i.e. greater than 95%) and has the absolute stereochemistry depicted in formula (XIII). In certain embodiments, the compound is in a substantially enantiomerically pure form (i.e. greater than 95%) and has the absolute stereochemistry the opposite to that depicted in formula (XIII).

The following statements apply to compounds of any of formulae (I) to (XIII). These statements are independent and interchangeable. In other words, any of the features described in any one of the following statements may (where chemically allowable) be combined with the features described in one or more other statements below. In particular, where a compound is exemplified or illustrated in this specification, any two or more of the statements below which describe a feature of that compound, expressed at any level of generality, may be combined so as to represent subject matter which is contemplated as forming part of the disclosure of this invention in this specification.

$\overline{- - -}$ may be a double bond. Typically, however, $\overline{- - -}$ is a single bond.

Where $\overline{- - -}$ is a single bond, it may be that the groups $Y^4$ and $Y^5$ are orientated cis to each other. Alternatively, it may be that the groups $Y^4$ and $Y^5$ are orientated trans to each other. Where $\overline{- - -}$ is a single bond, it may be that the groups $Y^1R^1$ and $Y^4$ are orientated cis to each other. Alternatively, it may be that the groups $Y^1R^1$ and $Y^4$ are orientated trans to each other. In certain embodiments, $Y^4$ and $Y^5$ are orientated cis to each other and $Y^1R^1$ and $Y^4$ are orientated trans to each other. In certain embodiments, $Y^4$ and $Y^5$ are orientated trans to each other and $Y^1R^1$ and $Y^4$ are orientated trans to each other. Where $\overline{- - -}$ is a single bond and m is 0, it may be that the groups $NR^3$ and $Y^5$ are orientated cis to each other. Alternatively, it may be that the groups $NR^3$ and $Y^5$ are orientated trans to each other. Thus, where $\overline{- - -}$ is a single bond and m is 0, it may be that the groups $Y^1R^1$ and $NR^3$ are orientated cis to each other. Alternatively, it may be that the groups $Y^1R^1$ and $NR^3$ are orientated trans to each other. In certain embodiments, $NR^3$ and $Y^5$ are orientated cis to each other and $Y^1R^1$ and $NR^3$ are orientated trans to each other. In certain embodiments, $Y^4$ and $Y^5$ are orientated trans to each other and $Y^1R^1$ and $Y^4$ are orientated trans to each other. Where $\overline{- - -}$ is a single bond and p is 0, it may be that the groups $Y^4$ and $Y^2$ are orientated cis to each other. Alternatively, it may be that the groups $Y^4$ and $Y^2$ are orientated trans to each other. In certain embodiments, $Y^4$ and $Y^2$ are orientated cis to each other and $Y^1R^1$ and $Y^4$ are orientated trans to each other. In certain embodiments, $Y^4$ and $Y^2$ are orientated trans to each other and $Y^1R^1$ and $Y^4$ are orientated trans to each other. Where $\overline{- - -}$ is a single bond and m and p are both 0, it may be that the groups $NR^3$ and $Y^2$ are orientated cis to each other. Alternatively, it may be that the groups $NR^3$ and $Y^2$ are orientated trans to each other. In certain embodiments, $NR^3$ and $Y^2$ are orientated cis to each other and $Y^1R^1$ and $NR^3$ are orientated trans to each other. In certain embodiments, $NR^3$ and $Y^2$ are orientated trans to each other and $Y^1R^1$ and $NR^3$ are orientated trans to each other. In certain embodiments, it has been observed that a trans relationship between $Y^4$ or $NR^3$ on the one hand and $Y^5$ or $Y^2$ on the other is associated with higher potencies against certain bacterial strains.

$Y^1$ may be O or S. $Y^1$ is preferably $NR^4$.

$R^4$ may be independently selected from: H, $C_1$-$C_4$-alkyl, C(O)—$C_1$-$C_4$-alkyl, and $C_1$-$C_3$-alkylene-$R^{12}$. $R^4$ may be $C_1$-$C_3$-alkylene-$R^{12}$. $R^4$ may be $CH_2R^{12}$. $R^4$ may be $CH_2CH_2R^{12}$. $R^{12}$ may be phenyl, e.g. unsubstituted phenyl. $R^{12}$ may be a monocyclic heteroaryl group. Thus, $R^{12}$ may be a 6-membered heteroaryl ring, e.g. pyridine. Alternatively, $R^{12}$ may be a 5-membered heteroaryl ring. $R^4$ may be $C_1$-$C_4$-alkyl, e.g. $C_1$-$C_4$-alkyl substituted with an OH or $NH_2$ group. $R^4$ may be unsubstituted $C_1$-$C_4$-alkyl, e.g. unsubstituted $C_1$-$C_2$-alkyl. $R^4$ may be H. Thus, $R^4$ may be selected from H and $C_1$-$C_4$-alkyl, e.g. $R^4$ may be selected from H and unsubstituted $C_1$-$C_2$-alkyl. $R^4$ may be C(O)—$C_1$-$C_4$-alkyl.

$Y^2$ may be S. Preferably, however, $Y^2$ is O.

$Y^3$ may be S. Preferably, however, $Y^3$ is O.

m may be 1. m may be 0. p may be 1. p may be 0. Preferably, the sum of m and p is 0 or 1. Thus, m and p may both be 0.

$R^1$ may be:

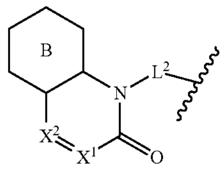

Throughout this specification, the group

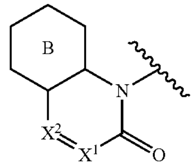

may be referred to as $R^{1a}$. Thus, $R^1$ may be -$L^2$-$R^{1a}$.

-$L^2$. may be —$C_2$-$C_3$-alkylene-. -$L^2$. may be —$C_2$-alkylene-. -$L^2$. may be —$C_3$-alkylene-. -$L^2$- may be substituted with 1 or 2 groups selected from =O, methyl, $CH_2OH$, $CO_2R^a$, and $CO_2NR^aR^a$. Where -$L^2$- is a $C_3$-alkylene, it may be that the central atom is substituted, e.g. with an $OR^a$ group. It may be that -$L^2$- is $CH_2CH(OH)CH_2$—. It may be, however, that -$L^2$- is unsubstituted alkylene. Thus, -$L^2$- may be —$CH_2CH_2$—. It may be that -$L^2$- is $CH_2CH_2CH_2$—.

It may be that -$L^2$- and $R^4$ together with the nitrogen to which they are attached form a 4- to 7-membered heterocyclic ring. Thus, it may be that -$L^2$- and $R^4$ together with the nitrogen to which they are attached form a 4- to 5-membered heterocyclic ring. -$L^2$- and $R^4$ together with the nitrogen to which they are attached may form a pyrrolidine or azetidine ring.

$X^1$ may be N. Thus, $R^{1a}$ may have the structure:

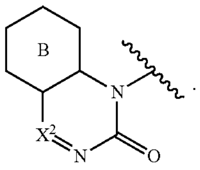

Alternatively, $X^1$ may be $CR^5$. Thus, $R^{1a}$ may have the structure:

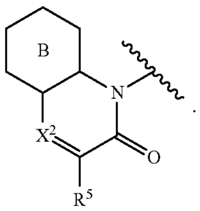

$X^2$ may be N. Thus, $R^{1a}$ may have the structure:

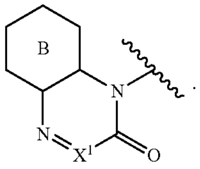

Alternatively, $X^2$ may be $CR^6$. Thus, $R^{1a}$ may have the structure:

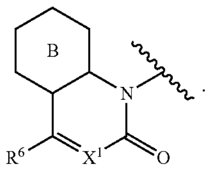

It may be that $X^1$ is N and $X^2$ is $CR^6$. Thus, $R^{1a}$ may have the structure:

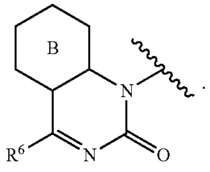

It may be that $X^1$ is N and $X^2$ is N. Thus, $R^{1a}$ may have the structure:

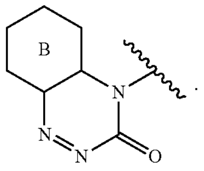

It may be that $X^1$ is $CR^5$ and $X^2$ is N. Thus, $R^{1a}$ may have the structure:

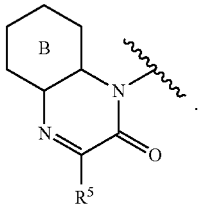

It may be that $X^1$ is $CR^5$ and $X^2$ is $CR^6$. Thus, $R^{1a}$ may have the structure:

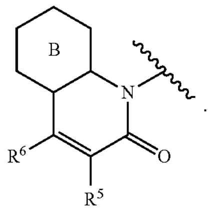

It may be that $R^5$ and $R^6$ are each independently selected from H, halo, cyano, $C_1$-$C_4$-alkyl and O—$C_1$-$C_4$-alkyl; or $R^5$ and $R^6$ together with the carbons to which they are attached together form a 5-membered heteroaryl ring. Compounds in which $R^5$ and $R^6$ together with the carbons to which they are attached together form a 5-membered heteroaryl ring are examples of compounds in which $X^1$ and $X^2$ together form a 5-membered heteroaryl group.

It may be that $R^5$ is independently selected from H or $C_1$-$C_4$-alkyl. It may be that $R^5$ is H. It may be that $R^6$ is independently selected from H or $C_1$-$C_4$-alkyl. It may be that $R^6$ is H.

It may be that $R^5$ and $R^6$ are each independently selected from: H, halo, cyano, $C_1$-$C_4$-alkyl and O—$C_1$-$C_4$-alkyl. It may be that $R^5$ and $R^6$ are each independently selected from H, $C_1$-$C_4$-alkyl and O—$C_1$-$C_4$-alkyl or that $R^5$ and $R^6$, together with the carbons to which they are attached together form a 5-membered heteroaryl ring. It may be that $R^5$ and $R^6$ are each independently at each occurrence selected from H or $C_1$-$C_4$-alkyl. It may be that $R^5$ and $R^6$ are at each occurrence H.

Alternatively, it may be that $R^5$ and $R^6$, together with the carbons to which they are attached together form a 5-membered heteroaryl ring. Exemplary heteroaryl rings include oxazole, thiazole, isoxazole, isothiazole, pyrazole, imidazole, triazole, pyrole, thiophene, furan and oxadiazole. For the absence of doubt, the double bond depicted in the structure above between $X^1$ and $X^2$ may be delocalised into the heteroaromatic ring.

Thus, $R^{1a}$ may have the structure:

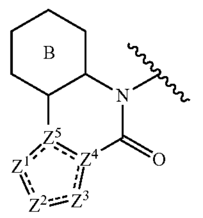

wherein $Z^4$ and $Z^5$ are each independently selected from C and N; $Z^1$, $Z^2$ and $Z^3$ are each independently selected from O, S, N, S(O), $NR^a$ and $CR^{14}$; wherein the ring formed by $Z^1$, $Z^2$, $Z^3$, $Z^4$ and $Z^5$ contains two endocyclic double bonds and with the further proviso that at least one of $Z^1$, $Z^2$, $Z^3$, $Z^4$ and $Z^5$ is O, S, N or $NR^a$; and wherein $R^{14}$ is independently selected from H, $C_1$-$C_4$-alkyl, $CR^aR^aOR^a$, $CR^aR^aNR^aR^a$, $CO_2R^a$ and $CONR^aR^a$.

In certain examples, the heteroaryl ring may be a ring selected from oxazole, thiazole, isoxazole and isothiazole. Thus, $R^{1a}$ may have the structure:

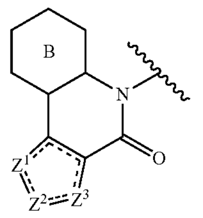

wherein one of $Z^1$, $Z^2$ and $Z^3$ is N, one of $Z^1$, $Z^2$ and $Z^3$ is $CR^{14}$ and the final one of $Z^1$, $Z^2$ and $Z^3$ is selected from O and S; provided that the ring comprising $Z^1$, $Z^2$ and $Z^3$ contains two endocyclic double bonds; and wherein $R^{14}$ is independently selected from H, $C_1$-$C_4$-alkyl, $CR^aR^aOR^a$, $CR^aR^aNR^aR^a$, $CO_2R^a$ and $CONR^aR^a$.

Thus, $R^{1a}$ may have the structure:

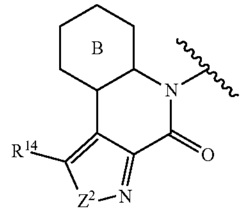

wherein $Z^2$ is independently selected from O and S. $Z^2$ may be O. $Z^2$ may be S.

Ring B may be selected from a phenyl ring or a 6-membered heteroaryl ring. Thus, Ring B may be a phenyl ring. Ring B may be a pyridine ring or a pyrimidine ring.

$R^{1a}$ may have the structure:

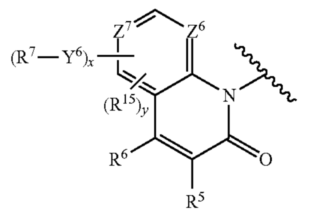

wherein x is 0 or 1; y is an integer from 0 to 2; $Z^6$ and $Z^7$ are each independently selected from carbon or nitrogen; and $R^{15}$ is independently selected from halo, nitro, cyano, $NR^aR^a$, $NR^aS(O)_2R^a$, $NR^aC(O)R^a$, $NR^aCONR^aR^a$, $NR^aCO_2R^a$, $OR^a$; $SR^a$, $SOR^a$, $SO_3R^a$, $SO_2R^a$, $SO_2NR^aR^a$, $CO_2R^a$, $C(O)R^a$, $CONR^aR^a$, $CR^aR^aNR^aR^a$, $CR^aR^aOR^a$, $C_1$-$C_4$-alkyl, $C_2$-$C_4$-alkenyl, $C_2$-$C_4$-alkynyl and $C_1$-$C_4$-haloalkyl.

Thus, $R^{1a}$ may have the structure:

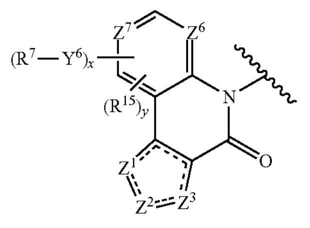

wherein one of $Z^1$, $Z^2$ and $Z^3$ is N, one of $Z^1$, $Z^2$ and $Z^3$ is $CR^{14}$ and the final one of $Z^1$, $Z^2$ and $Z^3$ is selected from O and S; provided that the ring comprising $Z^1$, $Z^2$ and $Z^3$ contains two endocyclic double bonds.

Likewise, $R^{1a}$ may have the structure:

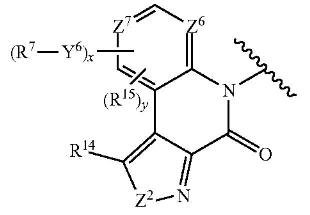

wherein $Z^2$ is independently selected from O and S. $Z^2$ may be O. $Z^2$ may be S.

x may be 0. Thus it may be that there is no $Y^6$—$R^7$ group on $R^1$.

Alternatively, x may be 1.

Thus, $R^{1a}$ may have the structure:

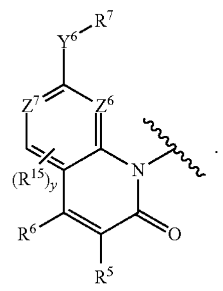

$R^{1a}$ may have the structure:

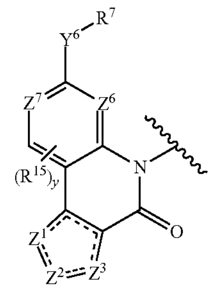

wherein one of $Z^1$, $Z^2$ and $Z^3$ is N, one of $Z^1$, $Z^2$ and $Z^3$ is $CR^{14}$ and the final one of $Z^1$, $Z^2$ and $Z^3$ is selected from O and S; provided that the ring comprising $Z^1$, $Z^2$ and $Z^3$ contains two endocyclic double bonds.

Likewise, $R^{1a}$ may have the structure:

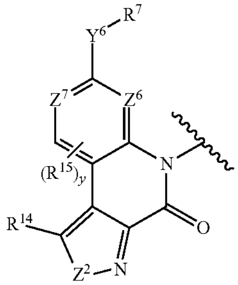

wherein $Z^2$ is independently selected from O and S. $Z^2$ may be O. $Z^2$ may be S.

$R^{1a}$ may have the structure:

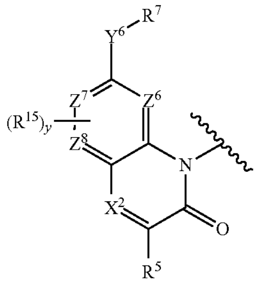

wherein y is an integer from 0 to 2; $Z^6$, $Z^7$ and $Z^8$ are each independently selected from carbon or nitrogen; providing that no more than 2 of $Z^6$, $Z^7$ and $Z^8$ are nitrogen; and $R^{15}$ is independently selected from halo, nitro, cyano, $NR^aR^a$, $NR^aS(O)_2R^a$, $NR^aC(O)R^a$, $NR^aCONR^aR^a$, $NR^aCO_2R^a$, $OR^a$; $SR^a$, $SOR^a$, $SO_3R^a$, $SO_2R^a$, $SO_2NR^aR^a$, $CO_2R^a$, $C(O)R^a$, $CONR^aR^a$, $CR^aR^aNR^aR^a$, $CR^aR^aOR^a$, $C_1$-$C_4$-alkyl, $C_2$-$C_4$-alkenyl, $C_2$-$C_4$-alkynyl and $C_1$-$C_4$-haloalkyl.

y may be 0.

$Z^6$ may be nitrogen. Alternatively, $Z^6$ may be carbon. $Z^7$ may be nitrogen. Alternatively, $Z^7$ may be carbon. It may be that $Z^6$ and $Z^7$ are each carbon. It may be that $Z^6$ and $Z^7$ are each nitrogen. It may be that $Z^6$ is nitrogen and $Z^7$ is carbon.

$Z^8$ may be carbon. $Z^8$ may be nitrogen.

$R^{14}$ may be selected from H and $C_1$-$C_4$-alkyl. In certain particular embodiments, $R^{14}$ is H.

If present, $R^{15}$ may at each occurrence be selected from halo and $C_1$-$C_4$-alkyl.

It may be that $Y^6$ is independently selected from $NR^8$, O and S. $Y^6$ is preferably O.

It may be that $R^7$ and $R^8$ together with the nitrogen to which they are attached form a 4- to 7-membered heterocycloalkyl ring. It may be that $R^7$ and $R^8$ together with the nitrogen to which they are attached form a 6-membered heterocycloalkyl ring, e.g. a piperidine, morpholine or piperazine ring.

Preferably, however, $R^7$ is independently selected from: H, $C_1$-$C_4$-alkyl, $C_2$-$C_4$-alkenyl, $C_2$-$C_4$-alkynyl, $C_1$-$C_4$-haloalkyl, $C_3$-$C_8$-cycloalkyl, $_{4-7}$-heterocycloalkyl, phenyl, monocyclic heteroaryl and $C_1$-$C_3$-alkylene-$R^{7a}$; wherein $R^{7a}$ is independently selected from $C_3$-$C_8$-cycloalkyl, $_{4-7}$-heterocycloalkyl, phenyl and monocyclic heteroaryl. $R^7$ is independently selected from: $C_1$-$C_4$-alkyl, $C_2$-$C_4$-alkenyl, $C_2$-$C_4$-alkynyl, $C_1$-$C_4$-haloalkyl, $C_3$-$C_8$-cycloalkyl, $_{4-7}$-heterocycloalkyl, phenyl, monocyclic heteroaryl and $C_1$-$C_3$-alkylene-$R^{7a}$; wherein $R^{7a}$ is independently selected from $C_3$-$C_8$-cycloalkyl, $_{4-7}$-heterocycloalkyl, phenyl and monocyclic heteroaryl. $R^7$ may be independently selected from: $C_1$-$C_4$-alkyl, phenyl and monocyclic heteroaryl.

$R^7$ may be alkyl. $R^7$ may be $C_1$-$C_4$-alkyl. $R^7$ may be $C_1$-$C_4$-haloalkyl. Alternatively, $R^7$ may be selected from phenyl and monocyclic heteroaryl. $R^7$ may be phenyl. $R^7$ may be unsubstituted phenyl or $R^7$ may be substituted. $R^7$ may be monocyclic heteroaryl, e.g. a 6-membered heteroaryl group. Thus, $R^7$ may be pyridyl, e.g. unsubstituted pyridyl. $R^7$ may be 3-pyridyl, e.g. unsubstituted 3-pyridyl. $R^7$ may be $C_3$-$C_8$-cycloalkyl, e.g. cyclohexyl. $R^7$ may be $_{4-7}$-heterocycloalkyl, e.g. piperidine or tetrahydropyran or azetidine.

It may be that $Y^6$ is O and $R^7$ is independently selected from: $C_1$-$C_4$-alkyl, $C_2$-$C_4$-alkenyl, $C_2$-$C_4$-alkynyl, $C_1$-$C_4$-haloalkyl, $C_3$-$C_8$-cycloalkyl, $_{4-7}$-heterocycloalkyl, phenyl, monocyclic heteroaryl and $C_1$-$C_3$-alkylene-$R^{7a}$; wherein $R^{7a}$ is independently selected from $C_3$-$C_8$-cycloalkyl, $_{4-7}$-heterocycloalkyl, phenyl and monocyclic heteroaryl.

Exemplary $R^{1a}$ groups include:

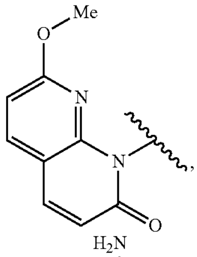
,
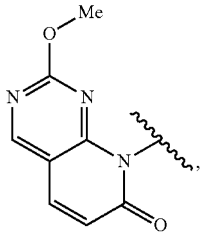
,
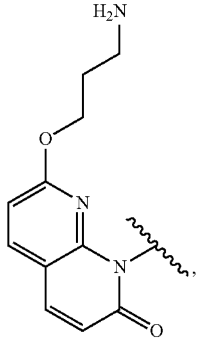
,
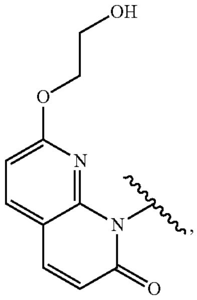
,

-continued
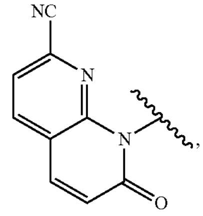,
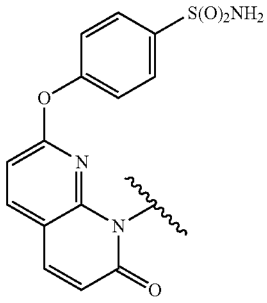,
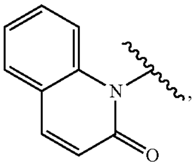,
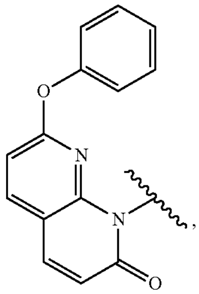,
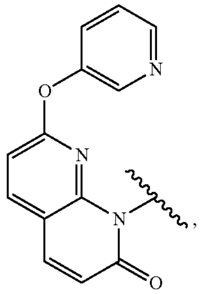,
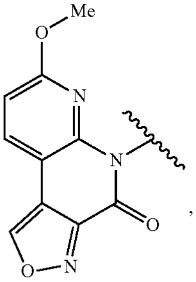,
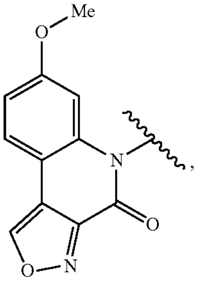,
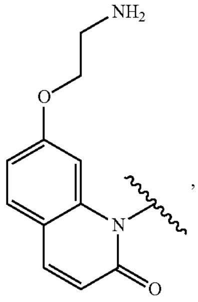,
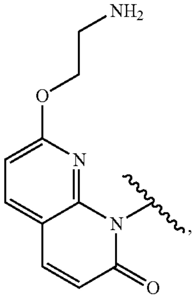,
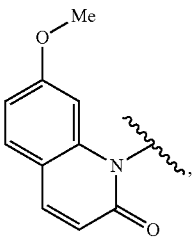,
-continued
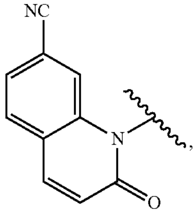,
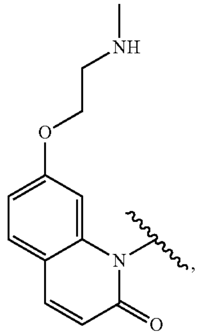,
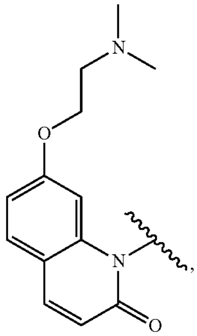,
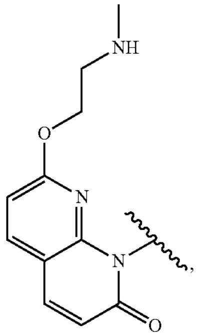,
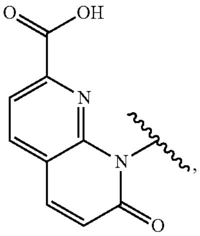,
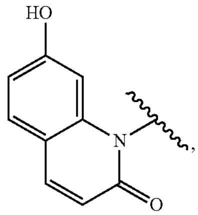,
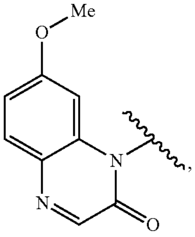,
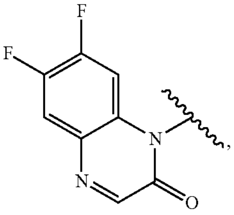,
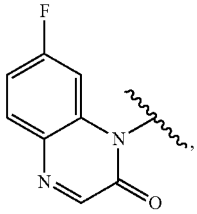,
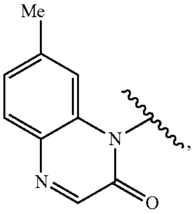,
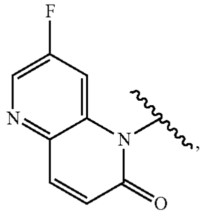,
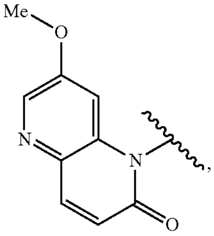, -continued

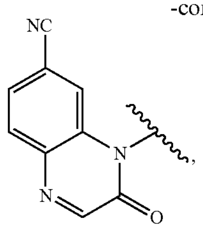,
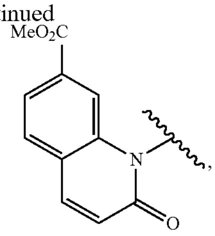,
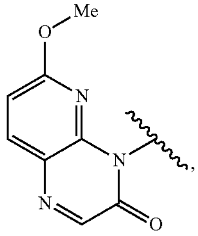,
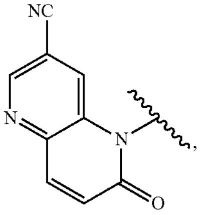,
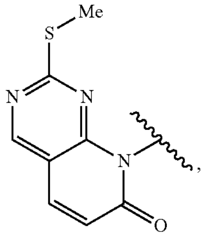,
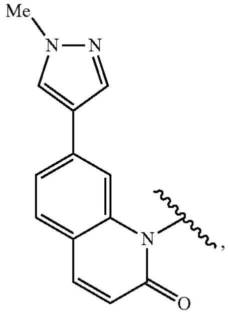,
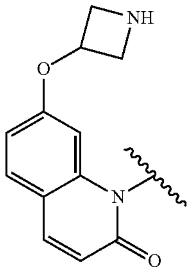,
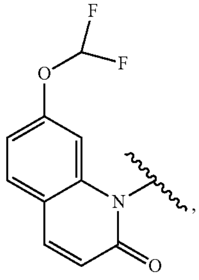,
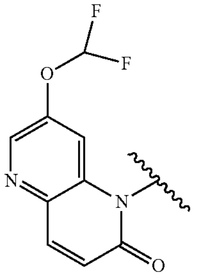
and
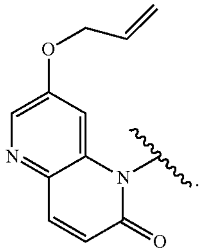.

In these embodiments, $-L^2-$ is typically an ethylene group. $-L^2-$ may also be a propylene group.

It may be that $R^1$ is $-L^1-Ar^1—Ar^2$; wherein $Ar^1$ is independently selected from a phenyl or monocyclic heteroaryl group; and wherein $Ar^2$ is a monocyclic heteroaryl group.

$-L^1$. may be $—C_1-C_2$-alkylene-. $-L^1$. may be $—C_1$-alkylene-. $-L^1$. may be $—C_2$-alkylene-. $-L^1-$ may be substituted with 1 or 2 groups selected from ═O, methyl, $CH_2OH$, $CO_2R^a$, and $CO_2NR^aR^a$. It may be, however, that $-L^1-$ is unsubstituted alkylene. Thus, $-L^1-$ may be $—CH_2—$.

It may be that $-L^1-$ and $R^4$ together with the nitrogen to which they are attached form a 4- to 7-membered heterocyclic ring. Thus, it may be that $-L^1-$ and $R^4$ together with the nitrogen to which they are attached form a 4- to 5-membered heterocyclic ring. $-L^1-$ and $R^4$ together with the nitrogen to which they are attached may form a pyrrolidine or azetidine ring.

It may be that at least one of $Ar^1$ and $Ar^2$ is a monocyclic heteroaryl group, e.g. a 6-membered monocyclic heteroaryl group, e.g. a pyridine. It may be that a single one of $Ar^1$ and $Ar^2$ is a monocyclic heteroaryl group, e.g. a 6-membered monocyclic heteroaryl group, e.g. a pyridine. It may be that a single one of $Ar^1$ and $Ar^2$ is phenyl, e.g. substituted phenyl.

It may be that $Ar^1$ is a phenyl group, e.g. a substituted phenyl group and $Ar^2$ is a 6-membered heteroaryl group, e.g. pyridine. It may be that $Ar^1$ is a 6-membered heteroaryl group, e.g. pyridine, and $Ar^2$ is a phenyl group.

$Ar^1$ may be a monocyclic heteroaryl group, e.g. a 6-membered monocyclic heteroaryl group.

$Ar^1$ may be pyridine. $Ar^1$ may be a phenyl group. $Ar^1$ may be unsubstituted. $Ar^1$ may be substituted, e.g. $Ar^1$ may be substituted with a single hydroxyl group.

Thus, $Ar^1$ may have the structure:

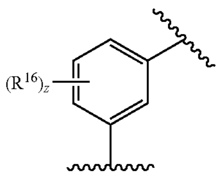

wherein z is an integer from 0 to 4; and $R^{16}$ is independently selected from halo, nitro, cyano, $NR^aR^a$, $NR^aS(O)_2R^a$, $NR^aC(O)R^a$, $NR^aCONR^aR^a$, $NR^aCO_2R^a$, $OR^a$; $SR^a$, $SOR^a$, $SO_3R^a$, $SO_2R^a$, $SO_2NR^aR^a$, $CO_2R^a$, $C(O)R^a$, $CONR^aR^a$, $CR^aR^aNR^aR^a$, $CR^aR^aOR^a$, $C_1$-$C_4$-alkyl, $C_2$-$C_4$-alkenyl, $C_2$-$C_4$-alkynyl and $C_1$-$C_4$ haloalkyl. $Ar^1$ may have the structure:

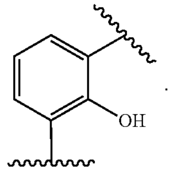 [SMILES: *c1cccc(*)c1O].

$Ar^2$ may be a monocyclic heteroaryl group. $Ar^2$ may be 6-membered heteroaryl group, e.g. a pyridyl group.

$Ar^2$ may have the structure:

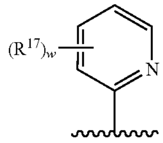

wherein w is an integer from 0 to 4; and $R^{17}$ is independently selected from halo, nitro, cyano, $NR^aR^a$, $NR^aS(O)_2R^a$, $NR^aC(O)R^a$, $NR^aCONR^aR^a$, $NR^aCO_2R^a$, $OR^a$; $SR^a$, $SOR^a$, $SO_3R^a$, $SO_2R^a$, $SO_2NR^aR^a$, $CO_2R^a$, $C(O)R^a$, $CONR^aR^a$, $CR^aR^aNR^aR^a$, $CR^aR^aOR^a$, $C_1$-$C_4$-alkyl, $C_2$-$C_4$-alkenyl, $C_2$-$C_4$-alkynyl and $C_1$-$C_4$-haloalkyl. $Ar^1$ may have the structure:

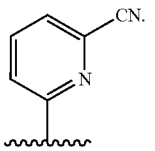 [SMILES: *c1cccc(C#N)n1]

Exemplary examples of $Ar^1$—$Ar^2$ include:

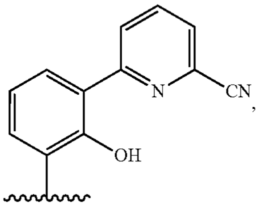
,
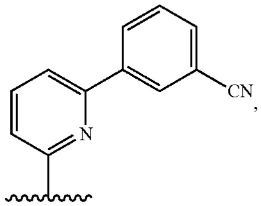
,
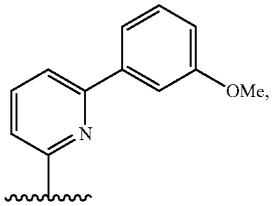

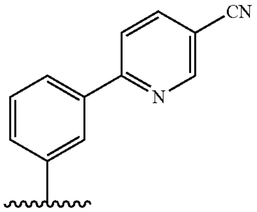
and
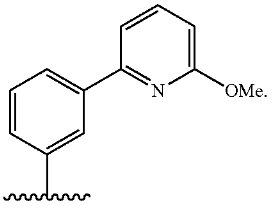

In these embodiments, $L^1$ is typically a methylene group.

$R^2$ may be independently at each occurrence selected from: $CO_2R^9$, $C(O)R^9$, $CONR^9R^9$, $C_1$-$C_4$-alkyl, $C_2$-$C_4$-alkenyl, $C_2$-$C_4$-alkynyl and $C_1$-$C_4$-haloalkyl. a may be 0.

n may be 0. Alternatively, n may be 1.

It may be that $R^3$ is a bicyclic carbocyclic or heterocyclic ring system in which at least one of the two rings is aryl or heteroaryl.

Thus, $R^3$ may take the form:

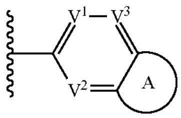
;

wherein $V^1$, $V^2$ and $V^3$ are each independently selected from: N and $CR^{13}$; with the proviso that no more than two of $V^1$, $V^2$ and $V^3$ are N; and wherein the ring A is a substituted or unsubstituted 5- or 6-membered saturated cycloalkyl or heterocycloalkyl ring; and wherein $R^{13}$ is independently at each occurrence selected from H, halo, nitro, cyano, $NR^aR^a$, $NR^aS(O)_2R^a$, $NR^aC(O)R^a$, $NR^aCONR^aR^a$, $NR^aCO_2R^a$, $OR^a$; $SR^a$, $SOR^a$, $SO_3R^a$, $SO_2R^a$, $SO_2NR^aR^a$, $CO_2R^a$, $C(O)R^a$, $CONR^aR^a$, $CR^aR^aNR^aR^a$, $CR^aR^aOR^a$, $C_1$-$C_4$-alkyl, $C_2$-$C_4$-alkenyl, $C_2$-$C_4$-alkynyl and $C_1$-$C_4$-haloalkyl.

Preferably, $R^3$ takes the form:

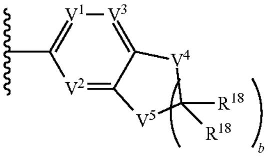
;

wherein $V^4$ and $V^5$ are each independently selected from O, S and $NR^a$; $R^{18}$ is independently at each occurrence selected from: H, fluoro, cyano, $CO_2R^a$, $C(O)R^a$, $CONR^aR^a$, $C_1$-$C_4$-alkyl, $C_2$-$C_4$-alkenyl, $C_2$-$C_4$-alkynyl and $C_1$-$C_4$-haloalkyl; or any two $R^{18}$ groups which are attached to the same carbon together form a group selected from: =O, $=NR^a$ and $=NOR^a$; and b is an integer selected from 1 and 2. For the absence of doubt, $V^1$, $V^2$, $V^3$, $V^4$, $V^5$, $R^{18}$ and b are selected such that the number of substituent groups (as defined above in relation to formula (I)) off the $R^3$ bicycle does not exceed 5.

It may be that $V^1$, $V^2$ and $V^3$ are each independently selected from: N and CH; with the proviso that no more than two of $V^1$, $V^2$ and $V^3$ are N. It may be that a single one of $V^1$, $V^2$ and $V^3$ is N. Preferably, $V^3$ is $CR^{13}$ (e.g. CH). Thus, it may be that $V^1$ is N and $V^2$ is $CR^{13}$ (e.g. CH). Alternatively, it may be that $V^2$ is N and $V^1$ is $CR^{13}$ (e.g. CH). In a further alternative, it may be that $V^1$ and $V^2$ are each N.

$R^{18}$ may be independently at each occurrence selected from: H, fluoro, cyano, $CO_2R^a$, $C(O)R^a$, $CONR^aR^a$, $C_1$-$C_4$-alkyl, $C_2$-$C_4$-alkenyl, $C_2$-$C_4$-alkynyl and $C_1$-$C_4$-haloalkyl; or any two $R^{18}$ groups which are attached to the same carbon together form a group selected from: =O, $=NR^a$ and $=NOR^a$. Preferably $R^{18}$ is independently at each occurrence selected from H, F, $C_1$-$C_4$-alkyl or $C_1$-$C_4$-haloalkyl; or any two $R^{18}$ groups which are attached to the same carbon together form a =O group. Preferably $R^{18}$ is independently at each occurrence selected from: H, $C_1$-$C_4$-alkyl or $C_1$-$C_4$-haloalkyl; or any two $R^{18}$ groups which are attached to the same carbon together form a =O group.

In a preferred embodiment, $V^4$ is O. Thus, it may be that both $V^4$ and $V^5$ are O. It may be that $V^4$ is O and $V^5$ is S. It may be that $V^4$ is O and $V^5$ is $NR^a$ (e.g. NH).

$V^4$ can also be S. Thus, it may be that $V^4$ is S and $V^5$ is $NR^a$ (e.g. NH).

It may be that $V^5$ is $NR^a$ (e.g. NH). In this case it is preferable that the —$CR^{18}R^{18}$— group attached to said $V^5$ is C=O.

b may be 1. Preferably, b is 2.

In a specific embodiment, $V^4$ is O, $V^5$ is O, b is 2 and $R^{18}$ is at each occurrence H. In another specific embodiment, $V^4$ is O, $V^5$ is S, b is 2 and $R^{18}$ is at each occurrence H. In yet another specific embodiment, $V^4$ is O, $V^5$ is NH, b is 2, the —$CR^{18}R^{18}$— group attached to $V^5$ is C=O and the —$CR^{18}R^{18}$— group attached to $V^4$ is $CH_2$.

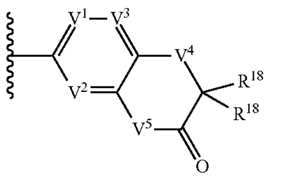

wherein $V^1$, $V^2$ and $V^3$ are each independently selected from: N and $CR^{13}$; with the proviso that no more than two of $V^1$, $V^2$ and $V^3$ are N; $V^4$ and $V^5$ are each independently selected from O, S and $NR^a$; wherein $R^{13}$ is independently at each occurrence selected from H, halo, nitro, cyano, $NR^aR^a$, $NR^aS(O)_2R^a$, $NR^aC(O)R^a$, $NR^aCONR^aR^a$, $NR^aCO_2R^a$, $OR^a$; $SR^a$, $SOR^a$, $SO_3R^a$, $SO_2R^a$, $SO_2NR^aR^a$, $CO_2R^a$, $C(O)R^a$, $CONR^aR^a$, $CR^aR^aNR^aR^a$, $CR^aR^aOR^a$, $C_1$-$C_4$-alkyl, $C_2$-$C_4$-alkenyl, $C_2$-$C_4$-alkynyl and $C_1$-$C_4$-haloalkyl; and $R^{18}$ is independently at each occurrence selected from: H, fluoro, cyano, $CO_2R^a$, $C(O)R^a$, $CONR^aR^a$, $C_1$-$C_4$-alkyl, $C_2$-$C_4$-alkenyl, $C_2$-$C_4$-alkynyl and $C_1$-$C_4$-haloalkyl.

$R^3$ may take the form:

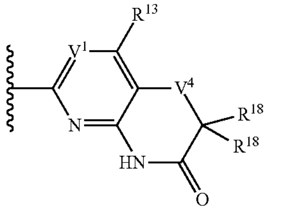

wherein $V^1$ is are each independently selected from: N and $CR^{13}$; $V^4$ is independently selected from O and S; wherein $R^{13}$ is independently at each occurrence selected from H, halo, nitro, cyano, $NR^aR^a$, $NR^aS(O)_2R^a$, $NR^aC(O)R^a$, $NR^aCONR^aR^a$, $NR^aCO_2R^a$, $OR^a$; $SR^a$, $SOR^a$, $SO_3R^a$, $SO_2R^a$, $SO_2NR^aR^a$, $CO_2R^a$, $C(O)R^a$, $CONR^aR^a$, $CR^aR^aNR^aR^a$, $CR^aR^aOR^a$, $C_1$-$C_4$-alkyl, $C_2$-$C_4$-alkenyl, $C_2$-$C_4$-alkynyl and $C_1$-$C_4$-haloalkyl; and $R^{18}$ is independently at each occurrence selected from: H, fluoro, cyano, $CO_2R^a$, $C(O)R^a$, $CONR^aR^a$, $C_1$-$C_4$-alkyl, $C_2$-$C_4$-alkenyl, $C_2$-$C_4$-alkynyl and $C_1$-$C_4$-haloalkyl.

Exemplary $R^3$ groups include:

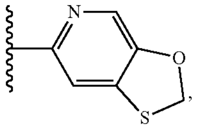
,
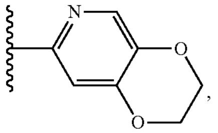
,
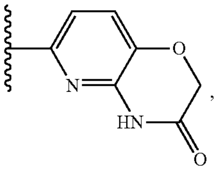
,
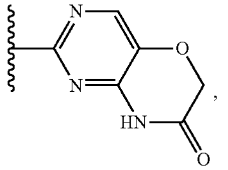
,
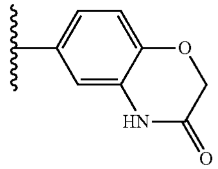

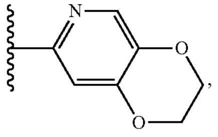
,

-continued

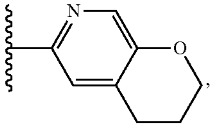
,
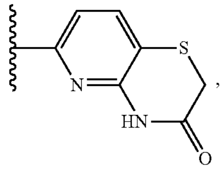
,
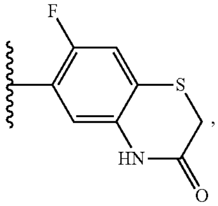
,
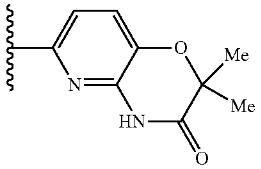
and
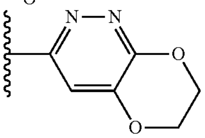

$R^3$ may be -$L^3$-phenyl.

$R^3$ may take the form:

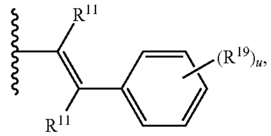

wherein $R^{19}$ is independently at each occurrence selected from halo, nitro, cyano, $NR^aR^a$, $NR^aS(O)_2R^a$, $NR^aC(O)R^a$, $NR^aCONR^aR^a$, $NR^aCO_2R^a$, $OR^a$; $SR^a$, $SOR^a$, $SO_3R^a$, $SO_2R^a$, $SO_2NR^aR^a$, $CO_2R^a$, $C(O)R^a$, $CONR^aR^a$, $CR^aR^aNR^aR^a$, $CR^aR^aOR^a$, $C_1$-$C_4$-alkyl, $C_2$-$C_4$-alkenyl, $C_2$-$C_4$-alkynyl and $C_1$-$C_4$-haloalkyl; and u is an integer from 0 to 5.

$R^{11}$ may at each occurrence be H.

$R^3$ may take the form:

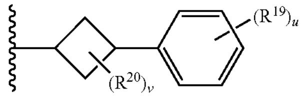

wherein $R^{19}$ is independently at each occurrence selected from halo, nitro, cyano, $NR^aR^a$, $NR^aS(O)_2R^a$, $NR^aC(O)R^a$, $NR^aCONR^aR^a$, $NR^aCO_2R^a$, $OR^a$; $SR^a$, $SOR^a$, $SO_3R^a$, $SO_2R^a$, $SO_2NR^aR^a$, $CO_2R^a$, $C(O)R^a$, $CONR^aR^a$, $CR^aR^aNR^aR^a$, $CR^aR^aOR^a$, $C_1$-$C_4$-alkyl, $C_2$-$C_4$-alkenyl, $C_2$-$C_4$-alkynyl and $C_1$-$C_4$-haloalkyl; $R^{20}$ is independently at each occurrence selected from oxo, fluoro, cyano, $CO_2R^a$, $C(O)R^a$, $CONR^aR^a$, $C_1$-$C_4$-alkyl, $C_2$-$C_4$-alkenyl, $C_2$-$C_4$-alkynyl and $C_1$-$C_4$-haloalkyl; u is an integer from 0 to 5; and v is an integer from 0 to 4;

$R^{20}$ may be selected from: fluoro, cyano, $CO_2R^a$, $C(O)R^a$, $CONR^aR^a$, $C_1$-$C_4$-alkyl, $C_2$-$C_4$-alkenyl, $C_2$-$C_4$-alkynyl and $C_1$-$C_4$-haloalkyl.

v may be 0.

$R^{19}$ may be independently at each occurrence selected from $C_1$-$C_4$-alkyl, halo, nitro and cyano.

u may be an integer from 1 to 5, e.g. from 1 to 3.

$R^3$ may also take the form

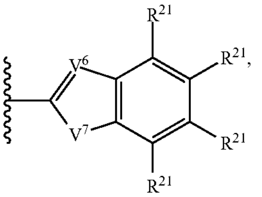

wherein $V^6$ is independently selected from N and $CR^{13}$ (e.g. CH); $V^7$ is independently selected from $NR^a$, S and O; and $R^{21}$ is independently at each occurrence selected from: H, halo, nitro, cyano, $NR^aR^a$, $NR^aS(O)_2R^a$, $NR^aC(O)R^a$, $NR^aCONR^aR^a$, $NR^aCO_2R^a$, $NR^aC(O)R^a$, $OR^a$; $SR^a$, $SOR^a$, $SO_3R^a$, $SO_2R^a$, $SO_2NR^aR^a$, $CO_2R^a$ $C(O)R^a$, $CONR^aR^a$, $C_1$-$C_4$-alkyl, $C_2$-$C_4$-alkenyl, $C_2$-$C_4$-alkynyl, $C_1$-$C_4$-haloalkyl, and $CR^aR^aNR^aR^a$. $R^{21}$ may be independently at each occurrence selected from H, F, CN, $OR^a$, nitro, $C_1$-$C_4$-alkyl, $C_2$-$C_4$-alkenyl, $C_2$-$C_4$-alkynyl and $C_1$-$C_4$-haloalkyl. For the absence of doubt, $V^6$, $V^7$ and $R^{21}$ are selected such that the number of substituent groups (as defined above in relation to formula (I)) off the $R^3$ bicycle does not exceed 5.

$R^3$ may take the form

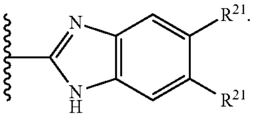

An exemplary $R^3$ group is

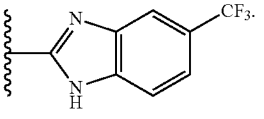 [SMILES: *c1nc2cc(C(F)(F)F)ccc2[nH]1]

The compound may be any one or more compound(s) selected from those prepared in Examples 1 to 107 and tested in Example 108 or a pharmaceutically acceptable salt or N-oxide thereof.

The compound may be as described in any of the following numbered clauses:

1. A compound of formula (I), or a pharmaceutically acceptable salt or N-oxide thereof:

(I)

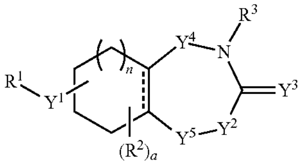

wherein ------ is a double bond or a single bond;

$Y^1$ is independently selected from $NR^4$, O and S;

$Y^2$ is independently selected from O and S;

$Y^3$ is independently selected from O and S;

$Y^4$ is $(CH_2)_m$;

$Y^5$ is $(CH_2)_p$;

$R^1$ is independently selected from -$L^1$-$Ar^1$—$Ar^2$ and

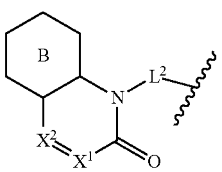

;

$Ar^1$ is independently selected from a phenyl or monocyclic heteroaryl group;

$Ar^2$ is a monocyclic heteroaryl group;

-$L^1$- is —$C_1$-$C_3$-alkylene-;

$X^1$ is independently selected from N and $CR^5$ and $X^2$ is independently selected from N and $CR^6$; or $X^1$ and $X^2$ together form a 5-membered heteroaryl ring;

-$L^2$- is —$C_2$-$C_3$-alkylene-;

Ring B is independently selected from: phenyl, monocyclic 6-membered heteroaryl and pyridinone, optionally substituted with a single —$Y^6$—$R^7$ group; $Y^6$ is independently selected from $NR^8$, O and S; where Ring B is a pyridinone ring, the nitrogen of the Ring B pyridinone may be attached to the proximal end of a —$C_1$-$C_3$-alkylene- group that is attached at its distal end to the group -$L^2$-

$R^2$ is independently at each occurrence selected from: halo, nitro, cyano, $NR^9R^{10}$, $NR^9S(O)_2R^9$, $NR^9CONR^9R^9$, $NR^9C(O)R^9$, $NR^9CO_2R^9$, $OR^9$, $SR^9$, $SOR^9$, $SO_3R^9$, $SO_2R^9$, $SO_2NR^9R^9$, $CO_2R^9$, $C(O)R^9$, $CONR^9R^9$, $C_1$-$C_4$-alkyl, $C_2$-$C_4$-alkenyl, $C_2$-$C_4$-alkynyl and $C_1$-$C_4$-haloalkyl;

$R^3$ is a bicyclic carbocyclic or heterocyclic ring system in which at least one of the two rings is aryl or heteroaryl;

or $R^3$ is -$L^3$-phenyl; wherein -$L^3$- is selected from —$CR^{11}$═$CR^{11}$— and —$C_4$-cycloalkyl-;

$R^4$ is independently selected from: H, $C_1$-$C_4$-alkyl and $C_1$-$C_3$-alkylene-$R^{12}$; wherein $R^{12}$ is independently selected from phenyl or monocyclic heteroaryl;

or wherein $R^4$ and either -$L^1$- or -$L^2$- and the nitrogen to which they are attached together form a 4- to 7-membered heterocycloalkyl ring;

$R^5$ and $R^6$ are each independently selected from H, halo, cyano, $C_1$-$C_4$-alkyl and O—$C_1$-$C_4$-alkyl;

$R^7$ is independently selected from: H, $C_1$-$C_4$-alkyl, $C_3$-$C_8$-cycloalkyl, $_{4-7}$-heterocycloalkyl, phenyl and monocyclic heteroaryl;

$R^8$ is independently selected from: H and $C_1$-$C_4$-alkyl;

or $R^7$ and $R^8$ together with the nitrogen to which they are attached form a 4- to 7-membered heterocycloalkyl ring;

$R^9$ is independently at each occurrence selected from: H and $C_1$-$C_4$-alkyl;

$R^{10}$ is independently selected from: H, $C_1$-$C_4$-alkyl, $C_1$-$C_4$-haloalkyl, $S(O)_2$—$C_1$-$C_4$-alkyl and $C(O)$—$C_1$-$C_4$-alkyl;

$R^{11}$ is independently at each occurrence selected from H and $C_1$-$C_4$-alkyl;

a is an integer from 0 to 4;

n is an integer selected from 0, 1 and 2;

m and p are each an integer selected from: 0 and 1;

wherein any of the aforementioned alkyl, alkylene, alkenyl, alkynyl, haloalkyl, cycloalkyl, carbocyclic, heterocyclic, heterocycloalkyl, aryl, phenyl and heteroaryl groups is optionally substituted, where chemically possible, by 1 to 5 substituents which are each independently at each occurrence selected from the group consisting of: oxo, ═$NR^a$, ═$NOR^a$, halo, nitro, cyano, $NR^aR^a$, $NR^aS(O)_2R^a$, $NR^aC(O)R^a$, $NR^aCONR^aR^a$, $NR^aCO_2R^a$, $OR^a$; $SR^a$, $SOR^a$, $SO_3R^a$, $SO_2R^a$, $SO_2NR^aR^a$, $CO_2R^a$, $C(O)R^a$, $CONR^aR^a$, $CR^aR^aNR^aR^a$, $CR^aR^aOR^a$, $C_1$-$C_4$-alkyl, $C_2$-$C_4$-alkenyl, $C_2$-$C_4$-alkynyl and $C_1$-$C_4$-haloalkyl; wherein $R^a$ is independently at each occurrence selected from H, $C_1$-$C_4$-alkyl.

2. A compound of clause 1, wherein the compound of formula (I) is a compound of formula (X):

(X)

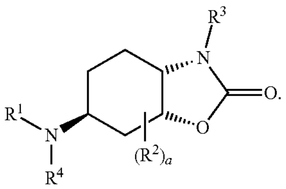

3. A compound of clause 1, wherein the compound of formula (I) is a compound of formula (XI):

(XI)

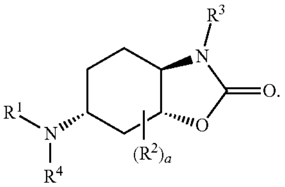

4. A compound of any preceding clause, wherein a is 0.

5. A compound of any preceding clause, wherein $R^1$ is:

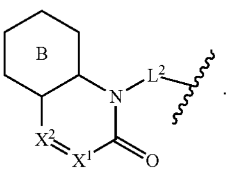

6. A compound of clause 5, wherein $-L^2$. is $-C_2$-alkylene-.

7. A compound of clause 5 or clause 6, wherein $X^1$ is $CR^5$ and $X^2$ is $CR^6$.

8. A compound of any one of clauses 5 to 7, wherein $R^5$ and $R^6$, together with the carbons to which they are attached together form a 5-membered heteroaryl ring.

9. A compound of clause 8, wherein the heteroaryl ring is a ring selected from oxazole, thiazole, isoxazole and isothiazole.

10. A compound of any one of clauses 5 to 9, wherein Ring B is a phenyl ring.

11. A compound of any one of clauses 5 to 9, wherein Ring B is a pyridine ring or a pyrimidine ring.

12. A compound of any one of clauses 1 to 4, wherein $R^1$ is $-L^1$-$Ar^1$—$Ar^2$; wherein $Ar^1$ is independently selected from a phenyl or monocyclic heteroaryl group; and wherein $Ar^2$ is a monocyclic heteroaryl group.

13. A compound of clause 12, wherein $-L^1$. is $-C_1$-alkylene-.

14. A compound of clause 13, wherein $Ar^1$ is a phenyl group.

15. A compound of clause 13 or clause 14, wherein $Ar^2$ is a 6-membered heteroaryl group.

16. A compound of any preceding clause, wherein $R^3$ takes the form:

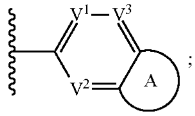

wherein $V^1$, $V^2$ and $V^3$ are each independently selected from: N and $CR^{13}$; with the proviso that no more than two of $V^1$, $V^2$ and $V^3$ are N; and wherein the ring A is a substituted or unsubstituted 5- or 6-membered saturated cycloalkyl or heterocycloalkyl ring; and wherein $R^{13}$ is independently at each occurrence selected from H, halo, nitro, cyano, $NR^aR^a$, $NR^aS(O)_2R^a$, $NR^aC(O)R^a$, $NR^aCONR^aR^a$, $NR^aCO_2R^a$, $OR^a$; $SR^a$, $SOR^a$, $SO_3R^a$, $SO_2R^a$, $SO_2NR^aR^a$, $CO_2R^a$, $C(O)R^a$, $CONR^aR^a$, $CR^aR^aNR^aR^a$, $CR^aR^aOR^a$, $C_1$-$C_4$-alkyl, $C_2$-$C_4$-alkenyl, $C_2$-$C_4$-alkynyl and $C_1$-$C_4$-haloalkyl.

17. A compound of any preceding clause, wherein $R^4$ is selected from H and $C_1$-$C_4$-alkyl

DETAILED DESCRIPTION

Throughout this specification, the term 'compound of the invention' is intended to refer to a compound of any one of formulae (I) to (XI) or a pharmaceutically acceptable salt or N-oxide thereof.

Where the compound of the invention is an N-oxide, it will typically be a pyridine N-oxide, i.e. where the compound of the invention comprises a pyridine ring (which may form part of a bicyclic or tricyclic ring system), the nitrogen of that pyridine may be $N^+$—$O^-$. Alternatively, it may be that the compound of the invention is not an N-oxide.

Included within the scope of the present invention are all stereoisomers, geometric isomers and tautomeric forms of the compounds of the invention, including compounds exhibiting more than one type of isomerism, and mixtures of one or more thereof. Also included are acid addition or base salts wherein the counter ion is optically active, for example, d-lactate or l-lysine, or racemic, for example, dl-tartrate or dl-arginine.

Compounds of the invention containing one or more asymmetric carbon atoms can exist as two or more stereoisomers. Where a compound of the invention contains a double bond such as a C═C or C═N group, geometric cis/trans (or Z/E) isomers are possible. Specifically, the oxime groups present in certain compounds of the invention may be present as the E-oxime, as the Z-oxime or as a mixture of both in any proportion. Cis/trans isomers may be separated by conventional techniques well known to those skilled in the art, for example, chromatography and fractional crystallisation.

Where structurally isomeric forms of a compound are interconvertible via a low energy barrier, tautomeric isomerism ('tautomerism') can occur. This can take the form of proton tautomerism in compounds of the invention containing, for example, an imino, keto, or oxime group, or so-called valence tautomerism in compounds which contain an aromatic moiety.

Conventional techniques for the preparation/isolation of individual enantiomers when necessary include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of the invention contains an acidic or basic moiety, a base or acid such as 1-phenylethylamine or tartaric acid.

The resulting diastereomeric mixture may be separated by chromatography and/or fractional crystallization and one or both of the diastereoisomers converted into the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, "Stereochemistry of Organic Compounds" by E. L. Eliel and S. H. Wilen (Wiley, 1994).

It follows that a single compound may exhibit more than one type of isomerism.

The term $C_m$-$C_n$ refers to a group with m to n carbon atoms.

The term "alkyl" refers to a monovalent linear or branched hydrocarbon chain. For example, $C_1$-$C_6$-alkyl may refer to methyl, ethyl, n-propyl, iso-propyl, n-butyl, sec-butyl, tert-butyl, n-pentyl and n-hexyl. An alkyl group may be unsubstituted or substituted by one or more substituents. Specific substituents for each alkyl group independently may be fluorine, $OR^a$ or $NHR^a$.

The term "alkylene" refers to a bivalent linear hydrocarbon chain. For example, —$C_1$-$C_3$-alkyl may refer to methylene, ethylene or propylene. An alkylene group may be unsubstituted or substituted by one or more substituents. Specific substituents for each alkyl group independently may be methyl or ethyl.

The term "haloalkyl" refers to a hydrocarbon chain substituted with at least one halogen atom independently chosen at each occurrence from: fluorine, chlorine, bromine and iodine. The halogen atom may be present at any position on the hydrocarbon chain. For example, $C_1$-$C_6$-haloalkyl may refer to chloromethyl, fluoromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl. A halo alkyl group may be a fluoroalkyl group, i.e. a hydrocarbon chain substituted with at least one halogen atom.

The term "alkenyl" refers to a branched or linear hydrocarbon chain containing at least one double bond. The double bond(s) may be present as the E or Z isomer. The double bond may be at any possible position of the hydrocarbon chain. For example, "$C_2$-$C_6$-alkenyl" may refer to ethenyl, propenyl, butenyl, butadienyl, pentenyl, pentadienyl, hexenyl and hexadienyl. An alkenyl group may be unsubstituted or substituted by one or more substituents. Specific substituents for any saturated carbon atom in each alkenyl group independently may be fluorine, $OR^a$ or $NHR^a$.

The term "alkynyl" refers to a branched or linear hydrocarbon chain containing at least one triple bond. The triple bond may be at any possible position of the hydrocarbon chain. For example, "$C_2$-$C_6$-alkynyl" may refer to ethynyl, propynyl, butynyl, pentynyl and hexynyl. An alkynyl group may be unsubstituted or substituted by one or more substituents. Specific substituents for any saturated carbon atom in each alkynyl group independently may be fluorine, $OR^a$ or $NHR^a$.

The term "cycloalkyl" refers to a saturated hydrocarbon ring system containing 3, 4, 5 or 6 carbon atoms. For example, "$C_3$-$C_6$-cycloalkyl" may refer to cyclopropyl, cyclobutyl, cyclopentyl, cyclohexyl. A cycloalkyl group may be unsubstituted or substituted by one or more substituents. Specific substituents for each cycloalkyl group independently may be fluorine, $OR^a$ or $NHR^a$.

The term "aromatic" when applied to a substituent as a whole means a single ring or polycyclic ring system with 4n+2 electrons in a conjugated π system within the ring or ring system where all atoms contributing to the conjugated π system are in the same plane.

The term "heteroaromatic" when applied to a substituent as a whole means a single ring or polycyclic ring system with 4n+2 electrons in a conjugated π system within the ring or ring system where all atoms contributing to the conjugated π system are in the same plane, the ring system comprising from 1 to 4 heteroatoms independently selected from O, S and N (in other words from 1 to 4 of the atoms forming the ring or ring system are selected from O, S and N).

The term "aryl" refers to an aromatic hydrocarbon ring system. The ring system has 4n+2 electrons in a conjugated π system within a ring where all atoms contributing to the conjugated π system are in the same plane. For example, the "aryl" may be phenyl and naphthyl. An aryl group may be unsubstituted or substituted by one or more substituents.

Specific substituents for each aryl group independently may be $C_1$-$C_4$-alkyl, $C_1$-$C_4$-haloalkyl, cyano, halogen, $OR^a$ or $NHR^a$.

Aryl groups may have from 6 to 20 carbon atoms as appropriate to satisfy valency requirements. Aryl groups comprise aromatic rings, i.e. rings which satisfy the Huckel rule.

Aryl groups may be optionally substituted phenyl groups, optionally substituted biphenyl groups, optionally substituted naphthalenyl groups or optionally substituted anthracenyl groups. Equally, aryl groups may include non-aromatic carbocyclic portions. An aromatic ring is a phenyl ring.

The term "heteroaryl" may refer to any aromatic (i.e. a ring system containing (4n+2) π-electrons or n-electrons in the π-system) 5-10 membered ring system comprising from 1 to 4 heteroatoms independently selected from O, S and N (in other words from 1 to 4 of the atoms forming the ring system are selected from O, S and N). Thus, any heteroaryl groups may be independently selected from: 5 membered heteroaryl groups in which the heteroaromatic ring is substituted with 1-4 heteroatoms independently selected from O, S and N; and 6-membered heteroaryl groups in which the heteroaromatic ring is substituted with 1-3 (e.g. 1-2) nitrogen atoms; 9-membered bicyclic heteroaryl groups in which the heteroaromatic system is substituted with 1-4 heteroatoms independently selected from O, S and N; 10-membered bicyclic heteroaryl groups in which the heteroaromatic system is substituted with 1-4 nitrogen atoms. Specifically, heteroaryl groups may be independently selected from: pyrrole, furan, thiophene, pyrazole, imidazole, oxazole, isoxazole, triazole, oxadiazole, thiadiazole, tetrazole; pyridine, pyridazine, pyrimidine, pyrazine, triazine, indole, isoindole, benzofuran, isobenzofuran, benzothiophene, indazole, benzimidazole, benzoxazole, benzthiazole, benzisoxazole, purine, quinoline, isoquinoline, cinnoline, quinazoline, quinoxaline, pteridine, phthalazine, naphthyridine. Heteroaryl groups may also be 6-membered heteroaryl groups in which the heteroaromatic ring is substituted with 1 heteroatomic group independently selected from O, S and NH and the ring also comprises a carbonyl group. Such groups include pyridones and pyranones. The heteroaryl system itself may be substituted with other groups. A heteroaryl group may be unsubstituted or substituted by one or more substituents. Specific substituents for each heteroaryl group independently may be $C_1$-$C_4$-alkyl, $C_1$-$C_4$-haloalkyl, cyano, halogen, $OR^a$ or $NHR^a$.

Heteroaryl groups may mean a 5- or 6-membered heteroaryl group. They may therefore comprise a 5- or 6-membered heteroaromatic ring, i.e. a 5- or 6-membered ring which satisfies the Huckel rule and comprises a heteroatom. Heteroaryl groups may be selected from: 5-membered heteroaryl groups in which the heteroaromatic ring is includes 1-4 heteroatoms selected from O, S and N; and 6-membered heteroaryl groups in which the heteroaromatic ring includes 1-2 nitrogen atoms. Specifically, heteroaryl groups and heteroaromatic rings may be selected from: pyrrole, furan, thiophene, pyrazole, imidazole, oxazole, isoxazole, triazole, oxadiazole, thiodiazole, pyridine, pyridazine, pyrimidine, pyrazine.

The term "$_{y-z}$-membered heterocycloalkyl" may refer to a monocyclic or bicyclic saturated or partially saturated group having from y to z atoms in the ring system and comprising 1 or 2 heteroatoms independently selected from O, S and N in the ring system (in other words 1 or 2 of the atoms forming the ring system are selected from O, S and N). By partially saturated it is meant that the ring may comprise one or two double bonds. This applies particularly to monocyclic rings with from 5 to 8 members. The double bond will typically be between two carbon atoms but may be between a carbon atom and a nitrogen atom. Examples of heterocycloalkyl groups include; piperidine, piperazine, morpholine, thiomorpholine, pyrrolidine, tetrahydrofuran, tetrahydrothiophene, dihydrofuran, tetrahydropyran, dihydropyran, dioxane, azepine. Bicyclic systems may be spiro-fused, i.e. where the rings are linked to each other through a single carbon atom; vicinally fused, i.e. where the rings are linked to each other through two adjacent carbon or nitrogen atoms; or they may be share a bridgehead, i.e. the rings are linked to each other two non-adjacent carbon or nitrogen atoms. A heterocycloalkyl groups may be unsubstituted or substituted by one or more substituents. Specific substituents for any saturated carbon atom in each heterocycloalkyl group may independently be fluorine, $OR^a$ or $NHR^a$.

An 'endocyclic' double bond is one where both of the atoms between which the double bond is formed are in the ring or ring system in which the atoms are situated.

A carbocyclic group consists of one or more rings which are entirely formed from carbon atoms. A carbocylic group can be a mono- or bicyclic cycloalkyl group, or it can comprise at least one phenyl ring.

A heterocyclic group consists of one or more rings wherein the ring system includes at least one heteroatom. A heterocyclic group comprises at least one heteroaryl or heterocycloalkyl rings. A heterocycloalkyl ring may be a saturated ring comprising at least one heteroatom selected from O, S and N.

Where a ring system is described as being a x-membered bicyclic group, that is intended to mean that the skeleton of the bicyclic ring system is formed from x atoms (i.e. the total number of atoms across the two rings of the bicycle is x).

Aryl and heteroaryl groups are optionally substituted with 1 to 5 substituents which are each independently at each occurrence selected from the group consisting of: halo, nitro, cyano, $NR^aR^a$, $NR^aS(O)_2R^a$, $NR^aCONR^aR^a$, $NR^aCO_2R^a$, $NR^aC(O)R^a$, $OR^a$; $SR^a$, $SOR^a$, $SO_3R^a$, $SO_2R^a$, $SO_2NR^aR^a$, $CO_2R^a$, $C(O)R^a$, $CONR^aR^a$, $C_1$-$C_4$-alkyl, $C_2$-$C_4$-alkenyl, $C_2$-$C_4$-alkynyl, $C_1$-$C_4$-haloalkyl and $CR^aR^aNR^aR^a$; wherein $R^a$ is independently at each occurrence selected from H, $C_1$-$C_4$-alkyl and $C_1$-$C_4$-haloalkyl.

The present invention also includes the synthesis of all pharmaceutically acceptable isotopically-labelled compounds of formulae (I) to (XI) wherein one or more atoms are replaced by atoms having the same atomic number, but an atomic mass or mass number different from the atomic mass or mass number most commonly found in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labelled compounds can generally be prepared by conventional techniques known to those skilled in the art or by processes analogous to those described using an appropriate isotopically-labelled reagent in place of the non-labelled reagent previously employed.

Uses, Methods of Treatment and Pharmaceutical Formulations

Each of the compounds of the present invention may be used as a medicament. Thus, in another aspect of the invention, there is provided a compound as defined above for the treatment of bacterial infections.

The compounds and formulations of the present invention may be used in the treatment of a wide range of bacterial infections. In some embodiments, the compounds can be used to treat bacterial infections caused by one or more resistant strains of bacteria e.g. a strain which is resistant to at least one approved antibiotic drug. In a further embodiment, the compounds can be used to treat bacterial infections caused by one or more resistant strains of Gram-positive bacteria e.g. a strain which is resistant to at least one approved antibiotic drug. In a further embodiment, the compounds can be used to treat bacterial infections caused by one or more resistant strains of Gram-negative bacteria, e.g. a strain which is resistant to at least one approved antibiotic drug.

The compounds and formulations of the invention may be used to treat infections caused by bacteria which are in the form of a biofilm.

The term 'resistant strains' is intended to mean strains of bacteria which have shown resistance to one or more known antibacterial drug. For example, it may refer to strains which are resistant to methicillin, strains that are resistant to one or more other β-lactam antibiotics, strains that are resistant to one or more fluoroquinolones and/or strains that are resistant to one or more other antibiotics (i.e. antibiotics other than β-lactams and fluoroquinolones). A resistant strain is one in which the MIC of a given compound or class of compounds for that strain has shifted to a significantly higher number than for the parent (susceptible) strain.

The term 'approved drug' is intended to mean that the drug is one which had been approved by the US FDA or the EMA prior to 1 Feb. 2016.

The bacterial strain (e.g. the MRSA strain or *E. coli* strain) may be resistant to one or more fluoroquinolone antibiotics, e.g. one or more antibiotics selected from levofloxacin, enoxacin, fleroxacin, lomefloxacin, nadifloxacin, norfloxacin, rufloxacin, balofloxacin, grepafloxacin, pazufloxacin, sparfloxacin, temafloxacin, tosufloxacin, besifloxacin, clinafloxacin, garenoxacin, gemifloxacin, gatifloxacin, sitafloxacin, trovafloxacin, prulifloxacin, ciprofloxacin, pefloxacin, moxifloxacin, ofloxacin, delafloxacin, zabofloxacin, avarofloxacin, finafloxacin.

The compounds of the invention may be particularly effective at treating infections caused by Gram-positive bacteria. The compounds of the invention may be particularly effective at treating infections caused by Gram-positive bacteria which are resistant to one or more fluoroquinolone antibiotics.

The compounds of the invention may be particularly effective at treating infections caused by Gram-negative bacteria. The compounds of the invention may be particularly effective at treating infections caused by Gram-negative bacteria which are resistant to one or more fluoroquinolone antibiotics.

The compounds of the invention may be particularly effective at treating infections caused by aerobic bacteria, e.g. *S. aureus*. The compounds of the invention may be particularly effective at treating infections caused by anaerobic bacteria, e.g. a *Clostridium* spp. such as *Clostridium difficile*.

The compounds and formulations of the present invention can be used to treat or to prevent infections caused by bacterial strains associated with biowarfare. These may be strains which are category A pathogens as identified by the US government (e.g. those which cause anthrax, plague etc.) and/or they may be strains which are category B pathogens as identified by the US government (e.g. those which cause Glanders disease, mellioidosis etc). In a specific embodiment, the compounds and formulations of the present invention can be used to treat or to prevent infections caused by Gram-positive bacterial strains associated with biowarfare (e.g. anthrax). More particularly, the compounds and formulations may be used to treat category A and/or category B pathogens as defined by the US government on 1 Jan. 2014.

The bacterial infection may be caused by a strain selected from: *Neisseria* spp., *Haemophilus* spp., *Legionella* spp., *Pasteurella* spp., *Bordetella* spp., *Brucella* spp., *Francisella* spp. and *Moraxella* spp. Like *Neisseria* spp., *Haemophilus* spp., *Legionella* spp., *Pasteurella* spp., *Bordetella* spp., *Brucella* spp., *Francisella* spp. and *Moraxella* spp. are fastidious Gram-negative organisms. A fastidious bacterium is one having a complex nutritional requirement, i.e. one which will only grow when specific nutrients are included in the culture medium. As an example *Neisseria gonorrhoeae* requires, amongst other supplements, iron, several amino acids, cofactors and vitamins in order to grow. Members of the fastidious Gram-negative bacteria group often share common antibiotic susceptibility profiles. Pathogenic *Neisseria* species include *Neisseria gonorrhoeae* (the pathogen responsible for gonorrhoea) and *Neisseria meningitidis* (one of the pathogens responsible for bacterial meningitis). Infections which can be treated by the compounds and methods of the invention include gonorrhoea. Infections which can be treated include secondary infections which can arise from lack of treatment of a primary *Neisseria gonorrhoeae* infection. Exemplary secondary infections include urethritis, dysuria, epididymitis, pelvic inflammatory disease, cervicitis and endometritis and also systemic gonococcal infections (e.g. those manifesting as arthritis, endocarditis or meningitis). The gonorrhoea infection may be one caused by a strain of *Neisseria gonorrhoeae* which is resistant to at least one known antibacterial drug, e.g. at least one β-lactam drug. The gonorrhoea infection may be one caused by a strain of *Neisseria gonorrhoeae* which is resistant to at least one approved drug. The at least one drug may be an antibiotic drug, e.g. one that is approved for use in treating one of the fastidious Gram-negative species mentioned in this specification. It may be approved for use in treating gonorrhoea. The approved drug may be a β-lactam drug. Further infections which can be treated by the compounds and methods of the invention include bacterial meningitis and *Neisseria meningitidis* infections of other parts of the human or animal body.

The compounds of the invention can be used to treat or prevent mycobacterial infections, e.g. mycobacterial infections caused by resistant strains of mycobacteria. Thus, for example, they can be used to treat TB or leprosy. Thus, it may be that the mycobacterial infection is caused by *M. tuberculosis*. It may also be that the mycobacterial infection is caused by a *mycobacterium* selected from: *M. avium* complex, *M. abscessus, M. leprae, M. bovis, M. kansasii, M. chelonae, M. africanum, M. canetti* and *M. microti*. The compounds may be used to treat resistant strains of TB, e.g. MDR-TB (i.e. TB infections caused by strains which are resistant to isoniazid and rifampicin), XDR-TB (i.e. TB infections caused by strains which are resistant to isoniazid, rifampicin, at least one fluoroquinolone and at least one of kanamycin, capreomycin and amikacin) and/or TDR-TB (i.e. TB infections caused by strains which have proved resistant to every drug tested against it with the exception of a compound of the invention). The *mycobacterium* is caused by a mycobacterial strain which is resistant to at least one approved antimycobacterial compound. The at least one approved antimycobacterial compound may be selected from: rifampicin, isoniazid, kanamycin, capreomycin, amikacin and a fluoroquinolone. The at least one approved antimycobacterial compound may be selected from: rifampicin, moxifloxacin, isoniazid, ciprofloxacin and levofloxacin. The compounds of the invention may be used to treat non-replicating TB.

The compounds of the invention may also be useful in treating other forms of infectious disease, e.g. fungal infections, parasitic infections and/or viral infections.

The compounds of the present invention can be used in the treatment of the human body. They may be used in the treatment of the animal body. In particular, the compounds of the present invention can be used to treat commercial animals such as livestock. Alternatively, the compounds of the present invention can be used to treat companion animals such as cats, dogs, etc.

The compounds of the invention may be obtained, stored and/or administered in the form of a pharmaceutically acceptable salt. Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate and hemicalcium salts. Also included are acid addition or base salts wherein the counter ion is optically active, for example, d-lactate or l-lysine, or racemic, for example, dl-tartrate or dl-arginine.

Compounds of the invention may exist in a single crystal form or in a mixture of crystal forms or they may be amorphous. Thus, compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

For the above-mentioned compounds of the invention the dosage administered will, of course, vary with the compound employed, the mode of administration, the treatment desired and the disorder indicated. For example, if the compound of the invention is administered orally, then the daily dosage of the compound of the invention may be in the range from 0.01 micrograms per kilogram body weight (μg/kg) to 100 milligrams per kilogram body weight (mg/kg).

A compound of the invention, or pharmaceutically acceptable salt thereof, may be used on their own but will generally be administered in the form of a pharmaceutical composition in which the compounds of the invention, or pharmaceutically acceptable salt thereof, is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

The compounds of the invention may be administered in combination with other active compounds (e.g. antifungal compounds, oncology compounds) and, in particular, with other antibacterial compounds. The compound of the invention and the other active (e.g. the other antibacterial compound) may be administered in different pharmaceutical formulations either simultaneously or sequentially with the other active. Alternatively, the compound of the invention and the other active (e.g. the other antibacterial compound) may form part of the same pharmaceutical formulation.

Examples of other bacterial compounds which could be administered with the compounds of the invention are penems, carbapenems, fluoroquinolones, β-lactams, vancomycin, erythromycin or any other known antibiotic drug molecule.

Depending on the mode of administration of the compounds of the invention, the pharmaceutical composition which is used to administer the compounds of the invention will preferably comprise from 0.05 to 99% w (percent by weight) compounds of the invention, more preferably from 0.05 to 80% w compounds of the invention, still more preferably from 0.10 to 70% w compounds of the invention, and even more preferably from 0.10 to 50% w compounds of the invention, all percentages by weight being based on total composition.

The pharmaceutical compositions may be administered topically (e.g. to the skin) in the form, e.g., of creams, gels, lotions, solutions, suspensions, or systemically, e.g. by oral administration in the form of tablets, capsules, syrups, powders, suspensions, solutions or granules; or by parenteral administration in the form of a sterile solution, suspension or emulsion for injection (including intravenous, subcutaneous, intramuscular, intravascular or infusion); or by rectal administration in the form of suppositories; or by inhalation (i.e. in the form of an aerosol or by nebulisation).

If administered topically, high-dosages of the compounds of the invention can be administered. Thus, a compound with an in vitro MIC of, for example, 16-64 μg/mL may still provide an effective treatment against certain bacterial infections.

For oral administration the compounds of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compounds of the invention may be admixed with, for example, a vegetable oil or polyethylene glycol. Hard gelatine capsules may contain granules of the compound using either the above-mentioned excipients for tablets. Also liquid or semi-solid formulations of the compound of the invention may be filled into hard gelatine capsules. Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, sweetening agents (such as saccharine), preservative agents and/or carboxymethylcellulose as a thickening agent or other excipients known to those skilled in the art.

For intravenous (parenteral) administration the compounds of the invention may be administered as a sterile aqueous or oily solution.

The size of the dose for therapeutic purposes of compounds of the invention will naturally vary according to the nature and severity of the conditions, the age and sex of the animal or patient and the route of administration, according to well known principles of medicine.

Dosage levels, dose frequency, and treatment durations of compounds of the invention are expected to differ depending on the formulation and clinical indication, age, and co-morbid medical conditions of the patient. The standard duration of treatment with compounds of the invention is expected to vary between one and seven days for most clinical indications. It may be necessary to extend the duration of treatment beyond seven days in instances of recurrent infections or infections associated with tissues or implanted materials to which there is poor blood supply including bones/joints, respiratory tract, endocardium, and dental tissues.

In another aspect the present invention provides a pharmaceutical formulation comprising a compound of the invention and a pharmaceutically acceptable excipient. The formulation may further comprise one or more other antibiotics, e.g. one or more fluoroquinolone antibiotics. Illustrative fluoroquinolone antibiotics include levofloxacin, enoxacin, fleroxacin, lomefloxacin, nadifloxacin, norfloxacin, rufloxacin, balofloxacin, grepafloxacin, pazufloxacin, sparfloxacin, temafloxacin, tosufloxacin, besifloxacin, clinafloxacin, garenoxacin, gemifloxacin, gatifloxacin, sitafloxacin, trovafloxacin, prulifloxacin, ciprofloxacin, pefloxacin, moxifloxacin, ofloxacin, delafloxacin, zabofloxacin, avarofloxacin, finafloxacin.

In another aspect of the invention is provided a method of treating a bacterial infection, the method comprising treating a subject in need thereof with a therapeutically effective amount of a compound of the invention.

Medical Uses

The compounds of the present invention can be used in the treatment of the human body.

The compounds of the invention may be for use in treating human bacterial infections such as infections of the genitourinary system, the respiratory tract, the gastrointestinal tract, the ear, the skin, the throat, soft tissue, bone and joints (including infections caused by *Staphylococcus aureus*). The compounds can be used to treat pneumonia, sinusitis, acute bacterial sinusitis, bronchitis, acute bacterial exacerbation of chronic bronchitis, anthrax, chronic bacterial prostatitis, acute pyelonephritis, pharyngitis, tuberculosis, tonsillitis, *Escherichia coli*, prophylaxis before dental surgery, cellulitis, acnes, cystitis, infectious diarrhoea, typhoid fever, infections caused by anaerobic bacteria, peritonitis, abdominal infection, bacteraemia, septicaemia, sexually transmitted bacterial infection (e.g. gonorrhoea, *Chlamydia*), bacterial vaginosis, pelvic inflammatory disease, pseudomembranous colitis, *Helicobacter pylori*, acute gingivitis, Crohn's disease, rosacea, fungating tumours, impetigo.

The compounds of the present invention may also be used in treating other conditions treatable by eliminating or reducing a bacterial infection. In this case they will act in a secondary manner alongside for example a chemotherapeutic agent used in the treatment of cancer.

In yet another aspect of the invention is provided a compound for use in the preparation of a medicament. The medicament may be for use in the treatment of any of the diseases, infections and indications mentioned in this specification.

In an aspect of the invention is provided a compound of the invention for medical use. The compound may be used in the treatment of any of the diseases, infections and indications mentioned in this specification.

Veterinary Uses

They may be used in the treatment of the animal body. In particular, the compounds of the present invention can be used to treat commercial animals such as livestock. The livestock may be mammal (excluding humans) e.g. cows, pigs, goats, sheep, llamas, alpacas, camels and rabbits. The livestock may be birds (e.g. chickens, turkeys, ducks, geese etc.).

Alternatively, the compounds of the present invention can be used to treat companion animals such as cats, dogs, etc. The veterinary use may be to treat wild populations of animals in order to prevent the spread of disease to humans or to commercial animals. In this case, the animals may be rats, badgers, deer, foxes, wolves, mice, kangaroos and monkeys and other apes.

In an aspect of the invention is provided a compound of the invention for veterinary use. The compound may be used in the treatment of any of the animal diseases and infections and indications mentioned in this specification.

In another aspect the present invention provides a veterinary formulation comprising a compound of the invention and a veterinarily acceptable excipient.

The methods by which the compounds may be administered for veterinary use include oral administration by capsule, bolus, tablet or drench, topical administration as an ointment, a pour-on, spot-on, dip, spray, mousse, shampoo, collar or powder formulation or, alternatively, they can be administered by injection (e.g. subcutaneously, intramuscularly or intravenously), or as an implant. Such formulations may be prepared in a conventional manner in accordance with standard veterinary practice. The formulations will vary with regard to the weight of active compound contained therein, depending on the species of animal to be treated, the severity and type of infection and the body weight of the animal. For parenteral, topical and oral administration, typical dose ranges of the active ingredient are 0.01 to 100 mg per kg of body weight of the animal. Preferably the range is 0.1 to 10 mg per kg. In any event, the veterinary practitioner, or the skilled person, will be able to determine the actual dosage which will be most suitable for an individual patient, which may vary with the species, age, weight and response of the particular patient. The above dosages are exemplary of the average case; there can, of course, be individual instances where higher or lower dosage ranges are merited, and such are within the scope of this invention.

As an alternative, when treating animals the compounds may be administered with the animal feedstuff and for this purpose a concentrated feed additive or premix may be prepared for mixing with the normal animal feed.

Certain compounds of the invention are of particular use in the treatment of mastitis. In this regard, a particularly preferred method of administration is by injection into the udder of a subject (e.g. a cow, a goat, a pig or sheep).

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

Synthesis

The skilled man will appreciate that adaptation of methods known in the art could be applied in the manufacture of the compounds of the present invention.

For example, the skilled person will be immediately familiar with standard textbooks such as "Comprehensive Organic Transformations—A Guide to Functional Group Transformations", R C Larock, Wiley-VCH (1999 or later editions), "March's Advanced Organic Chemistry—Reactions, Mechanisms and Structure", M B Smith, J. March, Wiley, (5th edition or later) "Advanced Organic Chemistry, Part B, Reactions and Synthesis", F A Carey, R J Sundberg, Kluwer Academic/Plenum Publications, (2001 or later editions), "Organic Synthesis—The Disconnection Approach", S Warren (Wiley), (1982 or later editions), "Designing Organic Syntheses" S Warren (Wiley) (1983 or later editions), "Guidebook To Organic Synthesis" R K Mackie and D M Smith (Longman) (1982 or later editions), etc., and the references therein as a guide.

The skilled chemist will exercise his judgement and skill as to the most efficient sequence of reactions for synthesis of a given target compound and will employ protecting groups as necessary. This will depend inter alia on factors such as the nature of other functional groups present in a particular substrate. Clearly, the type of chemistry involved will influence the choice of reagent that is used in the said synthetic steps, the need, and type, of protecting groups that are employed, and the sequence for accomplishing the protection/deprotection steps. These and other reaction parameters will be evident to the skilled person by reference to standard textbooks and to the examples provided herein.

Sensitive functional groups may need to be protected and deprotected during synthesis of a compound of the invention. This may be achieved by conventional methods, for example as described in "Protective Groups in Organic Synthesis" by T W Greene and P G M Wuts, John Wiley & Sons Inc (1999), and references therein.

Throughout this specification these abbreviations have the following meanings:

| | |
|---|---|
| ACN—Acetonitrile | CDI—Carbonyl diimidazole |
| BOC—tert-Butyl carbonate | dba—Dibenzylideneacetone |
| DCM—Dichloromethane | DMF—N,N-Dimethylformamide |
| DMSO—Dimethylsulfoxide | IPA—iso-Propyl alcohol |
| NMP—N-Methylpyrolidinone | PMB—para-Methoxybenzyl |
| TFA—Trifluoroacetic acid | THF—Tetrahydrofuran |
| DMA—N,N-Dimethylacetamide | |
| EDCI—N-(3-Dimethylaminopropyl)-N'-ethylcarbodiimide hydrochloride | |

Certain compounds of the invention can be made according to the following general schemes. Certain compounds of the invention can be made according to or analogously to the methods described in Examples 1 to 107.

Certain compounds of the invention in which $Y^1$ is NH can be made by Scheme A:—

Scheme A

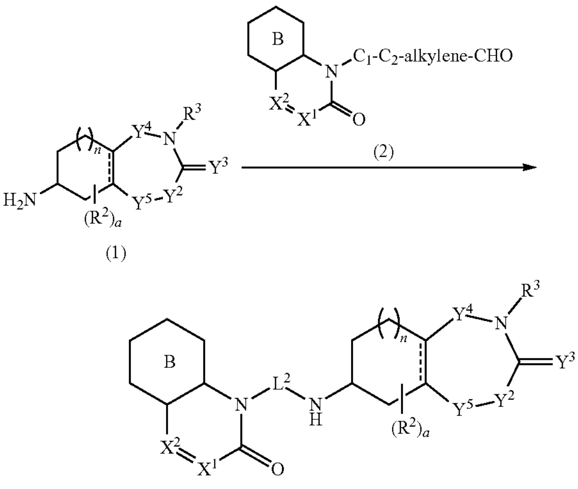

(1) (2) (3)

Amine (1) can be converted to (3) via reductive amination with aldehyde (2). The reaction can be performed using a borohydride reagent, such as tetramethylammonium triacetoxyborohydride or sodium triacetoxyborohydride, in a solvent, such as THF or 1,2-dichloroethane, at a temperature from room temperature to 80° C. In certain examples, 4 Å sieves can be added to the reaction mixture.

Certain compounds of the invention in which $Y^1$ is O can be made by Scheme B:—

Scheme B

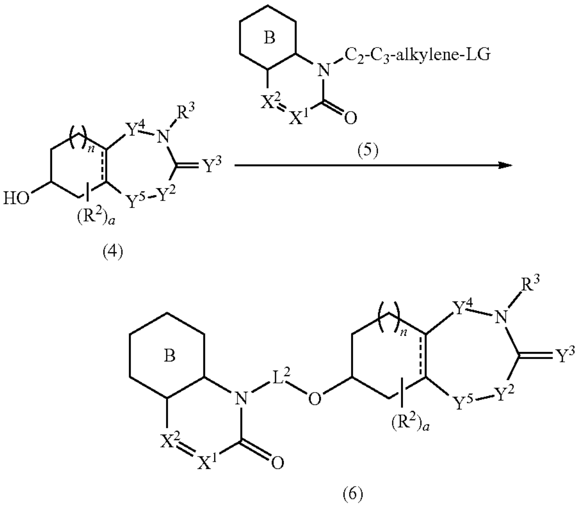

(4) (5) (6)

Alcohol (4) can be converted to (6) via alkylation with (5), where LG represents a leaving group, such as a halide. The reaction can be performed in a solvent, such as DMF or THF, in the presence of a base, such as $K_2CO_3$, with optional heating.

Following Scheme B, but using thiol (7), compound (8) (a subset of compounds of the invention in which $Y^1$ is S) can be prepared.

(7)

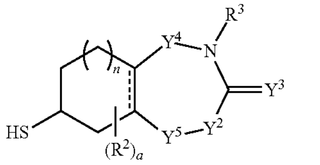

(8)

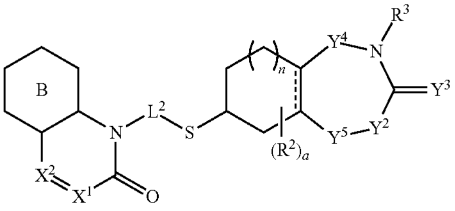

Following Scheme A but using aldehyde (9), compound (10) (a subset of compounds of the invention in which $Y^1$ is NH) can be prepared.

(9)

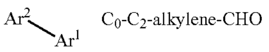

-continued (10)

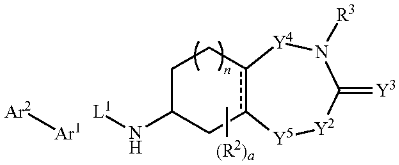

Following Scheme B but using alkylating agent (11), compound (12) (a subset of compounds of the invention in which $Y^1$ is O) can be prepared.

(11)

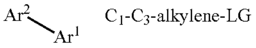

(12)

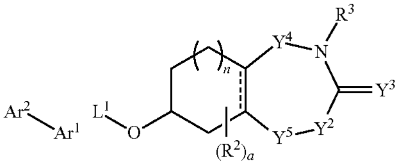

Following Scheme B but using thiol (7) and alkylating agent (11) compound (13) (a subset of compounds of the invention in which $Y^1$ is S) can be prepared.

(13)

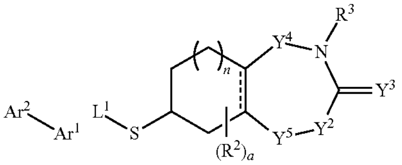

Certain compounds of the invention can be made by Scheme C:—

Scheme C

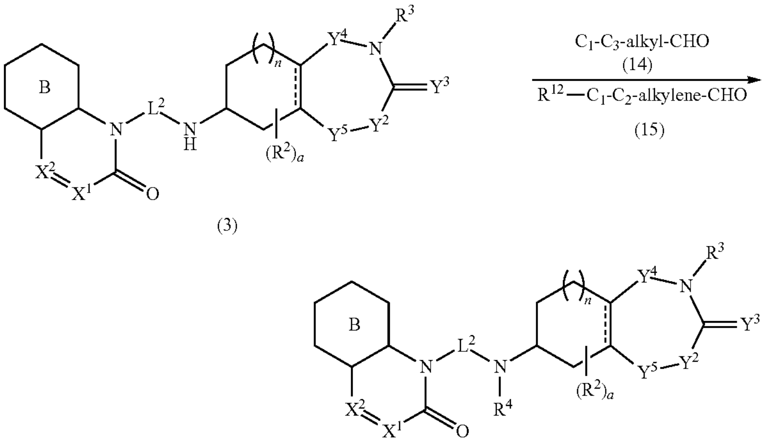

(3)

(16)

Reductive amination of (3) (prepared as described in Scheme A) with aldehyde (14) or (15) can afford (16) (a subset of compounds of the invention in which $Y^1$ is $NR^4$) The reaction can be performed using a borohydride reagent, such as tetramethylammonium triacetoxyborohydride or sodium triacetoxyborohydride, in a solvent, such as THF or 1,2-dichloroethane or DCM, at a temperature from room temperature to 80° C. In certain examples, 4 Å sieves can be added to the reaction mixture.

Following Scheme C, but using amine (10), compound (17) (a subset of compounds of formula (II)) can be prepared.

(17)

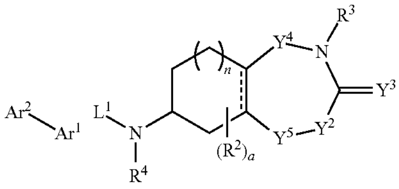

Following Scheme A, but using amine (18), compound (19) (a subset of compounds of formula (IV)) can be prepared.

(18)

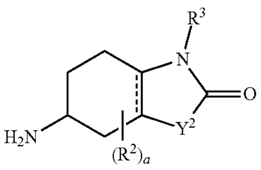

(19)

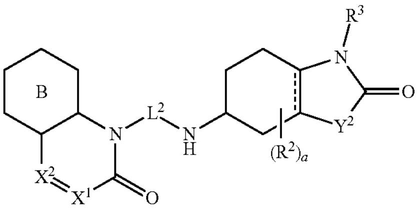

Following Scheme A, but using aldehyde (9) and amine (18), compound (20) (a subset of compounds of formula (IV)) can be prepared.

(20)

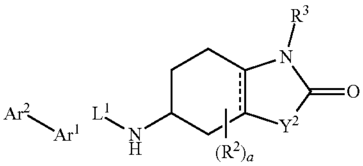

Following Scheme C, amine (19) and amine (20) can be converted to compounds (21) and (22) representing a subset of compounds of formula (IV).

(21)

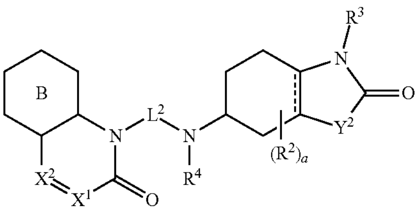

-continued (22)

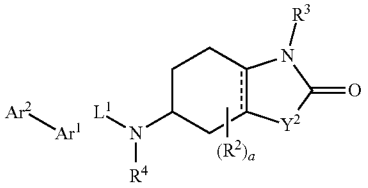

Following Scheme A, but using aldehyde (9) and amine (23), compound (24) (a subset of compounds of formula (VII)) can be prepared.

(23)

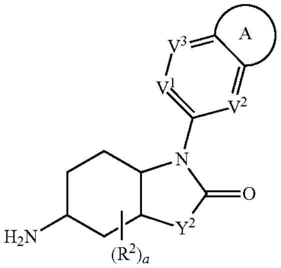

(24)

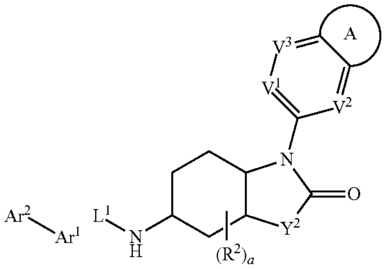

Following Scheme A, but using amine (23), compound (25) (a subset of compounds of formula (VIII)) can be prepared.

(25)

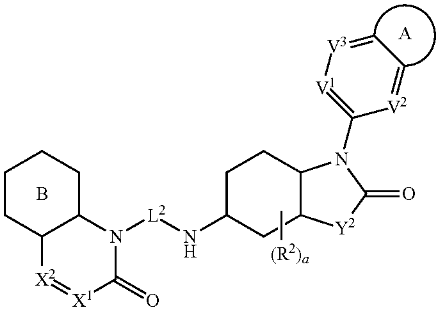

Following Scheme C, amine (24) and amine (25) can be converted to compounds (26) and (27) representing subsets of compounds of formula (VI).

(26)

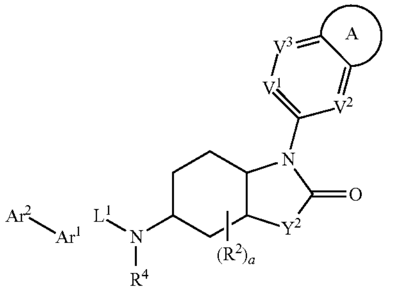

(27)

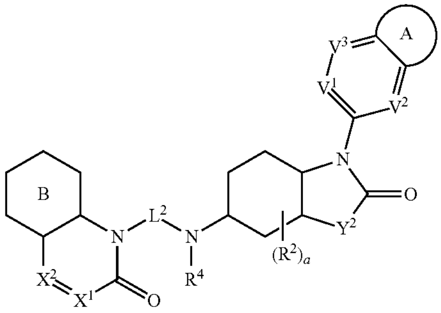

Following Scheme A, but using aldehyde (28) and amine (23), compound (29) (a subset of compounds of formula (VII)) can be prepared.

(28)

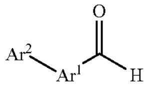

(29)

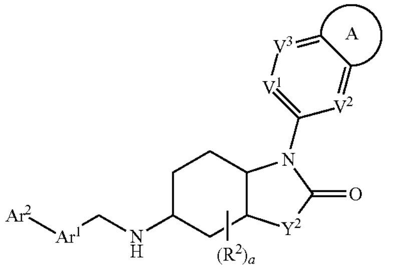

Certain compounds of formula (VIII) can be made by Scheme D:—

Scheme D

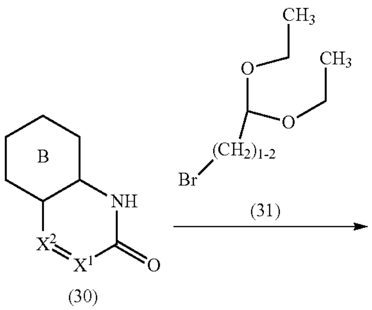

(30)

-continued

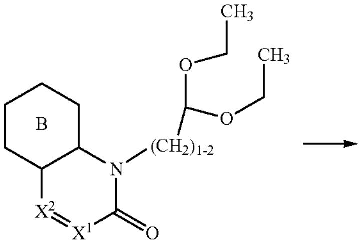

(32)

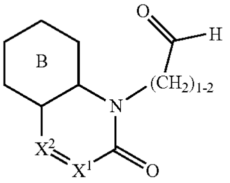

(33)

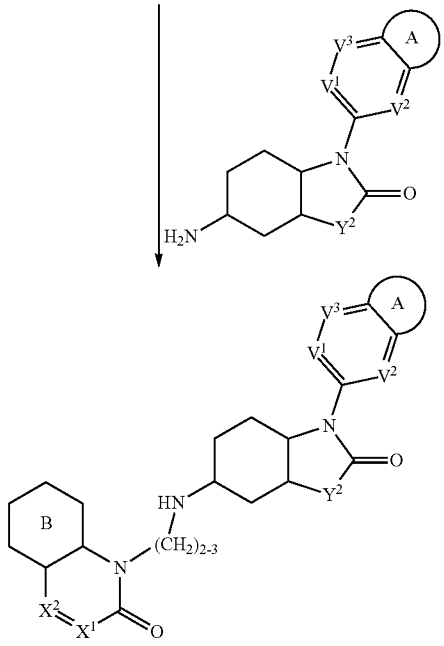

(35)

Reaction of pyridone (30) with commercially available bromo acetals (31) can generate pyridone acetals (32). The alkylation reaction can be carried out in the presence of a base, such as $Cs_2CO_3$, in a solvent, such as dry NMP, at a temperature from 50-100° C. Hydrolysis of pyridone acetals (32) to give the requisite aldehydes (33) can be effected using a strong acid, such as concentrated HCl, in a solvent, such as ACN, at room temperature. Aldehydes (33) can be converted to pyridones (35) (a subset of compounds of formula (VIII)) via reductive amination with amine (34). The reaction can be performed using a borohydride reagent, such as tetramethylammonium triacetoxyborohydride or sodium triacetoxyborohydride, in a solvent, such as THF or 1,2-dichloroethane, at a temperature from room temperature to 80° C. In certain examples, 4 Å sieves can be added to the reaction mixture.

Amine (34) can be made by Scheme E:

Scheme E

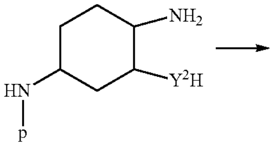

(36)

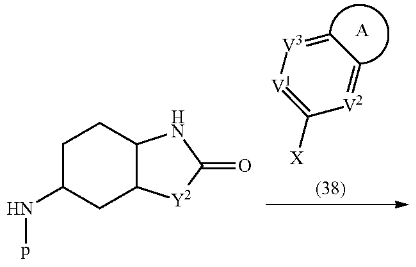

(38)

(37)

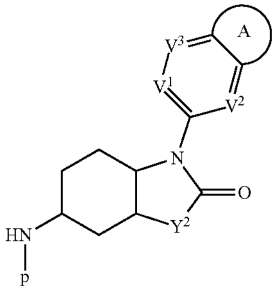

(39)

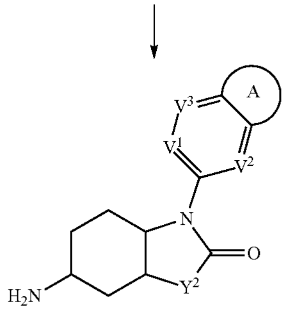

(34)

Reaction of protected amine (36), where P represents a standard nitrogen protecting group, such as BOC, with a carbonylating reagent, such as CDI, in a solvent, such as dioxane or ACN, at a temperature from 80-100° C. can generate (37). Addition of a base, such as $K_2CO_3$, is optional. Cross coupling reaction of (37), with (38), where X═Br or Cl, can generate protected amine (39). The cross coupling reaction can be copper catalysed, using for example CuI, in the presence of a diamine, such as 1,2-diaminocyclohexane or N,N-dimethyl-1,2-ethanediamine, in the presence of a base, such as $K_2CO_3$, in a solvent, such as dioxane or toluene, at a temperature from 70-110° C. The cross coupling reaction can be palladium catalysed, using for example, $Pd_2(dba)_3$ or $Pd(OAc)_2$ in the presence of a phosphine, such as Xantphos or $P(t\text{-}Bu)_3$ or X-Phos, in the presence of a base, such as t-BuONa or $Cs_2CO_3$, in a solvent, such as dioxane or toluene, at a temperature from 80-120° C.

The nitrogen protecting group in (39) can be deprotected to give the free amine (34) under standard conditions. Where the nitrogen protecting group is BOC the deprotection can be achieved by the action of TFA in DCM at room temperature.

Following Scheme C, but using amine (35), compound (40) (a subset of compounds of formula (VIII)) can be prepared.

(40)

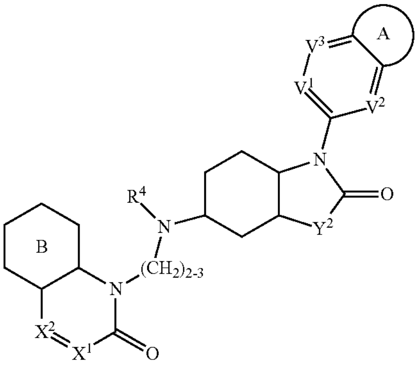

Following Scheme D, but using tricyclic pyridone (41), amine (42) (a subset of compounds of formula (IX)) can be prepared.

(41)

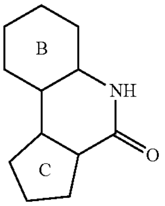

(42)

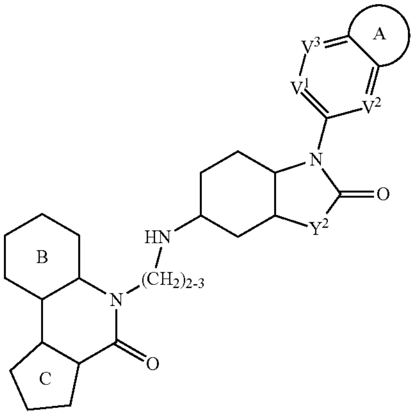

EXPERIMENTAL

Analytical Methods

NMR spectra were obtained on a LC Bruker AV400 using a 5 mm QNP probe (Method A), a Bruker AVIII 400 Nanobay using a 5 mm BBFQ with z-gradients (Method B), a Bruker AV1 Avance using a 5 mm QNP probe (Method C), a BrukerAV1 Avance using a $^{1}H/^{13}C$ Dual probe (Method D) or a Bruker ASCEND 400 MHz spectrometer (Method E).

MS was carried out on either a Waters ZQ MS (Method A and B), an Agilent Technologies 1200 series (Method C and D) using $H_2O$ and ACN (0.1% formic acid—acidic pH; 0.1% ammonia—basic pH)—wavelengths were 254 and 210 nM, or a Shimadzu LCMS-2020 (Method E) using $H_2O$ and MeOH (0.1% formic acid—acidic pH; 0.1% ammonia—basic pH)—wavelengths were 254 and 210 nM.

Method A

Column: YMC-Triart C18, 5 μm, 50×2 mm. Flow rate: 0.8 mL/min. Injection volume 5 μL.

| Time (min) | $H_2O$ % | ACN % |
|---|---|---|
| 0 | 95 | 0 |
| 4 | 0 | 95 |
| 4.4 | 0 | 95 |
| 4.5 | 95 | 5 |
| 4.5 | STOP | |

Method B

Column: YMC-Triart C18, 5 μm, 50×2 mm. Flow rate: 0.8 mL/min. Injection volume 5-10 μL

| Time (min) | $H_2O$ (%) | ACN (%) |
|---|---|---|
| 0 | 95 | 0 |
| 2.0 | 95 | 0 |
| 12.0 | 0 | 95 |
| 14.0 | 0 | 95 |
| 14.2 | 95 | 0 |

Method C

Column: Poroshell 120, 2.7 μm, 50×2.1 mm. Flow rate: 0.8 mL/min. Injection volume 5-10 μL

| Time (min) | $H_2O$ (%) | ACN (%) |
|---|---|---|
| 0.0 | 90 | 10 |
| 0.5 | 90 | 10 |
| 4.0 | 20 | 80 |
| 5.0 | 20 | 80 |
| 5.1 | 90 | 10 |
| 6.0 | 90 | 10 |

Method D

Column: Poroshell 120, 2.7 μm, 50×2.1 mm. Flow rate: 0.8 mL/min. Injection volume 5-10 μL

| Time (min) | $H_2O$ (%) | ACN (%) |
|---|---|---|
| 0.0 | 90 | 10 |
| 0.5 | 90 | 10 |
| 5.0 | 20 | 80 |
| 6.0 | 20 | 80 |
| 6.1 | 90 | 10 |
| 7.0 | 90 | 10 |

Method E

Column: Atlantis T3, 3 μm, 3.0×75 mm. Flow rate: 0.8 mL/min. Injection volume 1-10 μL

| Time (min) | $H_2O$ (%) | MeOH (%) |
|---|---|---|
| 0.01 | 50 | 50 |
| 0.05 | 50 | 50 |
| 3.5 | 95 | 5 |

-continued

| Time (min) | $H_2O$ (%) | MeOH (%) |
|---|---|---|
| 7.0 | 95 | 5 |
| 8.5 | 50 | 50 |
| 9.5 | 50 | 50 |

Preparative HPLC was performed using a Waters 3100 Mass detector (Method A) or Waters 2767 Sample Manager (Method B) using $H_2O$ and ACN (0.1-% formic acid—acidic pH; 0.1% ammonia—basic pH).

Method A

Column: XBridge™ prep C18, 5 μm OBD 19×100 mm. Flow rate: 20 mL/min.

Method B

Column: XBridge™ prep C18, 5 μm OBD 19×100 mm. Flow rate: 20 mL/min.

Example 1:—1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydro-1,8-naphthyridin-2-one

1

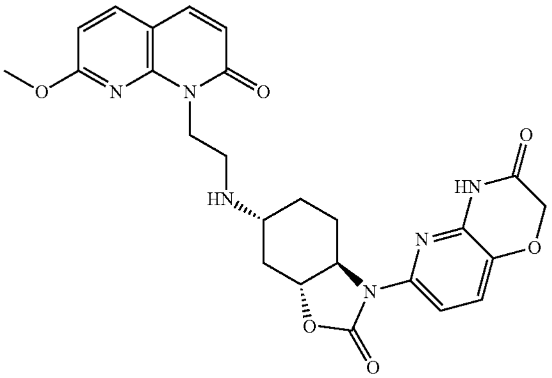

a) tert-butyl N-[(3aR, 6R, 7aR)-2-oxo-octahydro-1,3-benzoxazol-6-yl]carbamate 1a Step 1: tert-butyl N-[(1R,3R,4R)-4-azido-3-hydroxycyclohexyl]carbamate To a 500 mL round bottom flask at 25° C. was added tert-butyl N-[(1R,3R,6S)-7-oxabicyclo[4.1.0]heptan-3-yl] carbamate (WO 2011146953 A1) (20.0 g, 93.7 mmol) and MeOH (200 mL) to form a solution. Lithium perchlorate (49.8 g, 468 mmol) was added at 25° C. and the mixture heated to 50° C. for 16 h. The reaction was allowed to cool to 25° C. and sodium azide (9.14 g, 140 mmol) added. The mixture was heated at 50° C. for 16 h and TLC (petroleum ether/EtOAc=1/1, $R_f$=0.43) showed the reaction was complete. Aqueous $NaHCO_3$ (500 mL) was added and the mixture extracted with EtOAc (500 mL). The organic layer was washed with $H_2O$ (300 mL×2) and concentrated. The crude material was purified by column chromatography (SiO2, 100-200 mesh, petroleum ether/EtOAc=20/1 to 5/1) to give tert-butyl N-[(1R,3R,4R)-4-azido-3-hydroxycyclohexyl]carbamate (1.40 g, 5.0% yield) as white solid. $^1H$ NMR (Method A) ($CDCl_3$): δ ppm 4.51 (br, 1H), 3.47-3.52

(m, 2H), 3.17-3.23 (m, 1H), 2.54 (d, J=3.2 Hz, 1H), 2.28 (d, J=10.4 Hz, 1H), 2.07-2.04 (m, 1H), 1.43 (s, 9H), 1.17-1.29 (m, 2H)

Step 2: tert-butyl N-[(1R,3R,4R)-4-amino-3-hydroxycyclohexyl]carbamate tert-butyl N-[(1R,3R,4R)-4-azido-3-hydroxycyclohexyl] carbamate (4.40 g, 17.1 mmol) was added to a 50 mL round bottom flask and THF (24.0 mL) added. Triphenylphosphine (9.01 g, 34.3 mmol) and $H_2O$ (4.00 mL) were added and the mixture stirred for 16 h at 25° C. TLC (petroleum ether/EtOAc=1/1, $R_f$=0.00) showed the reaction was complete. The mixture was directly concentrated and purified by column chromatography (SiO2, 100-200 mesh, DCM/MeOH=1/0 to 10/1) to give tert-butyl N-[(1R,3R,4R)-4-amino-3-hydroxycyclohexyl]carbamate (3.60 g, 91% yield) as white solid. TLC (DCM/MeOH=5/1, $R_f$=0.32). $^1$H NMR (Method C) (CDCl3): δ ppm 4.45 (br. s, 1H), 3.57 (br. s, 1H), 3.27-3.17 (m, 1H), 2.45-2.37 (m, 1H), 2.34-2.37 (m, 1H), 2.06-1.97 (m, 1H), 1.93-1.84 (m, 1H), 1.84-1.59 (m, 2H), 1.47 (s, 9H), 1.28-1.11 (m, 3H).

Step 3: tert-butyl N-[(3aR, 6R, 7aR)-2-oxo-octahydro-1,3-benzoxazol-6-yl]carbamate 1a To a mixture of tert-butyl N-[(1R,3R,4R)-4-amino-3-hydroxycyclohexyl]carbamate (20 g, 86.84 mmol) and triethylamine (36.3 mL, 260.5 mmol) in THF (350 mL) was added portionwise triphosgene (10.31 g, 34.7 mmol)—the reaction exothermed, liberating gas.

The mixture was stirred at 25° C. for 24 h then quenched with aqueous HCl (1.0 N, 100 mL), extracted with DCM (150 mL), dried over $MgSO_4$ and the solvent evaporated to afford a yellow solid. This was triturated with DCM/EtOAc (1:1) to afford a solid which was filtered and dried to give tert-butyl N-[(3aR,6R,7aR)-2-oxo-octahydro-1,3-benzoxazol-6-yl]carbamate 1a (16.5 g, 64.38 mmol, 74.1% yield) as a white solid. $^1$H NMR (Method C) (CDCl3): δ ppm 5.42 (s 1H), 4.53 (d, J=8.5 Hz, 1H), 3.89 (ddd, J=12.0, 10.8, 3.5 Hz, 1H), 3.81-3.59 (m, 1H), 3.45-3.26 (m, 1H), 2.57 (dt, J=10.8, 3.6 Hz, 1H), 2.19-2.10 (m, 1H), 2.10-2.06 (m, 1H), 1.65-1.47 (m, 2H), 1.44 (s, 9H), 1.25 (qd, J=12.8, 4.1 Hz, 1H).

b) tert-butyl N-[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]carbamate 1b A mixture of tert-butyl N-[(3aR, 6R, 7aR)-2-oxo-octahydro-1,3-benzoxazol-6-yl]carbamate 1a (0.3 g, 1.17 mmol), 6-bromo-4-[(4-methoxyphenyl)methyl]-2H,3H,4H-pyrido[3,2-b][1,4]oxazin-3-one (prepared as described in WO2014108832) (0.53 g, 1.52 mmol), $K_2CO_3$ (320 mg, 2.34 mmol), trans-1,2-diaminocyclohexane (27 mg, 0.23 mmol) and CuI (45 mg, 0.23 mmol) in dioxane (25 mL) was heated at reflux for 18 h under $N_2$. The mixture was cooled to room temperature, poured into $H_2O$ and extracted with EtOAc (200 mL). The organic layer was washed with brine, dried over $Na_2SO_4$, filtered and concentrated. The residue was purified by silica gel chromatography using DCM/EtOAc, 2:1 to 1:1, v/v to give tert-butyl N-[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]carbamate 1b (400 mg, 65%). TLC: $R_f$=0.4 (silica gel, DCM/EtOAc=2:1, v/v). LC-MS (Method D) 525.2 [M+H]$^+$; RT 5.03 min.

c) (3aR,6R,7aR)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 1c To a solution of tert-butyl N-[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]carbamate 1b (0.40 g, 0.76 mmol) in DCM (10 mL) at room temperature was added TFA (3 mL) and the mixture was stirred for 2 h, then concentrated under reduced pressure. The residue was adjusted to pH 8~9 with saturated aqueous $Na_2CO_3$, then partitioned between brine and DCM. The organic phase was dried over $Na_2SO_4$, filtered and concentrated to give (3aR,6R,7aR)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 1c (380 mg), which was used without further purification. TLC: $R_f$=0.3 (silica gel, DCM/MeOH=10:1, v/v). LC-MS (Method D) 425.1 [M+H]$^+$; RT 2.77 min.

d) 1-({[(3aR,6R, 7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}methyl)-7-methoxy-1,2-dihydro-1,8-napthyridin-2-one 1d To a solution of (3aR,6R,7aR)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 1c (380 mg, 0.90 mmol) and 2-(7-methoxy-2-oxo-1,2-dihydro-1,8-naphthyridin-1-yl)acetaldehyde (prepared as described in WO2008009700) (200 mg, 0.91 mmol) in DCM (40 mL) was added $NaBH(OAc)_3$ (570 mg, 2.69 mmol) and the mixture was stirred at room temperature for 17 h. The mixture was adjusted to pH 8~9 with saturated aqueous $Na_2CO_3$ and extracted with DCM (100 mL). The organic layer was washed with brine, dried ($Na_2SO_4$), filtered and concentrated. The residue was purified by silica gel chromatography using 2% MeOH in DCM to give 1-({[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}methyl)-7-methoxy-1,2-dihydro-1,8-napthyridin-2-one 1d (100 mg, 17%). TLC: $R_f$=0.3 (silica gel, DCM/MeOH=10:1, v/v). LC-MS (Method D) 627.2 [M+H]$^+$; RT 3.38 min.

e) 1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydro-1,8-naphthyridin-2-one 1

To a solution of 1-({[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}methyl)-7-methoxy-1,2-dihydro-1,8-napthyridin-2-one 1d (100 mg, 0.16 mmol) in DCM (20 mL) was added TFA (3 mL) followed by $CF_3SO_3H$ (1 mL) and the mixture was stirred at room temperature for 1 h. The reaction was quenched with MeOH and the mixture was adjusted to pH 8~9 with saturated aqueous $Na_2CO_3$ and extracted with DCM (100 mL). The organic extract was washed with brine, dried ($Na_2SO_4$), filtered and concentrated under reduced pressure. The residue was purified by chromatography to give 1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydro-1,8-naphthyridin-2-one 1 (60 mg, 74%). TLC: $R_f$=0.4 (silica gel, DCM/MeOH=20:1, v/v). LC-MS (Method D) 507.2 $[M+H]^+$; RT 2.75 min. $^1$H NMR (Method E) (DMSO-d6): δ ppm 11.2 (br s, 1H), 8.06 (d, J=8.4 Hz, 1H), 7.87 (d, J=9.2 Hz, 1H), 7.42 (d, J=8.4 Hz, 1H), 7.17 (d, J=8.4 Hz, 1H), 6.74 (d, J=8.4 Hz, 1H), 6.51 (d, J=9.2 Hz, 1H), 4.62 (s, 2H), 4.45 (m, 2H), 4.04 (m, 1H), 4.00 (s, 3H), 3.74 (m, 1H), 2.90-2.73 (m, 4H), 2.45 (m, 1H), 2.00 (m, 1H), 1.49 (m, 1H), 1.34-1.16 (m, 3H).

Example 2:—(3aR,6R,7aR)-6-[(2-{2-methoxy-7-oxo-7H,8H-pyrido[2,3-d]pyrimidin-8-yl}ethyl)amino]-3-(3-oxo-2H,3H,4H-pyrido[3,2-b][1,4]oxazin-6-yl}-octahydro-1,3-benzoxazol-2-one

2

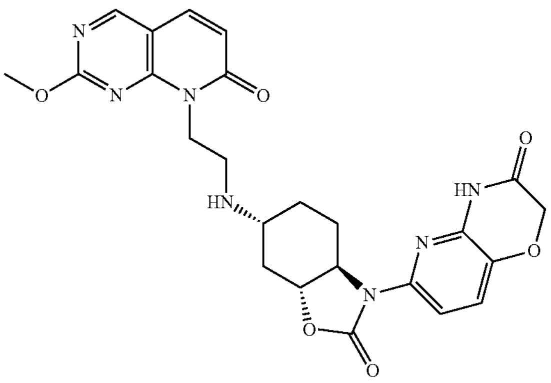

a) 8-(2,2-diethoxyethyl)-2-methoxy-7H,8H-pyrido[2,3-d]pyrimidin-7-one 2a $K_2CO_3$ (143 mg, 1.04 mmol) was added to a suspension of 2-methoxy-7H,8H-pyrido[2,3-d]pyrimidin-7-one (prepared as described in J. Med. Chem., 54(22), 7834-7847; 2011) (100 mg, 0.56 mmol) in DMF (2 mL). The mixture was stirred at room temperature for 1 h. Bromoacetaldehyde diethyl acetal (0.09 mL, 0.62 mmol) was added and the mixture heated at 103° C. for 4 h. The reaction mixture was allowed to cool to room temperature then diluted with $H_2O$ and extracted with DCM (3×20 mL). The combined organic extracts were washed with saturated brine (3 mL), dried over anhydrous $MgSO_4$, filtered, and concentrated to afford a brown residue of 8-(2,2-diethoxyethyl)-2-methoxy-7H,8H-pyrido[2,3-d]pyrimidin-7-one 2a (91 mg, 55%) which was used without further purification.

(b) 2-(2-methoxy-7-oxo-7H,8H-pyrido[2,3-d]pyrimidin-8-yl)acetaldehyde 2b

A solution of TFA (6 mL, 1.02 mmol) in $H_2O$ (1.5 mL) was added to 8-(2,2-diethoxyethyl)-2-methoxy-7H,8H-pyrido[2,3-d]pyrimidin-7-one 2a (300 mg, 1.02 mmol) and the reaction mixture stirred at room temperature for 3 h. The reaction was basified with saturated aqueous $NaHCO_3$ to pH 8. The mixture was extracted with DCM (20 mL) and IPA/DCM (1:3, 4×20 mL). The combined organic extracts were washed with brine, dried over anhydrous $MgSO_4$, filtered, and concentrated under reduced pressure. The resulting residue was purified by chromatography eluting with 100% EtOAc to afford a white solid of 2-(2-methoxy-7-oxo-7H,8H-pyrido[2,3-d]pyrimidin-8-yl)acetaldehyde 2b (173 mg, 77%). LC-MS (Method A) 220.4 $[M+H]^+$; RT 1.39 min.

c) (3aR,6R,7aR)-6-[(2-{2-methoxy-7-oxo-7H,8H-pyrido[2,3-d]pyrimidin-8-yl}ethyl)amino]-3-{4-[(4-methoxyphenyl)methyl]-3-oxo-2H,3H,4H-pyrido[3,2-b][1,4]oxazin-6-yl}-octahydro-1,3-benzoxazol-2-one 2c A solution of (3aR,6R,7aR)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 1c (228 mg, 0.54 mmol) and 2-(2-methoxy-7-oxo-7H,8H-pyrido[2,3-d]pyrimidin-8-yl)acetaldehyde 2b (59 mg, 0.27 mmol) in DCM (2 mL) was stirred at room temperature over molecular sieves (4 Å) for 2 h. $NaBH(OAc)_3$ (170 mg, 0.80 mmol) was added and the reaction stirred for 17 h. Further 2-(2-methoxy-7-oxo-pyrido[2,3-d]pyrimidin-8-yl)acetaldehyde 2b (20 mg) was added and the reaction stirred for 2 h then quenched with saturated aqueous $NaHCO_3$. The resulting mixture was passed through a SPE phase separator and the DCM filtrate concentrated under reduced pressure and purified by chromatography using 0-20% DCM/MeOH. Concentration of the clean fractions gave a white solid of (3aR,6R,7aR)-6-[(2-{2-methoxy-7-oxo-7H,8H-pyrido[2,3-d]pyrimidin-8-yl}ethyl)amino]-3-{4-[(4-methoxyphenyl)methyl]-3-oxo-2H,3H,4H-pyrido[3,2-b][1,4]oxazin-6-yl}-octahydro-1,3-benzoxazol-2-one 2c (116 mg, 69%). LC-MS (Method A) 628.1 $[M+H]^+$; RT 1.95 min.

d) (3aR,6R,7aR)-6-[(2-{2-methoxy-7-oxo-7H,8H-pyrido[2,3-d]pyrimidin-8-yl}ethyl)amino]-3-(3-oxo-2H,3H,4H-pyrido[3,2-b][1,4]oxazin-6-yl}-octahydro-1,3-benzoxazol-2-one 2

To a stirred solution of (3aR,6R,7aR)-6-[(2-{2-methoxy-7-oxo-7H,8H-pyrido[2,3-d]pyrimidin-8-yl}ethyl)amino]-3-{4-[(4-methoxyphenyl)methyl]-3-oxo-2H,3H,4H-pyrido[3,2-b][1,4]oxazin-6-yl}-octahydro-1,3-benzoxazol-2-one 2c (116 mg, 0.18 mmol) in DCM (20 mL), was added TFA (3.6 mL, 47 mmol) and $CF_3SO_3H$ (1.2 mL, 13.56 mmol). Stirring was continued for 1 h at room temperature then MeOH (1 mL) added. Saturated aqueous $Na_2CO_3$ was added adjusting the pH between 8-9. The mixture was extracted with DCM (2×25 mL) and 10% MeOH/DCM (2×25 mL) and the combined DCM extracts were passed through a SPE phase separator. Concentration gave a residue which was purified by chromatography using 0-20% DCM/MeOH to give a solid of (3aR,6R,7aR)-6-[(2-{2-methoxy-7-oxo-7H,8H-pyrido[2,3-d]pyrimidin-8-yl}ethyl)amino]-3-(3-oxo-2H,3H,4H-pyrido[3,2-b][1,4]oxazin-6-yl}-octahydro-1,3-benzoxazol-2-one 2 (37 mg, 39%). LC-MS (Method B) 508.2 $[M+H]^+$; RT 4.93 min. $^1$H NMR (Method D) (DMSO-d6): δ ppm 11.24 (s, 1H), 8.92 (s, 1H), 7.95 (d, J=9.4 Hz, 1H), 7.43 (d, J=8.6 Hz, 1H), 7.18 (d, J=8.5 Hz, 1H), 6.57 (d, J=9.5 Hz, 1H), 4.63 (s, 2H), 4.34 (t, J=6.7 Hz, 2H), 4.06 (m, 1H), 4.03 (s, 3H), 3.74 (m, 1H), 2.86 (m, 2H), 2.76 (m, 2H), 2.45 (m, 1H), 1.98 (d, J=13.3 Hz, 1H), 1.46 (q, J=11.1 Hz, 1H), 1.27 (m, 2H).

Example 3:—1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-(3-aminopropoxy)-1,2-dihydroquinolin-2-one

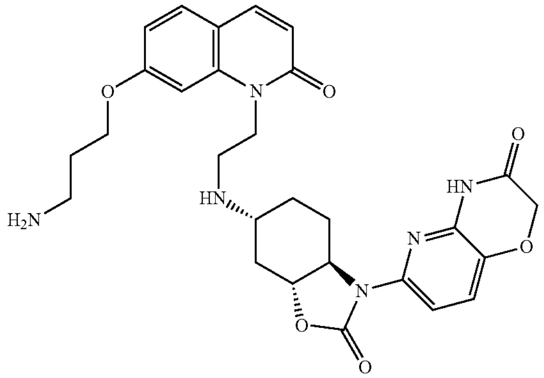

a) benzyl N-{3-[(2-oxo-1,2-dihydroquinolin-7-yl)oxy]propyl}carbamate 3a

To a suspension of 7-hydroxy-1H-quinolin-2-one (2.10 g, 13.0 mmol) and $Cs_2CO_3$ (6.37 g, 19.6 mmol) in anhydrous DMF (40 mL) was added a solution of benzyl N-(3-bromopropyl)carbamate (3.55 g, 13.0 mmol) in anhydrous DMF (10 mL) and the resulting mixture heated to 90° C. After 2 h the reaction was diluted with EtOAc (100 mL) and $H_2O$ (50 mL). A precipitate formed in the organic phase. The organic and aqueous phases were separated and the organic phase filtered to remove the precipitate. The resulting filtrate was concentrated to give a brown residue and combined with the initial precipitate using DCM. Concentration of the DCM solution gave a residue which on trituration with EtOAc gave a precipitate. The precipitate was filtered and dried to give a yellow solid of benzyl N-{3-[(2-oxo-1,2-dihydroquinolin-7-yl)oxy]propyl}carbamate 3a (2.5 g, 54%) which was used without further purification. LC-MS (Method A) 353.5 $[M+H]^+$; RT 2.42 min.

b) benzyl N-(3-{[1-(2,2-diethoxyethyl)-2-oxo-1,2-dihydroquinolin-7-yl]oxy}propyl)carbamate 3b A solution of benzyl N-{3-[(2-oxo-1,2-dihydroquinolin-7-yl)oxy]propyl}carbamate 3a (654 mg, 1.86 mmol) in anhydrous DMF (150 mL) was heated to 50° C. for 15 min. The reaction was cooled to 40° C. and $Cs_2CO_3$ (907 mg, 2.78 mmol) added followed by bromoacetaldehyde diethyl acetal (279 μL, 1.86 mmol). The mixture was heated to 70° C. for 21.5 h and further bromoacetaldehyde diethyl acetal (279 μL, 1.86 mmol) added. After 65.5 h the reaction was allowed to cool and then concentrated down. The resulting crude was diluted with EtOAc (100 mL) and saturated aqueous $NaHCO_3$ (30 mL). The aqueous phase was separated and extracted using EtOAc (3×20 mL). The combined organic extracts were washed with brine (20 mL), dried over $MgSO_4$, filtered and concentrated. The resulting crude was purified by chromatography using 0 to 10% DCM/EtOAc to give a colourless oil of benzyl N-(3-{[1-(2,2-diethoxyethyl)-2-oxo-1,2-dihydroquinolin-7-yl]oxy}propyl)carbamate 3b (520 mg, 64%).

c) benzyl N-(3-{[2-oxo-1-(2-oxoethyl)-1,2-dihydroquinolin-7-yl]oxy}propyl)carbamate 3c To a solution of benzyl N-(3-{[1-(2,2-diethoxyethyl)-2-oxo-1,2-dihydroquinolin-7-yl]oxy}propyl)carbamate 3b (400 mg, 0.91 mmol) in THF (20 mL) was added HCl (2.0 M, 15 mL) and the resulting mixture heated to 50° C. After 2 h the reaction was allowed to cool to room temperature. EtOAc (20 mL) was added and the aqueous phase was separated and extracted using EtOAc (3×20 mL). The combined organic extracts were washed with brine (30 mL), dried over $MgSO_4$, filtered, and concentrated. The resulting residue was purified by chromatography using 0 to 10% DCM/MeOH to give a yellow solid of benzyl N-(3-{[2-oxo-1-(2-oxoethyl)-1,2-dihydroquinolin-7-yl]oxy}propyl)carbamate 3c (155 mg, 43%). LC-MS (Method A) 395.5 $[M+H]^+$; RT 2.50 min.

d) benzyl N-(3-{[1-(2-{[(3aR.6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-2-oxo-1,2-dihydroquinolin-7-yl]oxy}propyl)carbamate 3d Benzyl N-(3-{[2-oxo-1-(2-oxoethyl)-1,2-dihydroquinolin-7-yl]oxy}propyl)carbamate 3c (67 mg, 0.17 mmol) and (3aR,6R,7aR)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 1c (144, 0.34 mmol) were dissolved in THF (3 mL) and heated to 70° C. for 2 h then cooled. $NaBH(OAc)_3$ (108 mg, 0.51 mmol) was added and the reaction stirred for 30 min. Excess volatiles were removed and the residue mixed with DCM (10 mL) and saturated aqueous $NaHCO_3$ (10 mL). The organic layer was separated and the aqueous phase further extracted with DCM. The organics extracts were combined, washed with saturated brine then passed through an SPE phase separator. The DCM filtrate was concentrated down to give a yellow residue. Purification by column chromatography using DCM/MeOH gave a white solid of benzyl N-(3-{[1-(2-{[(3aR.6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-2-oxo-1,2-dihydroquinolin-7-yl]oxy}propyl)carbamate 3d (95 mg, 70%). LC-MS (Method A) 803.8 $[M+H]^+$; RT 3.21 min.

e) 1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-(3-aminopropoxy)-1,2-dihydroquinolin-2-one 3

To a solution of benzyl N-(3-{[1-(2-{[(3aR.6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-2-oxo-1,2-dihydroquinolin-7-yl]oxy}propyl)carbamate 3d (95 mg, 0.11 mmol) in DCM (2 mL) was added TFA (3 mL) and $CF_3SO_3H$ (1 mL). Stirring was continued at room temperature for 1 h, then saturated aqueous $Na_2CO_3$ was added adjusting the pH to 8. The solution was extracted with DCM (3×20 mL), organics extracts were combined and passed through a SPE phase separator. The filtrate was concentrated to afford a dark yellow solid. The solid was purified by chromatography (Biotage 10 g KP-Si cartridge, 0-20% DCM/MeOH, then 0-20% DCM/(2M $NH_3$ in MeOH) affording a white solid of 1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]

amino}ethyl)-7-(3-aminopropoxy)-1,2-dihydroquinolin-2-one 3 (14 mg, 22%). LC-MS (Method A) 549.6 $[M+H]^+$; RT 2.23 min. $^1H$ NMR (Method C) ($CDCl_3$): δ ppm 7.57 (d, J=9.4 Hz, 1H), 7.45 (d, J=8.7 Hz, 1H), 7.27 (m, 2H), 6.92 (d, J=2.3 Hz, 1H), 6.83 (dd, J=8.6, 2.2 Hz, 1H), 6.50 (d, J=9.4 Hz, 1H), 4.56 (d, 2H), 4.50-4.39 (m, 1H), 4.32 (m, 1H), 4.18 (m, 2H), 3.96 (m, 1H), 3.81 (m, 1H), 3.15-3.00 (m, 3H), 3.00-2.96 (m, 2H), 2.91 (m, 2H), 2.68 (m, 1H), 2.61-2.56 (m, 1H), 2.22-2.13 (m, 1H), 2.02 (m, 1H), 1.69-1.57 (m, 1H), 1.45-1.32 (m, 1H).

Example 4:—1-(2-{[(3aS,6S,7aR)-2-oxo-2H,3H,4H-pyrido[3,2-b][1,4]oxazin-6-yl}-octahydro-1,3-benzoxazol-6-yl]amino}ethyl)-7-methoxy-1,2-dihydro-1,8-naphthyridin-2-one

4

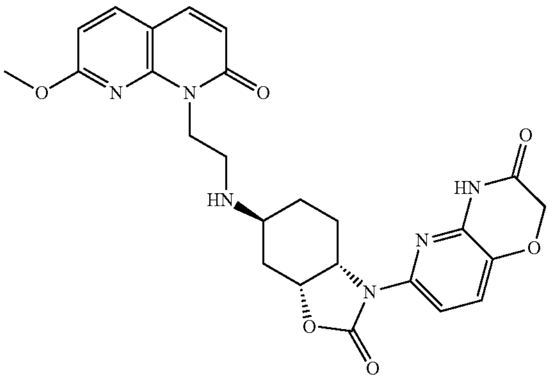

(a) tert-butyl N-[(3aS,6S,7aR)-2-oxo-octahydro-1,3-benzoxazol-6-yl]carbamate 4a

To a suspension of tert-butyl N-[(1S,3R,4S)-4-amino-3-hydroxy-cyclohexyl]carbamate (prepared from tert-butyl N-[(1S,3S,4S)-4-amino-3-hydroxycyclohexyl]carbamate following the methods described in Example 25a-d) (0.50 g, 2.17 mmol) in dioxane (30 mL) at 60° C. was added CDI (0.52 g, 3.26 mmol) and the mixture was heated at 60° C. for 4.5 h. After cooling to room temperature, 5% aqueous $Na_2CO_3$ (5 mL) was added and the mixture extracted with EtOAc. The organic layer was washed with brine, dried over $Na_2SO_4$, filtered and concentrated. The residue was purified by chromatography using 30% DCM/EtOAc to give a solid tert-butyl N-[(3aS,6S,7aR)-2-oxo-octahydro-1,3-benzoxazol-6-yl]carbamate 4a (0.30 g). TLC: $R_f$=0.73 (MeOH/DCM=1:10, v/v). $^1H$-NMR (Method E) ($CDCl_3$) δ ppm: 5.41 (s, 1H), 4.70 (m, 1H), 4.45 (m, 1H), 3.66-3.60 (m, 2H), 2.44 (m, 1H), 2.02 (m, 2H), 1.60-1.51 (m, 1H), 1.44 (s, 9H), 1.18-1.25 (m, 2H).

(b) tert-butyl N-[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]carbamate 4b A mixture of tert-butyl N-[(3aS,6S,7aR)-2-oxo-octahydro-1,3-benzoxazol-6-yl]carbamate 4a (0.20 g, 0.78 mmol), 6-bromo-4-[(4-methoxyphenyl)methyl]-2H,3H,4H-pyrido[3,2-b][1,4]oxazin-3-one (prepared as described in WO2014108832) (0.27 g, 0.77 mmol), $K_2CO_3$ (210 mg, 1.56 mmol), trans-1,2-diaminocyclohexane (18 mg, 0.16 mmol) and CuI (30 mg, 0.16 mmol) in dioxane (30 mL) was heated at reflux for 18 h under $N_2$. The mixture was cooled to room temperature, poured into $H_2O$ and exacted with EtOAc (200 mL). The organic layer was washed with brine, dried over $Na_2SO_4$, filtered and concentrated. The residue was purified by chromatography using 20% EtOAc in petroleum ether then 40% EtOAc in DCM to give a solid of tert-butyl N-[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]carbamate 4b (300 mg, 73%). TLC: $R_f$=0.2 (silica gel, DCM/EtOAc=4:1, v/v). LC-MS (Method D) 525.2 $[M+H]^+$; RT 5.00 min.

(c) (3aS,6S,7aR)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 4c To a solution of tert-butyl N-[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]carbamate 4b (0.16 g, 0.30 mmol) in DCM (1.5 mL) was added TFA (2 mL) and the mixture was stirred at room temperature for 30 min then concentrated under reduced pressure. The residue was adjusted to pH 8~9 with saturated aqueous $Na_2CO_3$, then partitioned between brine and DCM. The organic phase was dried over $Na_2SO_4$, filtered and concentrated to give a yellow solid of (3aS,6S,7aR)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 4c (130 mg, 52%) which was used without further purification. TLC: $R_f$=0.3 (silica gel, DCM/MeOH=15:1, v/v). LC-MS (Method D) 425.2 $[M+H]^+$; RT 2.87 min.

(d) 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl-7-methoxy-1,2-dihydro-1,8-naphthyridin-2-one 4d To a solution of (3aS,6S,7aR)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 4c (130 mg, 0.31 mmol) and 2-(7-methoxy-2-oxo-1,2-dihydro-1,8-naphthyridin-1-yl)acetaldehyde (prepared as described in WO2008009700) (70 mg, 0.32 mmol) in DCM (25 mL) was added $NaBH(OAc)_3$ (325 mg, 1.50 mmol) and the mixture was stirred for 22 h. The mixture was adjusted to pH 8~9 with saturated aqueous $Na_2CO_3$ and extracted with DCM (100 mL). The organic layer was washed with brine, dried ($Na_2SO_4$), filtered and concentrated. The residue was purified by chromatography using 2% MeOH in DCM to give a solid of 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl-7-methoxy-1,2-dihydro-1,8-naphthyridin-2-one 4d (100 mg, 50%). TLC: $R_f$=0.4 (silica gel, DCM/MeOH=20:1, v/v). LC-MS (Method D) 627.3 $[M+H]^+$; RT 3.49 min.

(e) 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydro-1,8-naphthyridin-2-one 4

To a solution of 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl-7- methoxy-1,2-dihydro-1,8-naphthyridin-2-one 4d (100 mg, 0.16 mmol) in DCM (15 mL) was added TFA (1.2 mL) followed by $CF_3SO_3H$ (0.4 mL) and the mixture was stirred for 1 h. The reaction was quenched with MeOH and the mixture adjusted to pH 8~9 with saturated aqueous $Na_2CO_3$ and extracted with DCM (100 mL). The organic layer was washed with brine, dried ($Na_2SO_4$), filtered and concentrated. The residue was purified by chromatography (DCM/MeOH, 50:1 to 20:1, v/v) to give a solid of 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydro-1,8-naphthyridin-2-one 4 (50 mg, 62%). TLC: $R_f$=0.4 (silica gel, DCM/MeOH=20:1, v/v). LC-MS (Method D) 505.2 $[M-H]^-$; RT 2.77 min. $^1H$ NMR (Method E) (DMSO-d6): δ ppm 11.2 (br s, 1H), 8.06 (d, J=8.4 Hz, 1H), 7.88 (d, J=9.6 Hz, 1H), 7.51 (d, J=8.4 Hz, 1H), 7.40 (d, J=8.4 Hz, 1H), 6.74 (d, J=8.4 Hz, 1H), 6.52 (d, J=9.2 Hz, 1H), 4.89-4.75 (m, 1H), 4.61 (s, 2H), 4.59-4.43 (m, 3H), 4.01 (s, 3H), 3.14-2.89 (m, 3H), 2.44-2.29 (m, 1H), 1.93-1.81 (m, 1H), 1.80-1.64 (m, 1H), 1.32-1.16 (m, 3H).

Example 5:—1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-(3-aminopropoxy)-1,2-dihydro-1,8-naphthyridin-2-one

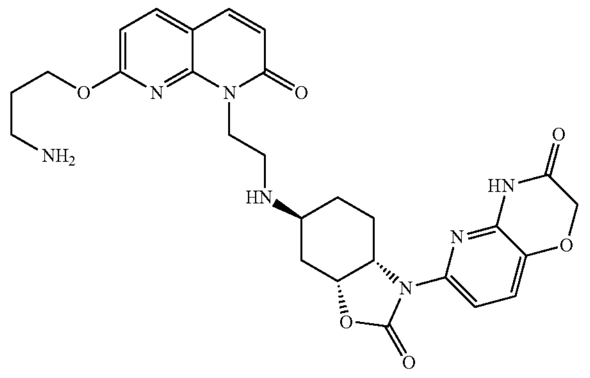

a) 7-chloro-1-(2,2-diethoxyethyl)-1,2-dihydro-1,8-naphthyridin-2-one 5a

To a solution of 7-chloro-1,2-dihydro-1,8-naphthyridin-2-one (1.80 g, 10.0 mmol) and bromoacetaldehyde diethyl acetal (4.92 g, 25.0 mmol) in DMF (25 mL) was added $Cs_2CO_3$ (4.90 g, 15.0 mmol) and the mixture heated at 70° C. under $N_2$ overnight. The mixture was diluted with $H_2O$ (200 mL), extracted with EtOAc (100 mL×3) and the combined organic extracts were washed with $H_2O$ (200 mL×2), brine (100 mL) and concentrated under reduced pressure. The residue was purified by chromatography (EtOAc/petroleum ether, 1:5 to 1:2, v/v) to afford a white solid of 7-chloro-1-(2,2-diethoxyethyl)-1,2-dihydro-1,8-naphthyridin-2-one 5a (1.80 g, 61%). TLC: $R_f$=0.45 (silica gel, petroleum ether/EtOAc=2:1, v/v). $^1H$ NMR (Method E) ($CDCl_3$): δ ppm 7.78 (d, J=8.0 Hz, 1H), 7.61 (d, J=9.6 Hz, 1H), 7.15 (d, J=8.0 Hz, 1H), 6.72 (d, J=9.6 Hz, 1H), 5.10 (t, J=5.6 Hz, 1H), 4.67 (d, J=5.6 Hz, 2H), 3.79 (m, 2H), 3.54 (m, 2H), 1.11 (t, J=7.2 Hz, 6H).

b) tert-butyl N-(3-{[8-(2,2-diethoxyethyl)-7-oxo-7,8-dihydro-1,8-naphthyridin-2-yl]oxy}propyl)carbamate 5b To a solution of 7-chloro-1-(2,2-diethoxyethyl)-1,2-dihydro-1,8-naphthyridin-2-one 5a (595 mg, 2.0 mmol) and tert-butyl N-(3-hydroxypropyl)carbamate (1.05 g, 6.0 mmol) in DMF (15 mL) was added a solution of t-BuOK (784 mg, 7.0 mmol) in dry THF (25 mL) and the mixture was stirred at room temperature overnight. The mixture was diluted with $H_2O$ (100 mL), extracted with EtOAc (100 mL×3) and the combined organic extracts were washed with $H_2O$ (100 mL×2), brine (100 mL) and concentrated under reduced pressure. The residue was purified by chromatography (petroleum ether/EtOAc, 3:1, v/v) to give a colourless oil of tert-butyl N-(3-{[8-(2,2-diethoxyethyl)-7-oxo-7,8-dihydro-1,8-naphthyridin-2-yl]oxy}propyl)carbamate 5b (540 mg). TLC: $R_f$=0.30 (silica gel, petroleum ether/EtOAc=2:1, v/v) $^1H$ NMR (Method E) (DMSO-d6): δ ppm 8.04 (d, J=8.4 Hz, 1H), 7.86 (d, J=9.4 Hz, 1H), 6.89 (m, 1H), 6.71 (d, J=8.4 Hz, 1H), 6.50 (d, J=9.4 Hz, 1H), 5.03 (t, J=5.7 Hz, 1H), 4.48 (d, J=5.7 Hz, 2H), 4.38 (m, 2H), 3.65 (m, 2H), 3.37 (m, 2H), 3.09 (m, 2H), 1.90 (m, 2H), 1.36 (s, 9H), 0.98 (t, J=7.0 Hz, 6H).

c) tert-butyl N-(3-{[7-oxo-8-(2-oxoethyl)-7,8-dihydro-1,8-naphthyridin-2-yl]oxy}propyl)carbamate 5c To a solution of tert-butyl N-(3-{[8-(2,2-diethoxyethyl)-7-oxo-7,8-dihydro-1,8-naphthyridin-2-yl]oxy}propyl)carbamate 5b (540 mg, 1.24 mmol) in THF (10 mL) was added 1 M HCl (6.0 mL, 6.0 mmol) and the mixture was stirred at room temperature for 20 h. The mixture was adjusted to pH 8-9 with a saturated aqueous $NaHCO_3$ solution and extracted with EtOAc (20 mL×3). The combined organic extracts were washed with $H_2O$ (50 mL), brine (50 mL), dried over $Na_2SO_4$, filtered and concentrated under reduced pressure. The residue was purified by chromatography (petroleum ether/EtOAc, 5:1 to 1:1, v/v) to give a white solid of tert-butyl N-(3-{[7-oxo-8-(2-oxoethyl)-7,8-dihydro-1,8-naphthyridin-2-yl]oxy}propyl)carbamate 5c (250 mg, 56%). TLC: $R_f$=0.14 (silica gel, petroleum ether/EtOAc=2:1, v/v). LC-MS (Method C) 362.3 $[M+H]^+$, RT 3.38 min. $^1H$-NMR (Method E) ($CDCl_3$) δ ppm: 9.65 (s, 1H), 7.77 (d, J=8.4 Hz, 1H), 7.65 (d, J=9.4 Hz, 1H), 6.63 (d, J=9.6 Hz, 1H), 6.62 (d, J=8.4 Hz, 1H), 5.20 (s, 2H), 4.32 (t, J=6.2 Hz, 2H), 3.29 (m, 2H), 1.95 (m, 2H), 1.43 (s, 9H).

d) tert-butyl N-(3-{[8-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-7-oxo-7,8-dihydro-1,8-naphthyridin-2-yl]oxy}propyl)carbamate 5d A mixture of tert-butyl N-(3-{[7-oxo-8-(2-oxoethyl)-7,8-dihydro-1,8-naphthyridin-2-yl]oxy}propyl)carbamate 5c (110 mg, 0.30 mmol) and (3aS,6S,7aR)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 4c (130 mg, 0.30 mmol) in DCM (20 mL) was stirred at room temperature for 30 min. $NaBH(OAc)_3$ (254 mg, 1.20 mmol) was then added and stirring was continued overnight. The mixture was diluted with a saturated aqueous $NaHCO_3$ solution and extracted with EtOAc (20 mL×3). The combined organic extracts were washed with $H_2O$, brine, dried over $Na_2SO_4$, filtered and concentrated under reduced pressure. The residue was purified by chromatography (DCM/MeOH, 50:1 to 20:1, v/v) to give a white foam of tert-butyl N-(3-{[8-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-7-oxo-7,8-dihydro-1,8-naphthyridin-2-yl]oxy}propyl)carbamate 5d (140 mg, 60%). TLC: $R_f$=0.35 (silica gel, DCM/MeOH=20:1, v/v). LC-MS (Method C) 770.4 $[M+H]^+$, RT 3.81 min.

e) 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-(3-aminopropoxy)-1,2-dihydro-1,8-naphthyridin-2-one 5

To a solution of tert-butyl N-(3-{[8-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-7-oxo-7,8-dihydro-1,8-naphthyridin-2-yl]oxy}propyl)carbamate 5d (140 mg, 0.18 mmol) in DCM (10 mL) was added TFA (2.0 mL) and the mixture stirred at room temperature for 4 h. $CF_3SO_3H$ (1.0 mL) was then added and stirring continued for a further 1 h. The mixture was adjusted to pH 8-9 with a saturated aqueous $K_2CO_3$ solution (40 mL) and then extracted with DCM/IPA (3:1, 20 mL×3). The combined organic extracts were washed with $H_2O$, brine, dried over $Na_2SO_4$, filtered and concentrated under reduced pressure. The residue was purified by preparative TLC (DCM/MeOH/$NH_3$.$H_2O$, 100:10:2, v/v) to give a white solid of 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-(3-aminopropoxy)-1,2-dihydro-1,8-naphthyridin-2-one 5 (72 mg, 72%). TLC: $R_f$=0.25 (silica gel, DCM/MeOH=10:1+1 drop $NH_3$.$H_2O$, v/v). LC-MS (Method C) 550.2 $[M+H]^+$, RT 1.80 min. $^1H$ NMR (Method E) (DMSO-d6): δ ppm: 8.07 (d, J=8.4 Hz, 1H), 7.87 (d, J=9.4 Hz, 1H), 7.51 (d, J=8.6 Hz, 1H), 7.41 (d, J=8.6 Hz, 1H), 6.74 (d, J=8.4 Hz, 1H), 6.51 (d, J=9.4 Hz, 1H), 4.77 (m, 1H), 4.61 (s, 2H), 4.55-4.39 (m, 5H), 2.96 (t, J=7.3 Hz, 2H), 2.89 (m, 2H), 2.76 (m, 1H), 2.45 (m, 1H), 2.31 (m, 1H), 2.10 (m, 2H), 1.80 (m, 1H), 1.58 (m, 1H), 1.27 (m, 1H), 1.06 (m, 1H).

Example 6:—1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-(2-hydroxyethoxy)-1,2-dihydro-1,8-naphthyridin-2-one

6

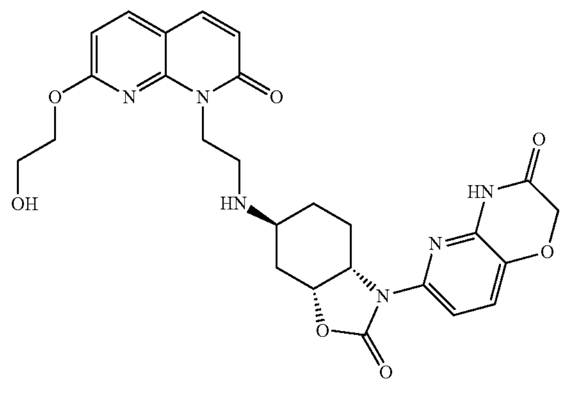

a) 1-(2,2-diethoxyethyl)-7-(2-hydroxyethoxy)-1,2-dihydro-1,8-naphthyridin-2-one 6a 7-chloro-1-(2,2-diethoxyethyl)-1,2-dihydro-1,8-naphthyridin-2-one 5a (592 mg, 2 mmol) and $Cs_2CO_3$ (978 mg, 3 mmol) were suspended in ethylene glycol (5 mL) and the mixture was heated at 100° C. in the microwave for 1 h. The mixture was diluted with $H_2O$ (30 mL), extracted with EtOAc (30 mL×3) and the combined organic extracts were washed with $H_2O$ (50 mL×2), brine (50 mL), dried over $Na_2SO_4$, filtered and concentrated under reduced pressure to give a yellow solid of 1-(2,2-diethoxyethyl)-7-(2-hydroxyethoxy)-1,2-dihydro-1,8-naphthyridin-2-one 6a (574 mg, 89%) which was used without further purification. TLC: $R_f$=0.33 (silica gel, petroleum ether/EtOAc=1:1, v/v). LC-MS (Method C) 277.1 $[M-OEt]^+$, RT 2.76 min.

b) 2-[7-(2-hydroxyethoxy)-2-oxo-1,2-dihydro-1,8-naphthyridin-1-yl]acetaldehyde 6b To a solution of 1-(2,2-diethoxyethyl)-7-(2-hydroxyethoxy)-1,2-dihydro-1,8-naphthyridin-2-one 6a (574 mg, 1.8 mmol) in dioxane (6 mL) was added 3 M HCl (6 mL, 18 mmol) and the mixture was stirred at room temperature for 2 h. The mixture was adjusted to pH 8-9 with a saturated aqueous $NaHCO_3$ solution and extracted with EtOAc (20 mL×3). The combined organic extracts were washed with $H_2O$ (30 mL), brine (30 mL), dried over $Na_2SO_4$, filtered and concentrated under reduced pressure. The residue was purified by chromatography using petroleum ether/EtOAc, 5:1 to 1:1, v/v to give a pale yellow oil of 2-[7-(2-hydroxyethoxy)-2-oxo-1,2-dihydro-1,8-naphthyridin-1-yl]acetaldehyde 6b (240 mg). TLC: $R_f$=0.20 (silica gel, petroleum ether/EtOAc=1:1, v/v). LC-MS (Method D) 249.1 $[M+H]^+$, RT 2.17 min.

c) 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-7-(2-hydroxyethoxy)-1,2-dihydro-1,8-naphthyridin-2-one 6c A mixture of 2-[7-(2-hydroxyethoxy)-2-oxo-1,2-dihydro-1,8-naphthyridin-1-yl]acetaldehyde 6b (114 mg, 0.46 mmol), (3aS,6S,7aR)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 4c (200 mg, 0.47 mmol) and AcOH (55 mg, 0.92 mmol) in DCM (10 mL) was stirred at room temperature for 10 min. $NaBH(OAc)_3$ (488 mg, 2.3 mmol) was added and stirring continued for 17 h. The mixture was diluted with a saturated aqueous $NaHCO_3$ solution and extracted with EtOAc (20 mL×3). The combined organic extracts were washed with $H_2O$, brine, dried over $Na_2SO_4$, filtered and concentrated under reduced pressure. The residue was purified by chromatography using DCM/MeOH, 40:1 to 20:1, v/v to give a white solid of 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-7-(2-hydroxyethoxy)-1,2-dihydro-1,8-naphthyridin-2-one 6c (260 mg, 86%). TLC: $R_f$=0.44 (silica gel, DCM/MeOH=15:1, v/v). LC-MS (Method C) 657.3 $[M+H]^+$, RT 2.86 min.

d) 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-(2-hydroxyethoxy)-1,2-dihydro-1,8-naphthyridin-2-one 6

To a solution of 1-(2-{[(3aS,6S,7aR)-3-{4-[(4-methoxyphenyl)methyl]-3-oxo-2H,3H,4H-pyrido[3,2-b][1,4]oxazin- 6-yl}-2-oxo-octahydro-1,3-benzoxazol-6-yl]amino}ethyl)-7-(2-hydroxyethoxy)-1,2-dihydro-1,8-naphthyridin-2-one 6c (260 mg, 0.39 mmol) in TFA (5.0 mL) at 00° C. was added $CF_3SO_3H$ (0.5 mL) and the mixture was allowed to warm to room temperature and stirred for 1 h. The mixture was adjusted to pH 8-9 with a saturated aqueous $K_2CO_3$ solution (40 mL) and then extracted with EtOAc (30 mL×3). The combined organic extracts were washed with $H_2O$, brine, dried over $Na_2SO_4$, filtered and concentrated under reduced pressure The residue was purified by preparative-TLC (DCM/MeOH, 10:1, v/v) to give a white solid of 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-(2-hydroxyethoxy)-1,2-dihydro-1,8-naphthyridin-2-one 6 (61 mg, 29%). TLC: $R_f$=0.50 (silica gel, DCM/MeOH=10:1, v/v). LC-MS (Method D) 537.2 $[M+H]^+$, RT 2.46 min. $^1H$ NMR (Method E) (DMSO-d6): δ ppm: 11.2 (br s, 1H), 8.05 (d, J=8.4 Hz, 1H), 7.86 (d, J=9.6 Hz, 1H), 7.51 (d, J=8.8 Hz, 1H), 7.40 (d, J=8.8 Hz, 1H), 6.72 (d, J=8.4 Hz, 1H), 6.49 (d, J=9.6 Hz, 1H), 4.89 (br s, 1H), 4.76 (m, 1H), 4.61 (s, 2H), 4.42 (m, 5H), 3.77 (m, 2H), 2.89 (m, 2H), 2.76 (m, 1H), 2.45 (m, 1H), 2.29 (m, 1H), 1.79 (m, 1H), 1.56 (m, 1H), 1.26 (m, 2H), 1.04 (m, 1H).

Example 7:—1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl](2-hydroxyethyl)amino}ethyl)-7-methoxy-1,2-dihydro-1,8-naphthyridin-2-one

7

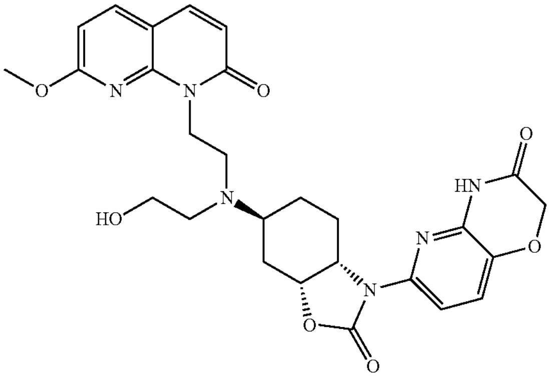

a) 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]({2-[(tert-butyldimethylsilyl)oxy]ethyl})amino}ethyl)-7-methoxy-1,2-dihydro-1,8-naphthyridin-2-one 7a To a solution of 1-(2-{[(3aS,6S,7aR)-2-oxo-2H,3H,4H-pyrido[3,2-b][1,4]oxazin-6-yl}-octahydro-1,3-benzoxazol-6-yl]amino}ethyl)-7-methoxy-1,2-dihydro-1,8-naphthyridin-2-one 4 (150 mg, 0.30 mmol) and 2-[tert-butyl(dimethyl)silyl]oxyacetaldehyde (164 mg, 0.94 mmol) in DCM (60 mL) was added $NaBH(OAc)_3$ (400 mg, 1.89 mmol) and the mixture was stirred at room temperature for 17 h. A saturated aqueous $NaHCO_3$ solution was added and the mixture was extracted with EtOAc (20 mL×3). The combined organic extracts were washed with $H_2O$, brine, dried over $Na_2SO_4$, filtered and concentrated under reduced pressure. The residue was purified by chromatography using DCM/EtOAc, 5:1 to 3:1, v/v to give a white solid of 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]({2-[(tert-butyldimethylsilyl)oxy]ethyl})amino}ethyl)-7-methoxy-1,2-dihydro-1,8-naphthyridin-2-one 7a (140 mg, 71%). TLC: $R_f$=0.59 (silica gel, DCM/MeOH=15:1, v/v). LC-MS (Method D) 665.2 $[M+H]^+$, RT 4.59 min.

b) 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl](2-hydroxyethyl)amino}ethyl)-7-methoxy-1,2-dihydro-1,8-naphthyridin-2-one 7

A mixture of 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]({2-[(tert-butyldimethylsilyl)oxy]ethyl})amino}ethyl)-7-methoxy-1,2-dihydro-1,8-naphthyridin-2-one 7a (140 mg, 0.21 mmol) and conc. HCl (1 mL) in THF/$H_2O$ (25 mL/3 mL) was stirred at room temperature for 3 h. The mixture was adjusted to pH 8-9 with a saturated aqueous $Na_2CO_3$ solution and extracted with DCM (20 mL×3). The combined organic extracts were washed with $H_2O$, brine, dried over $Na_2SO_4$, filtered and concentrated under reduced pressure The residue was purified by chromatography using DCM/MeOH, 40:1 to 10:1, v/v to give a white solid of 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl](2-hydroxyethyl)amino}ethyl)-7-methoxy-1,2-dihydro-1,8-naphthyridin-2-one 7 (50 mg, 43%). TLC: $R_f$=0.24 (silica gel, DCM/MeOH=10:1, v/v). LC-MS (Method D) 551.2 $[M+H]^+$, RT 2.77 min. $^1H$ NMR (Method E) (DMSO-d6): δ ppm 11.2 (br s, 1H), 8.06 (d, J=8.4 Hz, 1H), 7.86 (d, J=9.6 Hz, 1H), 7.52 (d, J=8.4 Hz, 1H), 7.40 (d, J=8.8 Hz, 1H), 6.73 (d, J=8.4 Hz, 1H), 6.50 (d, J=9.6 Hz, 1H), 4.78 br (s, 1H), 4.61 (s, 2H), 4.49-4.33 (m, 4H), 4.00 (s, 3H), 3.38 (m, 2H), 2.83 (m, 1H), 2.74 (m, 2H), 2.65 (m, 2H), 2.10 (m, 1H), 1.75 (m, 1H), 1.60 (m, 1H), 1.31-1.16 (m, 3H).

Example 8:—4-{[8-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-oxo-7,8-dihydro-1,8-naphthyridin-2-yl]oxy}benzene-1-sulphonamide

8

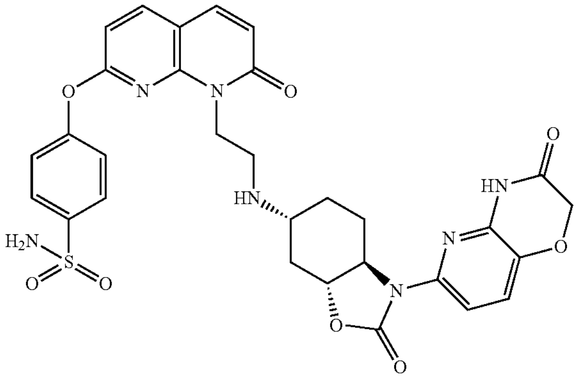

a) 4-{[8-(2,2-diethoxyethyl)-7-oxo-7,8-dihydro-1,8-naphthyridin-2-yl]oxy}benzene-1-sulfonamide 8a A solution of 7-chloro-1-(2,2-diethoxyethyl)-1,2-dihydro-1,8-naphthyridin-2-one 5a (547 mg, 1.54 mmol) and $K_2CO_3$ (425 mg, 3.08 mmol) in DMF (10 mL) was stirred for 30 min. 4-hydroxybenzene-1-sulfonamide (400 mg, 2.31 mmol) was added and the stirred mixture was heated to 90° C. for 17 h. The mixture was concentrated under reduced pressure and the residue was mixed with DCM and saturated aqueous $NaHCO_3$ then passed through a SPE phase separator. The organic phase was concentrated under reduced pressure and purified by chromatography (DCM/MeOH, 100:1 to 10:1, v/v) to give a pale yellow solid of 4-{[8-(2,2-diethoxyethyl)-7-oxo-7,8-dihydro-1,8-naphthyridin-2-yl]oxy}benzene-1-sulfonamide 8a (322 mg, 0.74 mmol). LC-MS (Method A) 388.5 $[M-OEt]^+$; RT 2.31 min.

b) 4-{[7-oxo-8-(2-oxoethyl)-7,8-dihydro-1,8-naphthyridin-2-yl]oxy}benzene-1-sulfonamide 8b To a solution of 4-{[8-(2,2-diethoxyethyl)-7-oxo-7,8-dihydro-1,8-naphthyridin-2-yl]oxy}benzene-1-sulfonamide 8a (322 mg, 0.74 mmol) in THF (10 mL) was added HCl (2.0 M, 7.43 mL) and the mixture heated to 50° C. for 2 h. The reaction was mixed with saturated aqueous $NaHCO_3$ and extracted with EtOAc (30 mL×3). The combined organics were washed with brine, dried over $MgSO_4$, filtered and concentrated under reduced pressure. The residue was purified via chromatography (DCM/MeOH, 100:1 to 10:1, v/v) to give a cream solid of 4-{[7-oxo-8-(2-oxoethyl)-7,8-dihydro-1,8-naphthyridin-2-yl]oxy}benzene-1-sulfonamide 8b (89.4 mg, 33.4%). LC-MS (Method A) 360.4 $[M+H]^+$; RT 1.71 min.

c) 4-{[8-(2-{[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-7-oxo-7,8-dihydro-1,8-naphthyridin-2-yl]oxy}benzene-1-sulfonamide 8c A mixture of 4-{[7-oxo-8-(2-oxoethyl)-7,8-dihydro-1,8-naphthyridin-2-yl]oxy}benzene-1-sulfonamide 8b (50 mg, 0.14 mmol) and (3aR,6R,7aR)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 1c (118 mg, 0.28 mmol) in THF (2 mL) was heated at 70° C. for 2 h. The reaction mixture was allowed to cool and $NaBH(OAc)_3$ (88.4 mg, 0.42 mmol) added. After 1.5 h further $NaBH(OAc)_3$ (88.4 mg, 0.42 mmol) was added and stirring continued at room temperature for 30 min. The resulting mixture was concentrated under reduced pressure, saturated aqueous $NaHCO_3$ added and the crude products extracted with DCM (3×30 mL). The combined organics were filtered through a SPE phase separator, concentrated under reduced pressure then purified by chromatography (DCM/MeOH, 10:1, v/v) to give an off white solid, which was further purified via chromatography using a Biotage KPNH cartridge 11 g (DCM/MeOH, 1:100 to 2:1, v.v) to give a white solid of 4-{[8-(2-{[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-7-oxo-7,8-dihydro-1,8-naphthyridin-2-yl]oxy}benzene-1-sulfonamide 8c (50 mg, 70%). LC-MS (Method A) 768.9 $[M+H]^+$; RT 2.70 min.

d) 4-{[8-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-oxo-7,8-dihydro-1,8-naphthyridin-2-yl]oxy}benzene-1-sulphonamide 8

To a solution of 4-{[8-(2-{[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-7-oxo-7,8-dihydro-1,8-naphthyridin-2-yl]oxy}benzene-1-sulfonamide 8c (31 mg, 0.04 mmol) in DCM (1.2 mL) was added TFA (2.0 mL) then $CF_3SO_3H$ (0.34 mL). After 10 min the mixture was adjusted to pH 8-9 with saturated aqueous $K_2CO_3$ (40 mL) and extracted with DCM (3×30 mL). The combined organics were filtered through an SPE phase separator and concentrated under reduced pressure. The residue was purified by chromatography (DCM/MeOH, 100:1 to 2:1 followed by DCM/2M $NH_3$ in MeOH, v/v) to give a white solid of 4-{[8-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-oxo-7,8-dihydro-1,8-naphthyridin-2-yl]oxy}benzene-1-sulphonamide 8 (9.8 mg, 26%). LC-MS (Method B) 648.5 $[M+H]^+$; RT 6.24 min. $^1H$ NMR (Method C) ($CDCl_3$): δ ppm: 8.11-8.05 (m, 2H), 7.86 (d, J=8.3 Hz, 1H), 7.54 (d, J=9.5 Hz, 1H), 7.40-7.35 (m, 2H), 7.25 (d, J=1.3 Hz, 2H), 6.88 (d, J=8.2 Hz, 1H), 6.59 (d, J=9.5 Hz, 1H), 4.56 (d, J=3.7 Hz, 2H), 4.29-4.22 (m, 2H), 3.87 (td, J=11.7, 3.4 Hz, 1H), 3.76 (m, 1H), 2.81 (m, 2H), 2.73 (td, J=11.7, 10.9, 6.2 Hz, 1H), 2.60 (d, J=11.7 Hz, 1H), 2.41 (d, J=10.9 Hz, 1H), 1.86 (d, J=12.8 Hz, 1H), 1.46 (dd, J=11.3, 11.3 Hz, 1H), 1.30-1.20 (m, 2H), 1.19-1.08 (m, 1H).

Example 9:—1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-(2-aminoethoxy)-1,2-dihydroquinolin-2-one

9

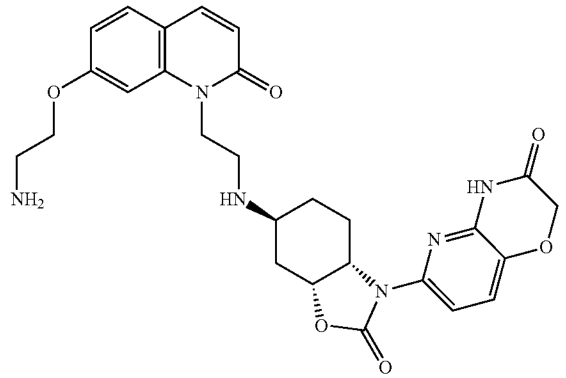

a) 7-(prop-2-en-1-yloxy)-1,2-dihydroquinolin-2-one 9a

A mixture of 7-hydroxy-1,2-dihydroquinolin-2-one (4.0 g, 24.82 mmol), $K_2CO_3$ (5.15 g, 37.23 mmol) and allyl bromide (2.6 mL, 29.78 mmol) in acetone (40 mL) was heated at 60° C. for 16 h. After cooling to room temperature the mixture was filtered and the solid collected was washed with acetone (2×15 mL). The filtrates were combined and the solvent removed in vacuo. The resulting residual solid was triturated with MeOH to furnish 7-(prop-2-en-1-yloxy)-1,2-dihydroquinolin-2-one 9a (3.7 g, 74% yield) as a white solid. LC-MS (Method A) 202.4 $[M+H]^+$; RT 2.14 min b) 2-[2-oxo-7-(prop-2-en-1-yloxy)-1,2-dihydroquinolin-1-yl]acetaldehyde 9b To a mixture of 7-(prop-2-en-1-yloxy)-1,2-dihydroquinolin-2-one 9a (28.5 g, 141.64 mmol) and $Cs_2CO_3$ (55.4 g, 167.97 mmol) in NMP (230 mL) was added 2-bromo-1,1-diethoxyethane (23.44 mL, 155.8 mmol) and the suspension heated at 100° C. for 16 h. On cooling $H_2O$ (500 mL) was added and the mixture was extracted with EtOAc (3×350 mL).

The combined organics were washed with $H_2O$ and brine, dried ($MgSO_4$) and concentrated in vacuo. The residue was taken up in THF (150 mL) and HCl (2M, 150 mL) and heated to 55° C. for 2 h. On cooling the reaction mixture was extracted with EtOAc (200 mL×3) and the combined organics were washed with $H_2O$ and brine, dried ($MgSO_4$) and concentrated in vacuo. The resulting residue was triturated with petroleum ether then $Et_2O$ and dried to give 2-[2-oxo-7-(prop-2-en-1-yloxy)-1,2-dihydroquinolin-1-yl]acetaldehyde 9b (10.4 g, 30% yield).

c) 1-(2,2-diethoxyethyl)-7-(prop-2-en-1-yloxy)-1,2-dihydroquinolin-2-one 9c

A mixture of 2-[2-oxo-7-(prop-2-en-1-yloxy)-1,2-dihydroquinolin-1-yl]acetaldehyde 9b (100 mg, 0.41 mmol), 4-methylbenzene-1-sulfonic acid (10 mg, 0.05 mmol), EtOH (1 mL) in Toluene (30 mL) was stirred at reflux for 7 h under azeotropic conditions. The reaction was allowed to cool and $Na_2CO_3$ (1M, 20 mL) added. The mixture was extracted with EtOAc (2×30 mL) and the combined extracts were washed with water, brine and dried over $Na_2SO_4$. The filtrate was concentrated under reduced pressure and purified by chromatography using 30% EtOAc in petroleum ether to give a yellow solid of 1-(2,2-diethoxyethyl)-7-(prop-2-en-1-yloxy)-1,2-dihydroquinolin-2-one 9c, (60 mg, 46%). TLC: $R_f$=0.54 (silica gel, DCM/MeOH=15:1, v/v). LC-MS (Method C) 318.2 $[M+H]^+$; RT 3.96 min.

d) 1-(2,2-diethoxyethyl)-7-hydroxy-1,2-dihydroquinolin-2-one 9d

A mixture of 1-(2,2-diethoxyethyl)-7-(prop-2-en-1-yloxy)-1,2-dihydroquinolin-2-one 9c (60 mg, 0.19 mmol), $Pd(PPh_3)_4$ (21.8 mg, 0.02 mmol) and $K_2CO_3$ in EtOH (10 mL) was stirred at room temperature for 17 h. The mixture was adjusted to pH 7.0-7.5 with saturated aqueous $NaHCO_3$ and extracted with EtOAc (20 mL×3). The combined extracts were washed with water, brine, dried over $Na_2SO_4$ and concentrated under reduced pressure. The residue was purified by preparative-TLC (DCM/MeOH, 15:1, v/v) to give a white solid of 1-(2,2-diethoxyethyl)-7-hydroxy-1,2-dihydroquinolin-2-one 9d, (55 mg, 81%). TLC: $R_f$=0.33 (silica gel, DCM/MeOH=15:1, v/v). LC-MS (Method C) 278.3 $[M+H]^+$; RT 2.80 min.

e) tert-butyl N-(2-{[1-(2,2-diethoxyethyl)-2-oxo-1,2-dihydroquinolin-7-yl]oxy}ethyl)carbamate 9e To a stirring suspension of 1-(2,2-diethoxyethyl)-7-hydroxy-1,2-dihydroquinolin-2-one 9d (45 mg, 0.16 mmol) and $K_2CO_3$ in DMF (10 mL) was added tert-butyl N-(2-bromoethyl)carbamate (73 mg, 0.32 mmol). The mixture was heated to 85° C. for 4 h then allowed to cool. Water was added and the mixture extracted with EtOAc (3×30 mL). The combined extracts were washed with water (30 mL), brine (30 mL), dried over $Na_2SO_4$ and concentrated under reduced pressure. The residue was purified using chromatography (DCM:MeOH 15:1 to 10:1) to give a yellow oil of tert-butyl N-(2-{[1-(2,2-diethoxyethyl)-2-oxo-1,2-dihydroquinolin-7-yl]oxy}ethyl)carbamate 9e (55 mg, 81%) TLC: $R_f$=0.52 (silica gel, DCM/MeOH=15:1, v/v). LC-MS (Method C) 375.2 $[M+OEt]^+$; RT 3.96 min.

f) tert-butyl N-(2-{[2-oxo-1-(2-oxoethyl)-1,2-dihydroquinolin-7-yl]oxy}ethyl)carbamate 9f To a solution of tert-butyl N-(2-{[1-(2,2-diethoxyethyl)-2-oxo-1,2-dihydroquinolin-7-yl]oxy}ethyl)carbamate 9e (55 mg, 0.13 mmol) in THF (20 mL) was added HCl (1.0 M, 1.3 mL) and heated to 35° C. for 20 h. Saturated aqueous $NaHCO_3$ was added and the mixture extracted with EtOAc (3×30 mL). The combined organics were washed with brine, dried over $Na_2SO_4$, filtered and concentrated under reduced pressure. The residue was purified using chromatography (petroleum ether/EtOAc, 5:1-1:1, v/v) to give a yellow oil of tert-butyl N-(2-{[2-oxo-1-(2-oxoethyl)-1,2-dihydroquinolin-7-yl]oxy}ethyl)carbamate 9f (55 mg, 81%) TLC: $R_f$=0.34 (silica gel, EtOAc/petroleum ether=1:2, v/v). LC-MS (Method C) 347.4 $[M+H]^+$; RT 3.26 min.

g) tert-butyl N-(2-{[1-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-2-oxo-1,2-dihydroquinolin-7-yl]oxy}ethyl)carbamate 9g To a mixture of tert-butyl N-(2-{[2-oxo-1-(2-oxoethyl)-1,2-dihydroquinolin-7-yl]oxy}ethyl)carbamate 9f (33 mg, 0.09 mmol) and (3aS,6S,7aR)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 4c (41 mg, 0.09 mmol) in DCM (15 mL) was added $NaBH(OAc)_3$ and stirred at room temperature for 4 h. Saturated aqueous $NaHCO_3$ was added and extracted with EtOAc (3×20 mL). The combined organics were washed with water, brine, dried over $Na_2SO_4$, and concentrated under reduced pressure. The residue was purified by preparative-TLC (DCM/MeOH, 10:1, v/v) to give a white solid of tert-butyl N-(2-{[1-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-2-oxo-1,2-dihydroquinolin-7-yl]oxy}ethyl)carbamate 9g (50 mg, 70%), which was used directly in the next step without further purification. TLC: $R_f$=0.52 (silica gel, DCM/MeOH=20:1, v/v).

h) 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-(2-aminoethoxy)-1,2-dihydroquinolin-2-one To a solution of tert-butyl N-(2-{[1-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-2-oxo-1,2-dihydroquinolin-7-yl]oxy}ethyl)carbamate 9g (50 mg, 0.07 mmol) in DCM (10 mL) was added TFA (2.0 mL, 26.1 mmol) and stirred at room temperature for 3 h. $CF_3SO_3H$ (1.0 mL, 11.3 mmol) was then added and stirring continued for a further 1 h. The resulting mixture was adjusted to pH 8-9 with saturated aqueous $K_2CO_3$ (40 mL) and extracted with EtOAc (3×30 mL). The combined extracts were washed with water, brine, dried over $Na_2SO_4$ and concentrated under reduced pressure. The residue was purified by preparative-TLC (DCM/MeOH, 10:1, v/v) to give a white solid of 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-(2-aminoethoxy)-1,2-dihydroquinolin-2-one (55 mg, 81%). TLC: $R_f$=0.31 (silica gel, DCM/MeOH=8:1, v/v). LC-MS (Method C) 535.5 $[M+H]^+$; RT 1.91 min. $^1H$ NMR (Method E) (DMSO-d6): δ ppm 7.81 (d, J=8.4 Hz, 1H), 7.63 (d, J=8.4 Hz, 1H), 7.51 (d, J=8.4 Hz, 1H), 7.40 (d, J=8.4 Hz, 1H), 7.05 (br s, 1H), 6.90 (d, J=9.6 Hz, 1H), 6.41 (d, J=9.6 Hz, 1H), 4.76 (m, 1H), 4.61 (s, 2H), 4.47 (m, 1H), 4.26 (m, 2H), 4.09 (m, 2H), 2.96 (m, 2H), 2.79 (m, 2H), 2.71 (m, 1H), 2.45 (m, 1H), 2.25 (m, 1H), 1.80 (m, 1H), 1.55 (m, 1H), 1.26 (m, 1H), 1.00 (m, 1H).

Example 10:—1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-(2-aminoethoxy)-1,2-dihydro-1,8-naphthyridin-2-one

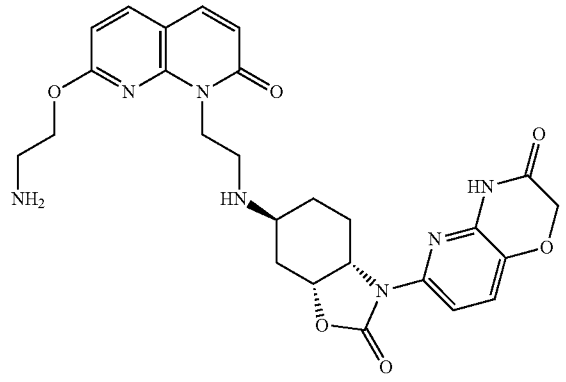

a) tert-butyl N-(2-{[8-(2,2-diethoxyethyl)-7-oxo-7,8-dihydro-1,8-naphthyridin-2-yl]oxy}ethyl)carbamate 10a To a solution of 7-chloro-1-(2,2-diethoxyethyl)-1,2-dihydro-1,8-naphthyridin-2-one 5a (500 mg, 1.7 mmol) and tert-butyl N-(2-hydroxyethyl)carbamate (815 mg, 5.1 mmol) in DMF (15 mL) was added a solution of t-BuOK (1M in THF, 5.1 mL, 5.1 mmol) dropwise and the mixture was stirred at room temperature for 17 h. The resulting mixture was diluted with water (100 mL), extracted with EtOAc (3×100 mL) and the combined extracts were washed with water (2×100 mL), brine (100 mL) and concentrated under reduced pressure. The residue was purified by chromatography (petroleum ether:EtOAc, 3:1, v/v) to give a colourless oil of tert-butyl N-(2-{[8-(2,2-diethoxyethyl)-7-oxo-7,8-dihydro-1,8-naphthyridin-2-yl]oxy}ethyl)carbamate 10a (430 mg, 60%). TLC: $R_f$=0.58 (silica gel, PE:EtOAc=1:1, v/v). $^1H$ NMR (Method E) (DMSO-d6): δ ppm 8.03 (d, J=8.4 Hz, 1H), 7.85 (d, J=9.5 Hz, 1H), 7.01 (t, J=5.8 Hz, 1H), 6.69 (d, J=8.4 Hz, 1H), 6.49 (d, J=9.4 Hz, 1H), 5.00 (t, J=5.7 Hz, 1H), 4.47 (d, J=5.57 Hz, 2H), 4.36 (t, J=5.8 Hz, 2H), 3.63 (m, 2H), 3.44-3.37 (m, 4H), 1.36 (s, 9H), 0.97 (t, J=7.0 Hz, 6H).

b) tert-butyl N-(2-{[7-oxo-8-(2-oxoethyl)-7,8-dihydro-1,8-naphthyridin-2-yl]oxy}ethyl)carbamate 10b To a solution of tert-butyl N-(2-{[8-(2,2-diethoxyethyl)-7-oxo-7,8-dihydro-1,8-naphthyridin-2-yl]oxy}ethyl)carbamate 10a (430 mg, 1.02 mmol) in THF was added aqueous HCl (1.0 M, 5.1 mL, 5.1 mmol) and the mixture was stirred at room temperature for 20 h. The mixture was adjusted to pH 8-9 with saturated aqueous $NaHCO_3$ and extracted with EtOAc (3×20 mL). The combined extracts were washed with water (50 mL), brine (50 mL), dried over $Na_2SO_4$ and concentrated under reduced pressure. The residue was purified by chromatography (Petroleum ether:EtOAc, 5:1 to 1:1, v/v) to give a white solid of tert-butyl N-(2-{[7-oxo-8-(2-oxoethyl)-7,8-dihydro-1,8-naphthyridin-2-yl]oxy}ethyl) carbamate 10b (174 mg, 50%). TLC: $R_f$=0.25 (silica gel, Petroleum ether/EtOAc=1:1, v/v). $^1H$ NMR (Method E) (DMSO-d6): δ ppm 9.69 (s, 1H), 8.09 (d, J=8.5 Hz, 1H), 7.94 (d, J=9.5 Hz, 1H), 7.00 (t, J=5.8 Hz, 1H), 6.71 (d, J=8.4 Hz, 1H), 6.55 (d, J=9.4 Hz, 1H), 5.24 (s, 2H), 4.27 (t, J=5.9 Hz, 2H), 3.28 (m, 2H), 1.36 (s, 9H).

c) tert-butyl N-(2-{[8-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-7-oxo-7,8-dihydro-1,8-naphthyridin-2-yl]oxy}ethyl)carbamate 10c A mixture of tert-butyl N-(2-{[7-oxo-8-(2-oxoethyl)-7,8-dihydro-1,8-naphthyridin-2-yl]oxy}ethyl)carbamate 10b (174 mg, 0.50 mmol) and (3aS,6S,7aR)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 4c (212 mg, 0.50 mmol) in DCE (15 mL) was prepared. $NaBH(OAc)_3$ (424 mg, 2 mmol) was added and stirred at room temperature for 4 h. The resulting mixture was diluted with saturated aqueous $NaHCO_3$ and extracted with EtOAc (3×20 mL). The combined extracts were washed with water (50 mL), brine (50 mL), dried over $Na_2SO_4$ and concentrated under reduced pressure. The residue was purified by chromatography (DCM/MeOH, 50:1 to 20:1, v/v) to give a white foam of tert-butyl N-(2-{[8-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-7-oxo-7,8-dihydro-1,8-naphthyridin-2-yl]oxy}ethyl)carbamate 10c (140 mg, 37%). TLC: $R_f$=0.35 (silica gel, DCM/MeOH=20:1, v/v). LC-MS (Method C) 756.3 $[M+H]^+$; RT 4.13 min.

d) 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-(2-aminoethoxy)-1,2-dihydro-1,8-naphthyridin-2-one 10

To a solution tert-butyl N-(2-{[8-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-7-oxo-7,8-dihydro-1,8-naphthyridin-2-yl]oxy}ethyl)carbamate 10c (140 mg, 0.18 mmol) in DCM (10 mL) was added TFA (2.0 mL, 26.1 mmol) and the mixture was stirred at room temperature for 3 h. $CF_3SO_3H$ (1.0 mL, 11.3 mmol) was then added and stirring was continued for a further 1 h. The resulting mixture was adjusted to pH 8-9 with saturated aqueous $K_2CO_3$ (40 mL) and extracted with DCM/IPA (3:1, 3×20 mL). The combined organic extracts were washed with water, brine, dried over $Na_2SO_4$, filtered and concentrated under pressure. The residue was purified by preparative-TLC ($DCM/MeOH/NH_3.H_2O$, 100:10:2, v/v) to give a white solid of 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-(2-aminoethoxy)-1,2-dihydro-1,8-naphthyridin-2-one 10 (30 mg, 31%). TLC: $R_f$=0.25 (silica gel, DCM/MeOH=10:1 drop of $NH_3$, v/v). LC-MS (Method C) 536.5 $[M+H]^+$; RT 1.72 min. $^1H$ NMR (Method E) (DMSO-d6): δ ppm 8.12 (d, J=8.5 Hz, 1H), 7.92 (d, J=9.5 Hz, 1H), 7.50 (d, J=8.7 Hz, 1H), 7.41 (d, J=8.8 Hz, 1H), 6.77 (d, J=8.4 Hz, 1H), 6.54 (d, J=9.4 Hz, 1H), 4.84 (m, 1H), 4.73 (m, 2H), 4.61 (m, 4H), 4.51 (m, 1H), 3.26 (m, 2H), 3.08 (m, 3H), 2.45 (m, 2H), 1.89 (m, 2H), 1.33 (m, 2H).

Example 11:—(3aS,6S,7aR)-6-[(2-{7-methoxy-4-oxo-4H,5H-[1,2]oxazolo[3,4-c]quinolin-5-yl}ethyl)amino]-3-{3-oxo-2H,3H,4H-pyrido[3,2-b][1,4]oxazin-6-yl}-octahydro-1,3-benzoxazol-2-one

11

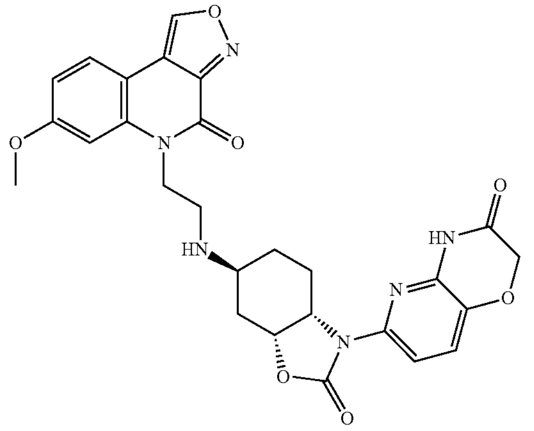

a) 5-(2-hydroxyethyl)-7-methoxy-4H,5H-[1,2]oxazolo[3,4-c]quinolin-4-one 11a

A mixture of 7-methoxy-4H,5H-[1,2]oxazolo[3,4-c]quinolin-4-one (preparation described in PCT 2016024096) (1.1 g, 5.1 mmol, 1 eq), 1,2-dibromoethane (5.2 g, 27.7 mmol, 5.4 eq) and $Cs_2CO_3$ (8.5 g, 26.1 mmol, 5.1 eq) in NMP (80 mL) was heated at 45° C. for 4 h. The mixture was then poured into water and extracted with EtOAc. The organic layer was washed with brine, dried over $Na_2SO_4$, filtered and concentrated under reduced pressure. The residue was purified by silica gel chromatography (Petroleum ether/EtOAc, 3:1 to 1:1, v/v) to give 5-(2-hydroxyethyl)-7-methoxy-4H,5H-[1,2]oxazolo[3,4-c]quinolin-4-one 11a (700 mg, 54%) as a grey solid. TLC: $R_f$=0.27 (silica gel, EtOAc/Petroleum ether=1:1, v/v). LC-MS (Method C) 261.1 $[M+H]^+$; RT 1.72 min. $^1H$ NMR (Method E) (DMSO-d6): δ ppm 9.92 (s, 1H), 7.94 (d, J=8.4 Hz, 1H), 7.16 (d, J=2.0 Hz, 1H), 6.95 (dd, J=8.4, 2.0 Hz, 1H), 4.96 (t, J=6.0 Hz, 1H), 4.33 (t, J=6.4 Hz, 2H), 3.87 (s, 3H), 3.71 (dt, J=6.0, 6.4 Hz, 2H). $^{13}C$ NMR (Method E) (DMSO-d6): δ ppm 160.6, 156.4, 154.9, 150.9, 138.8, 127.4, 117.3, 109.9, 106.5, 102.9, 58.3, 56.0, 44.7.

b) 2-{7-methoxy-4-oxo-4H,5H-[1,2]oxazolo[3,4-c]quinolin-5-yl}acetaldehyde 11b

A mixture of 5-(2-hydroxyethyl)-7-methoxy-4H,5H-[1,2]oxazolo[3,4-c]quinolin-4-one 11a (150 mg, 0.38 mmol, 1 eq) and PCC (800 mg, 3.7 mmol, 9.7 eq) in DCM (20 mL) was stirred at room temperature for 6 h. The mixture was filtered through silica gel and the filtrate was concentrated under reduced pressure to afford 2-{7-methoxy-4-oxo-4H,5H-[1,2]oxazolo[3,4-c]quinolin-5-yl}acetaldehyde 11 b (80 mg) as a grey solid, which was used directly in the next step without further purification. TLC: $R_f$=0.5 (silica gel, EtOAc/petroleum ether, 1:1, v/v). LC-MS (Method C) 259.0 $[M+H]^+$; RT 3.16 min.

c) (3aS,6S,7aR)-6-[(2-{7-methoxy-4-oxo-4H,5H-[1,2]oxazolo[3,4-c]quinolin-5-yl}ethyl)amino]-3-{4-[(4-methoxyphenyl)methyl]-3-oxo-2H,3H,4H-pyrido[3,2-b][1,4]oxazin-6-yl}-octahydro-1,3-benzoxazol-2-one 11c To a mixture of (3aS,6S,7aR)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 4c (30 mg, 0.17 mmol) and 2-{7-methoxy-4-oxo-4H,5H-[1,2]oxazolo[3,4-c]quinolin-5-yl}acetaldehyde 11b (50 mg, 0.12 mmol) in DCM (20 mL) was added $NaBH(OAc)_3$ (150 mg, 0.71 mmol) and stirred at room temperature for 20 h. The resulting mixture was adjusted to pH 8-9 with saturated aqueous $Na_2CO_3$ solution and extracted with DCM. The organic layer was washed with brine, dried over $Na_2SO_4$, filtered and concentrated under reduced pressure. The residue was purified via chromatography (DCM/EtOAc, 2:1 to 1:1, v/v) to give a white solid of (3aS,6S,7aR)-6-[(2-{7-methoxy-4-oxo-4H,5H-[1,2]oxazolo[3,4-c]quinolin-5-yl}ethyl)amino]-3-{4-[(4-methoxyphenyl)methyl]-3-oxo-2H,3H,4H-pyrido[3,2-b][1,4]oxazin-6-yl}-octahydro-1,3-benzoxazol-2-one 11c (40 mg, 52%) TLC: $R_f$=0.31 (silica gel, DCM/EtOAc=1:1, v/v). LC-MS (Method C) 667.2 $[M+H]^+$; RT 3.92 min.

d) (3aS,6S,7aR)-6-[(2-{7-methoxy-4-oxo-4H,5H-[1,2]oxazolo[3,4-c]quinolin-5-yl}ethyl)amino]-3-{3-oxo-2H,3H,4H-pyrido[3,2-b][1,4]oxazin-6-yl}-octahydro-1,3-benzoxazol-2-one 11

To a solution of (3aS,6S,7aR)-6-[(2-{7-methoxy-4-oxo-4H,5H-[1,2]oxazolo[3,4-c]quinolin-5-yl}ethyl)amino]-3-{4-[(4-methoxyphenyl)methyl]-3-oxo-2H,3H,4H-pyrido[3,2-b][1,4]oxazin-6-yl}-octahydro-1,3-benzoxazol-2-one 11c (40 mg, 0.06 mmol) in DCM was added TFA (1.5 mL, 19.6 mmol) and $CF_3SO_3H$ (0.7 mL, 7.9 mmol) and stirred at room temperature for 1 h. The resulting mixture was diluted with MeOH (1.5 mL), the pH adjusted to pH 8-9 with saturated aqueous $Na_2CO_3$ solution and extracted with DCM (100 mL). The organic layer was washed with brine, dried over $Na_2SO_4$, filtered and concentrated under reduced pressure. The residue was purified by chromatography (DCM/MeOH, 15:1, v/v) to give a pale yellow solid of (3aS,6S,7aR)-6-[(2-{7-methoxy-4-oxo-4H,5H-[1,2]oxazolo[3,4-c]quinolin-5-yl}ethyl)amino]-3-{3-oxo-2H,3H,4H-pyrido[3,2-b][1,4]oxazin-6-yl}-octahydro-1,3-benzoxazol-2-one 11. TLC: $R_f$=0.28 (silica gel, DCM/MeOH=15:1, v/v). LC-MS (Method B) 547.2 $[M+H]^+$; RT 3.04 min. $^1H$ NMR (Method E) (DMSO-d6): δ ppm 11.20 (s, 1H), 9.95 (s, 1H), 7.99 (d, J=8.4 Hz, 1H), 7.51 (d, J=8.8 Hz, 1H), 7.40 (d, J=8.4 Hz, 1H), 7.10 (d, J=2.4 Hz, 1H), 7.00 (dd, J=8.8, 2.4 Hz, 1H), 4.77 (dt, J=6.7, 3.2 Hz, 1H), 4.61 (m, 2H), 4.48 (d, J=9.4 Hz, 1H), 4.33 (m, 2H), 3.89 (s, 3H), 2.89 (m, 2H), 2.77 (m, 1H), 2.29 (m, 1H), 1.81 (m, 1H), 1.57 (m, 1H), 1.26 (m, 2H), 1.03 (m, 1H), 0.85 (m, 1H).

Example 12:—1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-(pyridin-3-yloxy)-1,2-dihydro-1,8-naphthyridin-2-one

12

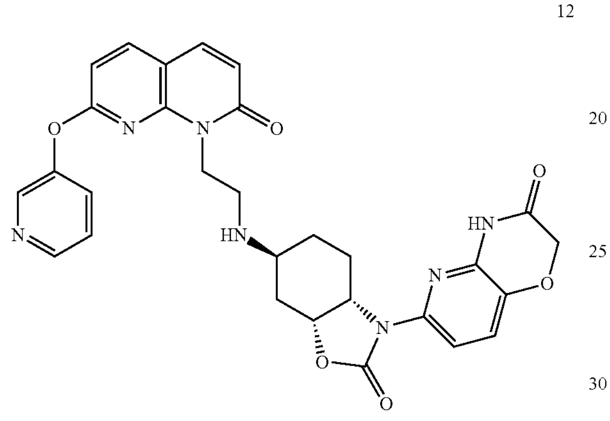

a) 1-(2,2-diethoxyethyl)-7-(pyridin-3-yloxy)-1,2-dihydro-1,8-naphthyridin-2-one 12a To a solution of 7-chloro-1-(2,2-diethoxyethyl)-1,2-dihydro-1,8-naphthyridin-2-one 5a (360 mg, 1.22 mmol) and pyridin-3-ol (174 mg, 1.83 mmol) in DMF (10 mL) was added $Cs_2CO_3$ (800 mg, 2.45 mmol) and the mixture was heated to 70° C. under a nitrogen atmosphere for 17 h. The mixture was diluted with water (100 mL), extracted with EtOAc (3×30 mL) and the combined organics extracts were washed with water (2×100 mL), brine (50 mL) and concentrated under reduced pressure to give a colourless oil of 1-(2,2-diethoxyethyl)-7-(pyridin-3-yloxy)-1,2-dihydro-1,8-naphthyridin-2-one 12a (430 mg, 100%). TLC: $R_f$=0.30 (silica gel, petroleum ether/EtOAc=2:1, v/v). LC-MS (Method C) 310.10 $[M+OEt]^+$; RT 3.29 min.

b) 2-[2-oxo-7-(pyridin-3-yloxy)-1,2-dihydro-1,8-naphthyridin-1-yl]acetaldehyde 12b To a solution of 1-(2,2-diethoxyethyl)-7-(pyridin-3-yloxy)-1,2-dihydro-1,8-naphthyridin-2-one 12a (430 mg, 1.22 mmol) in THF (20 mL) was added HCl (2.0 M, 12.2 mL, 24.4 mmol) and the mixture was stirred at room temperature for 2 h. The mixture was adjusted to pH 8-9 with saturated aqueous $NaHCO_3$ and extracted with EtOAc (20 mL×3). The combined organic extracts were washed with brine (50 mL), dried over $Na_2SO_4$, filtered and concentrated under reduced pressure. The residue was purified by chromatography (Petroleum ether:EtOAc, 5:1 to 1:1, v/v) to give a waxy solid of 2-[2-oxo-7-(pyridin-3-yloxy)-1,2-dihydro-1,8-naphthyridin-1-yl]acetaldehyde 12b (240 mg, 70%). TLC: $R_f$=0.14 (silica gel, Petroleum ether/EtOAc=2:1, v/v). LC-MS (Method C) 282.1 $[M+H]^+$; RT 2.46 min. $^1$H NMR (Method E) ($CDCl_3$): δ ppm 9.40 (s, 1H), 8.54 (br s, 2H), 7.92 (d, J=8.4 Hz, 1H), 7.68 (d, J=9.5 Hz, 1H), 7.44 (d, J=8.0 Hz, 1H), 7.40 (br s, 1H), 6.89 (d, J=8.4 Hz, 1H), 6.66 (d, J=9.5 Hz, 1H), 4.94 (s, 2H).

c) 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-7-(pyridin-3-yloxy)-1,2-dihydro-1,8-naphthyridin-2-one 12c A mixture of (3aS,6S,7aR)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 4c (100 mg, 0.23 mmol) and 2-[2-oxo-7-(pyridin-3-yloxy)-1,2-dihydro-1,8-naphthyridin-1-yl]acetaldehyde 12b (66 mg, 0.23 mmol) in DCE (15 mL) was stirred at room temperature for 30 min. $NaBH(OAc)_3$ (150 mg, 0.71 mmol) was added and the reaction stirred at room temperature for 17 h. The mixture was diluted with DCM (30 mL) and washed with water, brine, dried $Na_2SO_4$, filtered and concentrated under reduced pressure. The residue was purified via chromatography (DCM/MeOH, 50:1 to 20:1, v/v) to give a white foam of 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-7-(pyridin-3-yloxy)-1,2-dihydro-1,8-naphthyridin-2-one 12c (140 mg, 88%). TLC: $R_f$=0.35 (silica gel, DCM/MeOH=20:1, v/v). LC-MS (Method C) 690.3 $[M+H]^+$; RT 3.22 min.

d) 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-(pyridin-3-yloxy)-1,2-dihydro-1,8-naphthyridin-2-one 12

To a solution of 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-7-(pyridin-3-yloxy)-1,2-dihydro-1,8-naphthyridin-2-one 12c (140 mg, 0.20 mmol) in DCM (10 mL) was added TFA (1.5 mL, 19.6 mmol) and $CF_3SO_3H$ (0.7 mL, 7.9 mmol) and the mixture was stirred at room temperature for 1 h. The mixture was diluted with water (40 mL) and the pH was adjusted to pH 8-9 with saturated aqueous $Na_2CO_3$ solution and extracted with DCM (20 mL×3). The combined organic layer was washed with brine, dried on $Na_2SO_4$, filtered and concentrated under reduced pressure. The residue was purified by chromatography (DCM/MeOH, 100:1 to 10:1, v/v) to give a white solid of 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-(pyridin-3-yloxy)-1,2-dihydro-1,8-naphthyridin-2-one 12 (30 mg, 30%). TLC: $R_f$=0.25 (silica gel, DCM/MeOH=10:1, v/v). LC-MS (Method C) 570.2 $[M+H]^+$; RT 2.37 min. $^1$H NMR (Method E) (DMSO-d6): δ ppm: 11.2 (s, 1H), 8.58 (s, 1H), 8.51 (d, J=3.2 Hz, 1H), 8.25 (d, J=8.4 Hz, 1H), 7.93 (d, J=9.6 Hz, 1H), 7.80 (m, 1H), 7.53 (m, 2H), 7.41 (d, J=8.4 Hz, 1H), 7.04 (d, J=9.6 Hz, 1H), 6.56 (d, J=9.6 Hz, 1H), 4.73 (m, 1H), 4.62 (s, 2H), 4.45 (m, 1H), 4.05 (m, 2H), 2.56 (m, 2H), 2.42 (m, 1H), 2.15 (m, 1H), 1.62 (m, 1H), 1.42 (m, 1H), 1.23 (m, 2H), 0.88 (m, 1H).

Example 13:—1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl](2-aminoethyl)amino}ethyl)-7-methoxy-1,2-dihydro-1,8-naphthyridin-2-one

13

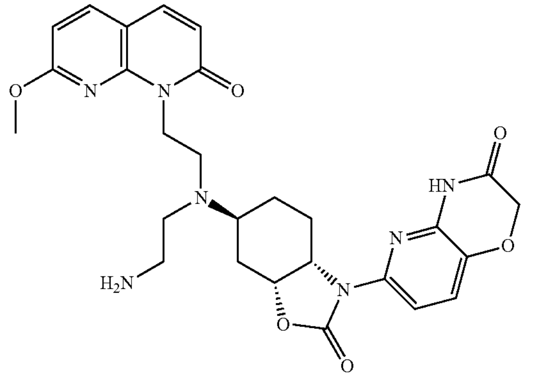

a) tert-butyl N-(2-{[(3aS,6S,7aR)-2-oxo-3-{3-oxo-2H,3H,4H-pyrido[3,2-b][1,4]oxazin-6-yl}-octahydro-1,3-benzoxazol-6-yl][2-(7-methoxy-2-oxo-1,2-dihydro-1,8-naphthyridin-1-yl)ethyl]amino}ethyl)carbamate 13a A solution of 1-(2-{[(3aS,6S,7aR)-2-oxo-2H,3H,4H-pyrido[3,2-b][1,4]oxazin-6-yl}-octahydro-1,3-benzoxazol-6-yl]amino}ethyl)-7-methoxy-1,2-dihydro-1,8-naphthyridin-2-one 4 (100 mg, 0.20 mmol) and tert-butyl N-(2-oxoethyl)carbamate (200 mg, 0.46 mmol) in DCM (10 mL) was added $NaBH(OAc)_3$ (488 mg, 2.3 mmol) and the mixture was stirred at room temperature for 17 h. The resulting mixture was diluted with saturated aqueous $NaHCO_3$ solution and extracted with EtOAc (3×20 mL). The combined organic extracts were washed with water, brine, dried over $Na_2SO_4$, filtered and concentrated under reduced pressure. The residue was purified by chromatography (DCM/EtOAc, 5:1 to 3:1, v/v) to give a white solid of tert-butyl N-(2-{[(3aS,6S,7aR)-2-oxo-3-{3-oxo-2H,3H,4H-pyrido[3,2-b][1,4]oxazin-6-yl}-octahydro-1,3-benzoxazol-6-yl][2-(7-methoxy-2-oxo-1,2-dihydro-1,8-naphthyridin-1-yl)ethyl]amino}ethyl)carbamate 13a (100 mg, 78%). TLC: $R_f$=0.59 (silica gel, DCM/MeOH=15:1, v/v). LC-MS (Method C) 630.3 $[M+H]^+$; RT 3.57 min.

b) 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl](2-aminoethyl)amino}ethyl)-7-methoxy-1,2-dihydro-1,8-naphthyridin-2-one 13

To a solution of tert-butyl N-(2-{[(3aS,6S,7aR)-2-oxo-3-{3-oxo-2H,3H,4H-pyrido[3,2-b][1,4]oxazin-6-yl}-octahydro-1,3-benzoxazol-6-yl][2-(7-methoxy-2-oxo-1,2-dihydro-1,8-naphthyridin-1-yl)ethyl]amino}ethyl)carbamate 13a (140 mg, 0.21 mmol) in DCM (30 mL) at 0° C. was added TFA (5 mL) and the mixture allowed to warm to room temperature and stirred for 5 h. The mixture was adjusted to pH 8-9 with saturated aqueous $K_2CO_3$ solution (40 mL) and extracted with DCM (30 mL×3). The combined organic extracts were washed with water, brine, dried over $Na_2SO_4$, filtered and concentrated under reduced pressure. The residue was purified by chromatography (DCM/MeOH, 25:1 to 10:1, v/v) to give a white solid of 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl](2-aminoethyl)amino}ethyl)-7-methoxy-1,2-dihydro-1,8-naphthyridin-2-one 13 (50 mg, 59%). TLC: $R_f$=0.24 (silica gel, DCM/MeOH=8:1, v/v). LC-MS (Method C) 550.2 $[M+H]^+$; RT 3.05 min. $^1H$ NMR (Method E) (DMSO-d6): δ ppm 8.05 (d, J=8.8 Hz, 1H), 7.86 (d, J=9.2 Hz, 1H), 7.53 (d, J=8.8 Hz, 1H), 7.41 (d, J=8.8 Hz, 1H), 6.73 (d, J=8.4 Hz, 1H), 6.50 (d, J=9.2 Hz, 1H), 4.79 (m, 1H), 4.61 (s, 2H), 4.41 (m, 3H), 4.00 (s, 3H), 2.85 (m, 1H), 2.73 (m, 2H), 2.55 (m, 3H), 2.48 (m, 1H), 2.11 (m, 1H), 1.77 (m, 1H), 1.61 (m, 1H), 1.33-1.23 (m, 3H).

Example 14:—1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-2-oxo-1,2-dihydroquinoline-7-carbonitrile

14

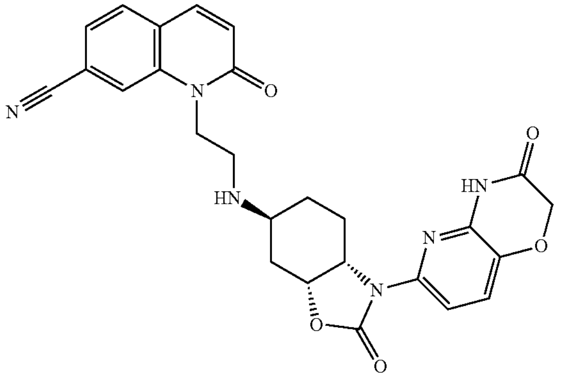

a) (3aS,6S,7aR)-6-amino-3-{3-oxo-2H,3H,4H-pyrido[3,2-b][1,4]oxazin-6-yl}-octahydro-1,3-benzoxazol-2-one 14a To a solution of (3aS,6S,7aR)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 4c (200 mg, 0.20 mmol) in DCM (40 mL) was added TFA (1.5 mL, 19.6 mmol) and $CF_3SO_3H$ (0.7 mL, 7.9 mmol). The mixture was stirred at room temperature for 1.5 h, diluted with MeOH (1.5 mL) and the pH adjusted to pH 8-9 with saturated aqueous $Na_2CO_3$ solution. The organic phase was separated and the aqueous layer was extracted with DCM/IPA (4:1). The organic phase was concentrated under reduced pressure and the residue purified by chromatography (DCM/MeOH, 100:1 to 10:1, v/v) to give a white solid of (3aS,6S,7aR)-6-amino-3-{3-oxo-2H,3H,4H-pyrido[3,2-b][1,4]oxazin-6-yl}-octahydro-1,3-benzoxazol-2-one 14a (140 mg, 97%). LC-MS (Method A) 305.6 $[M+H]^+$; RT 1.45 min.

b) 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-2-oxo-1,2-dihydroquinoline-7-carbonitrile 14

A mixture of (3aS,6S,7aR)-6-amino-3-{3-oxo-2H,3H,4H-pyrido[3,2-b][1,4]oxazin-6-yl}-octahydro-1,3-benzoxazol-2-one 14a (70 mg, 0.23 mmol) and 2-oxo-1-(2-oxo-ethyl)-1,2-dihydroquinoline-7-carbonitrile (49 mg, 0.23 mmol) (J. Med. Chem (2014) 57 (11), 4889-4905) in MeOH (2 mL) was stirred at room temperature for 2 h over molecular sieves (4 Å). $NaBH(OAc)_3$ (146 mg, 0.69 mmol) was added and stirred at room temperature for 2 h. The mixture was diluted with saturated aqueous $NaHCO_3$, the resulting mixture passed through a SPE phase separator and the organic filtrate collected and concentrated under reduced pressure. The residue was purified via silica gel chromatography using 0-100% EtOAc/petroleum ether and 0-20% MeOH/DCM to give a yellow solid of 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-2-oxo-1,2-dihydroquinoline-7-carbonitrile 14 (30 mg, 26.2%) LC-MS (Method B) 501.4 $[M+H]^+$; RT 5.64 min. $^1H$ NMR (Method D) (DMSO-d6): 11.19 (s, 1H), 8.18 (d, J=1.3 Hz, 1H), 8.00 (d, J=9.5 Hz, 1H), 7.91 (d, J=8.0 Hz, 1H), 7.65 (dd, J=8.0, 1.3 Hz, 1H), 7.50 (d, J=8.7 Hz, 1H), 7.40 (d, J=8.7 Hz, 1H), 6.78 (d, J=9.5 Hz, 1H), 4.75 (dt, J=6.3, 3.2 Hz, 1H), 4.60 (d, J=1.0 Hz, 2H), 4.46 (dt, J=9.5, 6.3 Hz, 1H), 4.30 (t, J=7.4 Hz, 2H), 2.85-2.74 (m, 2H), 2.68 (dd, J=20.0, 9.8 Hz, 1H), 2.24 (m, 1H), 2.12-1.95 (m, 1H), 1.76 (d, J=12.8 Hz, 2H), 1.51 (ddd, J=15.0, 11.1, 4.2 Hz, 1H), 1.32-1.21 (m, 1H), 1.02-0.92 (m, 1H).

Example 15:—8-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-oxo-7,8-dihydro-1,8-naphthyridine-2-carbonitrile

15

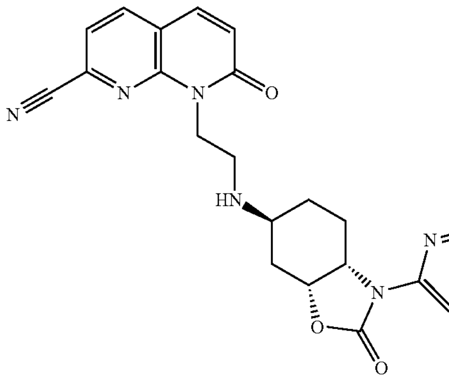

a) 8-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-oxo-7,8-dihydro-1,8-naphthyridine-2-carbonitrile 15

A mixture of (3aS,6S,7aR)-6-amino-3-{3-oxo-2H,3H,4H-pyrido[3,2-b][1,4]oxazin-6-yl}-octahydro-1,3-benzoxazol-2-one 14a (70 mg, 0.23 mmol) and 7-oxo-8-(2-oxo-ethyl)-1,8-naphthyridine-2-carbonitrile (49 mg, 0.23 mmol) (Eur. Pat. Appl. (2008) EP1992628A1 20081119) in DCM (2 mL) was stirred at room temperature for 2 h. $NaBH(OAc)_3$ (146 mg, 0.69 mmol) was added and stirred at room temperature for 2 h. The mixture was diluted with $NaHCO_3$, passed through an SPE phase separator and the organic extracts collected and concentrated under reduced pressure. The residue was purified via silica gel chromatography using 50-100% EtOAc/petroleum ether and 0-20% MeOH/DCM to give an off white solid of 8-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-oxo-7,8-dihydro-1,8-naphthyridine-2-carbonitrile 15 (2.6 mg, 2.2%) LC-MS (Method B) 502.4 $[M+H]^+$; RT 5.38 min. $^1H$ NMR (Method C) (DMSO-d6) δ 11.19 (s, 1H), 8.42 (d, J=7.7 Hz, 1H), 8.06 (d, J=9.6 Hz, 1H), 7.92 (d, J=7.7 Hz, 1H), 7.52 (d, J=8.7 Hz, 1H), 7.41 (d, J=8.7 Hz, 1H), 6.88 (d, J=9.6 Hz, 1H), 4.77 (s, 1H), 4.62 (d, J=1.9 Hz, 1H), 4.55-4.32 (m, 2H), 2.65 (p, J=1.9 Hz, 1H), 2.55 (p, J=1.9 Hz, 3H), 1.80 (m, 1H), 1.54 (m, 2H), 1.41-1.18 (m, 2H), 1.00 (s, 1H), 0.88 (d, J=6.8 Hz, 1H).

Example 16:—1-(2-{[(3aS,6S,7aR)-2-oxo-3-{7-oxo-6H,7H,8H-pyrimido[5,4-b][1,4]oxazin-6-yl}-octahydro-1,3-benzoxazol-6-yl]amino}ethyl)-7-methoxy-1,2-dihydro-1,8-naphthyridin-2-one

16

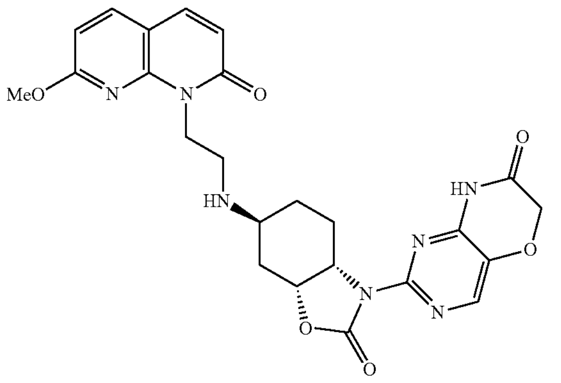

a) 2:1 mixture of 2-bromo-8-[(4-methoxyphenyl)methyl]-6H,7H,8H-pyrimido[5,4-b][1,4]oxazin-7-one and 2-chloro-8-[(4-methoxyphenyl)methyl]-6H,7H,8H-pyrimido[5,4-b][1,4]oxazin-7-one 16a To a solution of a 2:1 mixture of 2-bromo-6H,7H,8H-pyrimido[5,4-b][1,4]oxazin-7-one and 2-chloro-6H,7H,8H-pyrimido[5,4-b][1,4]oxazin-7-one (preparation described in PCT int. application 2011141848)(4.3 g, 20.6 mmol) in DMF under $N_2$ conditions, was added 1-(chloromethyl)-4-methoxybenzene (3.57 g, 22.7 mmol) and $K_2CO_3$ (5.69 g, 41.2 mmol). The mixture was stirred at room temperature for 5 h. Water was added slowly whilst stirring was continued. The resulting precipitate was collected via filtration, washed with water and dried to give a white solid of a 2:1 mixture of 2-bromo-8-[(4-methoxyphenyl)methyl]-6H,7H,8H-pyrimido[5,4-b][1,4]oxazin-7-one and 2-chloro-8-[(4-methoxyphenyl)methyl]-6H,7H,8H-pyrimido[5,4-b][1,4]oxazin-7-one 16a (4.3 g, 64%). TLC: $R_f$=0.78 (silica gel, Petroleum ether/EtOAc=4:1, v/v). LC-MS (Method C) 306.1 $[M+H]^+$ and 350.1 $[M+H]^+$; RT 4.24 min. $^1H$ NMR (Method E) ($CDCl_3$): δ ppm: 8.09 (s, 0.33H), 8.04 (s, 0.66H), 7.48 (d, J=8.8 Hz, 2H), 6.86 (d, J=8.4 Hz, 2H), 5.20/5.19 (2×s, 2H total), 4.76 (s, 2H), 3.79 (s, 3H).

b) tert-butyl N-[(3aS,6S,7aR)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]carbamate 16b To a solution of tert-butyl N-[(3aS,6S,7aR)-2-oxo-octahydro-1,3-benzoxazol-6-yl]carbamate 4a (256 mg, 1.0 mmol) in toluene (10 mL) was added a 2:1 mixture of 2-bromo-8-[(4-methoxyphenyl)methyl]-6H,7H,8H-pyrimido[5,4-b][1,4]oxazin-7-one and 2-chloro-8-[(4-methoxyphenyl)methyl]-6H,7H,8H-pyrimido[5,4-b][1,4]oxazin-7-one 16a (330 mg, 1.0 mmol), trans-1,2-diaminocyclhexane (48 mg, 0.4 mmol), $K_2CO_3$ (280 mg, 2.00 mmol) and CuI (160 mg, 0.8 mmol) under $N_2$ conditions. The mixture was heated to reflux and stirred for 17 h. The mixture was allowed to cool to room temperature, filtered and the filtrate was concentrated under reduced pressure. The residue was purified by chromatography (30% EtOAc in DCM) to give a colourless oil of tert-butyl N-[(3aS,6S,7aR)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]carbamate 16b (210 mg, 40%). TLC: $R_f$=0.39 (silica gel, Petroleum ether/EtOAc=2:1, v/v). LC-MS (Method C) 526.3 $[M+H]^+$; RT 4.02 min.

c) (3aS,6S,7aR)-6-amino-3-{8-[(4-methoxyphenyl)methyl]-7-oxo-6H,7H,8H-pyrimido[5,4-b][1,4]oxazin-2-yl}-octahydro-1,3-benzoxazol-2-one 16c To a solution of tert-butyl N-[(3aS,6S,7aR)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]carbamate 16b (210 mg, 0.40 mmol) in DCM (4 mL), TFA (2 mL, 26.1 mmol) was added and the resulting mixture was stirred at room temperature for 1.5 h. The mixture was adjusted to pH 8-9 with saturated aqueous $NaHCO_3$ and extracted with EtOAc (3×20 mL). The combined organics were washed with water (30 mL), brine (30 mL), dried over $Na_2SO_4$, filtered and concentrated under reduced pressure. The residue was purified by chromatography (DCM/MeOH, 15:1 to 10:1, v/v) to give a white solid of (3aS,6S,7aR)-6-amino-3-{8-[(4-methoxyphenyl)methyl]-7-oxo-6H,7H,8H-pyrimido[5,4-b][1,4]oxazin-2-yl}-octahydro-1,3-benzoxazol-2-one 16c (83 mg, 49%). TLC: $R_f$=0.20 (silica gel, DCM/MeOH=10:1, v/v). LC-MS (Method C) 426.2 $[M+H]^+$; RT 2.61 min.

d) 1-(2-{[(3aS,6S,7aR)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]amino}ethyl)-7-methoxy-1,2-dihydro-1,8-naphthyridin-2-one 16d A mixture of (3aS,6S,7aR)-6-amino-3-{8-[(4-methoxyphenyl)methyl]-7-oxo-6H,7H,8H-pyrimido[5,4-b][1,4]oxazin-2-yl}-octahydro-1,3-benzoxazol-2-one 16c (83 mg, 0.19 mmol) and 2-(7-methoxy-2-oxo-1,2-dihydro-1,8-naphthyridin-1-yl)acetaldehyde (41 mg, 0.19 mmol) (prepared as described in WO2008009700) in DCM (2 mL) was stirred at room temperature for 10 min. $NaBH(OAc)_3$ (212 mg, 1.0 mmol) was added and the mixture stirred at room temperature for 17 h. Saturated aqueous $NaHCO_3$ was added and the mixture extracted with EtOAc (3×20 mL). The combined organics were washed with water, brine, dried over $Na_2SO_4$, filtered and concentrated under reduced pressure to give 1-(2-{[(3aS,6S,7aR)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]amino}ethyl)-7-methoxy-1,2-dihydro-1,8-naphthyridin-2-one 16d (65 mg, 52%). TLC: $R_f$=0.49 (silica gel, DCM/MeOH=10:1, v/v). LC-MS (Method C) 628.3 $[M+H]^+$; RT 3.09 min.

e) 1-(2-{[(3aS,6S,7aR)-2-oxo-3-{7-oxo-6H,7H,8H-pyrimido[5,4-b][1,4]oxazin-6-yl}-octahydro-1,3-benzoxazol-6-yl]amino}ethyl)-7-methoxy-1,2-dihydro-1,8-naphthyridin-2-one dihydrochloride 16

To a stirring solution of 1-(2-{[(3aS,6S,7aR)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]amino}ethyl)-7-methoxy-1,2-dihydro-1,8-naphthyridin-2-one 16d (65 mg, 0.10 mmol) in TFA (4.0 mL, 52.2 mmol) at 0° C., was added $CF_3SO_3H$ (0.40 mL, 4.52 mmol). The mixture was allowed to warm to room temperature and stirred for 1 h. The mixture was adjusted to pH 8-9 with saturated aqueous $Na_2CO_3$ and extracted with EtOAc (3×30 mL). The combined organic extracts were washed with water, brine, dried over $Na_2SO_4$, filtered and concentrated under reduced pressure. The residue was purified by preparative TLC (DCM/MeOH, 10:1, v/v) and converted to the dihydrochloride salt to give a white solid of 1-(2-{[(3aS,6S,7aR)-2-oxo-3-{7-oxo-6H,7H,8H-pyrimido[5,4-b][1,4]oxazin-6-yl}-octahydro-1,3-benzoxazol-6-yl]amino}ethyl)-7-methoxy-1,2-dihydro-1,8-naphthyridin-2-one 16 (15 mg, 28%). TLC: $R_f$=0.39 (silica gel, DCM/MeOH=10:1, v/v). LC-MS (Method C) 508.2 $[M+H]^+$; RT 2.41 min. $^1H$ NMR (Method E) (DMSO-d6): δ ppm 11.75 (br s, 1H), 9.47 (br s, 1H), 8.21 (s, 1H), 8.09 (d, J=8.4 Hz, 1H), 7.92 (d, J=9.2 Hz, 1H), 7.29 (br s, 2H), 6.77 (d, J=8.4 Hz, 1H), 6.54 (d, J=9.2 Hz, 1H), 4.84 (m, 1H), 4.71 (m, 4H), 4.49 (m, 1H), 4.04 (s, 3H), 2.00 (m, 4H), 1.39-1.49 (m, 3H), 1.10 (m, 1H), 0.88 (m, 1H).

Example 17:—(3aS,6S,7aR)-6-[(2-{2-methoxy-7-oxo-7H,8H-pyrido[2,3-d]pyrimidin-8-yl}ethyl)amino]-3-{3-oxo-2H,3H,4H-pyrido[3,2-b][1,4]oxazin-6-yl}-octahydro-1,3-benzoxazol-2-one

17

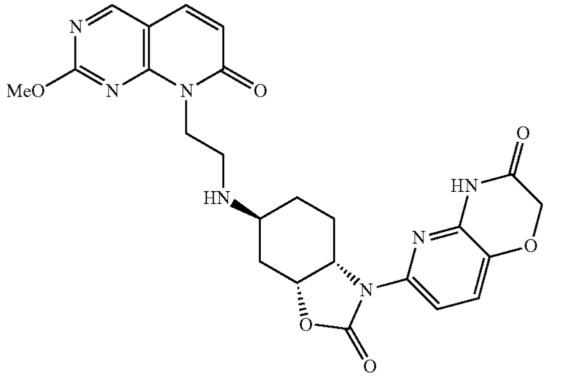

a) (3aS,6S,7aR)-6-[(2-{2-methoxy-7-oxo-7H,8H-pyrido[2,3-d]pyrimidin-8-yl}ethyl)amino]-3-{4-[(4-methoxyphenyl)methyl]-3-oxo-2H,3H,4H-pyrido[3,2-b][1,4]oxazin-6-yl}-octahydro-1,3-benzoxazol-2-one 17a A mixture of (3aS,6S,7aR)-6-amino-3-{4-[(4-methoxyphenyl)methyl]-3-oxo-2H,3H,4H-pyrido[3,2-b][1,4]oxazin- 6-yl}-octahydro-1,3-benzoxazol-2-one 4c (91 mg, 0.21 mmol) and 2-(2-methoxy-7-oxo-7H,8H-pyrido[2,3-d]pyrimidin-8-yl)acetaldehyde 2b (49 mg, 0.12 mmol) in DCM (1.5 mL) was stirred at room temperature for 2 h. NaBH$(OAc)_3$ (75 mg, 0.36 mmol) was added and the mixture stirred at room temperature for 2 h. The mixture was basified with saturated aqueous $NaHCO_3$ and the resulting mixture was passed through a SPE phase separator. The organic phase was washed with brine, dried over $MgSO_4$, filtered and concentrated under reduced pressure to give (3aS,6S,7aR)-6-[(2-{2-methoxy-7-oxo-7H,8H-pyrido[2,3-d]pyrimidin-8-yl}ethyl)amino]-3-{4-[(4-methoxyphenyl)methyl]-3-oxo-2H,3H,4H-pyrido[3,2-b][1,4]oxazin-6-yl}-octahydro-1,3-benzoxazol-2-one 17a (31 mg, 41%). LC-MS (Method A) 628.4 $[M+H]^+$; RT 2.13 min.

b) (3aS,6S,7aR)-6-[(2-{2-methoxy-7-oxo-7H,8H-pyrido[2,3-d]pyrimidin-8-yl}ethyl)amino]-3-{3-oxo-2H,3H,4H-pyrido[3,2-b][1,4]oxazin-6-yl}-octahydro-1,3-benzoxazol-2-one 17

To a solution of (3aS,6S,7aR)-6-[(2-{2-methoxy-7-oxo-7H,8H-pyrido[2,3-d]pyrimidin-8-yl}ethyl)amino]-3-{4-[(4-methoxyphenyl)methyl]-3-oxo-2H,3H,4H-pyrido[3,2-b][1,4]oxazin-6-yl}-octahydro-1,3-benzoxazol-2-one 17a (31 mg, 0.05 mmol) in DCM (5 mL) was added TFA (0.93 mL, 12.2 mmol) and $CF_3SO_3H$ (0.31 mL, 3.46 mmol). After 2 h the mixture was quenched with MeOH (1.5 mL) and the pH adjusted to pH 8-9 with saturated aqueous $Na_2CO_3$. The mixture was diluted with DCM and passed through a SPE phase separator. The organic filtrate was collected, washed with brine, dried over $MgSO_4$, filtered and concentrated under reduced pressure. The residue was purified by chromatography (0-10% MeOH in DCM) to give an off white solid of (3aS,6S,7aR)-6-[(2-{2-methoxy-7-oxo-7H,8H-pyrido[2,3-d]pyrimidin-8-yl}ethyl)amino]-3-{3-oxo-2H,3H,4H-pyrido[3,2-b][1,4]oxazin-6-yl}-octahydro-1,3-benzoxazol-2-one 17 (15.9 mg, 63%). LC-MS (Method B) 508.5 $[M+H]^+$; RT 2.13 min. $^1H$ NMR (Method C) (DMSO-d6): δ ppm δ 11.19 (s, 1H), 8.90 (s, 1H), 7.93 (d, J=9.5 Hz, 1H), 7.51 (d, J=8.7 Hz, 1H), 7.40 (d, J=8.7 Hz, 1H), 6.55 (d, J=9.5 Hz, 1H), 4.74 (dt, J=6.3, 3.1 Hz, 1H), 4.58 (s, 2H), 4.45 (dt, J=9.5, 6.3 Hz, 1H), 4.38-4.29 (m, 2H), 4.00 (s, 3H), 2.90-2.76 (m, 2H), 2.70 (dt, J=11.1, 6.3 Hz, 1H), 2.30-2.19 (m, 1H), 1.77 (d, J=12.9 Hz, 1H), 1.50 (ddd, J=15.1, 11.1, 4.2 Hz, 1H), 1.39-1.15 (m, 2H), 1.04 (m, 1H), 0.85 (m, 1H).

Example 18:—6-[3-({[(3aS,6S,7aR)-2-oxo-3-{3-oxo-2H,3H,4H-pyrido[3,2-b][1,4]oxazin-6-yl}-octahydro-1,3-benzoxazol-6-yl]amino}methyl)-2-hydroxyphenyl]pyridine-2-carbonitrile

18

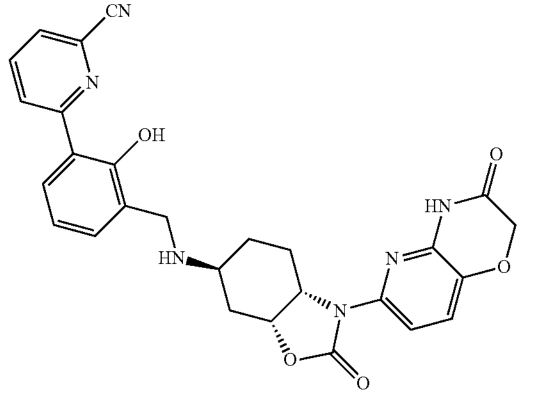

a) 2-(benzyloxy)-3-bromobenzaldehyde 18a

To a solution of 3-bromo-2-hydroxybenzaldehyde (6.03 g, 30.0 mmol) and triethylamine (12.4 mL, 89.1 mmol) in DCM (100 mL) was added (bromomethyl)benzene (6.63 g, 39.0 mmol) dropwise and the mixture stirred at room temperature for 17 h. The mixture was diluted with DCM (100 mL), washed with water (200 mL×2), brine (100 mL) and concentrated under reduced pressure. The residue was purified via chromatography (0-5% EtOAc in petroleum ether) to give a white solid of 2-(benzyloxy)-3-bromobenzaldehyde 18a (6.0 g, 70%). TLC: $R_f$=0.60 (silica gel, petroleum ether/EtOAc=20:1, v/v). $^1H$ NMR (Method E) ($CDCl_3$): δ ppm 10.1 (d, J=0.63 Hz, 1H), 7.86 (m, 1H), 7.81-7.75 (m, 1H), 7.44 (m, 2H), 7.42-7.37 (m, 3H), 7.15 (m, 1H), 5.14 (s, 2H).

b) 6-[2-(benzyloxy)-3-formylphenyl]pyridine-2-carbonitrile 18b

To a solution of 2-(benzyloxy)-3-bromobenzaldehyde 18a (6.00 g, 20.6 mmol) and bis(pinacolato)diboron (6.10 g and 24.0 mmol) in dioxane (60 mL), was added KOAc (6.00 g, 61.2 mmol) and $Pd(PPh_3)_4$ (700 mg, 0.0 mmol). The mixture was heated at reflux for 3 h.

The mixture was cooled to room temperature and 6-chloropyridine-2-carbonitrile (2.20 g, 16.0 mmol), $K_2CO_3$ (8.18 g, 60 mmol), $Pd(PPh_3)_4$ (700 mg, 6.0 mmol) and water (20 mL) were added and the mixture heated to reflux for 17 h. The solvent was removed under reduced pressure and the resulting residue was diluted with water (100 mL) and then extracted with EtOAc (100 mL×2). The combined organic extracts were washed with brine, dried over $Na_2SO_4$, filtered and concentrated under reduced pressure. The residue was purified by chromatography (petroleum ether/EtOAc, 10:1 to 5:1, v/v) to give a pale yellow solid of 6-[2-(benzyloxy)-3-formylphenyl]pyridine-2-carbonitrile 18b (1.60 g, 33%). TLC: $R_f$=0.20 (silica gel, petroleum ether/EtOAc=10:1, v/v). $^1H$ NMR (Method E) ($CDCl_3$): δ ppm 10.30 (s, 1H), 8.12 (d, J=8.0 Hz, 1H), 8.06 (d, J=7.6 Hz, 1H), 7.96 (d, J=7.7 Hz, 1H), 7.84 (t, J=7.8 Hz, 1H), 7.67 (d, J=7.6 Hz, 1H), 7.41 (t, J=7.70 Hz, 1H), 7.30 (m, 3H), 7.09 (d, J=6.9 Hz, 2H), 4.75 (s, 2H).

c) 6-(3-formyl-2-hydroxyphenyl)pyridine-2-carbonitrile 18c

To a solution of 6-[2-(benzyloxy)-3-formylphenyl]pyridine-2-carbonitrile 18b (1.6 g, 5.10 mmol) in EtOH (230 mL) was added palladium on carbon (10%, 160 mg, 0.15 mmol) and the mixture was stirred at room temperature under a hydrogen atmosphere for 24 h. The mixture was filtered and the filtrate concentrated under reduced pressure. The residue was purified by chromatography (petroleum ether/EtOAc, 5:1 to 3:1, v/v) to give a yellow solid of 6-(3-formyl-2-hydroxyphenyl)pyridine-2-carbonitrile 18c (800 mg, 70%). TLC: $R_f$=0.7 (silica gel, petroleum ether/EtOAc=10:1, v/v). LC-MS (Method D) 225.1 $[M+H]^*$; RT 4.31 min. $^1H$ NMR (Method E) (DMSO-d6): δ ppm 12.6 (s, 1H), 10.30 (s, 1H), 8.45 (dd, J=8.3, 0.8 Hz, 1H), 8.28-8.21 (m, 2H), 8.09 (dd, J=7.6, 0.8 Hz, 1H), 7.90 (dd, J=7.6, 1.7 Hz, 1H), 7.21 (t, J=7.6 Hz, 1H).

d) 6-[3-({[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}methyl)-2-hydroxyphenyl]pyridine-2-carbonitrile 18d A mixture of (3aS,6S,7aR)-6-amino-3-{4-[(4-methoxyphenyl)methyl]-3-oxo-2H,3H,4H-pyrido[3,2-b][1,4]oxazin- 6-yl}-octahydro-1,3-benzoxazol-2-one 4c (220 mg, 0.53 mmol) and 6-(3-formyl-2-hydroxyphenyl)pyridine-2-carbonitrile 18c (119 mg, 0.53 mmol) in DCE (20 mL) was stirred at room temperature for 0.5 h. $NaBH(OAc)_3$ (450 mg, 2.12 mmol) was added and stirred at room temperature for 17 h. The mixture was diluted with DCM (30 mL), washed with water, brine and concentrated under reduced pressure. The residue was purified by chromatography (DCM/MeOH, 50:1 to 20:1, v/v) to give a yellow solid of 6-[3-({[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}methyl)-2-hydroxyphenyl]pyridine-2-carbonitrile 18d (320 mg, 95%). TLC: $R_f$=0.38 (silica gel, DCM/MeOH=20:1, v/v). LC-MS (Method D) 633.2 $[M+H]^+$; RT 3.79 min. $^1H$ NMR (Method E) ($CDCl_3$): δ ppm 8.18 (d, J=8.4 Hz, 1H), 7.95 (t, J=8.0 Hz, 1H), 7.74 (m, 2H), 7.64 (d, J=7.5 Hz, 1H), 7.33-7.24 (m, 2H), 7.19 (d, J=8.5 Hz, 2H), 6.93 (t, J=7.7 Hz, 1H), 6.82 (d, J=8.6 Hz, 2H), 5.24 (d, J=14.7 Hz, 1H), 5.12 (d, J=14.7 Hz, 1H), 4.71 (s, 2H), 4.40 (m, 1H), 3.98 (s, 2H), 3.76 (s, 3H), 2.85 (m, 1H), 2.54 (m, 1H), 2.04 (m, 1H), 1.87 (m, 1H), 1.65 (m, 1H). 1.33-1.09 (m, 3H).

e) 6-[3-({[(3aS,6S,7aR)-2-oxo-3-{3-oxo-2H,3H,4H-pyrido[3,2-b][1,4]oxazin-6-yl}-octahydro-1,3-benzoxazol-6-yl]amino}methyl)-2-hydroxyphenyl]pyridine-2-carbonitrile 18

To a solution of 6-[3-({[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}methyl)-2-hydroxyphenyl]pyridine-2-carbonitrile 18d (320 mg, 0.50 mmol) in DCM (3 mL) was added TFA (2.0 mL, 26.1 mmol) and $CF_3SO_3H$ (1.0 mL, 11.3 mmol). The resulting mixture was stirred at room temperature for 1 h. Water (40 mL) was added and the pH adjusted to pH 8-9 with saturated aqueous $Na_2CO_3$ and extracted with DCM (20 mL×3). The combined organic extracts were washed with brine, dried over $MgSO_4$, filtered and concentrated under reduced pressure. The residue was purified by chromatography (DCM/MeOH, 100:1 to 10:1, v/v) to give a white solid of 6-[3-({[(3aS,6S,7aR)-2-oxo-3-{3-oxo-2H,3H,4H-pyrido[3,2-b][1,4]oxazin-6-yl}-octahydro-1,3-benzoxazol-6-yl]amino}methyl)-2-hydroxyphenyl]pyridine-2-carbonitrile 18 (180 mg, 70%). TLC: $R_f$=0.40 (silica gel, DCM/MeOH=10:1, v/v). LC-MS (Method C) 513.2 $[M+H]^+$; RT 2.79 min. $^1H$ NMR (Method E) ($CDCl_3$): δ ppm 8.18 (d, J=8.4 Hz, 1H), 7.95 (t, J=8.0 Hz, 1H), 7.79-7.72 (m, 2H) 7.64 (d, J=7.5 Hz, 1H), 7.29 (m, 2H), 6.93 (t, J=7.7 Hz, 1H), 4.73 (m, 1H), 4.62 (m, 2H), 4.54 (m, 1H), 3.98 (s, 2H), 2.89 (m, 1H), 2.59-2.48 (m, 2H), 2.00 (m, 1H), 1.66 (m, 1H), 1.42 (m, 1H), 1.22 (m, 1H).

Example 19:—1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl](2-aminoethyl)amino}ethyl)-2-oxo-1,2-dihydroquinoline-7-carbonitrile

19

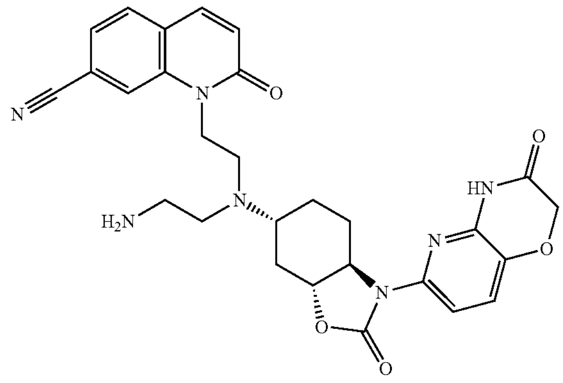

a) tert-butyl N-(2-{[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl][2-(7-cyano-2-oxo-1,2-dihydroquinolin-1-yl)ethyl]amino}ethyl)carbamate 19a A solution of 1-(2-{[(3aR,6R,7aR)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl]amino}ethyl)-2-oxo-1,2-dihydroquinoline-7-carbonitrile 60a (180 mg, 0.29 mmol) and tert-butyl N-(2-oxoethyl)carbamate (189 mg, 1.18 mmol) in DCM (5 mL) was stirred, at room temperature, over molecular sieves (3 Å) for 2 h. $NaBH(OAc)_3$ (307 mg, 1.45 mmol) was added and stirred for 17 h. The reaction was basified to pH 8~9 with saturated aqueous $NaHCO_3$ (10 mL), extracted with DCM (2×25 mL), passed through an SPE phase separator and the organic portion concentrated under reduced pressure to give tert-butyl N-(2-{[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl][2-(7-cyano-2-oxo-1,2-dihydroquinolin-1-yl)ethyl]amino}ethyl)carbamate 19a (230 mg, 104%) which was used without further purification. LC-MS (Method A) 764.3 $[M+H]^+$; RT 3.32 min.

b) 1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl](2-aminoethyl)amino}ethyl)-2-oxo-1,2-dihydroquinoline-7-carbonitrile 19

To a stirring solution of tert-butyl N-(2-{[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl][2-(7-cyano-2-oxo-1,2-dihydroquinolin-1-yl)ethyl]amino}ethyl)carbamate 19a (230 mg, 0.30 mmol) in DCM (20 mL) was added TFA (0.15 mL) followed by $CF_3SO_3H$ (0.08 mL). The reaction was stirred at room temperature for 90 min then quenched with MeOH (10 mL) and basified to pH 9 with saturated $Na_2CO_3$. The resulting mixture was diluted with 20 mL DCM, passed through an SPE phase separator and the organic portion was concentrated under reduced pressure. The residue was purified via silica gel chromatography using 0-20% MeOH in DCM to give 1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl](2-aminoethyl)amino}ethyl)-2-oxo-1,2-dihydroquinoline-7-carbonitrile 19 (7 mg, 4%). LC-MS (Method B) 544.3 $[M+H]^+$; RT 5.68 min. $^1H$ NMR (Method C) (DMSO-d6): δ ppm 8.15 (s, 1H), 8.12 (d, J=9.5 Hz, 1H), 8.03 (d, J=8.1 Hz, 1H), 7.77 (dd, J=7.9, 1.3 Hz, 1H), 7.48 (d, J=8.6 Hz, 1H), 7.23 (d, J=8.6 Hz, 1H), 6.90 (d, J=9.5 Hz, 1H), 4.68 (s, 2H), 4.45-4.39 (m, 2H), 4.05 (td, J=11.5, 3.4 Hz, 1H), 3.75 (td, J=11.1, 3.3 Hz, 1H), 3.01-2.91 (m, 1H), 2.89-2.77 (m, 6H), 2.27 (m, 1H), 1.82 (m, 1H), 1.66 (q, J=11.3 Hz, 1H), 1.47-1.27 (m, 3H).

Example 20:—1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-hydroxy-1,2-dihydroquinolin-2-one

20

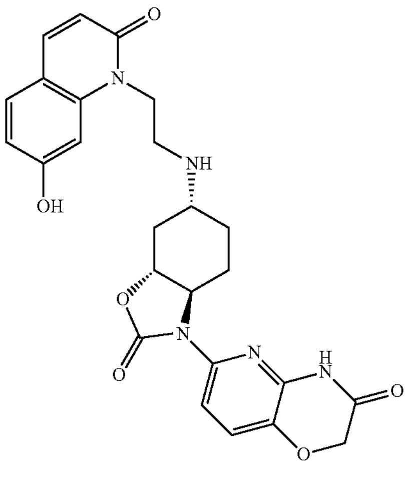

a) 2-(7-hydroxy-2-oxo-1,2-dihydroquinolin-1-yl)acetaldehyde 20a

To a solution of 1-(2,2-diethoxyethyl)-7-hydroxy-1,2-dihydroquinolin-2-one 9d (1 g, 4 mmol) in THF (10 mL) was added aqueous HCl (2.0 M, 10 mL). The mixture was heated at reflux for 1 h then allowed to cool. Excess THF was removed under reduced pressure and the resultant yellow precipitate was filtered, washed with water and dried in vacuo to afford 2-(7-hydroxy-2-oxo-1,2-dihydroquinolin-1-yl)acetaldehyde 20a (848 mg, 104%). $^1H$ NMR (Method C) (DMSO-d6): δ ppm: 10.27 (s, 1H), 9.63 (s, 1H), 7.84 (d, J=9.4 Hz, 1H), 7.55 (d, J=8.5 Hz, 1H), 6.76 (dd, J=8.5, 2.1 Hz, 1H), 6.65 (s, 1H), 6.39 (d, J=9.3 Hz, 1H), 5.14 (s, 2H).

b) 1-(2-{[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-7-hydroxy-1,2-dihydroquinolin-2-one 20b 2-(7-hydroxy-2-oxo-1,2-dihydroquinolin-1-yl)acetaldehyde 20a (146 mg, 0.72 mmol) and (3aR,6R,7aR)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 1c (305 mg, 0.72 mmol) were dissolved in DCM (8 mL). Molecular sieves (4 Å) were added and the mixture stirred at room temperature for 10 min followed by the addition of $NaBH(OAc)_3$ (457 mg, 2.16 mmol). After 3 h, 2-(7-hydroxy-2-oxo-1,2-dihydroquinolin-1-yl)acetaldehyde 20a (50 mg, 0.25 mmol) and $NaBH(OAc)_3$ (152 mg, 0.72 mmol) were added and stirring continued for 17 h. The reaction was quenched with saturated aqueous $NaHCO_3$ and the mixture passed through a SPE phase separator. The DCM fraction was evaporated and the residue purified by chromatography eluting with 0-100% EtOAc in petroleumether followed by 0-20% MeOH in EtOAc to afford 1-(2-{[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-7-hydroxy-1,2-dihydroquinolin-2-one 20b (161 mgs, 36.6%) as a white solid. LC-MS (Method A) 612.1 $[M+H]^+$; RT 2.34 min.

c) 1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-hydroxy-1,2-dihydroquinolin-2-one 20

TFA (0.3 mL, 3.92 mmol) and $CF_3SO_3H$ (0.08 mL, 0.85 mmol) were added to a stirred solution of 1-(2-{[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-7-hydroxy-1,2-dihydroquinolin-2-one 20b (60 mg, 0.1 mmol) in DCM (15 mL) at room temperature. After 1 h the reaction was diluted with MeOH (5 mL) and DCM (10 mL). Saturated aqueous $Na_2CO_3$ was added adjusting the pH to 8 and the mixture was passed through a SPE phase separator. The aqueous phase was further extracted with 5:1 DCM/MeOH (2×30 mL) and the combined organic extracts evaporated. The residue was purified by chromatography (0-20% MeOH in DCM) to afford 1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-hydroxy-1,2-dihydroquinolin-2-one 20 (27 mg, 50%) as a white solid. LC-MS (Method B) 492.1 $[M+H]^+$; RT 5.06 min. $^1H$ NMR (Method C) (DMSO-d6): δ ppm 11.22 (s, 1H), 10.24 (s, 1H), 7.76 (d, J=9.4 Hz, 1H), 7.53 (d, J=8.5 Hz, 1H), 7.42 (d, J=8.5 Hz, 1H), 7.17 (d, J=8.6 Hz, 1H), 6.90 (d, J=2.2 Hz, 1H), 6.73 (dd, J=8.5, 2.1 Hz, 1H), 6.34 (d, J=9.3 Hz, 1H), 4.62 (s, 2H), 4.19 (m, 2H), 4.05 (td, J=11.8, 3.3 Hz, 1H), 3.76 (td, J=11.2, 3.3 Hz, 1H), 2.79 (m, 3H), 2.52-2.45 (m, 3H), 1.49 (m, 1H), 1.32-1.17 (m, 2H).

Example 21:—1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydroquinoxalin-2-one

21

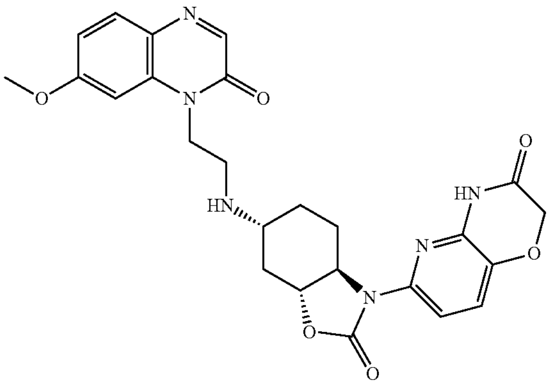

a) 1-(2-{[(3aR,6R,7aR)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl]amino}ethyl)-7-methoxy-1,2-dihydroquinoxalin-2-one 21a A solution of (3aR,6R,7aR)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 1c (136 mg, 0.32 mmol) and 2-(7-methoxy-2-oxo-1,2-dihydroquinoxalin-1-yl)acetaldehyde (prepared as described in WO2013080156A1) (70 mg, 0.32 mmol) in DCM (10 mL) was stirred, at room temperature, over molecular sieves (3 Å) for 2 h. $NaBH(OAc)_3$ (340 mg, 1.60 mmol) was added and stirred for 90 min. The reaction was basified to pH 8~9 with saturated aqueous $NaHCO_3$ (5 mL) and passed through an SPE phase separator. The organic phase was concentrated under reduced pressure to give 1-(2-{[(3aR,6R,7aR)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl]amino}ethyl)-7-methoxy-1,2-dihydroquinoxalin-2-one 21a (160 mg, 79%) which was used without further purification. LCMS (Method A) 627.3 $[M+H]^+$; RT 2.24 min.

b) 1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydroquinoxalin-2-one 21

To a stirring solution of 1-(2-{[(3aR,6R,7aR)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl]amino}ethyl)-7-methoxy-1,2-dihydroquinoxalin-2-one 21a (160 mg, 0.26 mmol) in DCM (30 mL) was added TFA (0.6 mL) followed by $CF_3SO_3H$ (0.15 mL). The reaction was stirred at room temperature for 90 min then quenched with MeOH (5 mL), basified to pH 8~9 with saturated aqueous $Na_2CO_3$ and passed through an SPE phase separator. The organic portion was concentrated under reduced pressure and the residue purified via silica gel chromatography using 0-20% MeOH in DCM to give 1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydroquinoxalin-2-one 21 (31.9 mg, 25%). LC-MS (Method B) 507.2 $[M+H]^+$; RT 5.18 min. $^1H$ NMR (Method C) (DMSO-d6): δ ppm 11.21 (s, 1H), 8.05 (s, 1H), 7.75 (d, J=8.8 Hz, 1H), 7.41 (d, J=8.5 Hz, 1H), 7.16 (d, J=8.5 Hz, 1H), 7.09 (d, J=2.5 Hz, 1H), 7.01 (dd, J=8.9, 2.5 Hz, 1H), 4.61 (s, 2H), 4.26 (t, J=7.0 Hz, 2H), 4.03 (td, J=11.8, 3.4 Hz, 1H), 3.92 (s, 3H), 3.74 (td, J=11.1, 3.3 Hz, 1H), 2.87-2.84 (m, 2H), 2.80-2.63 (m, 2H), 2.4 (m, 1H), 2.13 (br. s, 1H), 1.96 (m, 1H), 1.45 (q, J=11.1 Hz, 1H), 1.36-1.26 (m, 1H), 1.25-1.15 (m, 1H).

Example 22:—1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-6,7-difluoro-1,2-dihydroquinoxalin-2-one

22

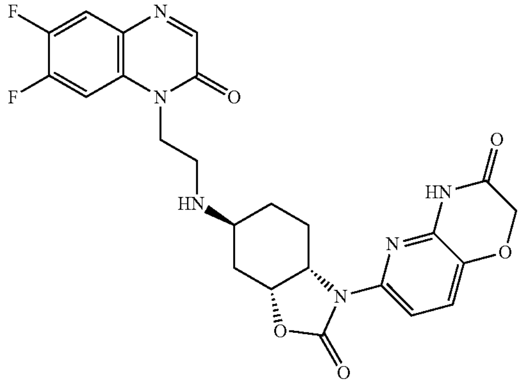

a) 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-6,7-difluoro-1,2-dihydroquinoxalin-2-one 22a To a solution of (3aS,6S,7aR)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 4c (133 mg, 0.31 mmol) and 2-(6,7-difluoro-2-oxo-1,2-dihydroquinoxalin-1-yl)acetaldehyde (prepared as described in WO2008009700 A1 20080124) (70 mg, 0.31 mmol) in DCM (15 mL) was stirred, at room temperature, over molecular sieves (3 Å) for 2 h. $NaBH(OAc)_3$ (331 mg, 1.56 mmol) was added and stirred for 17 h. The molecular sieves were filtered through Celite and washed with DCM/MeOH. The filtrate was basified to pH 8~9 with saturated aqueous $NaHCO_3$ and passed through an SPE phase separator. The organic portion was concentrated under reduced pressure to give 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl]amino}ethyl)-6,7-difluoro-1,2-dihydroquinoxalin-2-one 22a (120 mg, 61%) which was used without further purification. LC-MS (Method A) 633.1 $[M+H]^+$; RT 2.24 min.

b) 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-6,7-difluoro-1,2-dihydroquinoxalin-2-one 22

To a stirring solution of 1-(2-{[(3aS,6S,7aR)-3-{4-[(4-methoxyphenyl)methyl]-3-oxo-2H,3H,4H-pyrido[3,2-b][1, 4]oxazin-6-yl}-2-oxo-octahydro-1,3-benzoxazol-6-yl]amino}ethyl)-6,7-difluoro-1,2-dihydroquinoxalin-2-one 22a (120 mg, 0.19 mmol) in DCM (20 mL) was added TFA (0.6 mL) followed by $CF_3SO_3H$ (0.15 mL). The reaction was stirred at room temperature for 90 min then quenched with MeOH (5 mL), diluted with DCM (10 mL), basified to pH 8~9 with saturated aqueous $Na_2CO_3$ and passed through an SPE phase separator. The organic portion was concentrated under reduced pressure and the residue purified via silica gel chromatography using 0-20% MeOH in DCM to give 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-6,7-difluoro-1,2-dihydroquinoxalin-2-one 22 (24.4 mg, 25%). LC-MS (Method B) 513.1 $[M+H]^+$; RT 5.20 min. $^1H$ NMR (Method C) (DMSO-d6): δ ppm 11.17 (s, 1H), 8.25 (s, 1H), 7.98-7.89 (m, 2H), 7.50 (d, J=8.8 Hz, 1H), 7.4 (d, J=8.6 Hz, 1H), 4.75-4.72 (m, 1H), 4.60 (s, 2H), 4.47-4.43 (m, 1H), 4.25-4.18 (m, 2H), 2.84-2.81 (m, 2H), 2.70-2.62 (m, 1H), 2.43 (m, 1H), 2.24-2.17 (m, 1H), 1.98 (br. s, 1H), 1.76-1.71 (m, 1H), 1.52-1.45 (m, 1H), 1.31-1.20 (m, 1H), 0.98-0.90 (m, 1H).

Example 23:—1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-(2-aminoethoxy)-1,2-dihydroquinolin-2-one

23

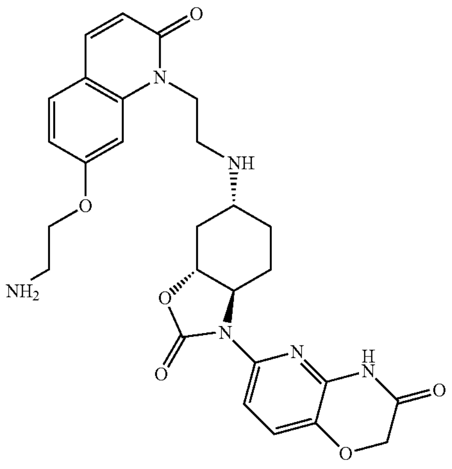

a) N-(2-{[1-(2-{[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-2-oxo-1,2-dihydroquinolin-7-yl]oxy}ethyl)carbamate 23a tert-Butyl N-(2-hydroxyethyl)carbamate (0.03 mL, 0.16 mmol), triphenylphosphine (42.9 mg, 0.16 mmol) and DIAD (0.04 mL, 0.21 mmol) were added to a stirred solution of 1-(2-{[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-7-hydroxy-1,2-dihydroquinolin-2-one 20b (100 mg, 0.16 mmol) in DCM (3 mL) at room temperature. The reaction was stirred for 3 h and purified directly by chromatography eluting with 0-100% EtOAc in petroleum ether followed by 0-20% MeOH in EtOAc to afford N-(2-{[1-(2-{[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-2-oxo-1,2-dihydroquinolin-7-yl]oxy}ethyl)carbamate 23a (46 mg, 37%) as an off white solid. LC-MS (Method A) 755.2 $[M+H]^+$; RT 2.98 min.

b) 1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-(2-aminoethoxy)-1,2-dihydroquinolin-2-one 23

TFA (0.2 mL, 2.61 mmol) and $CF_3SO_3H$ (0.05 mL, 0.57 mmol) were added to a stirred solution of N-(2-{[1-(2-{[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-2-oxo-1,2-dihydroquinolin-7-yl]oxy}ethyl)carbamate 23a (46 mg, 0.06 mmol) in DCM (15 mL). After 1 h the reaction was diluted with MeOH (250 mL) and loaded onto an ion exchange cartridge (10 g Isolute SCX-2). The column was flushed with MeOH and DCM followed by methanolic ammonia solution (1.5 M, 50 mL). The ammoniacal fraction was evaporated and the residue purified by chromatography (11 g Biotage KP-NH cartridge) eluting with 0-100% EtOAc in petroleum ether followed by 0-10% MeOH in EtOAc to give 1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-(2-aminoethoxy)-1,2-dihydroquinolin-2-one 23 (2.7 mg, 8.3%). LC-MS (Method B) 535.1 $[M+H]^+$; RT 4.09 min. NMR (Method C) (DMSO-d6): δ ppm: 7.79 (d, J=9.6 Hz, 1H), 7.61 (d, J=8.7 Hz, 1H), 7.39 (d, J=8.7 Hz, 1H), 7.14 (d, J=8.7 Hz, 1H), 7.01 (s, 1H), 6.88 (d, J=10.2 Hz, 1H), 6.39 (d, J=9.5 Hz, 1H), 4.59 (s, 2H), 4.22 (t, J=7.5 Hz, 2H), 4.02-3.92 (m, 4H), 3.72 (t, J=11.1 Hz, 1H), 2.91 (m, 2H), 2.82-2.64 (m, 5H), 1.97 (m, 2H), 1.54-1.40 (m, 2H).

Example 24:—1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydroquinoxalin-2-one

24

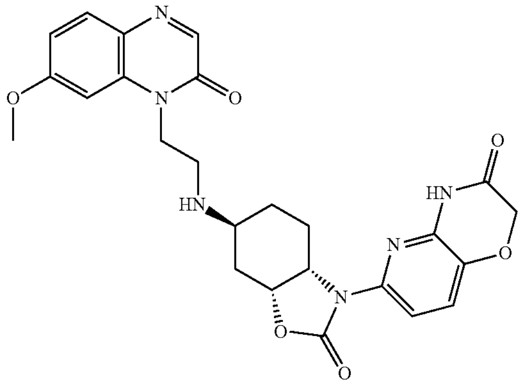

a) 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-7-methoxy-1,2-dihydroquinoxalin-2-one 24a To a solution of (3aS,6S,7aR)-6-amino-3-{4-[(4-methoxyphenyl)methyl]-3-oxo-2H,3H,4H-pyrido[3,2-b][1, 4]oxazin-6-yl}-octahydro-1,3-benzoxazol-2-one 4c (136 mg, 0.32 mmol) and 2-(7-methoxy-2-oxo-1,2-dihydroquinoxalin-1-yl)acetaldehyde (prepared as described in WO2013080156 A1 20130606) (70 mg, 0.32 mmol) in DCM (10 mL) was stirred, at room temperature, over molecular sieves (3 Å) for 2 h. $NaBH(OAc)_3$ (340 mg, 1.60 mmol) was added and stirred for 4 h. The reaction was basified to pH 8~9 with saturated aqueous $NaHCO_3$ (5 mL) and passed through an SPE phase separator. The organic portion was concentrated under reduced pressure to give 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl]amino}ethyl)-7-methoxy-1,2-dihydroquinoxalin-2-one 24a (175 mg, 88%) which was used without further purification. LC-MS (Method A) 627.3 $[M+H]^+$; RT 2.18 min.

b) 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydroquinoxalin-2-one 24

To a stirring solution of 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl]amino}ethyl)-7-methoxy-1,2-dihydroquinoxalin-2-one 24a (175 mg, 0.28 mmol) in DCM (30 mL) was added TFA (0.6 mL) followed by $CF_3SO_3H$ (0.15 mL). The reaction was stirred at room temperature for 2.5 h, then quenched with MeOH (5 mL), basified to pH 8~9 with saturated $Na_2CO_3$ and passed through an SPE phase separator. The organic portion was concentrated under reduced pressure and resulting residue purified via silica gel chromatography using 0-20% MeOH in DCM to give 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydroquinoxalin-2-one 24 (57.2 mg, 41%). LC-MS (Method B) 507.1 $[M+H]^+$; RT 5.20 min. $^1H$ NMR (Method C) (DMSO-d6): δ ppm 11.18 (s, 1H), 8.04 (s, 1H), 7.75 (d, J=8.8 Hz, 1H), 7.51 (d, J=8.6 Hz, 1H), 7.40 (d, J=8.6 Hz, 1H), 7.09 (d, J=2.5 Hz, 1H), 7.00 (dd, J=8.8, 2.5 Hz, 1H), 4.76-4.73 (m, 1H), 4.60 (s, 2H), 4.48-4.44 (m, 1H), 4.29-4.19 (m, 2H), 3.92 (s, 3H), 2.86-2.81 (m, 2H), 2.71-2.66 (m, 1H), 2.43 (m, 1H), 2.26-2.23 (m, 1H), 1.78-1.75 (m, 1H), 1.97-2.12 (br s, 1H), 1.54-1.48 (m, 1H), 1.29-1.22 (m, 1H), 1.02-0.92 (m, 1H).

Example 25:—1-(2-{[(3aR,6R,7aS)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydro-1,8-naphthyridin-2-one

25

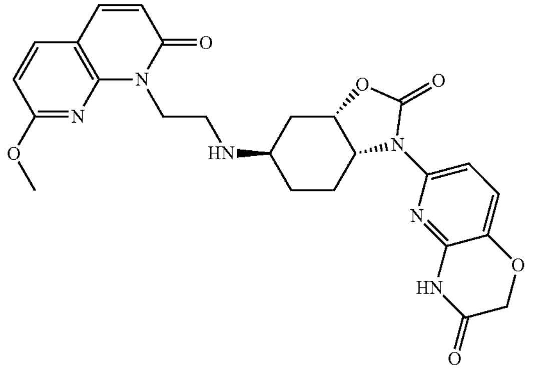

a) benzyl N-[(1R,2R,4R)-4-{[(tert-butoxy)carbonyl]amino}-2-hydroxycyclohexyl]carbamate 25a To a suspension of tert-butyl N-[(1R,3R,4R)-4-amino-3-hydroxy-cyclohexyl]carbamate (2.00 g, 8.68 mmol, (may be prepared according to the methods described in Example 1a, steps 1 to 2)) in DCM (120 mL) was added benzyl 2,5-dioxopyrrolidin-1-yl carbonate (2.38 g, 9.55 mmol) and allowed to stir at 25° C. for 20 hours. The reaction mixture was evaporated and the residue purified via column chromatography eluting with 0-10% MeOH in DCM to afford benzyl N-[(1R,2R,4R)-4-{[(tert-butoxy)carbonyl]amino}-2-hydroxycyclohexyl]carbamate 25a (1.97 g, 62%) as a white solid. LC-MS (Method A) 387.6 $[M+Na]^+$; RT 2.52 min.

b) (1S,2R,5R)-2-{[(benzyloxy)carbonyl]amino}-5-{[(tert-butoxy)carbonyl]amino}cyclohexyl 4-nitrobenzoate 25b To a solution of benzyl N-[(1R,2R,4R)-4-{[(tert-butoxy)carbonyl]amino}-2-hydroxycyclohexyl]carbamate 25a (1.97 g, 5.40 mmol) in anhydrous THF (60 mL) was added triphenylphosphine (1.56 g, 5.94 mmol) and 4-nitrobenzoic acid (0.99 g, 5.94 mmol) followed by dropwise addition of diisopropyl azodicarboxylate (1.17 mL, 5.94 mmol) at 25° C. The reaction mixture was allowed to stir for 3 hours. The reaction mixture was evaporated to dryness, dissolved in EtOAc (200 mL), washed with water (100 mL), brine (100 mL) and dried over $MgSO_4$. The crude product was purified via column chromatograph eluting with 0-50% EtOAc in pet-ether to afford (1S,2R,5R)-2-{[(benzyloxy)carbonyl]amino}-5-{[(tert-butoxy)carbonyl]amino}cyclohexyl 4-nitrobenzoate 25b (2.14 g, 77%) as a white solid. LC-MS (Method A) 512.3 $[M-H]^-$; RT 3.45 min.

c) benzyl N-[(1R,2S,4R)-4-{[(tert-butoxy)carbonyl]amino}-2-hydroxycyclohexyl]carbamate 25c To a solution of (1S,2R,5R)-2-{[(benzyloxy)carbonyl]amino}-5-{[(tert-butoxy)carbonyl]amino}cyclohexyl 4-nitrobenzoate 25b (2.09 g, 4.07 mmol) in anhydrous THF (60 mL) was added 1M lithium hydroxide solution (7.33 mL, 7.33 mmol) and the reaction was allowed to stir at 25° C. for 3 hours. The reaction mixture was diluted with EtOAc (200 mL), washed with water (100 mL), brine (100 mL) and dried over $MgSO_4$ to afford benzyl N-[(1R,2S,4R)-4-{[(tert-butoxy)carbonyl]amino}-2-hydroxycyclohexyl]carbamate 25c (1.42 g, 95%) as a cream solid. LC-MS (Method A) 387.1 $[M+Na]^+$; RT 2.69 min.

d) tert-butyl N-[(1R,3S,4R)-4-amino-3-hydroxycyclohexyl]carbamate 25d

To a solution of benzyl N-[(1R,2S,4R)-4-{[(tert-butoxy)carbonyl]amino}-2-hydroxycyclohexyl]carbamate 25c (1.36 g, 3.73 mmol) in ethanol (100 mL) was added 10% Pd/C paste (100 mg, 0.94 mmol) and the reaction mixture was allowed to stir for 20 hours at 25° C. under a hydrogen atmosphere. The reaction mixture was filtered through a pad of celite, washed with ethanol (100 mL) and the filtrate evaporated to dryness to afford tert-butyl N-[(1R,3S,4R)-4-amino-3-hydroxycyclohexyl]carbamate 25d (0.85 g, 99%) as a cream solid.

e) tert-butyl N-[(3aR,6R,7aS)-2-oxo-octahydro-1,3-benzoxazol-6-yl]carbamate 25e

To a mixture of tert-butyl N-[(1R,3S,4R)-4-amino-3-hydroxycyclohexyl]carbamate 25d (850 mg, 3.69 mmol) and triethylamine (1.54 mL, 11.07 mmol) in anhydrous THF (50 mL) was added triphosgene (438.15 mg, 1.48 mmol) and the mixture was allowed to stir at 25° C. for 24 hours. The reaction temperature was increased to 60° C. and heated for a further 5 hours. The reaction mixture was evaporated to dryness, taken up into water (100 mL) and extracted with EtOAc (2×100 mL). The combined organics were washed with brine (50 mL) and dried over $MgSO_4$ to give a crude solid. The solid was triturated with diethyl ether and filtered to afford tert-butyl N-[(3aR,6R,7aS)-2-oxo-octahydro-1,3-benzoxazol-6-yl]carbamate 25e (177 mg, 19%) as a cream solid.

f) tert-butyl N-[(3aR,6R,7aS)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]carbamate 25f To a mixture of tert-butyl N-[(3aR,6R,7aS)-2-oxo-octahydro-1,3-benzoxazol-6-yl]carbamate 25 e (177 mg, 0.69 mmol), 6-bromo-4-[(4-methoxyphenyl)methyl]-2H,3H,4H-pyrido[3,2-b][1,4]oxazin-3-one (prepared as described in WO2014108832) (313.49 mg, 0.90 mmol), potassium carbonate (190.89 mg, 1.38 mmol) in anhydrous 1,4-dioxane (25 mL) under nitrogen was added copper(I) iodide (26.31 mg, 0.14 mmol) and then (±)-trans-1,2-diaminocyclohexane (3.28 uL, 0.03 mmol) a few minutes later. The reaction mixture was heated at 110° C. for 4 days. The reaction mixture was diluted with water (50 mL) and extracted with EtOAc (2×75 mL). The combined organics were washed with brine (50 mL) and dried over $MgSO_4$. The crude was purified via column chromatography eluting with 0-100% EtOAc in pet-ether followed by 0-50% EtOAc in DCM to afford tert-butyl N-[(3aR,6R,7aS)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]carbamate 25 f (163 mg, 45%) as a white solid. LC-MS (Method A) 525.2 $[M+H]^+$; RT 3.22 min.

g) (3aR,6R,7aS)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 25g To a solution of tert-butyl N-[(3aR,6R,7aS)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]carbamate 25f (147 mg, 0.28 mmol) in DCM (25 mL) was added trifluoroacetic acid (2.0 mL, 26.12 mmol) and the reaction mixture was allowed to stir at 25° C. for 3 hours. The reaction mixture was carefully quenched with sat. sodium carbonate solution (25 mL), diluted with DCM (50 mL) and the layers separated. The aqueous layer was extracted with DCM (50 mL) and the combined organics washed with brine (30 mL) then dried over $MgSO_4$ to afford (3aR,6R,7aS)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 25g (103 mg, 87%) as a beige solid. LC-MS (Method A) 425.1 $[M+H]^+$; RT 1.99 min.

h) 1-(2-{[(3aR,6R,7aS)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl]amino}ethyl)-7-methoxy-1,2-dihydro-1,8-naphthyridin-2-one 25h To a mixture of (3aR,6R,7aS)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 25g (89 mg, 0.21 mmol) and 2-(7-methoxy-2-oxo-1,2-dihydro-1,8-naphthyridin-1-yl)acetaldehyde (prepared as described in WO2008009700) (45.76 mg, 0.21 mmol) in DCM (10 mL) (with some molecular sieves) was added a few drops of acetic acid and allowed to stir at 25° C. for 24 hours. To the reaction mixture was added sodium triacetoxyborohydride (133.32 mg, 0.63 mmol) and allowed to stir for a further 2 hours. The reaction mixture was diluted with DCM (50 mL) and washed with sat sodium carbonate solution (30 mL). The aqueous layer was extracted with DCM (2×50 mL), the combined organics washed with brine (50 mL) and dried over $MgSO_4$ to afford crude 1-(2-{[(3aR,6R,7aS)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl]amino}ethyl)-7-methoxy-1,2-dihydro-1,8-naphthyridin-2-one 25h (95 mg, 0.15 mmol, 72%) as a beige solid. LC-MS (Method A) 627.2 $[M+H]^+$; RT 2.88 min.

i) 1-(2-{[(3aR,6R,7aS)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydro-1,8-naphthyridin-2-one 25

To a solution of 1-(2-{[(3aR,6R,7aS)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl]amino}ethyl)-7-methoxy-1,2-dihydro-1,8-naphthyridin-2-one 25 h (95 mg, 0.15 mmol) in DCM (10 mL) under nitrogen at 25° C. was added trifluoroacetic acid (174 uL, 2.27 mmol) followed by trifluoromethanesulfonic acid (67 uL, 0.76 mmol). The reaction mixture was allowed to stir for 1 hour and then diluted with MeOH (1 mL) followed by the careful addition of sat. sodium carbonate solution (30 mL). The mixture was diluted with DCM (50 mL), the layers separated and the aqueous extracted with DCM (2×50 mL). The combined organics were washed with brine (30 mL) and dried over $Na_2SO_4$ to give a crude solid. The crude was purified by column chromatography eluting with 0-20% MeOH in DCM to afford 1-(2-{[(3aR,6R,7aS)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydro-1,8-naphthyridin-2-one 25 (44 mg, 57%) as a white solid. LC-MS (Method A) 507.1 $[M+H]^+$; RT 2.29 min. $^1H$ NMR (Method C) (DMSO-d6): δ ppm 11.2 (br s, 1H), 8.06 (d, J=8.4 Hz, 1H), 7.88 (d, J=9.6 Hz, 1H), 7.51 (d, J=8.4 Hz, 1H), 7.40 (d, J=8.4 Hz, 1H), 6.74 (d, J=8.4 Hz, 1H), 6.52 (d, J=9.2 Hz, 1H), 4.85-4.75 (m, 1H), 4.60 (s, 2H), 4.53-4.41 (m, 3H), 4.00 (s, 3H), 3.00-2.70 (m, 3H), 2.40-2.29 (m, 1H), 1.83-1.75 (m, 1H), 1.60-1.50 (m, 1H), 1.32-1.22 (m, 2H), 1.05-0.95 (m, 1H).

Example 26:—1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-fluoro-1,2-dihydroquinoxalin-2-one

26

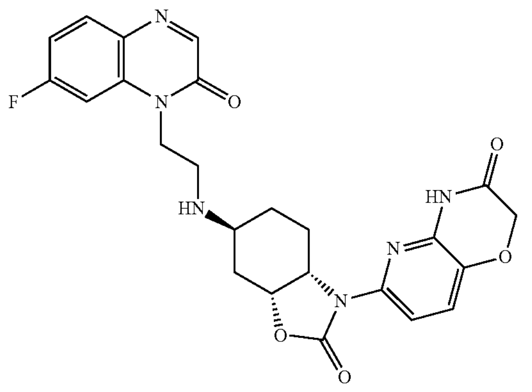

a) 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-7-fluoro-1,2-dihydroquinoxalin-2-one 26a To a solution of (3aS,6S,7aR)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 4c (144 mg, 0.34 mmol) and 2-(7-fluoro-2-oxo-1,2-dihydroquinoxalin-1-yl)acetaldehyde (prepared as described in WO2008009700 A1 20080124) (70 mg, 0.34 mmol) in DCM (15 mL) was stirred, at room temperature, over molecular sieves (3 Å) for 2 h. $NaBH(OAc)_3$ (340 mg, 1.60 mmol) was added and stirred for 17 h. The reaction was basified to pH 8~9 with saturated aqueous $NaHCO_3$ and passed through an SPE phase separator. The organic portion was concentrated under reduced pressure to give 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl]amino}ethyl)-7-fluoro-1,2-dihydroquinoxalin-2-one 26a (195 mg, 93%) which was used without further purification. LC-MS (Method A) 615.2 $[M+H]^+$; RT 2.23 min.

b) 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-fluoro-1,2-dihydroquinoxalin-2-one 26

To a stirring solution of 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl]amino}ethyl)-7-fluoro-1,2-dihydroquinoxalin-2-one 26a (195 mg, 0.32 mmol)) in DCM (30 mL) and MeOH (5 mL) was added TFA (0.85 mL) followed by $CF_3SO_3H$ (0.2 mL). The reaction was stirred at room temperature for 45 min then quenched with MeOH (5 mL), diluted with DCM (10 mL), basified to pH 8~9 with saturated $Na_2CO_3$ and passed through an SPE phase separator. The organic portion was concentrated under reduced pressure and the residue purified via silica gel chromatography using 0-20% MeOH in DCM to give 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-fluoro-1,2-dihydroquinoxalin-2-one 26 (43 mg, 28%). LC-MS (Method B) 495.1 $[M+H]^+$; RT 4.94 min. $^1H$ NMR (Method C) (DMSO-d6): δ ppm 11.18 (s, 1H), 8.19 (s, 1H), 7.88 (dd, J=8.9, 6.1 Hz, 1H), 7.62 (dd, J=11.2, 2.6 Hz, 1H), 7.51 (d, J=8.7 Hz, 1H), 7.40 (d, J=8.7 Hz, 1H), 7.24 (td, J=8.5, 2.6 Hz, 1H), 4.75-4.73 (m, 1H), 4.60 (s, 2H), 4.48-4.44 (m, 1H), 4.29-4.16 (m, 2H), 2.83 (br s, 2H), 2.24-2.21 (m, 1H), 2.01 (m, 1H), 1.75 (m, 1H), 1.50 (m, 1H), 1.25 (m, 2H), 0.96 (m, 1H).

Example 27:—1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-methyl-1,2-dihydroquinoxalin-2-one

27

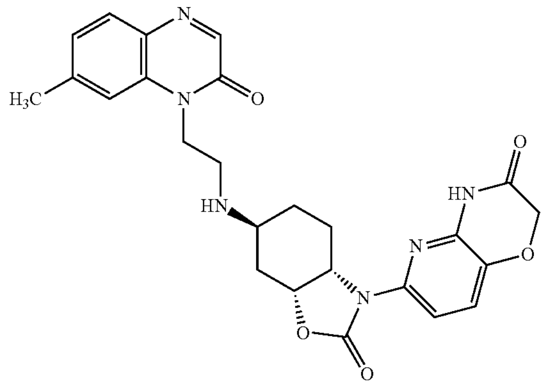

a) 7-bromo-1-(2,2-diethoxyethyl)-1,2-dihydroquinoxalin-2-one 27a 7-bromo-1,2-dihydroquinoxalin-2-one (12.1 g, 53.77 mmol), 2-bromo-1,1-diethoxyethane (7.6 mL, 50.74 mmol) and $CsCO_3$ (19.3 g, 59.15 mmol) were added to DMF (100 mL) and heated at 90° C. for 17 h. $H_2O$ (200 mL) was added to the cooled mixture and extracted with diethyl ether (2×200 mL, mL). The combined organic extracts were dried over $MgSO_4$, concentrated under reduced pressure and purified by silica gel chromatography using 50-60% $Et_2O$ in petroleum ether. The orange residue was mixed with 50% $Et_2O$ in heptane and the precipitate filtered to give 7-bromo-1-(2,2-diethoxyethyl)-1,2-dihydroquinoxalin-2-one (5.9 g, 17.3 mmol, 32% yield) as a yellow solid. LC-MS (Method A) 341, 343 $[M+H]^+$; RT 3.13 min.

b) 1-(2,2-diethoxyethyl)-7-methyl-1,2-dihydroquinoxalin-2-one 27b

A mixture of 7-bromo-1-(2,2-diethoxyethyl)-1,2-dihydroquinoxalin-2-one 27a (2.0 g, 5.86 mmol), $CsCO_3$ (5.72 g, 17.6 mmol), XPhos-Pd-G2 (230 mg, 0.29 mmol) and trimethylboroxine (2.21 g, 17.59 mmol) in dioxane (50 mL) and water (4 mL) was stirred at 100° C. for 17 h. The reaction was allowed to cool, diluted with water (70 mL) and extracted with $Et_2O$ (2×70 mL). The combined organic extracts were dried over $MgSO_4$, concentrated under reduced pressure and purified by silica gel chromatography using 10-50% $Et_2O$ in heptane to afford 1-(2,2-diethoxyethyl)-7-methyl-quinoxalin-2-one 27a (1.28 g, 4.54 mmol, 77%) as a yellow gum. $^1$H NMR (Method C) ($CDCl_3$): δ ppm 8.23 (s, 1H), 7.72 (d, J=7.5 Hz, 1H), 7.46 (s, 1H), 7.14 (d, J=7.5 Hz, 1H), 4.82 (t, J=7.2 HZ, 2H), 4.35 (d, J=7.2 HZ, 1H), 3.8-3.73 (m, 2H), 3.55-3.47 (m, 2H), 2.49 (s, 3H), 1.14-1.09 (t, J=7.5 HZ, 6H).

c) 2-(7-methyl-2-oxo-1,2-dihydroquinoxalin-1-yl) acetaldehyde 27c 1-(2,2-diethoxyethyl)-7-methyl-1,2-dihydroquinoxalin-2-one 27b (1.28 g, 4.63 mmol) was added to a mixture of aqueous HCl (3 N, 20 mL) and THF (20 mL) and heated at reflux for 17 h. After cooling, $H_2O$ (100 mL) was added and the mixture extracted with EtOAc (2×75 ml). The combined organic extracts were dried over $MgSO_4$, filtered and concentrated under reduced pressure to afford an orange solid. The solid was purified by silica gel chromatography using 10-50% $Et_2O$ in petroleum ether to afford 2-(7-methyl-2-oxo-1,2-dihydroquinoxalin-1-yl)acetaldehyde 27c (0.75 g, 80%) as an orange solid. LC-MS (Method A) 203.1 $[M+H]^+$; RT 1.65 min. $^1$H NMR (Method C) ($CDCl_3$): δ ppm 9.71 (s, 1H), 8.21 (s, 1H), 7.74 (d, J=7.5 Hz, 1H), 7.34 (s, 1H), 7.22 (d, J=7.5 Hz, 1H), 5.26 (s, 2H), 2.43 (s, 3H).

d) 1-(2-{[(3aS,6S,7aR)-3-{4-[(4-methoxyphenyl) methyl]-3-oxo-2H,3H,4H-pyrido[3,2-b][1,4]oxazin-6-yl}-2-oxo- octahydro-1,3-benzoxazol-6-yl] amino}ethyl)-7-methyl-1,2-dihydroquinoxalin-2-one 27d A solution of 6-[(3R, 6S)-6-amino-2-oxo-3a,4,5,6,7,7a-hexahydro-1,3-benzoxazol-3-yl]-4H-pyrido[3,2-b][1,4]oxazin-3-one 4c (105 mg, 0.25 mmol) and 2-(7-methyl-2-oxo-1,2-dihydroquinoxalin-1-yl)acetaldehyde 27c (50 mg, 0.25 mmol) in DCM (10 mL) was stirred over molecular sieves (3 Å) for 2 h. $NaBH(OAc)_3$ (262 mg, 1.25 mmol) was added and stirring continued for 2 h. The reaction was basified to pH 8~9 with saturated aqueous $NaHCO_3$ and passed through an SPE phase separator. The organic portion was concentrated under reduced pressure to give a rel-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-7-methyl-1,2-dihydroquinoxalin-2-one 27d (176 mg, 117%) which was used without further purification. LC-MS (Method A) 611.2 $[M+H]^+$; RT 2.24 min.

e) 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-methyl-1,2-dihydroquinoxalin-2-one 27

To a stirring solution of 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl] amino}ethyl)-7-methyl-1,2-dihydroquinoxalin-2-one 27e (176 mg, 0.29 mmol) in DCM (30 mL) was added TFA (0.78 mL) followed by $CF_3SO_3H$ (0.18 mL). The reaction was stirred at room temperature for 45 min, diluted with MeOH (8 mL) followed by DCM (20 mL), basified to pH 8~9 with saturated aqueous $Na_2CO_3$ and passed through an SPE phase separator. The organic portion was concentrated under reduced pressure and the residue purified via silica gel chromatography using 0-20% MeOH in DCM to give 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-methyl-1,2-dihydroquinoxalin-2-one 27 (55 mg, 39%). LC-MS (Method B) 491.1 $[M+H]^+$; RT 5.07 min. $^1$H NMR (Method C) (DMSO-d6): δ ppm 11.18 (s, 1H), 8.15 (s, 1H), 7.71 (d, J=8.1 Hz, 1H), 7.51 (d, J=8.6 Hz, 1H), 7.50 (s, 1H), 7.40 (d, J=8.7 Hz, 1H), 7.21 (dd, J=8.1, 1.6 Hz, 1H), 4.76-4.74 (m, 1H), 4.64-4.58 (m, 2H), 4.49-4.44 (m, 1H), 4.27-4.24 (m, 2H), 2.84 (m, 2H), 2.70 (m, 1H), 3.52 (m, 1H), 2.54 (s, 3H), 2.27-2.20 (m, 1H), 1.94-2.06 (br. s, 1H), 1.77 (m, 1H), 1.56-1.46 (m, 1H), 1.33-1.22 (m, 1H), 1.03-0.91 (m, 1H).

Example 28:—1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-fluoro-1,2-dihydro-1,5-naphthyridin-2-one

28

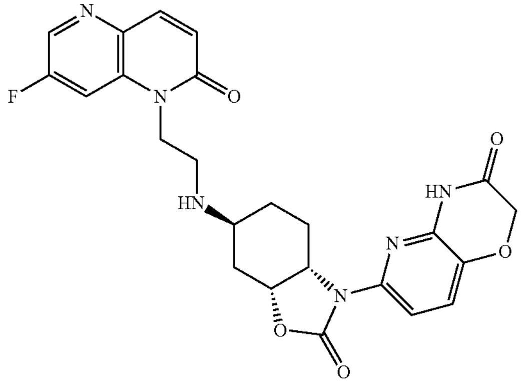

a) 1-(2-{[(3aS,6S,7aR)-3-{4-[(4-methoxyphenyl) methyl]-3-oxo-2H,3H,4H-pyrido[3,2-b][1,4]oxazin-6-yl}-2-oxo-octahydro-1,3-benzoxazol-6-yl] amino}ethyl)-7-fluoro-1,2-dihydro-1,5-naphthyridin-2-one 28a A solution of 6-[(3R, 6S)-6-amino-2-oxo-3a,4,5,6,7,7a-hexahydro-1,3-benzoxazol-3-yl]-4H-pyrido[3,2-b][1,4]oxazin-3-one 4c (144 mg, 0.34 mmol) and 2-(7-fluoro-2-oxo-1,2-dihydro-1,5-naphthyridin-1-yl)acetaldehyde (prepared as described in WO2012108376 A1 20120816) (70 mg, 0.34 mmol) in DCM (20 mL) was stirred, at room temperature, over molecular sieves (3 Å) for 2 h. $NaBH(OAc)_3$ (287 mg, 1.36 mmol) was added and stirred for 2 h. The reaction was basified to pH 8~9 with saturated aqueous $NaHCO_3$ and passed through an SPE phase separator. The organic portion was concentrated under reduced pressure to give 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl]amino}ethyl)-7-fluoro-1,2-dihydro-1,5-naphthyridin-2-one 28a (250 mg, 120%) which was used without further purification. LC-MS (Method A) 615.1 $[M+H]^+$; RT 2.24 min.

b) 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-fluoro-1,2-dihydro-1,5-naphthyridin-2-one 28

To a stirring solution of 1-(2-{[(3aS,6S,7aR)-3-{4-[(4-methoxyphenyl)methyl]-3-oxo-2H,3H,4H-pyrido[3,2-b][1, 4]oxazin-6-yl}-2-oxo-octahydro-1,3-benzoxazol-6-yl]amino}ethyl)-7-fluoro-1,2-dihydro-1,5-naphthyridin-2-one 28a (250 mg, 0.41 mmol) in DCM (30 mL) was added TFA (1.10 mL) followed by $CF_3SO_3H$ (0.25 mL). The reaction was stirred at room temperature for 1 h then quenched with MeOH (5 mL), basified to pH 8~9 with saturated aqueous $Na_2CO_3$ and passed through an SPE phase separator. The organic portion was concentrated under reduced pressure and the residue purified via silica gel chromatography using 0-20% MeOH in DCM to give 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-fluoro-1,2-dihydro-1,5-naphthyridin-2-one 28 (89.7 mg, 45%). LC-MS (Method B) 495.1 $[M+H]^+$; RT 4.81 min. $^1H$ NMR (Method C) (DMSO-d6): δ ppm 11.17 (s, 1H), 8.55 (d, J=2.4 Hz, 1H), 8.12 (dd, J=11.3, 2.5 Hz, 1H), 7.95 (d, J=9.5 Hz, 1H), 7.50 (d, J=8.6 Hz, 1H), 7.40 (d, J=8.8 Hz, 1H), 6.83 (d, J=9.8 Hz, 1H), 4.75-4.72 (m, 1H), 4.60 (s, 2H), 4.47-4.43 (m, 1H), 4.28-4.28 (m, 2H), 2.83-2.74 (m, 2H), 2.71-2.61 (m, 1H), 2.43 (m, 1H), 2.26-2.17 (m, 1H), 1.99 (br. s, 1H), 1.74 (m, 1H), 1.52-1.46 (m, 1H), 1.31-1.20 (m, 1H), 1.01-0.88 (m, 1H).

Example 29:—1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydro-1,8-naphthyridin-2-one

29

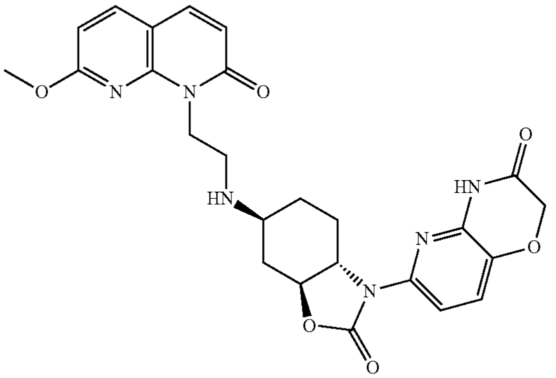

a) tert-butyl N-[(3aS,6S,7aS)-2-oxo-octahydro-1,3-benzoxazol-6-yl]carbamate 29a

To a suspension of tert-butyl N-[(1S,3S,4S)-4-amino-3-hydroxycyclohexyl]carbamate (prepared from tert-butyl N-[(1S,3S,6R)-7-oxabicyclo[4.1.0]heptan-3-yl]carbamate using the methods described in example 1a, steps 1 to 2) (500 mg, 2.17 mmol) in THF (5 mL) was added triethylamine (0.91 mL, 6.510 mmol) followed by careful addition of triphosgene (258 mg, 0.87 mmol) and the mixture was stirred at room temperature for 24 h. The reaction temperature was increased to 60° C. and stirred for a further 3 h. The reaction mixture was concentrated under reduced pressure to give a residue which was suspended in water and extracted with EtOAc (100 mL). The organic extracts were washed with brine, dried over $MgSO_4$, filtered and concentrated under reduced pressure to give tert-butyl N-[(3aS,6S,7aS)-2-oxo-octahydro-1,3-benzoxazol-6-yl]carbamate 29a (493 mg, 75%) as a white solid. $^1H$ NMR (Method C) (DMSO-d6): δ ppm 7.59 (s, 1H), 6.94 (d, J=8.2 Hz, 1H), 3.77 (td, J=11.8, 3.5 Hz, 1H), 3.49 (m, 1H), 3.13 (td, J=11.3, 3.5 Hz, 1H), 2.18 (m, 1H), 1.82 (m, 2H), 1.54 (q, J=11.3 Hz, 1H), 1.37 (s, 9H), 1.27 (m, 1H).

b) tert-butyl N-[(3aS,6S,7aS)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]carbamate 29b To a mixture of tert-butyl N-[(3aS,6S,7aS)-2-oxo-3a,4,5,6,7,7a-hexahydro-3H-1,3-benzoxazol-6-yl]carbamate 29a (490 mg, 1.91 mmol), 6-bromo-4-[(4-methoxyphenyl)methyl]pyrido[3,2-b][1,4]oxazin-3-one (prepared as described in WO2014108832) (868 mg, 2.49 mmol), $K_2CO_3$ (528 mg, 3.82 mmol) in anhydrous 1,4-Dioxane (45 mL) under nitrogen was added CuI (73 mg, 0.38 mmol) followed by trans-1,2-diaminocyclohexane (3.3 μL, 0.03 mmol) a few minutes later. The mixture was heated to 110° C. for 18 h under $N_2$. Another batch of CuI (73 mg, 0.38 mmol) and trans-1,2-diaminocyclohexane (3.3 μL, 0.03 mmol) was added and the mixture stirred at 110° C. for a further 50 h. The reaction was cooled to room temperature and evaporated under reduced pressure. The residue was diluted with EtOAc (200 mL), washed with brine, dried over $MgSO_4$, filtered and concentrated. The residue was purified by chromatography (Biotage 100 g KP-Si cartridge) using 0-100% EtOAc in DCM to give tert-butyl N-[(3aS,6S,7aS)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]carbamate 29b (759 mg, 75%) as a brown solid. LC-MS (Method A) 525.2 $[M+H]^+$; RT 3.23 min. $^1H$ NMR (Method C) ($CDCl_3$): δ ppm 7.30 (m, 2H), 7.17 (m, 2H), 6.82 (m, 2H), 5.18 (m, 2H), 4.72 (s, 2H), 4.53 (m, 1H), 3.94 (td, J=11.5, 3.3 Hz, 1H), 3.77 (s, 3H), 3.69 (td, J=11.0, 3.3 Hz, 1H), 2.63 (m, 1H), 2.26 (m, 1H), 2.03 (m, 1H), 1.61 (q, J=11.5 Hz, 1H), 1.46 (s, 9H), 1.25 (m, 2H).

c) (3aS,6S,7aS)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 29c To solution of tert-butyl N-[(3aS,6S,7aS)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]carbamate 29b (720 mg, 1.37 mmol) in DCM (25 mL) was added TFA (2 mL, 26.10 mmol) and the reaction was stirred at room temperature for 16 h. The reaction mixture was adjusted to pH 8~9 with saturated aqueous $Na_2CO_3$, then partitioned between brine and DCM. The organic phase was dried over $MgSO_4$, filtered and concentrated to give (3aS,6S,7aS)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 29c (438 mg, 75%), which was used without further purification. LC-MS (Method A) 425.2 $[M+H]^+$; RT 2.47 min.

d) 1-(2-{[(3aS,6S,7aS)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-7-methoxy-1,2-dihydro-1,8-naphthyridin-2-one 29d To a solution of (3aS,6S,7aS)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 29c (210 mg, 0.49 mmol) and 2-(7-methoxy-2-oxo-1,2-dihydro-1,8- naphthyridin-1-yl)acetaldehyde (108 mg, 0.49 mmol, prepared as described in WO2008009700) in DCM (20 mL) was added a few drops of AcOH and the mixture stirred at room temperature for 18 h. $NaBH(OAc)_3$ (314 mg, 1.48 mmol) was added and the reaction mixture stirred at room temperature for 30 min. The mixture was adjusted to pH 8~9 with saturated $Na_2CO_3$ and extracted with DCM (150 mL). The organic layer was washed with brine, dried over $MgSO_4$, filtered and concentrated to give 1-(2-{[(3aS,6S,7aS)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl]amino}ethyl)-7-methoxy-1,2-dihydro-1,8-naphthyridin-2-one 29d, (298 mg, 96%), which was used without further purification. LC-MS (Method A) 627.2 $[M+H]^+$; RT 2.90 min.

e) 8-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-2-methoxy-7,8-dihydroquinolin-7-one 29

To a solution of 1-(2-{[(3aS,6S,7aS)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl]amino}ethyl)-7-methoxy-1,2-dihydro-1,8-naphthyridin-2-one 29d (290 mg, 0.46 mmol) in DCM (30 mL) was added TFA (531 μL, 6.94 mmol) followed by $CF_3SO_3H$ (204 μL, 2.31 mmol) and the mixture was stirred at room temperature for 1 h. The reaction was quenched with MeOH (1 mL) and the mixture was adjusted to pH 8~9 with saturated aqueous $Na_2CO_3$ and extracted with DCM (100 mL). The organic extract was washed with brine, dried over $MgSO_4$, filtered and concentrated under reduced pressure. The residue was purified by chromatography (Biotage 10 g KP-Si cartridge) using 0-50% MeOH in DCM to give 8-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-2-methoxy-7,8-dihydroquinolin-7-one 29 (32 mg, 13%) as an off-white solid. LC-MS (Method A) 507.1 $[M+H]^+$; RT 2.34 min. $^1H$ NMR (Method C) ($CDCl_3$): δ ppm 8.25 (s, 1H), 7.71 (d, J=8.4 Hz, 1H), 7.54 (d, J=9.4 Hz, 1H), 7.29 (d, J=1.9 Hz, 2H), 6.63 (d, J=8.4 Hz, 1H), 6.56 (d, J=9.4 Hz, 1H), 4.65 (t, J=6.6 Hz, 2H), 4.59 (s, 2H), 4.04 (s, 3H), 3.95 (m, 1H), 3.77 (td, J=10.9, 3.4 Hz, 1H), 3.15 (t, J=6.6 Hz, 2H), 2.91 (m, 1H), 2.63 (m, 2H), 2.13 (m, 1H), 1.5 (q, J=11.4, 1H), 1.37 (m, 2H).

Example 30:—1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydro-1,5-naphthyridin-2-one

30

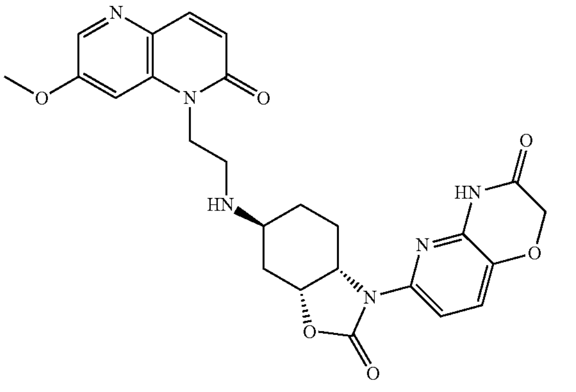

a) 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-7-methoxy-1,2-dihydro-1,5-naphthyridin-2-one 30a A solution of 6-[(3R, 6S)-6-amino-2-oxo-3a,4,5,6,7,7a-hexahydro-1,3-benzoxazol-3-yl]-4H-pyrido[3,2-b][1,4]oxazin-3-one 4c (117 mg, 0.28 mmol) and 2-(7-methoxy-2-oxo-1,2-dihydro-1,5-naphthyridin-1-yl)acetaldehyde (prepared as described in WO2011148962A1) (60 mg, 0.28 mmol) in DCM (20 mL) was stirred at room temperature over molecular sieves (3 Å) for 2 h. $NaBH(OAc)_3$ (233 mg, 1.10 mmol) was added and stirred for 3 h. The reaction was basified to pH 8~9 with saturated aqueous $NaHCO_3$ and passed through an SPE phase separator. The organic portion was concentrated under reduced pressure to give 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl]amino}ethyl)-7-methoxy-1,2-dihydro-1,5-naphthyridin-2-one 30a (160 mg, 93%) which was used without further purification. LC-MS (Method A) 627.2 $[M+H]^+$; RT 2.23 min.

b) 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydro-1,5-naphthyridin-2-one 30

To a stirring solution of 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl]amino}ethyl)-7-methoxy-1,2-dihydro-1,5-naphthyridin-2-one 30a (160 mg, 0.26 mmol) in DCM (20 mL) was added TFA (0.90 mL) followed by $CF_3SO_3H$ (0.20 mL). The reaction was stirred at room temperature for 1 h then quenched with MeOH (5 mL), diluted with DCM (10 ml), basified to pH 8~9 with saturated aqueous $Na_2CO_3$ and passed through an SPE phase separator. The organic portion was concentrated under reduced pressure and the residue purified via silica gel chromatography using 0-20% MeOH in DCM to give 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydro-1,5-naphthyridin-2-one 30 (83 mg, 51%). LC-MS (Method B) 507.1 $[M+H]^+$; RT 4.70 min. $^1H$ NMR (Method C) (DMSO-d6): δ ppm 11.18 (s, 1H), 8.28 (d, J=2.3 Hz, 1H), 7.87 (d, J=9.6 Hz, 1H), 7.51 (d, J=8.8 Hz, 1H), 7.49 (s, 1H), 7.40 (d, J=8.7 Hz, 1H), 6.66 (d, J=9.7 Hz, 1H), 4.76 (m, 1H), 4.64-4.57 (m, 2H), 4.50-4.42 (m, 1H), 4.32-4.25 (m, 2H), 3.98 (s, 3H), 2.81 (m, 2H), 2.69 (m, 1H), 2.43 (m, 1H), 2.24 (m, 1H), 2.02 (br. s, 1H), 1.76 (m, 1H), 1.58-1.45 (m, 1H), 1.32-1.19 (m, 1H), 1.03-0.90 (m, 1H).

Example 31:—4-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-3-oxo-3,4-dihydroquinoxaline-6-carbonitrile

31

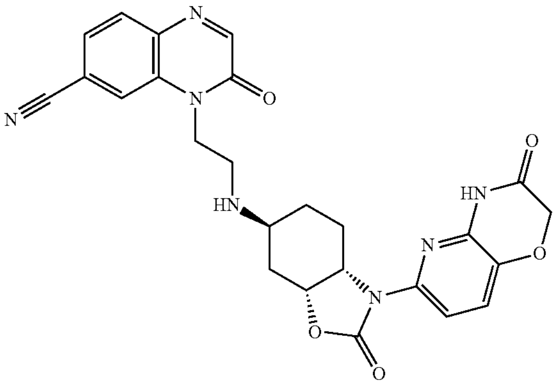

a) 4-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-3-oxo-3,4-dihydroquinoxaline-6-carbonitrile 31a A solution of 6-[(3R, 6S)-6-amino-2-oxo-3a,4,5,6,7,7a-hexahydro-1,3-benzoxazol-3-yl]-4H-pyrido[3,2-b][1,4]oxazin-3-one 4c (100 mg, 0.23 mmol) and 3-oxo-4-(2-oxoethyl)-3,4-dihydroquinoxaline-6-carbonitrile (prepared as described in WO 2006137485 A1 20061228) (50 mg, 0.23 mmol) in DCM (20 mL) was stirred, at room temperature, over molecular sieves (3 Å) for 2 h. $NaBH(OAc)_3$ (233 mg, 1.10 mmol) was added and stirred for 3 h. The reaction was basified to pH 8~9 with saturated aqueous $NaHCO_3$ and passed through an SPE phase separator. The organic portion was concentrated under reduced pressure to give 4-(2-{[(3aS,6S,7aR)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl]amino}ethyl)-3-oxo-3,4-dihydroquinoxaline-6-carbonitrile 31a (140 mg, 96%) which was used without further purification. LC-MS (Method A) 622.2 $[M+H]^+$; RT 2.29 min.

b) 4-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-3-oxo-3,4-dihydroquinoxaline-6-carbonitrile 31

To a stirring solution of 4-(2-{[(3aS,6S,7aR)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl]amino}ethyl)-3-oxo-3,4-dihydroquinoxaline-6-carbonitrile 31a (140 mg, 0.23 mmol) in DCM (14 mL) was added TFA (0.60 mL) followed by $CF_3SO_3H$ (0.14 mL). The reaction was stirred at room temperature for 1 h then quenched with MeOH (5 mL), diluted with DCM (10 ml), basified to pH 8~9 with saturated aqueous $Na_2CO_3$ and passed through an SPE phase separator. The organic portion was concentrated under reduced pressure and the residue purified via silica gel chromatography using 0-20% MeOH in DCM to give 4-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-3-oxo-3,4-dihydroquinoxaline-6-carbonitrile 31 (34 mg, 30%). LC-MS (Method B) 502.1 $[M+H]^+$; RT 5.10 min. $^1H$ NMR (Method C) (DMSO-d6): δ ppm 11.17 (s, 1H), 8.38 (s, 1H), 8.28 (d, J=1.3 Hz, 1H), 7.98 (d, J=8.2 Hz, 1H), 7.77 (dd, J=8.3, 1.6 Hz, 1H), 7.50 (d, J=8.7 Hz, 1H), 7.40 (d, J=8.7 Hz, 1H), 4.75-4.73 (m, 1H), 4.60 (m, 2H), 4.48-4.42 (m, 1H), 4.28-4.25 (m, 2H), 2.84 (m, 2H), 2.62 (m, 1H), 2.44 (m, 1H), 2.22 (m, 1H), 2.00 (m, 1H), 1.74 (m, 1H), 1.49 (m, 1H), 1.25 (m, 1H), 0.95 (m, 1H).

Example 32:—1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-[2-(dimethylamino)ethoxy]-1,2-dihydroquinolin-2-one

32

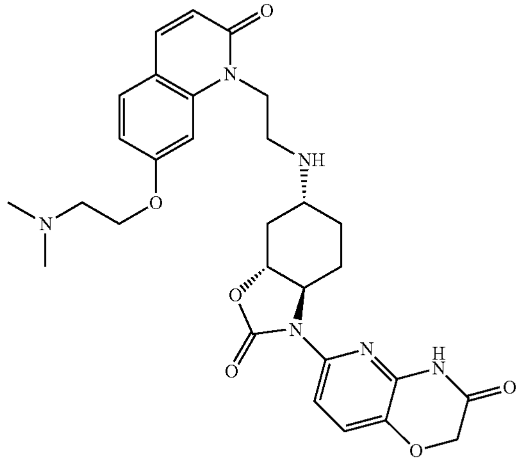

a) 1-(2,2-diethoxyethyl)-7-[2-(dimethylamino)ethoxy]-1,2-dihydroquinolin-2-one 32a Triphenylphosphine (179 mg, 0.68 mmol) and 2-(dimethylamino)ethan-1-ol (0.07 mL, 0.68 mmol) were added to a stirred solution of 1-(2,2-diethoxyethyl)-7-hydroxy-1,2-dihydroquinolin-2-one 9c (170 mg, 0.68 mmol) in DCM (2 mL) and cooled in an ice bath for 30 min. DIAD (0.17 mL, 0.89 mmol) was added and the mixture allowed to reach ambient temperature. After 17 h the mixture was purified by chromatography eluting with 0-100% EtOAc in petroleum ether and 0-10% MeOH in EtOAc to afford 1-(2,2-diethoxyethyl)-7-[2-(dimethylamino)ethoxy]-1,2-dihydroquinolin-2-one 32a (61 mg, 28.5%). TLC: $R_f$=0.31 (silica gel, MeOH/DCM=1:9, v/v). LC-MS (Method A) 349.1 $[M+H]^+$; RT 1.48 min.

b) 2-{7-[2-(dimethylamino)ethoxy]-2-oxo-1,2-dihydroquinolin-1-yl}acetaldehyde 32b A solution of 1-(2,2-diethoxyethyl)-7-[2-(dimethylamino)ethoxy]-1,2-dihydroquinolin-2-one 32a (105 mg, 0.30 mmol) in THF (1 mL) and aqueous HCl (2M, 1 mL) was stirred for 17 h at room temperature. The mixture was basified to pH 8 with saturated aqueous $NaHCO_3$. MeOH/DCM (1:4, 50 mL) was added and the mixture passed through an SPE phase separator. The organic portion was concentrated under reduced pressure to give a brown oil of 2-{7-[2-(dimethylamino)ethoxy]-2-oxo-1,2-dihydroquinolin-1-yl}acetaldehyde 32b (90 mg, 108%). LC-MS (Method A) 275.11 $[M+H]^+$; RT 1.13 min.

c) 1-(2-{[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-7-[2-(dimethylamino)ethoxy]-1,2-dihydroquinolin-2-one 32c A solution of 2-{7-[2-(dimethylamino)ethoxy]-2-oxo-1,2-dihydroquinolin-1-yl}acetaldehyde 32b (90 mg, 0.33 mmol) in DCM (9 mL) was stirred over molecular sieves (4 Å) at room temperature. After 15 min (3aR,6R,7aR)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 1c (133.5 mg, 0.31 mmol) and $NaBH(OAc)_3$ (209 mg, 0.98 mmol) were added and the reaction stirred for 5 h. Saturated aqueous $NaHCO_3$ (5 mL) was added and the mixture passed through an SPE phase separator. The organic phase was evaporated and the residue purified by chromatography eluting with 0-20% MeOH in DCM to give 1-(2-{[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-7-[2-(dimethylamino)ethoxy]-1,2-dihydroquinolin-2-one 32c (75 mg, 34.8%) as a white solid. LC-MS (Method A) 683.3 $[M+H]^+$; RT 1.76 min.

d) 1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-[2-(dimethylamino)ethoxy]-1,2-dihydroquinolin-2-one 32

TFA (0.4 mL, 5.22 mmol) and $CF_3SO_3H$ (0.1 mL, 1.13 mmol) were added to a stirred solution of 1-(2-{[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-7-[2-(dimethylamino)ethoxy]-1,2-dihydroquinolin-2-one 32c (75 mg, 0.11 mmol) in DCM (15 mL) at room temperature. After 1 h the reaction was diluted with MeOH (5 mL) and DCM (10 mL). Saturated aqueous $Na_2CO_3$ was added, adjusting the pH to 8, and the mixture was passed through an SPE phase separator. The aqueous phase was further extracted with DCM/MeOH (4:1, 2×30 mL) and the combined organics evaporated and the residue purified by chromatography eluting with 0-20% MeOH in DCM to give 1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-[2-(dimethylamino)ethoxy]-1,2-dihydroquinolin-2-one 32 (20 mg, 29%). LC-MS (Method B) 563.2 $[M+H]^+$; RT 4.18 min. $^1H$ NMR (Method C) (DMSO-d6): δ ppm 11.27 (s, 1H), 7.83 (d, J=9.4 Hz, 1H), 7.64 (d, J=8.5 Hz, 1H), 7.42 (d, J=8.7 Hz, 1H), 7.17 (d, J=8.6 Hz, 1H), 7.06 (d, J=2.3 Hz, 1H), 6.92 (dd, J=8.5, 2.1 Hz, 1H), 6.43 (d, J=9.3 Hz, 1H), 4.62 (s, 2H), 4.30 (t, J=7.4 Hz, 2H), 4.23 (t, J=5.7 Hz, 2H), 4.05 (td, J=11.7, 3.3 Hz, 1H), 3.76 (dt, J=11.0, 5.5 Hz, 1H), 2.87 (m, 3H), 2.80-2.67 (m, 3H), 2.47 (m, 1H), 2.28 (s, 6H), 2.02 (m, 1H), 1.53 (q, J=11.2 Hz, 1H), 1.40-1.21 (m, 2H).

Example 33:—(3aR,6R,7aR)-6-[(2-{2-methoxy-7-oxo-7H,8H-pyrido[2,3-d]pyrimidin-8-yl}ethyl)amino]-3-{7-oxo-6H,7H,8H-pyrimido[5,4-b][1,4]oxazin-2-yl}-octahydro-1,3-benzoxazol-2-one

33

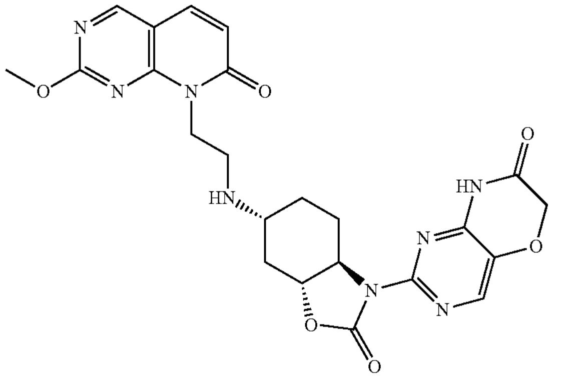

a) tert-butyl N-[(3aR,6R,7aR)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]carbamate 33a To a stirring solution of tert-butyl N-[(3aR, 6R, 7aR)-2-oxo-octahydro-1,3-benzoxazol-6-yl]carbamate 1a (1 g, 3.90 mmol) in toluene (30 mL) under $N_2$ conditions, was added a 2:1 mixture of 2-bromo-8-[(4-methoxyphenyl)methyl]-6H,7H,8H-pyrimido[5,4-b][1,4]oxazin-7-one and 2-chloro-8-[(4-methoxyphenyl)methyl]-6H,7H,8H-pyrimido[5,4-b][1,4]oxazin-7-one 16a (1.36 g, 3.90 mmol), trans-1,2-diaminocyclohexane (0.2 mL, 1.60 mmol), $K_2CO_3$ (1.078 g, 7.80 mmol) and CuI (594 mg, 3.12 mmol). The reaction was heated to reflux and stirred for 17 h. The reaction was allowed to cool to room temperature, and then filtered, washed with EtOAc (10 mL) and the filtrate concentrated under reduced pressure. The residue was purified via silica gel chromatography using 0-100% EtOAc in DCM to give tert-butyl N-[(3aR,6R,7aR)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]carbamate 33a (614 mg, 30%). LC-MS (Method A) 526.2 $[M+H]^+$; RT 3.03 min.

b) (3aR,6R,7aR)-6-amino-3-{8-[(4-methoxyphenyl)methyl]-7-oxo-6H,7H,8H-pyrimido[5, 4-b][1,4]oxazin-2-yl}-octahydro-1,3-benzoxazol-2-one 33b To a stirring solution of tert-butyl N-[(3aR,6R,7aR)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]carbamate 33a (614 mg, 1.17 mmol) in DCM (15 mL) was added TFA (4.8 mL) and the reaction stirred for 1 h. The volatiles were removed under reduced pressure, and the residue basified to pH 9 with saturated aqueous $Na_2CO_3$, and partitioned between DCM (20 mL) and brine (3 mL). This was passed through an SPE phase separator and the organic portion concentrated under reduced pressure to give (3aR,6R,7aR)-6-amino-3-{8-[(4-methoxyphenyl)methyl]-7-oxo-6H,7H,8H-pyrimido[5,4-b][1,4]oxazin-2-yl}-octahydro-1, 3-benzoxazol-2-one 33b (400 mg, 80%) which was used without further purification. LC-MS (Method A) 426.1 $[M+H]^+$; RT 1.55 min.

c) (3aR,6R,7aR)-6-[(2-{2-methoxy-7-oxo-7H,8H-pyrido[2,3-d]pyrimidin-8-yl}ethyl)amino]-3-{8-[(4-methoxyphenyl)methyl]-7-oxo-6H,7H,8H-pyrimido[5,4-b][1,4]oxazin-2-yl}-octahydro-1,3-benzoxazol-2-one 33c A solution of (3aR,6R,7aR)-6-amino-3-{8-[(4-methoxyphenyl)methyl]-7-oxo-6H,7H,8H-pyrimido[5,4-b][1,4]oxazin-2-yl}-octahydro-1,3-benzoxazol-2-one 33b (78 mg, 0.18 mmol) and 2-(2-methoxy-7-oxo-7H,8H-pyrido[2,3-d]pyrimidin-8-yl)acetaldehyde 2b (40 mg, 0.18 mmol) in DCM (15 mL) was stirred, at room temperature, over molecular sieves (3 Å) for 2 h. $NaBH(OAc)_3$ (174 mg, 0.82 mmol) was added and stirring continued for 90 min. The reaction was basified to pH 8~9 with saturated aqueous $NaHCO_3$ and passed through an SPE phase separator. The organic portion was concentrated under reduced pressure to give a crude residue containing (3aR,6R,7aR)-6-[(2-{2-methoxy-7-oxo-7H,8H-pyrido[2,3-d]pyrimidin-8-yl}ethyl)amino]-3-{8-[(4-methoxyphenyl)methyl]-7-oxo-6H,7H,8H-pyrimido[5,4-b][1,4]oxazin-2-yl}-octahydro-1,3-benzoxazol-2-one 33c (127 mg, 110%) which was used without further purification. LC-MS (Method A) 629.2 $[M+H]^+$; RT 2.02 min.

d) (3aR,6R,7aR)-6-[(2-{2-methoxy-7-oxo-7H,8H-pyrido[2,3-d]pyrimidin-8-yl}ethyl)amino]-3-{7-oxo-6H,7H,8H-pyrimido[5,4-b][1,4]oxazin-2-yl}-octahydro-1,3-benzoxazol-2-one 33

To a stirring solution of (3aR,6R,7aR)-6-[(2-{2-methoxy-7-oxo-7H,8H-pyrido[2,3-d]pyrimidin-8-yl}ethyl)amino]-3-{8-[(4-methoxyphenyl)methyl]-7-oxo-6H,7H,8H-pyrimido[5,4-b][1,4]oxazin-2-yl}-octahydro-1,3-benzoxazol-2-one 33c (127 mg, 0.20 mmol) in DCM (15 mL) was added TFA (1 mL) followed by $CF_3SO_3H$ (0.20 mL). The reaction was stirred at room temperature for 17 h then diluted with MeOH (5 mL) and DCM (10 ml), basified to pH 8~9 with saturated $Na_2CO_3$ and passed through an SPE phase separator. The organic portion was concentrated under reduced pressure and the residue purified via silica gel chromatography using 0-20% MeOH in DCM to give (3aR,6R,7aR)-6-[(2-{2-methoxy-7-oxo-7H,8H-pyrido[2,3-d]pyrimidin-8-yl}ethyl)amino]-3-{7-oxo-6H,7H,8H-pyrimido[5,4-b][1,4]oxazin-2-yl}-octahydro-1,3-benzoxazol-2-one 33 (22 mg, 22%). LC-MS (Method A) 509.1 $[M+H]^+$; RT 1.38 min. $^1H$ NMR (Method C) (DMSO-d6): δ ppm 8.91 (s, 1H), 8.25 (s, 1H), 7.94 (d, J=9.5 Hz, 1H), 6.56 (d, J=9.5 Hz, 1H), 5.77 (s, 1H), 4.75 (m, 2H), 4.33 (m, 2H), 4.10-4.03 (m, 1H), 4.02 (s, 3H), 3.78 (td, J=11.1, 3.3 Hz, 1H), 2.88-2.77 (m, 3H), 2.46-2.37 (m, 2H), 2.00-1.94 (m, 1H), 1.46 (q, J=11.1 Hz, 1H), 1.37-1.27 (m, 1H), 1.25-1.18 (m, 1H).

Example 34:—1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-6,7-difluoro-1,2-dihydroquinoxalin-2-one

34

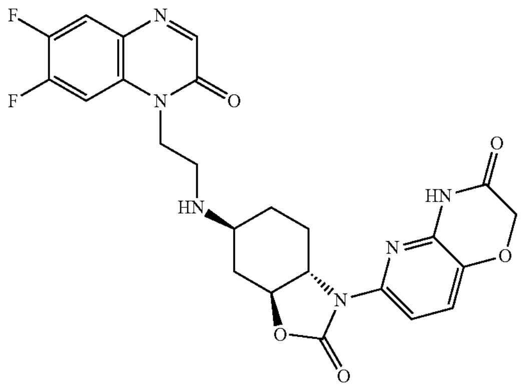

a) 1-(2-{[(3aS,6S,7aS)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-6,7-difluoro-1,2-dihydroquinoxalin-2-one 34a To a solution of (3aS,6S,7aS)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 29c (230 mg, 0.54 mmol) and 2-(6,7-difluoro-2-oxo-1,2-dihydroquinoxalin-1-yl)acetaldehyde (121 mg, 0.54 mmol, prepared as described in WO2008009700A1) in DCM (20 mL) was added a few drops of AcOH and the mixture stirred at room temperature for 20 h. $NaBH(OAc)_3$ (344 mg, 1.63 mmol) was added and the reaction mixture stirred at room temperature for 30 min. The mixture was adjusted to pH 8~9 with saturated $Na_2CO_3$ and extracted with DCM (100 mL). The organic layer was washed with brine, dried over $MgSO_4$, filtered and concentrated to give 1-(2-{[(3aS,6S,7aS)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-6,7-difluoro-1,2-dihydroquinoxalin-2-one 34a, (290 mg, 84%), which was used without further purification. LC-MS (Method A) 633.1 $[M+H]^+$; RT 3.01 min.

b) 1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-6,7-difluoro-1,2-dihydroquinoxalin-2-one 34

To a solution of 1-(2-{[(3aS,6S,7aS)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-6,7-difluoro-1,2-dihydroquinoxalin-2-one 34a (280 mg, 0.44 mmol) in DCM (25 mL) was added TFA (508 μL, 6.64 mmol) followed by $CF_3SO_3H$ (196 μL, 2.21 mmol) and the mixture was stirred at room temperature for 1 h. The reaction was quenched with MeOH (1 mL), adjusted to pH 8~9 with saturated aqueous $Na_2CO_3$ and extracted with DCM (100 mL). The organic extract was washed with brine, dried over $MgSO_4$, filtered and concentrated under reduced pressure.

The residue was purified by chromatography (Biotage 10 g KP-Si cartridge) using 0-50% MeOH in DCM to give 1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-6,7-difluoro-1,2-dihydroquinoxalin-2-one 34 (117 mg, 49%) as a yellow solid. LC-MS (Method A) 513.1 $[M+H]^+$; RT 2.29 min. $^1H$ NMR (Method C) (DMSO): δ ppm 11.28 (br s, 1H), 8.32 (s, 1H), 8.00 (m, 2H), 7.47 (d, J=8.5 Hz, 1H), 7.22 (d, J=8.5 Hz, 1H), 4.68 (s, 2H), 4.27 (t, J=6.9 Hz, 2H), 4.09 (td, J=11.7, 3.3 Hz, 1H), 3.79 (td, J=11.2, 3.3 Hz, 1H), 2.90 (m, 2H), 2.81 (m, 2H), 2.46 (m, 1H), 2.17 (br s, 1H), 2.00 (m, 1H), 1.49 (q, J=11.2 Hz, 1H), 1.37 (m, 1H), 1.24 (m, 1H).

Example 35:—(3aS,6S,7aR)-6-[(2-{6-methoxy-3-oxo-3H,4H-pyrido[2,3-b]pyrazin-4-yl}ethyl)amino]-3-{3-oxo-2H,3H,4H-pyrido[3,2-b][1,4]oxazin-6-yl}-octahydro-1,3-benzoxazol-2-one

35

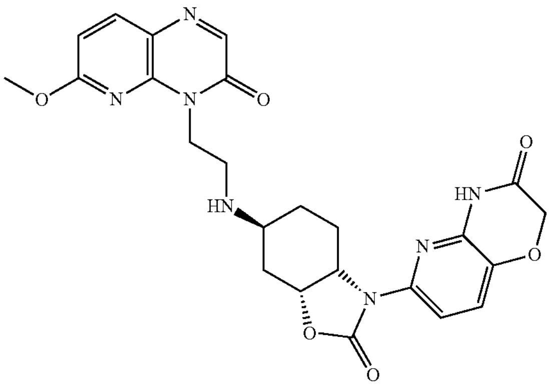

a) (3aS,6S,7aR)-6-[(2-{6-methoxy-3-oxo-3H,4H-pyrido[2,3-b]pyrazin-4-yl}ethyl)amino]-3-{4-[(4-methoxyphenyl)methyl]-3-oxo-2H,3H,4H-pyrido[3,2-b][1,4]oxazin-6-yl}-octahydro-1,3-benzoxazol-2-one 35a To a solution of 2-{6-methoxy-3-oxo-3H,4H-pyrido[2,3-b]pyrazin-4-yl}acetaldehyde (129 mg, 0.59 mmol) (prepared as described in EP2022793A1) in DCM (5 mL) over 4 Å molecular sieves was added (3aS,6S,7aR)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 4c (250 mg, 0.59 mmol) and the reaction stirred at room temperature for 2 h. Sodium triacetoxyborohydride (560 mg, 2.65 mmol) was added and the mixture was left to stir at room temperature for 1.5 h. The reaction was diluted with saturated aqueous $NaHCO_3$ and extracted with DCM (20 mL). The organic extracts were dried over $MgSO_4$, filtered and concentrated under reduced pressure to give (3aS,6S,7aR)-6-[(2-{6-methoxy-3-oxo-3H,4H-pyrido[2,3-b]pyrazin-4-yl}ethyl)amino]-3-{4-[(4-methoxyphenyl)methyl]-3-oxo-2H,3H,4H-pyrido[3,2-b][1,4]oxazin-6-yl}-octahydro-1,3-benzoxazol-2-one (60 mg, 36%) as a brown solid. LC-MS (Method A) 628.3 $[M+H]^+$; RT 1.83 min b) (3aS,6S,7aR)-6-[(2-{6-methoxy-3-oxo-3H,4H-pyrido[2,3-b]pyrazin-4-yl}ethyl)amino]-3-{3-oxo-2H,3H,4H-pyrido[3,2-b][1,4]oxazin-6-yl}-octahydro-1,3-benzoxazol-2-one 35

To a solution of (3aS,6S,7aR)-6-[(2-{6-methoxy-3-oxo-3H,4H-pyrido[2,3-b]pyrazin-4-yl}ethyl)amino]-3-{4-[(4-methoxyphenyl)methyl]-3-oxo-2H,3H,4H-pyrido[3,2-b][1,4]oxazin-6-yl}-octahydro-1,3-benzoxazol-2-one (60 mg, 0.10 mmol) in DCM (5 mL) was added TFA (2 mL) and $CF_3SO_3H$ (0.2 mL) dropwise and the reaction mixture was left to stir at room temperature for 1 h. The reaction was quenched with MeOH (5 mL) and the mixture evaporated. The residue was neutralised with saturated aqueous $NaHCO_3$ (50 mL), and extracted with DCM (25 mL). The organic extracts were washed with $H_2O$, brine, dried ($Na_2SO_4$), filtered and concentrated under reduced pressure. The residue was purified by silica gel chromatography (0-10% MeOH in EtOAc) to give an orange solid. The solid was dissolved in DCM (2 mL), triturated with diethyl ether (10 mL) and the precipitate filtered and dried to give (3aS,6S,7aR)-6-[(2-{6-methoxy-3-oxo-3H,4H-pyrido[2,3-b]pyrazin-4-yl}ethyl)amino]-3-{3-oxo-2H,3H,4H-pyrido[3,2-b][1,4]oxazin-6-yl}-octahydro-1,3-benzoxazol-2-one (40 mg, 16%) as a white solid. LC-MS (Method A) 508.1 $[M+H]^+$; RT 2.22 min. $^1H$ NMR (Method C) ($CDCl_3$) δ ppm: 8.17 (s, 1H), 8.03 (d, J=8.5, 1H), 7.76 (d, J=8.5, 1H), 7.28 (d, J=8.5, 1H), 6.75 (d, J=8.5, 1H), 4.69 (m, 1H), 4.62 (s, 2H), 4.58 (t, J=6.5, 2H), 4.50 (m, 1H), 4.04 (s, 3H), 3.11 (t, J=6.5, 2H), 2.89 (m, 1H), 2.47-2.42 (m, 2H), 1.88 (m, 1H), 1.54 (ddd, J=15.0, 11.0, 4.0, 1H), 1.39 (m, 1H), 1.11 (m, 1H)

Example 36:—methyl 1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-2-oxo-1,2-dihydroquinoline-7-carboxylate

36

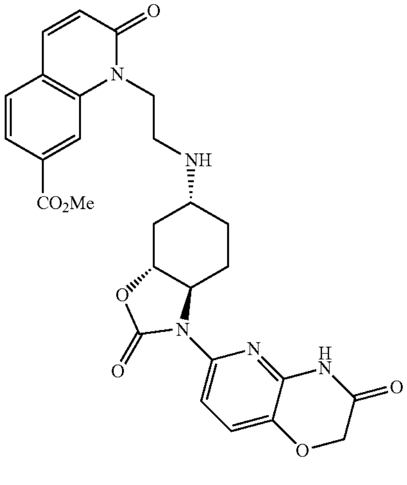

a)methyl 1-(2-{[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-2-oxo-1,2-dihydroquinoline-7-carboxylate 36a A solution of (3aR,6R,7aR)-6-amino-3-{4-[(4-methoxyphenyl)methyl]-3-oxo-2H,3H,4H-pyrido[3,2-b][1,4]oxazin- 6-yl}-octahydro-1,3-benzoxazol-2-one 1c and methyl 2-oxo-1-(2-oxoethyl)-1,2-dihydroquinoline-7-carboxylate (prepared from 7-bromo-1,2-dihydroquinolin-2-one using similar methods to those described in EP 1,900732A1 p 98) in DCM (8 mL) was stirred over molecular sieves (4 Å) at room temperature. After 20 min, $NaBH(OAc)_3$ (205 mg, 0.97 mmol) was added and the reaction stirred for 1 h. The reaction was quenched with saturated aqueous $Na_2CO_3$ (8 mL) and the mixture passed through an SPE phase separator. The organic phase was concentrated under reduced pressure and purified by chromatography eluting with 0-12% MeOH in DCM to give methyl 1-(2-{[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-2-oxo-1,2-dihydroquinoline-7-carboxylate 36a (114 mg, 61%) (Method A) 654.2 $[M+H]^+$; RT 2.82 min.

b)methyl 1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-2-oxo-1,2-dihydroquinoline-7-carboxylate 36

TFA (0.5 mL, 6.53 mmol) and $CF_3SO_3H$ (0.1 mL, 1.13 mmol) were added to a stirred solution of 1-(2-{[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-2-oxo-1,2-dihydroquinoline-7-carboxylate 36a (110 mg, 0.17 mmol) in DCM (10 mL) at room temperature. After 1 h the reaction was diluted with MeOH (5 mL) and DCM (5 mL). Saturated aqueous $Na_2CO_3$ was added, adjusting the pH to 9, and the mixture was passed through an SPE phase separator. The organic portion was concentrated under reduced pressure to give methyl 1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-2-oxo-1,2-dihydroquinoline-7-carboxylate 36 (76 mg, 84.7%) as a pale green solid. (Method B) 534.2 $[M+H]^+$; RT 5.47 min. $^1$H NMR (Method C) (DMSO-d6): δ ppm 11.24 (s, 1H), 8.13 (s, 1H), 8.02 (d, J=9.5 Hz, 1H), 7.88 (d, J=8.0 Hz, 1H), 7.81 (dd, J=8.0, 1.4 Hz, 1H), 7.43 (d, J=8.5 Hz, 1H), 7.18 (d, J=8.5 Hz, 1H), 6.77 (d, J=9.5 Hz, 1H), 4.63 (s, 2H), 4.33 (t, J=6.9 Hz, 2H), 4.06 (td, J=11.7, 3.2 Hz, 1H), 3.93 (s, 3H), 3.77-3.70 (m, 2H), 2.89-2.75 (m, 4H), 2.05-1.97 (m, 1H), 1.53-1.43 (m, 1H), 1.42-1.30 (m, 1H), 1.24-1.18 (m, 2H).

Example 37:—1-(2-{[(3aR,6R,7aR)-2-oxo-3-{7-oxo-6H,7H,8H-pyrimido[5,4-b][1,4]oxazin-2-yl}-octahydro-1,3-benzoxazol-6-yl]amino}ethyl)-2-oxo-1,2-dihydroquinoline-7-carbonitrile

37

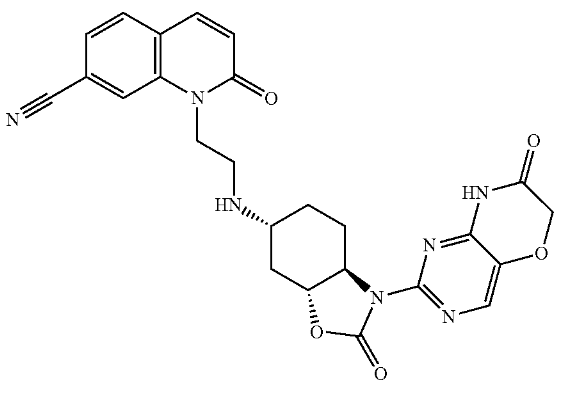

a) 1-(2-{[(3aR,6R,7aR)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]amino}ethyl)-2-oxo-1,2-dihydroquinoline-7-carbonitrile 37a A solution of (3aR,6R,7aR)-6-amino-3-{8-[(4-methoxyphenyl)methyl]-7-oxo-6H,7H,8H-pyrimido[5,4-b][1,4]oxazin-2-yl}-octahydro-1,3-benzoxazol-2-one 33b (80 mg, 0.19 mmol) and 2-oxo-1-(2-oxoethyl)quinolone-7-carbonitrile (40 mg, 0.19 mmol) (J. Med. Chem (2014) 57 (11), 4889-4905) in DCM (8 mL) was stirred, at room temperature, over molecular sieves (3 Å) for 2 h. $NaBH(OAc)_3$ (180 mg, 0.85 mmol) was added and stirred for 3 h. The reaction was basified to pH 8~9 with saturated aqueous $NaHCO_3$ and passed through an SPE phase separator. The organic portion was concentrated under reduced pressure to give a crude residue containing 1-(2-{[(3aR,6R,7aR)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]amino}ethyl)-2-oxo-1,2-dihydroquinoline-7-carbonitrile 37a (197 mg, 168%) which was used without further purification. LC-MS (Method A) 622.2 $[M+H]^+$; RT 2.34 min.

b) 1-(2-{[(3aR,6R,7aR)-2-oxo-3-{7-oxo-6H,7H,8H-pyrimido[5,4-b][1,4]oxazin-2-yl}-octahydro-1,3-benzoxazol-6-yl]amino}ethyl)-2-oxo-1,2-dihydroquinoline-7-carbonitrile 37

To a stirring solution of 1-(2-{[(3aR,6R,7aR)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]amino}ethyl)-2-oxo-1,2-dihydroquinoline-7-carbonitrile 37a (197 mg, 0.32 mmol) in DCM (15 mL) was added TFA (1.26 mL) followed by $CF_3SO_3H$ (0.30 mL). The reaction was stirred at room temperature for 17 h then diluted with MeOH (5 mL) and DCM (10 mL), basified to pH 8~9 with saturated aqueous $Na_2CO_3$ and passed through an SPE phase separator. The organic portion was concentrated under reduced pressure and the residue purified via silica gel chromatography using 0-10% MeOH in DCM to give 1-(2-{[(3aR,6R,7aR)-2-oxo-3-{7-oxo-6H,7H,8H-pyrimido[5,4-b][1,4]oxazin-2-yl}-octahydro-1, 3-benzoxazol-6-yl]amino}ethyl)-2-oxo-1,2-dihydroquinoline-7-carbonitrile 37 (7 mg, 4%). LC-MS (Method B) 502.1 $[M+H]^+$; RT 4.67 min. $^1$H NMR (Method C) (DMSO-d6): δ ppm 8.25 (s, 1H), 8.18 (s, 1H), 8.01 (d, J=9.5 Hz, 1H), 7.92 (d, J=8.0 Hz, 1H), 7.66 (dd, J=8.0, 1.3 Hz, 1H), 6.79 (d, J=9.5 Hz, 1H), 4.75 (m, 2H), 4.29 (t, J=7.3 Hz, 2H), 4.10-4.00 (m, 1H), 3.80 (td, J=11.1, 3.3 Hz, 1H), 2.85-2.76 (m, 3H), 2.46-2.41 (m, 2H), 2.01-1.93 (m, 1H), 1.47 (q, J=11.2 Hz, 1H), 1.37-1.27 (m, 1H), 1.26-1.14 (m, 2H).

Example 38:—1-(2-{[(3aR,6R,7aR)-2-oxo-3-{7-oxo-6H,7H,8H-pyrimido[5,4-b][1,4]oxazin-2-yl}-octahydro-1,3-benzoxazol-6-yl]amino}ethyl)-6,7-difluoro-1,2-dihydroquinoxalin-2-one

38

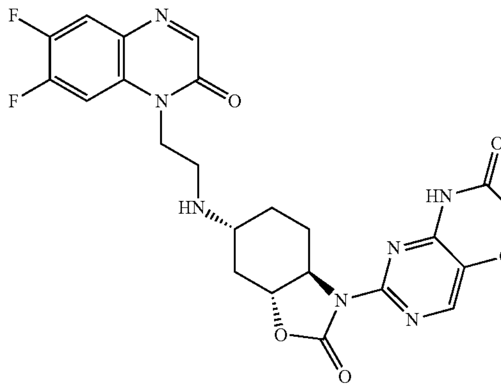

a) 1-(2-{[(3aR,6R,7aR)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]amino}ethyl)-6,7-difluoro-1,2-dihydro quinoxalin-2-one 38a A solution of (3aR,6R,7aR)-6-amino-3-{8-[(4-methoxyphenyl)methyl]-7-oxo-6H,7H,8H-pyrimido[5,4-b][1,4]oxazin-2-yl}-octahydro-1,3-benzoxazol-2-one 33b (76 mg, 0.18 mmol) and 2-(6,7-difluoro-2-oxo-1,2-dihydroquinoxalin-1-yl)acetaldehyde (prepared as described in WO2008009700 A1 20080124) (40 mg, 0.18 mmol) in DCM (10 mL) was stirred, at room temperature, over molecular sieves (3 Å) for 2 h. $NaBH(OAc)_3$ (189 mg, 0.89 mmol) was added and stirred for 90 min. The reaction was basified to pH 8~9 with saturated aqueous $NaHCO_3$ and passed through an SPE phase separator. The organic portion was concentrated under reduced pressure to give 1-(2-{[(3aR,6R,7aR)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]amino}ethyl)-6,7-difluoro-1,2-dihydroquinoxalin-2-one 38a (110 mg, 97%) which was used without further purification. LC-MS (Method A) 634.1 $[M+H]^+$; RT 2.38 min b) 1-(2-{[(3aR,6R,7aR)-2-oxo-3-{7-oxo-6H,7H,8H-pyrimido[5,4-b][1,4]oxazin-2-yl}-octahydro-1,3-benzoxazol-6-yl]amino}ethyl)-6,7-difluoro-1,2-dihydroquinoxalin-2-one 38

To a stirring solution of 1-(2-{[(3aR,6R,7aR)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]amino}ethyl)-6,7-difluoro-1,2-dihydroquinoxalin-2-one 38a (110 mg, 0.17 mmol) in DCM (10 mL) was added TFA (0.94 mL) followed by $CF_3SO_3H$ (0.22 mL). The reaction was stirred at room temperature for 72 h then diluted with MeOH (5 mL) and DCM (10 mL), basified to pH 8~9 with saturated aqueous $Na_2CO_3$ and passed through an SPE phase separator. The organic portion was concentrated under reduced pressure and the residue purified via silica gel chromatography using 0-10% MeOH in DCM to give 1-(2-{[(3aR,6R,7aR)-2-oxo-3-{7-oxo-6H,7H,8H-pyrimido[5,4-b][1,4]oxazin-2-yl}-octahydro-1, 3-benzoxazol-6-yl]amino}ethyl)-6,7-difluoro-1,2-dihydroquinoxalin-2-one 38 (15 mg, 17%). LC-MS (Method B) 514.0 $[M+H]^+$; RT 4.75 min. $^1H$ NMR (Method C) (DMSO-d6): δ ppm 8.26 (s, 1H), 8.25 (s, 1H), 7.98 (dd, J=10.7, 8.5 Hz, 1H), 7.92 (dd, J=12.7, 7.4 Hz, 1H), 4.75 (m, 2H), 4.22 (t, J=6.9 Hz, 2H), 4.05 (td, J 11.8, 3.4 Hz, 1H), 3.79 (td, J=11.2, 3.4 Hz, 1H), 2.88-2.76 (m, 3H), 2.44-2.34 (m, 2H), 2.01-1.8 (m, 1H), 1.45 (q, J=10.9 Hz, 2H), 1.33-1.17 (m, 2H).

Example 39:—(3aR,6R,7aR)—N-(2-{7-[2-(methylazaniumyl)ethoxy]-2-oxo-1,2-dihydroquinolin-1-yl}ethyl)-2-oxo-3-{3-oxo-2H,3H,4H-pyrido[3,2-b][1,4]oxazin-6-yl}-octahydro-1,3-benzoxazol-6-aminium dichloride

39

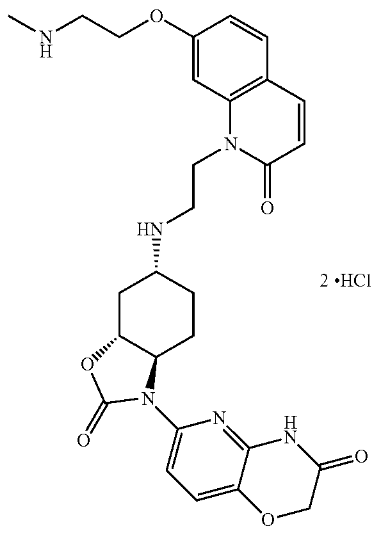

a) tert-butyl N-(2-{[1-(2,2-diethoxyethyl)-2-oxo-1,2-dihydroquinolin-7-yl]oxy}ethyl)-N-methylcarbamate 39a A solution of tert-butyl N-(2-{[1-(2,2-diethoxyethyl)-2-oxo-1,2-dihydroquinolin-7-yl]oxy}ethyl)carbamate 9d (200 mg, 0.48 mmol) in THF (7 mL) was cooled in a NaCl ice bath. NaH (60% dispersion in mineral oil, 30 mg, 0.75 mmol) was added and the mixture stirred for 30 min. Iodomethane (0.1 mL, 1.61 mmol) was added and the mixture stirred at ambient temperature for 17 h. The mixture was evaporated in vacuo and the residue dissolved in DCM (20 mL), MeOH (1 mL), DI water (5 mL) and passed through an SPE phase separator. The organic fraction was evaporated to give tert-butyl N-(2-{[1-(2,2-diethoxyethyl)-2-oxo-1,2-dihydroquinolin-7-yl]oxy}ethyl)-N-methylcarbamate 39a (210 mg, 102%) as a light brown oil. $^1H$ NMR (Method C) ($CDCl_3$): δ ppm 7.47 (d, J=9.4 Hz, 1H), 7.26 (d, J=8.6 Hz, 1H), 7.04 (s, 1H), 6.64 (dd, J=8.5, 2.1 Hz, 1H), 6.38 (d, J=9.2 Hz, 1H), 4.65 (t, J=5.2 Hz, 1H), 4.21 (d, J=5.3 Hz, 2H), 4.00 (d, J=17.0 Hz, 2H), 3.67-3.58 (m, 2H), 3.49 (s, 2H), 3.42-3.33 (m, 2H), 2.85 (s, 3H), 1.31 (s, 9H), 0.98 (t, J=6.9 Hz, 6H).

b) tert-butyl N-methyl-N-(2-{[2-oxo-1-(2-oxoethyl)-1,2-dihydroquinolin7yl]oxy}ethyl)carbamate 39b To a stirred solution of tert-butyl N-(2-{[1-(2,2-diethoxyethyl)-2-oxo-1,2-dihydroquinolin-7-yl]oxy}ethyl)-N-methylcarbamate 39a (100 mg, 0.23 mmol) in THF (5 mL) at room temperature was added aqueous HCl (1M, 1 mL). After stirring for 120 h, saturated aqueous $NaHCO_3$ was added and the mixture extracted with EtOAc (3×5 mL). The combined organic extracts were washed with saturated brine, dried ($MgSO_4$), filtered and concentrated to give tert-butyl N-methyl-N-(2-{[2-oxo-1-(2-oxoethyl)-1,2-dihydroquinolin7yl]oxy}ethyl)carbamate 39b (67 mg, 80.8%). (Method A) 361+H [M+H]$^+$; RT 2.46 min.

c) tert-butyl N-(2-{[1-(2-{[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-2-oxo-1,2-dihydroquinolin-7-yl]oxy}ethyl)-N-methylcarbamate 39c A solution of tert-butyl N-methyl-N-(2-{[2-oxo-1-(2-oxoethyl)-1,2-dihydroquinolin7yl]oxy}ethyl)carbamate 39b (76.6 mg, 0.15 mmol) and (3aR,6R,7aR)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 1c (60 mg, 0.14 mmol) in DCM (6 mL) was stirred at room temperature over molecular sieves (4 Å) for 10 min. $NaBH(OAc)_3$ (106.8 mg, 0.50 mmol) was added and stirring continued for 2 h. Saturated aqueous $NaHCO_3$ (5 mL) was added and the resulting mixture passed through an SPE phase separator. The organic phase was concentrated under reduced pressure and the residue purified by chromatography eluting with 0-100% EtOAc in petroleum ether and 0-20% MeOH in DCM. The fractions were concentrated under reduced pressure to give tert-butyl N-(2-{[1-(2-{[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-2-oxo-1,2-dihydroquinolin-7-yl]oxy}ethyl)-N-methylcarbamate 39c (43 mg, 37.6%) as a white solid. (Method A) 769.3 [M+H]$^+$; RT 3.49 min.

d) (3aR,6R,7aR)—N-(2-{7-[2-(methylazaniumyl)ethoxy]-2-oxo-1,2-dihydroquinolin-1-yl}ethyl)-2-oxo-3-{3-oxo-2H,3H,4H-pyrido[3,2-b][1,4]oxazin-6-yl}-octahydro-1,3-benzoxazol-6-aminium dichloride 39

TFA (0.2 mL, 2.6 mmol) and $CF_3SO_3H$ (0.05 mL, 0.56 mmol) were added to a stirred solution of tert-butyl N-(2-{[1-(2-{[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-2-oxo-1,2-dihydroquinolin-7-yl]oxy}ethyl)-N-methylcarbamate 39c (43 mg, 0.06 mmol)) in DCM (6 mL) at room temperature. After 1 h the reaction was diluted with MeOH (5 mL) and DCM (5 mL). Saturated aqueous $Na_2CO_3$ was added, adjusting the pH to 9, and the mixture was passed through an SPE phase separator. The aqueous phase was further extracted with DCM/MeOH (2:1, 2×20 mL) and the combined organic fractions concentrated under reduced pressure and the residue purified by chromatography eluting with 0-20% 2M $NH_3$/MeOH in DCM. The relevant fractions were evaporated, re-dissolved in MeOH, treated with 1M HCl in ether and evaporated to afford (3aR,6R,7aR)—N-(2-{7-[2-(methylazaniumyl)ethoxy]-2-oxo-1,2-dihydroquinolin-1-yl}ethyl)-2-oxo-3-{3-oxo-2H,3H,4H-pyrido[3,2-b][1,4]oxazin-6-yl}-octahydro-1,3-benzoxazol-6-aminium dichloride 39 (7 mg, 15.6%) as a white solid. MS (Method B) 549.2 [M+H]$^+$; RT 4.22 min. (Method C) (DMSO-d6): δ ppm 11.30 (s, 1H), 9.92 (br s, 2H), 9.06 (br s, 2H), 7.92 (d, J=9.5 Hz, 1H), 7.73 (d, J=8.7 Hz, 1H), 7.44 (d, J=8.5 Hz, 1H), 7.40 (d, J=2.2 Hz, 1H), 7.18 (d, J=8.6 Hz, 1H), 6.98 (dd, J=8.5, 2.1 Hz, 1H), 6.51 (d, J=9.4 Hz, 1H), 4.71-4.62 (m 1H), 4.64 (s, 3H), 4.59 (d, J=5.9 Hz, 2H), 4.11 (td, J=11.6, 3.3 Hz, 1H), 3.82 (td, J=11.3, 3.3 Hz, 1H), 3.52 (m, 1H), 3.26-3.11 (m, 2H), 2.88 (dq, J=11.9, 3.7 Hz, 1H), 2.73 (dt, J=9.6, 4.0 Hz, 1H), 2.66 (q, J=7.0, 6.1 Hz, 3H), 2.52 (m, 2H), 2.33-2.23 (m, 1H), 2.01 (q, J=11.4 Hz, 1H), 1.79-1.66 (m, 1H), 1.43 (qd, J=12.2, 3.7 Hz, 1H).

Example 40:—6-[3-({[(3aR,6R,7aR)-2-oxo-3-{3-oxo-2H,3H,4H-pyrido[3,2-b][1,4]oxazin-6-yl}-octahydro-1,3-benzoxazol-6-yl]amino}methyl)-2-hydroxyphenyl]pyridine-2-carbonitrile

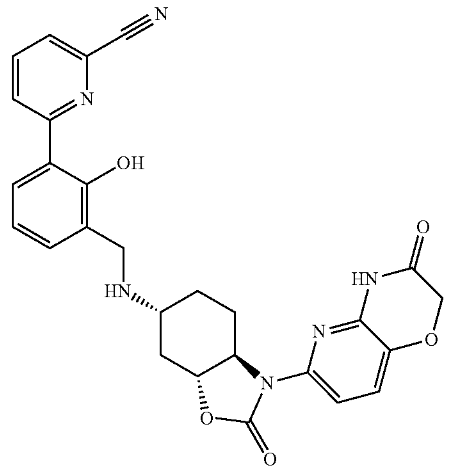

a) 6-[3-({[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}methyl)-2-hydroxyphenyl]pyridine-2-carbonitrile 40a To a solution of (3aR,6R,7aR)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 1c (151 mg, 0.36 mmol) in DCM (10 mL) at room temperature was added 6-(3-formyl-2-hydroxyphenyl)pyridine-2-carbonitrile 18c (83 mg, 0.37 mmol) and molecular sieves (4 Å). The reaction was stirred at room temperature for 2 h. $NaBH(OAc)_3$ (226 mg, 1.07 mmol) was added and the mixture stirred for a further 16 h. Saturated aqueous $K_2CO_3$ (10 mL) was added and the organic phase separated, dried over $MgSO_4$, filtered and concentrated to give 6-[3-({[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}methyl)-2-hydroxyphenyl]pyridine-2-carbonitrile 40a (170 mg, 75.5%), which was used without further purification. LC-MS (Method A) 633.2 [M+H]$^+$, RT 2.81 min.

b) 6-[3-({[(3aR,6R,7aR)-2-oxo-3-{3-oxo-2H,3H,4H-pyrido[3,2-b][1,4]oxazin-6-yl}-octahydro-1,3-benzoxazol-6-yl]amino}methyl)-2-hydroxyphenyl]pyridine-2-carbonitrile 40

To a solution of 6-[3-({[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}methyl)-2-hydroxyphenyl]pyridine-2-carbonitrile 40a (169 mg, 0.27 mmol) in DCM (10 mL), under nitrogen was added TFA (0.2 mL, 2.67 mmol) and $CF_3SO_3H$ (0.12 mL, 1.34 mmol). The reaction mixture was allowed to stir at room temperature for 1 h then quenched with MeOH (1 mL). Saturated aqueous $K_2CO_3$ (10 mL) was added and the layers were separated. The aqueous layer was extracted with DCM (10 mL). The combined organic extracts were dried over $MgSO_4$, filtered and concentrated. The residue was purified by chromatography using 0-40% MeOH in DCM to give 6-[3-({[(3aR,6R,7aR)-2-oxo-3-{3-oxo-2H,3H,4H-pyrido[3,2-b][1,4]oxazin-6-yl}-octahydro-1,3-benzoxazol-6-yl]amino}methyl)-2-hydroxyphenyl]pyridine-2-carbonitrile 40 (25.3 mg, 18.5%) TLC: $R_f$=0.34 (silica gel, DCM/MeOH 19:1, v/v). LC-MS (Method B) 513.1 $[M+H]^+$. RT 6.13 min. $^1$H NMR (Method E) ($CDCl_3$): δ ppm 8.19 (d, J=8.5 Hz, 1H), 7.97 (t, J=8.5 Hz, 1H), 7.85-7.73 (br s, 1H), 7.77 (d, J=8.1 Hz, 1H), 7.66 (d, J=8.1 Hz, 1H), 7.34 (d, J=8.5 Hz, 1H), 7.33 (d, J=7.5 Hz, 1H), 7.32 (d, J=8.5 Hz, 1H), 6.96 (t, J=7.5 Hz, 1H), 4.64 (s, 2H), 4.05-3.93 (m, 3H), 3.83 (td, J=12.2 Hz, 2.6 Hz, 1H), 2.97-2.81 (m, 1H), 2.79-2.64 (m, 2H), 2.21 (d, J=10.2 Hz, 1H), 1.79-1.60 (m, 1H), 1.54-1.36 (m, 1H), 1.35-1.21 (m, 1H).

Example 41:—1-(2-{[(3aR,6R,7aR)-2-oxo-3-{7-oxo-6H,7H,8H-pyrimido[5,4-b][1,4]oxazin-2-yl}-octahydro-1,3-benzoxazol-6-yl]amino}ethyl)-7-methoxy-1,2-dihydro-1,5-naphthyridin-2-one

41

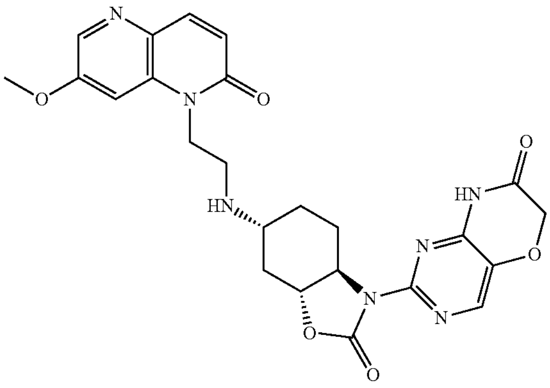

a) 1-(2-{[(3aR,6R,7aR)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]amino}ethyl)-7-methoxy-1,2-dihydro-1,5-naphthyridin-2-one 41a A solution of (3aR,6R,7aR)-6-amino-3-{8-[(4-methoxyphenyl)methyl]-7-oxo-6H,7H,8H-pyrimido[5,4-b][1,4]oxazin-2-yl}-octahydro-1,3-benzoxazol-2-one 33b (78 mg, 0.18 mmol) and 2-(7-methoxy-2-oxo-1,2-dihydro-1,5-naphthyridin-1-yl)acetaldehyde (prepared as described in WO 2011148962 A1 (40 mg, 0.18 mmol) in DCM (10 mL) was stirred, at room temperature, over molecular sieves (3 Å) for 2 h. $NaBH(OAc)_3$ (155 mg, 0.73 mmol) was added and stirred for 90 min. The reaction was basified to pH 8~9 with saturated aqueous $NaHCO_3$ and passed through an SPE phase separator. The organic portion was concentrated under reduced pressure to give 1-(2-{[(3aR,6R,7aR)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]amino}ethyl)-7-methoxy-1,2-dihydro-1,5-naphthyridin-2-one 41a (107 mg, 93%) which was used without further purification. LC-MS (Method A) 628.2 $[M+H]^+$; RT 2.10 min.

b) 1-(2-{[(3aR,6R,7aR)-2-oxo-3-{7-oxo-6H,7H,8H-pyrimido[5,4-b][1,4]oxazin-2-yl}-octahydro-1,3-benzoxazol-6-yl]amino}ethyl)-7-methoxy-1,2-dihydro-1,5-naphthyridin-2-one 41

To a stirring solution of 1-(2-{[(3aR,6R,7aR)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]amino}ethyl)-7-methoxy-1,2-dihydro-1,5-naphthyridin-2-one 41a (107 mg, 0.17 mmol) in TFA (4 mL), cooled to 0° C., was added $CF_3SO_3H$ (0.22 mL). The reaction was allowed to warm to room temperature and stirred for 17 h, then quenched with MeOH (5 mL), diluted with DCM (40 mL), basified to pH 8~9 with saturated aqueous $Na_2CO_3$ and passed through an SPE phase separator. The organic portion was concentrated under reduced pressure and the residue purified via silica gel chromatography using 0-10% MeOH in DCM to give 1-(2-{[(3aR,6R,7aR)-2-oxo-3-{7-oxo-6H,7H,8H-pyrimido[5,4-b][1,4]oxazin-2-yl}-octahydro-1,3-benzoxazol-6-yl]amino}ethyl)-7-methoxy-1,2-dihydro-1,5-naphthyridin-2-one 41 (13 mg, 15%). LC-MS (Method B) 508.1 $[M+H]^+$; RT 4.39 min. $^1$H NMR (Method C) (DMSO-d6): δ ppm 8.29 (d, J=2.4 Hz, 1H), 8.25 (s, 1H), 7.88 (d, J=9.7 Hz, 1H), 7.50 (d, J 2.5 Hz, 1H), 6.67 (d, J=9.7 Hz, 1H), 4.75 (m, 2H), 4.29 (t, J=7.1 Hz, 2H), 4.05 (td, J=11.7, 3.4 Hz, 1H), 3.99 (s, 3H), 3.80 (td, J=11.2, 3.3 Hz, 1H), 2.88-2.74 (m, 3H), 2.44-2.39 (m, 2H), 2.02-1.91 (m, 1H), 1.47 (q, J=11.2 Hz, 1H), 1.38-1.15 (m, 3H).

Example 42:—7-methoxy-1-{2-[(2-oxo-3-{3-oxo-2H,3H,4H-pyrido[3,2-b][1,4]oxazin-6-yl}-octahydro-1, 3-benzoxazol-6-yl)amino]ethyl}-1,2-dihydro-1,5-naphthyridin-2-one

42

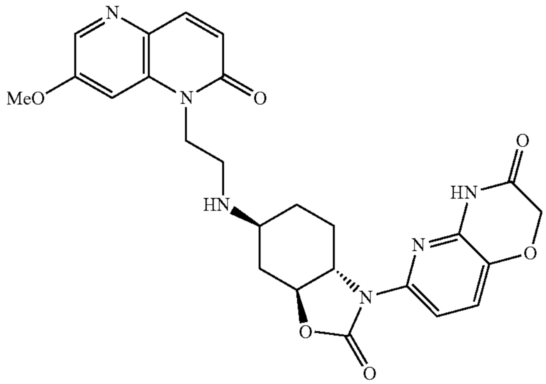

a) 7-methoxy-1-{2-[(3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl)amino]ethyl}-1,2-dihydro-1,5-naphthyridin-2-one 42a 6-[(3aS,6S,7aS)-6-amino-2-oxo-3a,4,5,6,7,7a-hexahydro-1,3-benzoxazol-3-yl]-4-[(4-methoxyphenyl)methyl]pyrido[3,2-b][1,4]oxazin-3-one 29c (150 mg, 0.35 mmol) and 2-(7-methoxy-2-oxo-1,5-naphthyridin-1-yl)acetaldehyde (77 mg, 0.35 mmol) (prepared as described in WO2011148962A1) were added to DCM (20 ml) over 3 angstrom molecular sieves and the mixture was stirred overnight. To this was added sodium triacetoxyborohydride (224 mg, 1.06 mmol) and the reaction was again stirred overnight. The reaction quenched with saturated $Na_2CO_3$ (50 ml) solution extracted with DCM (2×30 ml), dried $MgSO_4$ and concentrated in vacuo to give 6-[(3aS,6S,7aS)-6-[2-(7-methoxy-2-oxo-1,5-naphthyridin-1-yl)ethylamino]-2-oxo-3a,4,5,6,7,7a-hexahydro-1,3-benzoxazol-3-yl]-4-[(4-methoxyphenyl)methyl]pyrido[3,2-b][1,4]oxazin-3-one 42a (221 mg, 100% yield) as a yellow solid. The product was used crude without further purification. LC-MS (Method A) 627.1 $[M+H]^+$; RT 2.66 min.

b) 7-methoxy-1-{2-[(2-oxo-3-{3-oxo-2H,3H,4H-pyrido[3,2-b][1,4]oxazin-6-yl}-octahydro-1,3-benzoxazol-6-yl)amino]ethyl}-1,2-dihydro-1,5-naphthyridin-2-one. 42

To a room temperature solution of 7-methoxy-1-{2-[(3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl)amino]ethyl}-1,2-dihydro-1,5-naphthyridin-2-one 42a (221 mg, 0.35 mmol) in DCM (15 mL) under $N_2$ was added $CF_3CO_2H$ (2.7 mL, 35.27 mmol) followed by $CF_3SO_3H$ (156 uL, 1.76 mmol). The orange/red coloured reaction mixture was allowed to stir for 1 hour, then diluted with MeOH (1 mL) which decolourised the reaction. The mixture was carefully poured on to saturated aqueous potassium carbonate solution (100 ml) and extracted with DCM (2×75 mL). The organic extracts were dried ($MgSO_4$), evaporated and the residue purified via column chromatography (5 to 20% MeOH in EtOAc) to afford a yellow foam. The foam was dissolved in DCM (5 ml), treated with diethyl ether (5 ml) and the precipitate filtered and dried to afford 7-methoxy-1-{2-[(2-oxo-3-{3-oxo-2H,3H,4H-pyrido[3,2-b][1,4]oxazin-6-yl}-octahydro-1,3-benzoxazol-6-yl)amino]ethyl}-1,2-dihydro-1,5-naphthyridin-2-one 42 (69 mg, 36% yield) as a white solid. LC-MS (Method A) 507.1 $[M+H]^+$; RT 2.05 min. $^1H$ NMR (Method C) ($CDCl_3$): δ 8.39 (s, 1H), 8.31 (d, J=2.5 Hz, 1H), 7.86 (d, J=9.7 Hz, 1H), 7.30 (s, 2H), 7.19 (d, J=2.5 Hz, 1H), 6.74 (d, J=9.7 Hz, 1H), 4.60 (s, 2H), 4.50-4.27 (m, 2H), 4.07-3.88 (m, 4H), 3.85-3.71 (m, 1H), 3.08 (t, J=6.9 Hz, 2H), 2.97-2.78 (m, 1H), 2.71-2.48 (m, 2H), 2.14 (brs, 1H), 1.55 (q, J=6.9 Hz, 2H), 1.45-1.30 (m, 2H).

Example 43: (3aR,6R,7aR)-6-[(2-{6-methoxy-3-oxo-3H,4H-pyrido[2,3-b]pyrazin-4-yl}ethyl)amino]-3-{3-oxo-2H,3H,4H-pyrido[3,2-b][1,4]oxazin-6-yl}-octahydro-1,3-benzoxazol-2-one

43

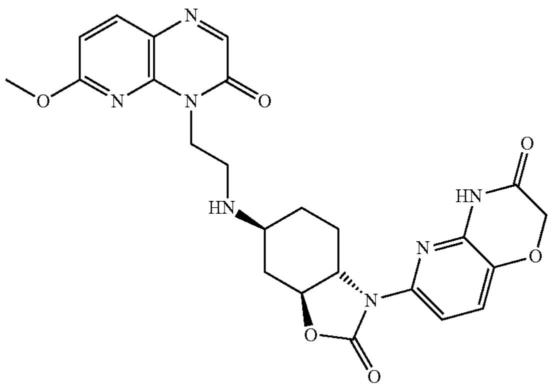

a) (3aR,6R,7aR)-6-[(2-{6-methoxy-3-oxo-3H,4H-pyrido[2,3-b]pyrazin-4-yl}ethyl)amino]-3-{4-[(4-methoxyphenyl)methyl]-3-oxo-2H,3H,4H-pyrido[3,2-b][1,4]oxazin-6-yl}-octahydro-1,3-benzoxazol-2-one, 43a To a solution of 2-{6-methoxy-3-oxo-3H,4H-pyrido[2,3-b]pyrazin-4-yl}acetaldehyde (90 mg, 0.41 mmol) (prepared as described in EP2022793A1) in DCM (5 mL) over 4 Å molecular sieves was added (3aR,6R,7aR)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 1c (174 mg, 0.41 mmol) and the reaction stirred at room temperature for 2 h. Sodium triacetoxyborohydride (391 mg, 1.84 mmol) was added and the reaction stirred at room temperature for 1.5 h. The reaction was basified with saturated aqueous $NaHCO_3$ and extracted with DCM (20 mL). The organic extracts were dried over $MgSO_4$, filtered and concentrated under reduced pressure to give (3aR,6R,7aR)-6-[(2-{6-methoxy-3-oxo-3H,4H-pyrido[2,3-b]pyrazin-4-yl}ethyl)amino]-3-{4-[(4-methoxyphenyl)methyl]-3-oxo-2H,3H,4H-pyrido[3,2-b][1,4]oxazin-6-yl}-octahydro-1,3-benzoxazol-2-one (200 mg, 99%) as a brown solid. LC-MS (Method A) 628.1 $[M+H]^+$; RT 2.86 min b) (3aR,6R,7aR)-6-[(2-{6-methoxy-3-oxo-3H,4H-pyrido[2,3-b]pyrazin-4-yl}ethyl)amino]-3-{3-oxo-2H,3H,4H-pyrido[3,2-b][1,4]oxazin-6-yl}-octahydro-1,3-benzoxazol-2-one 43

To a solution of (3aR,6R,7aR)-6-[(2-{6-methoxy-3-oxo-3H,4H-pyrido[2,3-b]pyrazin-4-yl}ethyl)amino]-3-{4-[(4-methoxyphenyl)methyl]-3-oxo-2H,3H,4H-pyrido[3,2-b][1,4]oxazin-6-yl}-octahydro-1,3-benzoxazol-2-one 43a (200 mg, 0.31 mmol) in DCM (5 mL) was added TFA (2 mL) and $CF_3SO_3H$ (0.2 mL) dropwise and the reaction mixture was left to stir at room temperature for 1 h. The reaction was quenched with MeOH (5 mL) and the mixture evaporated. The residue was basified with saturated aqueous $NaHCO_3$ (50 mL) and extracted with DCM (25 mL). The organic extracts were washed with $H_2O$, brine, dried ($Na_2SO_4$), filtered and concentrated under reduced pressure. The residue was purified by silica gel chromatography (0-10% MeOH in EtOAc) to give an orange solid. The solid was dissolved in DCM (2 mL), triturated with diethyl ether (10 mL) and the precipitate filtered, dried and evaporated to give (3aR,6R,7aR)-6-[(2-{6-methoxy-3-oxo-3H,4H-pyrido[2,3-b]pyrazin-4-yl}ethyl)amino]-3-{3-oxo-2H,3H,4H-pyrido[3,2-b][1,4]oxazin-6-yl}-octahydro-1,3-benzoxazol-2-one 43 (40 mg, 21%) as a white solid. LC-MS (Method A) 508.1 $[M+H]^+$; RT 2.22 min.

NMR (Method C) ($CDCl_3$) δ ppm: 8.16 (s, 1H), 8.03 (d, J=8.5, 1H), 7.32 (d, J=8.5, 1H), 7.30 (d, J=8.5, 1H), 6.75 (d, J=8.5, 1H), 4.61 (s, 2H), 4.58 (t, J=6.5, 2H), 4.04 (s, 3H), 3.95 (m, 1H), 3.78 (m, 1H), 3.18-3.10 (m, 2H), 2.89 (m, 1H), 2.66 (m, 1H), 2.60 (m, 1H), 2.10 (m, 1H), 1.55-1.65 (m, 1H), 1.42-1.31 (m, 2H).

Example 44:—1-(2-{[(3aR,6R,7aR)-2-oxo-3-{7-oxo-6H,7H,8H-pyrimido[5,4-b][1,4]oxazin-2-yl}-octahydro-1,3-benzoxazol-6-yl]amino}ethyl)-7-methoxy-1,2-dihydro-1,8-naphthyridin-2-one

44

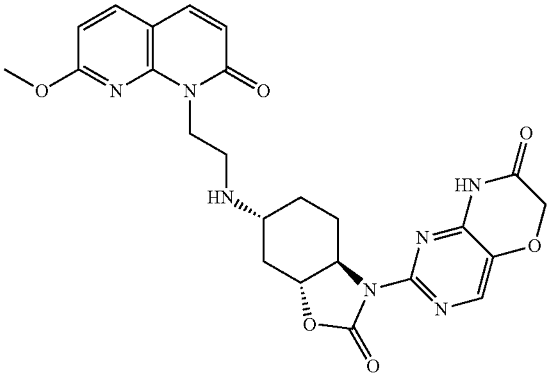

a) 1-(2-{[(3aR,6R,7aR)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]amino}ethyl)-7-methoxy-1,2-dihydro-1,8-naphthyridin-2-one 44a A solution of (3aR,6R,7aR)-6-amino-3-{8-[(4-methoxyphenyl)methyl]-7-oxo-6H,7H,8H-pyrimido[5,4-b][1,4]oxazin-2-yl}-octahydro-1,3-benzoxazol-2-one 33b (78 mg, 0.18 mmol) and 2-(7-methoxy-2-oxo-1,2-dihydro-1,8-naphthyridin-1-yl)acetaldehyde (prepared as described in WO2008009700) (40 mg, 0.18 mmol) in DCM (10 mL) was stirred, at room temperature, over molecular sieves (3 Å) for 2 h. $NaBH(OAc)_3$ (194 mg, 0.92 mmol) was added and stirred for 90 min. The reaction was basified to pH 8~9 with saturated aqueous $NaHCO_3$ and passed through an SPE phase separator. The organic portion was concentrated under reduced pressure and purified via silica gel chromatography using 0-10% MeOH in DCM to give 1-(2-{[(3aR,6R,7aR)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]amino}ethyl)-7-methoxy-1,2-dihydro-1,8-naphthyridin-2-one 44a (40 mg, 35%). LC-MS (Method A) 628.2 $[M+H]^+$; RT 2.39 min.

b) 1-(2-{[(3aR,6R,7aR)-2-oxo-3-{7-oxo-6H,7H,8H-pyrimido[5,4-b][1,4]oxazin-2-yl}-octahydro-1,3-benzoxazol-6-yl]amino}ethyl)-7-methoxy-1,2-dihydro-1,8-naphthyridin-2-one 44

To a stirring solution of 1-(2-{[(3aR,6R,7aR)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]amino}ethyl)-7-methoxy-1,2-dihydro-1,8-naphthyridin-2-one 44a (40 mg, 0.06 mmol) in DCM (5 mL) was added TFA (0.17 mL) followed by $CF_3SO_3H$ (0.04 mL). The reaction was stirred at room temperature for 17 h then diluted with MeOH (5 mL) and DCM (15 mL), basified to pH 8~9 with saturated aqueous $Na_2CO_3$ and passed through an SPE phase separator. The organic portion was concentrated under reduced pressure and the residue purified via silica gel chromatography using 0-10% MeOH in DCM to give 1-(2-{[(3aR,6R,7aR)-2-oxo-3-{7-oxo-6H,7H,8H-pyrimido[5,4-b][1,4]oxazin-2-yl}-octahydro-1, 3-benzoxazol-6-yl]amino}ethyl)-7-methoxy-1,2-dihydro-1,8-naphthyridin-2-one 44 (13 mg, 41%). LC-MS (Method B) 508.1 $[M+H]^+$; RT 4.65 min. $^1H$ NMR (Method C) (DMSO-d6): δ ppm 8.25 (s, 1H), 8.05 (d, J=8.5 Hz, 1H), 7.86 (d, J=9.4 Hz, 1H), 6.74 (d, J=8.3 Hz, 1H), 6.50 (d, J=9.4 Hz, 1H), 4.75 (m, 2H), 4.45-4.42 (m, 2H), 4.05 (td, J=11.8, 3.5 Hz, 1H), 4.00 (s, 3H), 3.79 (td, J=11.1, 3.3 Hz, 1H), 2.91-2.77 (m, 3H), 2.47-2.37 (m, 2H), 2.01-1.98 (m, 1H), 1.48 (q, J=11.2 Hz, 1H), 1.39-1.15 (m, 2H).

Example 45:—(3aS,6S,7aS)-6-[(2-{6-methoxy-3-oxo-3H,4H-pyrido[2,3-b]pyrazin-4-yl}ethyl)amino]-3-{3-oxo-2H,3H,4H-pyrido[3,2-b][1,4]oxazin-6-yl}-octahydro-1,3-benzoxazol-2-one

45

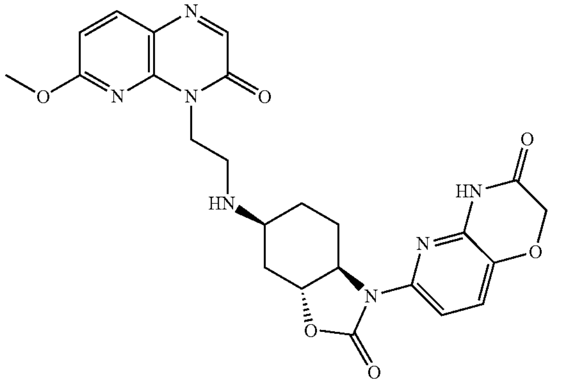

a) (3aS,6S,7aS)-6-[(2-{6-methoxy-3-oxo-3H,4H-pyrido[2,3-b]pyrazin-4-yl}ethyl)amino]-3-{4-[(4-methoxyphenyl)methyl]-3-oxo-2H,3H,4H-pyrido[3,2-b][1,4]oxazin-6-yl}-octahydro-1,3-benzoxazol-2-one, 45a To a solution of 2-{6-methoxy-3-oxo-3H,4H-pyrido[2,3-b]pyrazin-4-yl}acetaldehyde (82 mg, 0.37 mmol) (prepared as described in EP2022793 A1) in DCM (5 mL) over 4 Å molecular sieves was added (3aS,6S,7aS)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 29c (160 mg, 0.37 mmol) and the reaction stirred at room temperature for 2 h. Sodium triacetoxyborohydride (393 mg, 1.69 mmol) was added and the mixture left to stir at room temperature for 0.5 h. The reaction was basified with saturated aqueous $NaHCO_3$ and extracted with DCM (20 mL). The organic extracts were dried over $MgSO_4$, filtered and concentrated under reduced pressure to give (3aS,6S,7aS)-6-[(2-{6-methoxy-3-oxo-3H,4H-pyrido[2,3-b]pyrazin-4-yl}ethyl)amino]-3-{4-[(4-methoxyphenyl)methyl]-3-oxo-2H,3H,4H-pyrido[3,2-b][1,4]oxazin-6-yl}-octahydro-1,3-benzoxazol-2-one (250 mg, 99%) as a brown solid. LC-MS (Method A) 628.1 $[M+H]^+$; RT 2.87 min b) (3aS,6S,7aS)-6-[(2-{6-methoxy-3-oxo-3H,4H-pyrido[2,3-b]pyrazin-4-yl}ethyl)amino]-3-{3-oxo-2H,3H,4H-pyrido[3,2-b][1,4]oxazin-6-yl}-octahydro-1,3-benzoxazol-2-one 45

To a solution of (3aS,6S,7aS)-6-[(2-{6-methoxy-3-oxo-3H,4H-pyrido[2,3-b]pyrazin-4-yl}ethyl)amino]-3-{4-[(4-methoxyphenyl)methyl]-3-oxo-2H,3H,4H-pyrido[3,2-b][1,4]oxazin-6-yl}-octahydro-1,3-benzoxazol-2-one (60 mg, 0.10 mmol) in DCM (5 mL) was added TFA (2 mL) and $CF_3SO_3H$ (0.2 mL) dropwise and the mixture was stirred at room temperature for 1 h. The reaction was quenched with MeOH (5 mL) and evaporated. The residue was basified with saturated aqueous $NaHCO_3$ (50 mL) and extracted with DCM. The combined organic extracts were washed with $H_2O$, brine, dried ($Na_2SO_4$), filtered and concentrated under reduced pressure. The residue was purified by silica gel chromatography (0-10% MeOH in EtOAc) to give an orange solid. The solid was dissolved in DCM (2 mL), triturated with diethyl ether (10 mL) and the precipitate filtered and dried to give (3aS,6S,7aS)-6-[(2-{6-methoxy-3-oxo-3H,4H-pyrido[2,3-b]pyrazin-4-yl}ethyl)amino]-3-{3-oxo-2H,3H,4H-pyrido[3,2-b][1,4]oxazin-6-yl}-octahydro-1,3-benzoxazol-2-one 45 (14 mg, 8%) as a white solid. LC-MS (Method A) 508.1 $[M+H]^+$; RT 2.22 min. NMR (Method C) ($CDCl_3$) δ ppm: 8.18 (s, 1H), 8.03 (d, J=8.5, 1H), 7.32 (d, J=8.5, 1H), 7.29 (d, J=8.5, 1H), 6.75 (d, J=8.5, 1H), 4.61 (m, 4H), 4.04 (s, 3H), 3.93 (m, 1H), 3.78 (m, 1H), 3.25-3.13 (m, 2H), 2.94 (m, 1H), 2.69 (m, 1H), 2.60 (m, 1H), 2.13 (m, 1H), 1.55-1.65 (m, 1H), 1.42-1.31 (m, 2H).

Example 46:—5-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-6-oxo-5,6-dihydro-1,5-naphthyridine-3-carbonitrile

46

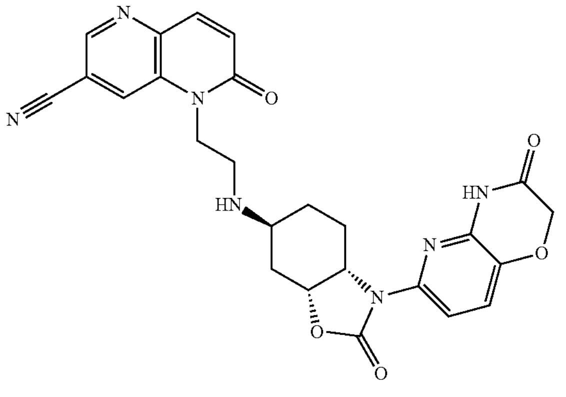

a) 5-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-6-oxo-5,6-dihydro-1,5-naphthyridine-3-carbonitrile 46a A solution of (3aS,6S,7aR)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 4c (100 mg, 0.23 mmol) and 6-oxo-5-(2-oxoethyl)-5,6-dihydro-1,5-naphthyridine-3-carbonitrile (prepared as described in WO 2008009700 A1 20080124) (50 mg, 0.23 mmol) in DCM (15 mL) was stirred, at room temperature, over molecular sieves (3 Å) for 2 h. $NaBH(OAc)_3$ (199 mg, 0.94 mmol) was added and stirred for 90 min. The reaction was basified to pH 8~9 with saturated aqueous $NaHCO_3$ and passed through an SPE phase separator. The organic portion was concentrated under reduced pressure to give 5-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-6-oxo-5,6-dihydro-1,5-naphthyridine-3-carbonitrile 46a (137 mg, 94%) which was used without further purification. LC-MS (Method A) 622.3 $[M+H]^+$; RT 1.28 min.

b) 5-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-6-oxo-5,6-dihydro-1,5-naphthyridine-3-carbonitrile 46

To a stirring solution of 5-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-6-oxo-5,6-dihydro-1,5-naphthyridine-3-carbonitrile 46a (137 mg, 0.22 mmol) in DCM (10 mL) was added TFA (0.60 mL) followed by $CF_3SO_3H$ (0.14 mL). The reaction was stirred at room temperature for 168 h then diluted with MeOH (5 mL) and DCM (15 mL), basified to pH 8~9 with saturated aqueous $Na_2CO_3$ and passed through an SPE phase separator. The organic portion was concentrated under reduced pressure and the residue purified via silica gel chromatography using 0-20% MeOH in DCM to give 5-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-6-oxo-5,6-dihydro-1,5-naphthyridine-3-carbonitrile 46 (41.5 mg, 38%). LC-MS (Method B) 502.1 $[M+H]^+$; RT 4.97 min. $^1H$ NMR (Method C) (DMSO-d6): δ ppm 11.18 (s, 1H), 8.88 (d, J=1.5 Hz, 1H), 8.70 (s, 1H), 8.01 (d, J=9.7 Hz, 1H), 7.51 (d, J=8.7 Hz, 1H), 7.40 (dd, J=8.6, 1.4 Hz, 1H), 7.05 (d, J=9.8 Hz, 1H), 4.76-4.73 (m, 1H), 4.61 (s, 2H), 4.48-4.44 (m, 1H), 4.30-4.26 (m, 2H), 2.85-2.78 (m, 2H), 2.73-2.63 (m, 1H), 2.47-2.40 (m, 1H), 2.27-2.20 (m, 1H), 1.74 (m, 1H), 1.53-1.47 (m, 2H), 1.01-0.90 (m, 1H).

Example 47:—1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl](methyl)amino}ethyl)-2-oxo-1,2-dihydroquinoline-7-carbonitrile

47

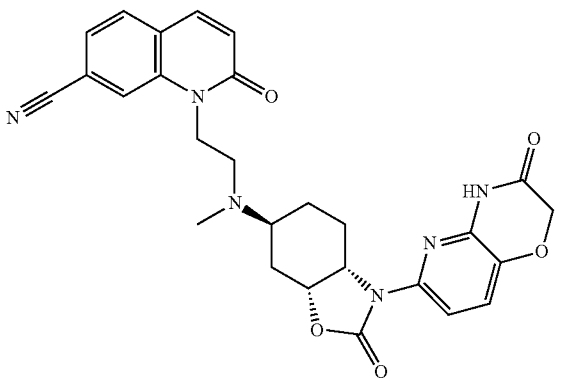

a) 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl](methyl)amino}ethyl)-2-oxo-1,2-dihydro quinoline-7-carbonitrile 47a A solution of 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl]amino}ethyl)-2-oxo-1,2-dihydroquinoline-7-carbonitrile 59a (97 mg, 0.16 mmol) in DCM (4 mL) and MeOH (10 mL) and formaldehyde solution (36.5-38%)(0.06 mL) were stirred at room temperature for 2 h. $NaBH(OAc)_3$ (132 mg, 0.6 mmol) was added and stirred for 90 min. The reaction was basified to pH 8 with saturated aqueous $NaHCO_3$ and passed through an SPE phase separator. The organic portion was concentrated under reduced pressure and the residue purified via silica gel chromatography using 0-10% MeOH in DCM to give a residue containing 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl](methyl)amino}ethyl)-2-oxo-1,2-dihydroquinoline-7-carbonitrile 47a (110 mg, 110%) which was used without further purification. LC-MS (Method A) 635.3 $[M+H]^+$; RT 1.34 min.

b) 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl](methyl)amino}ethyl)-2-oxo-1,2-dihydroquinoline-7-carbonitrile 47

To a stirring solution of 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl](methyl)amino}ethyl)-2-oxo-1,2-dihydroquinoline-7-carbonitrile 47a (110 mg, 0.17 mmol) in DCM (10 mL) was added TFA (0.47 mL) followed by $CF_3SO_3H$ (0.08 mL). The reaction was stirred at room temperature for 1 hour then diluted with MeOH (5 mL) and DCM (15 mL), basified to pH 8~9 with saturated aqueous $Na_2CO_3$ and passed through an SPE phase separator. The organic portion was concentrated under reduced pressure and the residue purified via silica gel chromatography using 0-20% MeOH in DCM to give 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl](methyl)amino}ethyl)-2-oxo-1,2-dihydroquinoline-7-carbonitrile 47 (14.7 mg, 16%). LC-MS (Method B) 515.1 $[M+H]^+$; RT 5.57 min. $^1H$ NMR (Method C) (DMSO-d6): δ ppm 11.17 (s, 1H), 8.09 (s, 1H), 8.00 (d, J=9.5 Hz, 1H), 7.90 (d, J=8.0 Hz, 1H), 7.64 (d, J=8.1 Hz, 1H), 7.49 (d, J=8.6 Hz, 1H), 7.38 (d, J=8.8 Hz, 1H), 6.78 (d, J=9.6 Hz, 1H), 4.74 (br. s, 1H), 4.60 (br. s, 2H), 4.42-4.31 (m, 3H), 2.66 (br. s, 3H), 2.43 (br. s, 1H), 2.35 (br. s, 3H), 1.99 (m, 1H), 1.69 (t, J=13.4 Hz, 1H), 1.48 (m, 1H), 1.26-1.22 (m, 1H), 1.15-1.05 (m, 1H).

Example 48:—1-(2-{[(3aS,6S,7aS)-3-{2,2-dimethyl-3-oxo-2H,3H,4H-pyrido[3,2-b][1,4]oxazin-6-yl}-2-oxo-octahydro-1,3-benzoxazol-6-yl]amino}ethyl)-7-methoxy-1,2-dihydro-1,8-naphthyridin-2-one

48

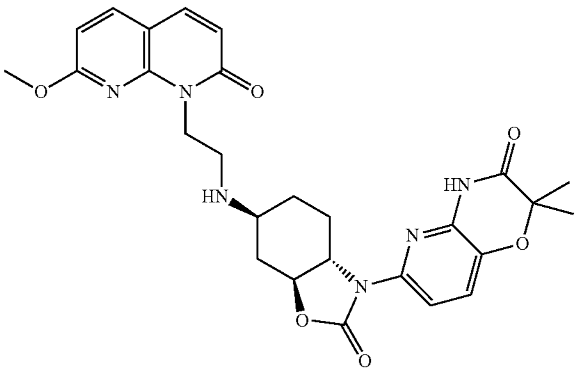

a) tert-butyl N-[(3aS,6S,7aS)-3-{2,2-dimethyl-3-oxo-2H,3H,4H-pyrido[3,2-b][1,4]oxazin-6-yl}-2-oxo-octahydro-1,3-benzoxazol-6-yl]carbamate 48a To a mixture of tert-butyl N-[(3aS,6S,7aS)-2-oxo-octahydro-1,3-benzoxazol-6-yl]carbamate (800 mg, 3.12 mmol), 6-bromo-2,2-dimethyl-2H,3H,4H-pyrido[3,2-b][1,4]oxazin-3-one (882 mg, 3.43 mmol) (BMCL, 2015, vol. 25, p. 3636-3643) and $K_2CO_3$ (862 mg, 6.24 mmol) in 1,4-dioxane (anhydrous, 15 mL) under $N_2$ was added CuI (148 mg, 0.78 mmol) and trans-1,2-diaminocyclohexane (94 uL, 0.78 mmol). The reaction mixture was heated at 110° C. for 2 h. Further CuI (148 mg, 0.78 mmol) and trans-1,2-diaminocyclohexane (94 uL, 0.78 mmol) were added and the mixture heated at reflux for 17 h. The reaction was allowed to cool and the mixture concentrated under reduced pressure. The isolated residue was mixed with $H_2O$ and extracted with EtOAc. The combined organic extracts were dried over $MgSO_4$, filtered and concentrated to afford a black gum. The residue was purified by silica gel chromatography using 50% $Et_2O$ in heptane to give tert-butyl N-[(3aS,6S,7aS)-3-{2,2-dimethyl-3-oxo-2H,3H,4H-pyrido[3,2-b][1,4]oxazin-6-yl}-2-oxo-octahydro-1,3-benzoxazol-6-yl]carbamate 48a (550 mg, 41% yield) as a yellow foam. LC-MS (Method A) 433.1 $[M+H]^+$; RT 2.87 min.

b) (3aS,6S,7aS)-6-amino-3-{2,2-dimethyl-3-oxo-2H,3H,4H-pyrido[3,2-b][1,4]oxazin-6-yl}octa hydro-1,3-benzoxazol-2-one 48b tert-butyl N-[(3aS,6S,7aS)-3-{2,2-dimethyl-3-oxo-2H,3H,4H-pyrido[3,2-b][1,4]oxazin-6-yl}-2-oxo-octahydro-1, 3-benzoxazol-6-yl]carbamate 48a (0.5 g, 1.16 mmol) was dissolved in HCl (5-6 N in IPA, 0.51 mL) and the mixture stirred for 1 h. $Et_2O$ (175 ml) was added and the reaction quenched with saturated aqueous $Na_2CO_3$ adjusting the pH to 8. The mixture was extracted with DCM (2×75 mL) and the organic extracts were dried ($MgSO_4$) and evaporated under reduced pressure to afford (3aS,6S,7aS)-6-amino-3-{2,2-dimethyl-3-oxo-2H,3H,4H-pyrido[3,2-b][1,4]oxazin-6-yl}octahydro-1,3-benzoxazol-2-one 48b (305 mg, 0.87 mmol, 75% yield) as a yellow foam. LC-MS (Method A) 333.1 $[M+H]^+$; RT 1.98 min.

c) 1-(2-{[(3aS,6S,7aS)-3-{2,2-dimethyl-3-oxo-2H,3H,4H-pyrido[3,2-b][1,4]oxazin-6-yl}-2-oxo-octahydro-1,3-benzoxazol-6-yl]amino}ethyl)-7-methoxy-1,2-dihydro-1,8-naphthyridin-2-one (3aS,6S,7aS)-6-amino-3-{2,2-dimethyl-3-oxo-2H,3H,4H-pyrido[3,2-b][1,4]oxazin-6-yl}octa hydro-1,3-benzoxazol-2-one 48b (126 mg, 0.38 mmol), 2-(7-methoxy-2-oxo-1,2-dihydro-1,8-naphthyridin-1-yl)acetaldehyde (prepared as described in WO2008009700) (83 mg, 0.38 mmol) and molecular sieves (3 Å) were added to DCM (10 mL) and stirred for 1 h at room temperature. $NaBH(OAc)_3$ (242 mg, 1.14 mmol) was added and the mixture stirred for 2 h. The reaction mixture was purified by silica gel chromatography using 10-20% MeOH in EtOAc to give a white foam. DCM (2 mL) and $Et_2O$ (20 mL) were added and the mixture sonicated. The precipitate was filtered, washed with $Et_2O$ and dried to afford 1-(2-{[(3aS,6S,7aS)-3-{2,2-dimethyl-3-oxo-2H,3H,4H-pyrido[3,2-b][1,4]oxazin-6-yl}-2-oxo-octahydro-1,3-benzoxazol-6-yl]amino}ethyl)-7-methoxy-1,2-dihydro-1,8-naphthyridin-2-one 48 (45 mg, 0.08 mmol, 21%) as a white solid. LC-MS (Method A) 535.2 $[M+H]^+$; RT 2.60 min. $^1H$ NMR (Method C) ($CDCl_3$): δ ppm 7.97 (s, 1H), 7.73 (d, J=8.3 Hz, 1H), 7.58 (d, J=9.3 Hz, 1H), 7.31 (d, J=8.6 Hz, 1H), 7.27 (d, J=8.6 Hz, 1H), 6.64 (d, J=8.3 Hz, 1H), 6.59 (d, J=9.3 Hz, 1H), 4.65 (t, J=6.6 Hz, 2H), 4.04 (s, 3H), 3.95 (td, J=11.8 Hz, J=3.4 Hz 1H), 3.79 (td, J=11.8 Hz, J=3.4 Hz, 1H), 3.19-3.06 (m, 2H), 2.99-2.81 (m, 1H), 2.75-2.64 (m, 1H), 2.64-2.56 (m, 1H), 2.20-1.87 (m, 1H), 1.62-1.55 (m, 2H), 1.54 (s, 3H), 1.52 (s, 3H), 1.43-1.34 (m, 2H).

Example 49:—1-(2-{[(3aR,6R,7aR)-3-{6H,7H-[1,4]dioxino[2,3-c]pyridazin-3-yl}-2-oxo-octahydro-1,3-benzoxazol-6-yl]amino}ethyl)-7-methoxy-1,2-dihydro-1,8-naphthyridin-2-one

49

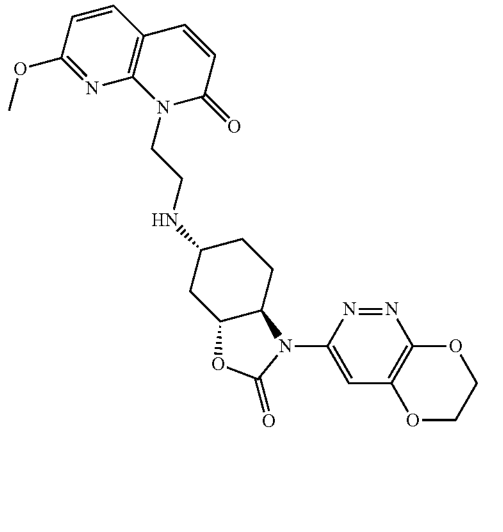

a) 2-[(3,6-dichloropyridazin-4-yl)oxy]ethan-1-ol 49a

To a solution of ethylene glycol (21.28 mL, 381.6 mmol) in THF (90 mL) at 00° C. was added NaH (60%, 1.31 g, 54.52 mmol). Once the addition was complete 3,4,6-trichloropyridazine (10 g, 54.52 mmol) in THF (10 mL) was added and the reaction stirred at 00° C. for 1 h. The reaction was allowed to warm to room temperature and stirred for 17 h. The mixture was reduced in volume by evaporation, saturated aqueous $NaHCO_3$ (30 mL) added and the mixture extracted with DCM (3×35 mL) and EtOAc (35 mL). The combined organic extracts were washed with water (40 mL), dried over $MgSO_4$ and concentrated under reduced pressure. The crude residue was purified by silica gel chromatography eluting with 3% MeOH in DCM to give 2-[(3,6-dichloropyridazin-4-yl)oxy]ethan-1-ol 49a (4.52 g, 39%). LC-MS (Method A) 210.9 $[M+H]^+$ 1.29 min.

b) 3-chloro-6H, 7H-[1, 4]dioxino[2,3-c]pyridazine 49b

To a solution of 2-[(3,6-dichloropyridazin-4-yl)oxy]ethan-1-ol 49a (4.52 g, 21.61 mmol) in 1, 4-dioxane (250 mL) was added NaH (60%, 2.07 g, 86.44 mmol) and the reaction heated to 110° C. for 18 h. After cooling, the reaction was quenched with iced water, reduced in volume and extracted with DCM (3×75 mL). The combined organic extracts were washed with $H_2O$, dried over $MgSO_4$ and concentrated. The crude material was purified by silica gel chromatography eluting with 0-3% MeOH in EtOAc to give 3-chloro-6H,7H-[1,4]dioxino[2,3-c]pyridazine 49b (1.22 g, 33%). LC-MS (Method A) 173.0 $[M+H]^+$ 1.27 min.

c) tert-butyl N-[(3aR,6R,7aR)-3-{6H,7H-[1,4]dioxino[2,3-c]pyridazin-3-yl}-2-oxo-octahydro-1,3-benzoxoazol-6-yl]carbamate 49c tert-butyl N-[(3aR,6R,7aR)-2-oxo-octahydro-1,3-benzoxazol-6-yl]carbamate 1a (1.01 g, 3.95 mmol), $Pd(OAc)_2$ (35.5 mg, 0.16 mmol), (+/−)-BINAP (197 mg, 0.32 mmol) and $K_3PO_4$ (2.1 g, 9.87 mmol) were added to a flask under a $N_2$ atmosphere. A solution of 3-chloro-6H, 7H-[1, 4]dioxino[2, 3-c]pyridazine 49b (0.681 g, 3.95 mmol) in 1, 4-dioxane (30 mL) was added and the reaction heated to 110° C. for 18 h. (+/−)-BINAP (197 mg, 0.32 mmol) and $Pd(OAc)_2$ (35.45 mg, 0.16 mmol) were added and the reaction stirred at 110° C. for a further 48 h. The reaction was allowed to cool, diluted with $H_2O$ and extracted with EtOAc (3×30 mL). The combined organic extracts were washed with brine, dried over $MgSO_4$ and concentrated to give a residue containing tert-butyl N-[(3aR,6R,7aR)-3-{6H,7H-[1,4]dioxino[2,3-c]pyridazin-3-yl}-2-oxo-octahydro-1,3-benzoxazol-6-yl]carbamate 49c (1.799 g, 116%) which was used without further purification. LC-MS (Method A) 393.1 $[M+H]^+$ 2.40 min.

d) (3aR,6R,7aR)-6-amino-3-{6H,7H-[1,4]dioxino[2,3-c]pyridazin-3-yl}-octahydro-1,3-benzoxazonol-2-one 49d HCl (5-6N in IPA, 20 mL) was added to a solution of tert-butyl N-[(3aR,6R,7aR)-3-{6H, 7H-[1, 4]dioxino[2,3-c]pyridazin-3-yl}-2-oxo-octahydro-1,3-benzoxoazol-6-yl]carbamate 49c (1.8 g, 4.58 mmol) in DCM (15 mL) and the reaction stirred at room temperature for 2 h. $H_2O$ was added and the phases separated. The organic phase was further extracted with $H_2O$ and the aqueous extracts combined. $K_2CO_3$ was added adjusting the pH to 8 and the mixture extracted with DCM. The organic extracts were dried over $MgSO_4$ and concentrated under reduced pressure to give (3aR,6R,7aR)-6-amino-3-{6H,7H-[1,4]dioxino[2,3-c]pyridazin-3-yl}-octahydro-1,3-benzoxazol-2-one 49d (116.3 mg, 9%). LC-MS (Method A) 293.1 $[M+H]^+$ 1.13 min.

e) 1-(2-{[3aR,6R,7aR)-3-{6H,7H-[1,4]dioxino[2,3-c]pyridazin-3-yl}-2-oxo-octahydro-1,3-benzoxazol-6-yl]amino}ethyl)-7-methoxy-1,2-dihydro-1,8-napthyridin-2-one 49

To a solution of (3aR,6R,7aR)-6-amino-3-{6H,7H-[1,4]dioxino[2,3-c]pyridazin-3-yl}-octahydro-1,3-benzoxazonol-2-one 49d (116 mg, 0.40 mmol) in DCM (10 mL) over molecular sieves (4 Å) was added 2-(7-methoxy-2-oxo-1,2-dihydro-1,8-naphthyridin-1-yl)acetaldehyde (87 mg, 0.40 mmol) (prepared as described in WO2008009700) and acetic acid (0.1 mL). The reaction was heated to 40° C. for 18 h. Sodium borohydride (45.16 mg, 1.19 mmol) was added and the reaction stirred at room temperature for 30 min. The mixture was decanted to remove the molecular sieves and saturated aqueous $NaHCO_3$ added, adjusting the pH to 8. The organic phase was washed with brine, dried over $MgSO_4$ and concentrated under reduced pressure. The crude residue was purified by silica gel chromatography (0-20% MeOH in EtOAc) followed by prep. HPLC (Method B) to give 1-(2-{[3aR,6R,7aR)-3-{6H,7H-[1,4]dioxino[2,3-c]pyridazin-3-yl}-2-oxo-octahydro-1,3-benzoxazol-6-yl]amino}ethyl)-7-methoxy-1, 2-dihydro-1,8-napthyridin-2-one 49 (23 mg, 12%). LC-MS (Method A) 495.1 $[M+H]^+$ 1.96 min. $^1H$ NMR (Method C) ($CH_3OD$): δ ppm 8.00 (d, J=8.5 Hz, 1H), 7.88 (d, J=9.3 Hz, 1H), 7.48 (s, 1H), 6.77 (d, J=8.5 Hz, 1H), 6.60 (d, J=9.4 Hz, 1H), 4.69 (t, J=7.2 Hz, 2H), 4.57 (dd, J=5.8, 3.0 Hz, 2H), 4.52-4.36 (m, 2H), 4.15 (d, J=3.2 Hz, 1H), 4.10 (s, 3H), 3.99 (s, 1H), 3.08 (td, J=6.9, 2.8 Hz, 2H), 3.00 (td, J=10.7, 5.2 Hz, 1H), 2.84-2.71 (m, 1H), 2.64 (s, 1H), 2.17 (d, J=12.6 Hz, 1H), 1.68-1.57 (m, 1H), 1.53-1.35 (m, 2H).

Example 50:—5-(2-{[(3aR,6R,7aR)-2-oxo-3-{3-oxo-2H,3H,4H-pyrido[3,2-b][,4]oxazin-6-yl}-octahydro-1,3-benzoxazol-6-yl]amino}ethyl)-6-oxo-5,6-dihydro-1,5-naphthyridine-3-carbonitrile

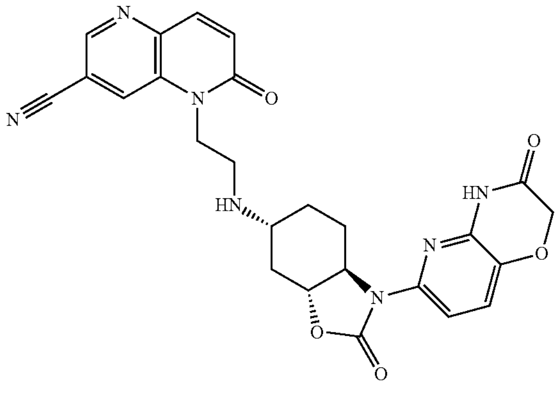

a) 5-(2-{[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-6-oxo-5,6-dihydro-1,5-naphthyridine-3-carbonitrile 50a A solution of (3aR,6R,7aR)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 1c (100 mg, 0.23 mmol) and 6-oxo-5-(2-oxoethyl)-5,6-dihydro-1,5-naphthyridine-3-carbonitrile (prepared as described in WO 2008009700 A1 20080124) (50 mg, 0.23 mmol) in DCM (15 mL) was stirred, at room temperature, over molecular sieves (3 Å) for 2 h. $NaBH(OAc)_3$ (199 mg, 0.94 mmol) was added and stirred for 2 h. The reaction was basified to pH 8~9 with saturated aqueous $NaHCO_3$ and passed through an SPE phase separator. The organic portion was concentrated under reduced pressure to give a residue containing 5-(2-{[(3aR,6R,7aR)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl]amino}ethyl)-6-oxo-5,6-dihydro-1,5-naphthyridine-3-carbonitrile 50a (182 mg, 125%) which was used without further purification. LC-MS (Method A) 622.1 $[M+H]^+$; RT 2.50 min.

b) 5-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-6-oxo-5,6-dihydro-1,5-naphthyridine-3-carbonitrile 50

To a stirring solution of 5-(2-{[(3aR,6R,7aR)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl]amino}ethyl)-6-oxo-5,6-dihydro-1,5-naphthyridine-3-carbonitrile 50a (182 mg, 0.29 mmol) in DCM (15 mL) was added TFA (0.80 mL) followed by $CF_3SO_3H$ (0.18 mL). The reaction was stirred at room temperature for 30 min then diluted with MeOH (5 mL) and DCM (15 mL), basified to pH 8~9 with saturated aqueous $Na_2CO_3$ and passed through an SPE phase separator. The organic portion was concentrated under reduced pressure and the residue purified via silica gel chromatography using 0-10% MeOH in DCM to give 5-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-6-oxo-5,6-dihydro-1,5-naphthyridine-3-carbonitrile 50 (60.5 mg, 41%). LC-MS (Method B) 502.0 $[M+H]^+$; RT 4.84 min. $^1H$ NMR (Method C) (DMSO-d6): δ ppm 11.22 (s, 1H), 8.89 (d, J=1.6 Hz, 1H), 8.72 (d, J=1.6 Hz, 1H), 8.02 (d, J=9.8 Hz, 1H), 7.42 (d, J=8.5 Hz, 1H), 7.17 (d, J=8.6 Hz, 1H), 7.06 (d, J=9.8 Hz, 1H), 4.62 (s, 2H), 4.30 (t, J=7.0 Hz, 2H), 4.04 (td, J=11.7, 3.3 Hz, 1H), 3.75 (td, J=11.1, 3.2 Hz, 1H), 2.87 (br. s, 2H), 2.77 (m, 2H), 2.46-2.39 (m, 1H), 1.96 (m, 1H), 1.47 (br. s, 1H), 1.34-1.29 (m, 1H), 1.25 (m, 1H).

Example 51:—1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl](methyl)amino}ethyl)-7-methoxy-1,2-dihydro-1,5-naphthyridin-2-one

51

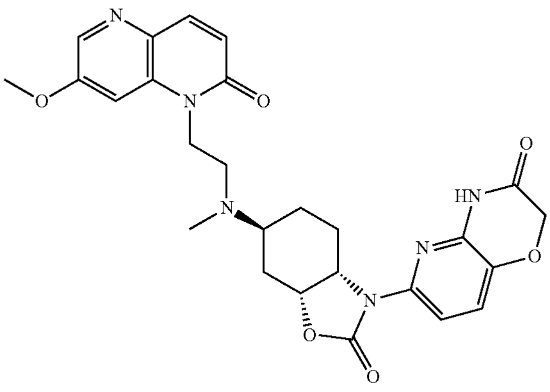

a) 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl](methyl)amino}ethyl)-7-methoxy-1,2-dihydro-1,5-naphthyridin-2-one 51a A solution of 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl]amino}ethyl)-7-methoxy-1,2-dihydro-1,5-naphthyridin-2-one 30a (110 mg, 0.18 mmol) in DCM (4 mL), MeOH (10 mL) and formaldehyde solution (36.5-38%)(0.07 mL) was stirred at room temperature for 2 h. $NaBH(OAc)_3$ (149 mg, 0.70 mmol) was added and the reaction stirred for 1 h. The reaction was basified to pH 8 with saturated aqueous $NaHCO_3$ and passed through an SPE phase separator. The organic portion was concentrated under reduced pressure to give a crude residue containing 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl](methyl)amino}ethyl)-7-methoxy-1,2-dihydro-1, 5-naphthyridin-2-one 51a which was used without further purification. LC-MS (Method A) 641.2 $[M+H]^+$; RT 2.48 min.

b) 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl](methyl)amino}ethyl)-7-methoxy-1,2-dihydro-1,5-naphthyridin-2-one 51

To a stirring solution of 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl](methyl)amino}ethyl)-7-methoxy-1,2-dihydro-1,5-naphthyridin-2-one 51a (114 mg, 0.18 mmol) in DCM (10 mL) was added TFA (0.47 mL) followed by $CF_3SO_3H$ (0.11 mL). The reaction was stirred at room temperature for 1 h then diluted with MeOH (5 mL) and DCM (15 ml), basified to pH 8~9 with saturated $Na_2CO_3$ and passed through an SPE phase separator. The organic portion was concentrated under reduced pressure and the residue purified via silica gel chromatography using 0-20% MeOH in DCM to give 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl](methyl)amino}ethyl)-7-methoxy-1,2-dihydro-1,5-naphthyridin-2-one 51 (29 mg, 31%). LC-MS (Method B) 521.2 $[M+H]^+$; 4.98 min, $^1H$ NMR (Method C) (DMSO-d6): δ ppm 11.18 (s, 1H), 8.27 (d, J=2.3 Hz, 1H), 7.87 (d, J=9.6 Hz, 1H), 7.49 (d, J=8.7 Hz, 1H), 7.42 (d, J=2.5 Hz, 1H), 7.38 (d, J=8.7 Hz, 1H), 6.66 (d, J=9.6 Hz, 1H), 4.77-4.72 (m, 1H), 4.62 (m, 2H), 4.42-4.38 (m, 1H), 4.35-4.30 (m, 2H), 3.99 (s, 3H), 2.68-2.64 (m, 3H), 2.45-2.42 (m, 1H), 2.38 (s, 3H), 2.05-1.97 (m, 1H), 1.73-1.66 (m, 1H), 1.54-1.48 (m, 1H), 1.28-1.20 (m, 1H), 1.15-1.08 (m, 1H).

Example 52:—(3aS,6S,7aS)-6-[(2-{2-methoxy-7-oxo-7H,8H-pyrido[2,3-d]pyrimidin-8-yl}ethyl)amino]-3-{3-oxo-2H,3H,4H-pyrido[3,2-b][1,4]oxazin-6-yl}-octahydro-1,3-benzoxazol-2-one

52

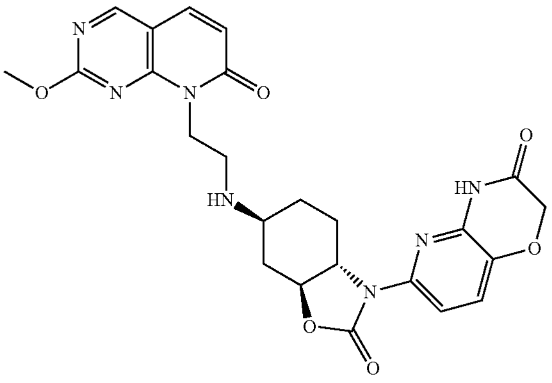

a) 1-(2-{[(3aS,6S,7aS)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-6,7-difluoro-1,2-dihydroquinoxalin-2-one 52a To a solution of (3aS,6S,7aS)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 29c (209 mg, 0.49 mmol) and 2-{2-methoxy-7-oxo-7H,8H-pyrido[2,3-d]pyrimidin-8-yl}acetaldehyde 2b (108 mg, 0.49 mmol) in DCM (20 mL) was added a few drops of AcOH and the mixture stirred at room temperature for 2 h. $NaBH(OAc)_3$ (313 mg, 1.48 mmol) was added and the reaction mixture stirred at room temperature for 18 h. The mixture was adjusted to pH 8~9 with saturated $Na_2CO_3$ and extracted with DCM (100 mL). The organic layer was washed with brine, dried over $MgSO_4$, filtered and concentrated to give 1-(2-{[(3aS,6S,7aS)-3-{4-[(4[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-6,7-difluoro-1,2-dihydroquinoxalin-2-one 52a, (209 mg, 67%), which was used without further purification. LC-MS (Method A) 628.2 $[M+H]^+$; RT 2.61 min.

b) (3aS,6S,7aS)-6-[(2-{2-methoxy-7-oxo-7H,8H-pyrido[2,3-d]pyrimidin-8-yl}ethyl)amino]3-{3-oxo-2H,3H,4H-pyrido[3,2-b][1,4]oxazin-6-yl}-octahydro-1,3-benzoxazol-2-one 52

To a solution of 1-(2-{[(3aS,6S,7aS)-3-{4-[(4-methoxyphenyl)methyl]-3-oxo-2H,3H,4H-pyrido[3,2-b][1,4]oxazin- 6-yl}-2-oxo-octahydro-1,3-benzoxazol-6-yl]amino}ethyl)-6,7-difluoro-1,2-dihydroquinoxalin-2-one 52a (209 mg, 0.33 mmol) in DCM (20 mL) was added TFA (382 μL, 5.00 mmol) followed by $CF_3SO_3H$ (147 μL, 1.67 mmol) and the mixture was stirred at room temperature for 1.5 h. The reaction was quenched with MeOH (1 mL), adjusted to pH 8~9 with saturated aqueous $Na_2CO_3$ and extracted with DCM (100 mL). The organic extract was washed with brine, dried over $MgSO_4$, filtered and concentrated under reduced pressure. The residue was purified by chromatography (Biotage 10 g KP-Si cartridge) using 0-50% MeOH in DCM to give (3aS,6S,7aS)-6-[(2-{2-methoxy-7-oxo-7H,8H-pyrido[2,3-d]pyrimidin-8-yl}ethyl)amino]-3-{3-oxo-2H,3H,4H-pyrido[3,2-b][1,4]oxazin-6-yl}-octahydro-1,3-benzoxazol-2-one 52 (39 mg, 23%) as a white solid. LC-MS (Method B) 508.1 $[M+H]^+$; RT 5.58 min. $^1H$ NMR (Method C) (DMSO): δ ppm 11.24 (br s, 1H), 8.92 (s, 1H), 7.95 (d, J=9.5 Hz, 1H), 7.42 (d, J=8.5 Hz, 1H), 7.17 (d, J=8.5 Hz, 1H), 6.57 (d, J=9.5 Hz, 1H), 4.62 (s, 2H), 4.34 (m, 2H), 4.06 (td, J=11.8, 3.3 Hz, 1H), 4.02 (s, 3H), 3.74 (td, J=11.2, 3.3 Hz, 1H), 2.86 (m, 2H), 2.77 (m, 2H), 2.44 (m, 1H), 1.98 (d, J=12.9 Hz, 1H), 1.46 (q, J=11.2 Hz, 1H), 1.32 (m, 1H), 1.22 (m, 1H).

Example 53:—(3aS,6S,7aR)-6-({2-[2-(methylsulfanyl)-7-oxo-7H,8H-pyrido[2,3-d]pyrimidin-8-yl]ethyl}amino)-3-{3-oxo-2H,3H,4H-pyrido[3,2-b][1,4]oxazin-6-yl}-octahydro-1,3-benzoxazol-2-one

53

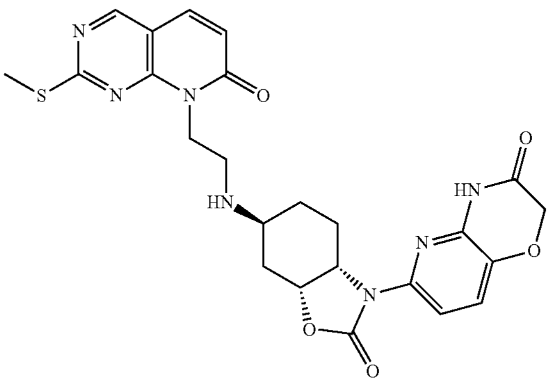

a) 5-bromo-N-(2,2-dimethoxyethyl)-2-(methylsulfanyl)pyrimidin-4-amine 53a 5-bromo-4-chloro-2-(methylsulfanyl)pyrimidine (25 g, 104.40 mmol), $K_2CO_3$ (19 g, 135.700 mmol) and 2,2-dimethoxyethan-1-amine (23 mL, 208.80 mmol) were added to DMF (200 mL) and the mixture was heated at 50° C. for 18 h. The reaction was evaporated to dryness and quenched with water (300 mL), extracted with diethyl ether (3×250 ml), washed with brine and dried over $MgSO_4$ and evaporated to give 5-bromo-N-(2,2-dimethoxyethyl)-2-(methylsulfanyl)pyrimidin-4-amine 53a (31 g, 96%) as a clear gum. $^1H$ NMR (Method C) ($CDCl_3$): δ ppm 8.02 (s, 1H), 5.49 (s, 1H), 4.44 (dd, J=5.5 Hz, 1H), 3.59 (dd, J=5.5 Hz, J=5.5 Hz, 2H), 3.37 (s, 6H), 2.43 (s, 3H).

b) Butyl (2E)-3-{4-[(2,2-dimethoxyethyl)amino]-2-(methylsulfanyl)pyrimidin-5-yl}prop-2-enoate 53b 5-bromo-N-(2,2-dimethoxyethyl)-2-(methylsulfanyl)pyrimidin-4-amine 53a (18.2 g, 59.10 mmol), triethylamine (20 mL, 143.50 mmol), butyl prop-2-enoate (84.8 mL, 591.20 mmol) and tetrakis(triphenylphosphine)palladium(0) (5.0 g, 4.30 mmol) were combined and heated to 100° C. for 18 h. Further butyl prop-2-enoate (100 mL, 402.30 mmol) was added followed by tetrakis(triphenylphosphine)palladium(0) (2.0 g, 2.48 mmol)). The reaction was heated at reflux for another 18 h. The reaction was evaporated to dryness and then quenched with water (150 mL), extracted with ether (3×500 mL) and dried over $MgSO_4$. The solvent was evaporated to afford an orange gum. The mixture was purified by chromatography using 0-50% EtOAc in heptane to give butyl (2E)-3-{4-[(2,2-dimethoxyethyl)amino]-2-(methylsulfanyl)pyrimidin-5-yl}prop-2-enoate 53b (20.1 g, 96%) as a very pale yellow oil. $^1H$ NMR (Method C) ($CDCl_3$): δ ppm 8.10 (s, 1H), 7.44 (d, J=15.9 Hz, 1H), 6.22 (d, J=15.9 Hz, 1H), 5.29 (t, J=5.4 Hz, 1H), 4.46 (t, J=5.4 Hz, 1H), 4.14 (t, J=6.4 Hz, 2H), 3.64 (dd, J=5.4 Hz, J=5.4 Hz, 2H), 3.37 (s, 6H), 2.46 (s, 3H), 1.61 (m, 2H), 1.36 (m, 2H), 0.90 (t, J=7.4 Hz, 3H).

c) 8-(2,2-dimethoxyethyl)-2-(methylsulfanyl)-7H,8H-pyrido[2,3-d]pyrimidin-7-one 53c Butyl (2E)-3-{4-[(2,2-dimethoxyethyl)amino]-2-(methylsulfanyl)pyrimidin-5-yl}prop-2-enoate 53b (4.04 g, 11.37 mmol) was taken up in methanol (40 mL) and to this was added catalytic sodium methoxide (31 mg, 0.57 mmol). The reaction was heated at 60° C. for 4 h.

The reaction was complete after this time and then treated with saturated aqueous $NH_4Cl$ solution (0.5 mL) and evaporated to dryness. The residue was taken up in DCM (50 mL) and the white solid formed ($NH_4Cl$) was filtered off, washed with further DCM (30 mL) and the supernatant evaporated to dryness. The residue was purified by chromatography using 0-40% EtOAc in DCM. Relevant fractions were combined and evaporated to dryness to afford a colourless oil which slowly solidified. Trituration with 10% EtOAc/heptane afforded 8-(2,2-dimethoxyethyl)-2-(methylsulfanyl)-7H,8H-pyrido[2,3-d]pyrimidin-7-one 53c as a fluffy white solid. $^1H$ NMR (Method C) ($CDCl_3$): δ ppm 8.53 (s, 1H), 7.53 (d, J=9.5 Hz, 1H), 6.57 (d, J=9.5 Hz, 1H), 4.89 (t, J=5.6 Hz, 1H), 4.53 (d, J=5.6 Hz, 2H), 3.31 (s, 6H), 2.55 (s, 3H).

d) 2-[2-(methylsulfanyl)-7-oxo-7H,8H-pyrido[2,3-d]pyrimidin-8-yl]acetaldehyde 53d 8-(2,2-dimethoxyethyl)-2-(methylsulfanyl)-7H,8H-pyrido[2,3-d]pyrimidin-7-one 53c (273 mg, 0.97 mmol) was added to 2M HCl (4.85 mL, 9.70 mmol) and THF (10 mL) and the reaction heated at 60° C. for 18 h. The mixture was adjusted to pH 8~9 with saturated $Na_2CO_3$ and extracted with EtOAc (2×50 mL). The organic layer was washed with brine, dried over $MgSO_4$, filtered and concentrated to give 2-[2-(methylsulfanyl)-7-oxo-7H,8H-pyrido[2,3-d]pyrimidin-8-yl]acetaldehyde 53d (209 mg, 91%) as a white solid, which was used without further purification. LC-MS (Method A) 236.1 $[M+H]^+$; RT 1.13 min.

e) (3aS,6S,7aR)-3-{4-[(4-methoxyphenyl)methyl]-3-oxo-2H,3H,4H-pyrido[3,2-b][1,4]oxazin-6-yl}-6-({2-[2-(methylsulfanyl)-7-oxo-7H,8H-pyrido[2,3-d]pyrimidin-8-yl]ethyl}amino)-octahydro-1,3-benzoxazol-2-one 53e To a solution of (3aS,6S,7aR)-6-amino-3-{4-[(4-methoxyphenyl)methyl]-3-oxo-2H,3H,4H-pyrido[3,2-b][1, 4]oxazin-6-yl}-octahydro-1,3-benzoxazol-2-one 4c (370 mg, 0.87 mmol) and 2-[2-(methylsulfanyl)-7-oxo-7H,8H-pyrido[2,3-d]pyrimidin-8-yl]acetaldehyde 53d (205 mg, 0.87 mmol) in DCM (40 mL) was added a few drops of AcOH and the mixture stirred at room temperature for 2 h. $NaBH(OAc)_3$ (554 mg, 2.62 mmol) was added and the reaction mixture stirred at room temperature for 1 h. The mixture was adjusted to pH 8~9 with saturated $Na_2CO_3$ and extracted with DCM (150 mL). The organic layer was washed with brine, dried over $MgSO_4$, filtered and concentrated. The crude was purified by chromatography (Biotage 25 g KP-Si cartridge) using 0-50% MeOH in DCM to give (3aS,6S,7aR)-3-{4-[(4-methoxyphenyl)methyl]-3-oxo-2H,3H,4H-pyrido[3,2-b][1,4]oxazin-6-yl}-6-({2-[2-(methylsulfanyl)-7-oxo-7H,8H-pyrido[2,3-d]pyrimidin-8-yl]ethyl}amino)-octahydro-1,3-benzoxazol-2-one 53e (183 mg, 32%). LC-MS (Method A) 644.2 $[M+H]^+$; RT 2.86 min.

f) (3aS,6S,7aR)-6-({2-[2-(methylsulfanyl)-7-oxo-7H,8H-pyrido[2,3-d]pyrimidin-8-yl]ethyl}amino)-3-{3-oxo-2H,3H,4H-pyrido[3,2-b][1,4]oxazin-6-yl}-octahydro-1,3-benzoxazol-2-one 53

To a solution of (3aS,6S,7aR)-3-{4-[(4-methoxyphenyl)methyl]-3-oxo-2H,3H,4H-pyrido[3,2-b][1,4]oxazin-6-yl}-6-({2-[2-(methylsulfanyl)-7-oxo-7H,8H-pyrido[2,3-d]pyrimidin-8-yl]ethyl}amino)-octahydro-1,3-benzoxazol-2-one 53e (180 mg, 0.28 mmol) in DCM (20 mL) was added TFA (320 μL, 4.19 mmol) followed by $CF_3SO_3H$ (124 μL, 1.40 mmol) and the mixture was stirred at room temperature for 1.5 h. The reaction was quenched with MeOH (1 mL), adjusted to pH 8~9 with saturated aqueous $Na_2CO_3$ and extracted with DCM (100 mL). The organic extract was washed with brine, dried over $MgSO_4$, filtered and concentrated under reduced pressure.

The residue was purified by chromatography (Biotage 10 g KP-Si cartridge) using 0-25% MeOH in DCM to give (3aS,6S,7aR)-6-({2-[2-(methylsulfanyl)-7-oxo-7H,8H-pyrido[2,3-d]pyrimidin-8-yl]ethyl}amino)-3-{3-oxo-2H,3H,4H-pyrido[3,2-b][1,4]oxazin-6-yl}-octahydro-1,3-benzoxazol-2-one 53 (24 mg, 16%). LC-MS (Method B) 524.1 $[M+H]^+$; RT 6.05 min. $^1H$ NMR (Method C) ($CDCl_3$): δ ppm 8.62 (s, 1H), 7.94 (br s, 1H), 7.77 (d, J=8.7 Hz, 1H), 7.60 (d, J=9.4 Hz, 1H), 7.28 (d, J=8.7 Hz, 1H), 6.64 (d, J=9.4 Hz, 1H), 4.69 (m, 1H), 4.63 (s, 2H), 4.54 (m, 3H), 3.05 (m, 2H), 2.89 (m, 1H), 2.63 (s, 3H), 2.48 (m, 1H), 2.44 (m, 1H) 1.90 (m, 1H), 1.54 (m, 1H), 1.42 (m, 1H), 1.11 (m, 1H).

Example 54:—(3aR,6R,7aR)—N-{2-[7-(2-azaniumylethoxy)-2-oxo-1,2-dihydroquinolin-1-yl]ethyl}-N-methyl-2-oxo-3-{3-oxo-2H,3H,4H-pyrido[3,2-b][1,4]oxazin-6-yl}-octahydro-1,3-benzoxazol-5-aminium dichloride

54

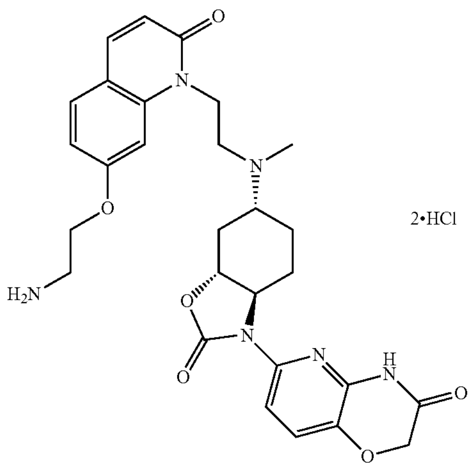

2•HCl a) tert-butyl N-(2-{[1-(2-{[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-5-yl](methyl)amino}ethyl)-2-oxo-1,2-dihydroquinolin-7-yl]oxy}ethyl)carbamate 54a Formaldehyde solution (36.5-38% in H2O, 0.05 mL) was added to a stirred solution of N-(2-{[1-(2-{[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-2-oxo-1,2-dihydroquinolin-7-yl]oxy}ethyl)carbamate 23a (99 mg, 0.13 mmol) in DCM (5 mL). The mixture was stirred for 10 min and $NaBH(OAc)_3$ (83.4 mg, 0.39 mmol) added. After 1 h, volatiles were removed under reduced pressure and the residue dissolved in DCM (5 mL) and MeOH (0.5 mL). Saturated aqueous $NaHCO_3$ (5 mL) was added and the mixture passed through an SPE phase separator. The organic phase was evaporated under reduced pressure and purified by chromatography eluting with 0-6% MeOH/DCM to give tert-butyl N-(2-{[1-(2-{[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-5-yl](methyl)amino}ethyl)-2-oxo-1,2-dihydroquinolin-7-yl]oxy}ethyl)carbamate 54a (151 mg, 149.7%). LC-MS (Method A) 769.3 $[M+H]^+$; RT 3.93 min.

b) (3aR,6R,7aR)—N-{2-[7-(2-azaniumylethoxy)-2-oxo-1,2-dihydroquinolin-1-yl]ethyl}-N-methyl-2-oxo-3-{3-oxo-2H,3H,4H-pyrido[3,2-b][1,4]oxazin-6-yl}-octahydro-1,3-benzoxazol-5-aminium dichloride 54

TFA (0.49 mL, 6.44 mmol) and $CF_3SO_3H$ (0.12 mL, 1.39 mmol) were added to a solution of tert-butyl N-(2-{[1-(2-{[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-5-yl](methyl)amino}ethyl)-2-oxo-1,2-dihydroquinolin-7-yl]oxy}ethyl)carbamate 54a (151 mg, 0.2 mmol)) in DCM (15 mL) at room temperature. After 1 h the reaction was diluted with MeOH (5 mL) and DCM (10 mL). Saturated aqueous $Na_2CO_3$ was added, adjusting the pH to 8, and the mixture was passed through an SPE phase separator. The aqueous phase was further extracted with DCM/MeOH (4:1, 2×30 mL) and the combined organics concentrated under reduced pressure. The residue was purified by preparative LCMS (Method B) to afford a white solid. This was dissolved in a minimum volume of MeOH, treated with 1M HCl in ether and evaporated to afford (3aR,6R,7aR)—N-{2-[7-(2-azaniumylethoxy)-2-oxo-1,2-dihydroquinolin-1-yl]ethyl}-N-methyl-2-oxo-3-{3-oxo-2H,3H,4H-pyrido[3,2-b][1,4]oxazin-6-yl}-octahydro-1,3-benzoxazol-5-aminium dichloride 54 (18 mg, 16.7%) as a white solid. LC-MS (Method B) 549.2 $[M+H]^+$; RT 4.51 min. $^1H$ NMR (Method C) (DMSO-d6): δ ppm 11.59 (br s, 1H), 11.27 (d, J=4.6 Hz, 1H), 8.19 (br s, 3H), 7.93 (dd, J=9.5, 1.5 Hz, 1H), 7.74 (d, J=8.7 Hz, 1H), 7.45 (d, J=8.5 Hz, 1H), 7.33 (t, J=2.7 Hz, 1H), 7.21 (dd, J=8.6, 6.8 Hz, 1H), 6.98 (dd, J=8.7, 2.0 Hz, 1H), 6.52 (dd, J=9.4, 3.7 Hz, 1H), 4.75 (m, 2H), 4.64 (d, J=2.6 Hz, 2H), 4.51 (m, 2H), 4.16 (dtd, J=14.8, 11.5, 3.3 Hz, 1H), 3.91-3.75 (m, 2H), 3.50-3.38 (m, 1H), 3.31-3.18 (m, 3H), 2.96 (m, 4H), 2.74 (dd, J=24.4, 9.9 Hz, 1H), 2.32 (m, 1H), 2.17 (m, 1H), 1.86-1.67 (m, 1H), 1.53-1.40 (m, 1H).

Example 55:—5-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-6-oxo-5,6-dihydro-1,5-naphthyridine-3-carbonitrile

55

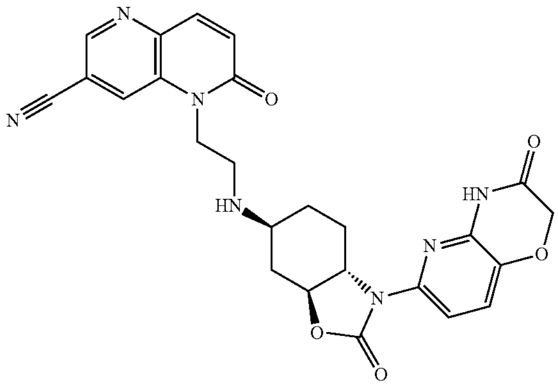

a) 5-(2-{[(3aS,6S,7aS)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-6-oxo-5,6-dihydro-1,5-naphthyridine-3-carbonitrile 55a A solution of (3aS,6S,7aS)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 29c (100 mg, 0.23 mmol) and 6-oxo-5-(2-oxoethyl)-5,6-dihydro-1,5-naphthyridine-3-carbonitrile (prepared as described in WO 2008009700 A1) (50 mg, 0.23 mmol) in DCM (15 mL) were stirred at room temperature for 2 h. $NaBH(OAc)_3$ (249 mg, 1.17 mmol) was added and stirred for 17 h. The reaction was basified to pH 8 with saturated aqueous $NaHCO_3$, diluted with DCM (10 mL) and passed through an SPE phase separator. The organic portion was concentrated under reduced pressure to give a crude residue containing 5-(2-{[(3aS,6S,7aS)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl]amino}ethyl)-6-oxo-5,6-dihydro-1,5-naphthyridine-3-carbonitrile 55a (198 mg, 136%) which was used without further purification. LC-MS (Method A) 622.2 $[M+H]^+$; RT 2.53 min.

b) 5-(2-{[(3aS,6S,7aS)-2-oxo-3-{3-oxo-2H,3H,4H-pyrido[3,2-b][1,4]oxazin-6-yl}-octahydro-1, 3-benzoxazol-6-yl]amino}ethyl)-6-oxo-5,6-dihydro-1,5-naphthyridine-3-carbonitrile 55

To a stirring solution of 5-(2-{[(3aS,6S,7aS)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl]amino}ethyl)-6-oxo-5,6-dihydro-1,5-naphthyridine-3-carbonitrile 55a (198 mg, 0.32 mmol) in DCM (15 mL) was added TFA (0.86 mL) followed by $CF_3SO_3H$ (0.20 mL). The reaction was stirred at room temperature for 1 h then diluted with MeOH (5 mL) and DCM (15 mL), basified to pH 8~9 with saturated aqueous $Na_2CO_3$ and passed through an SPE phase separator. The organic portion was concentrated under reduced pressure and the residue purified via silica gel chromatography using 0-20% MeOH in DCM to give 5-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-6-oxo-5,6-dihydro-1,5-naphthyridine-3-carbonitrile 55 (39 mg, 25%). LC-MS (Method B) 502.2 $[M+H]^+$; RT 5.11 min. $^1H$ NMR (Method C) (DMSO-d6): δ ppm 11.21 (br. s, 1H), 8.89 (d, J=2.0 Hz, 1H), 8.71 (d, J=1.7 Hz, 1H), 8.02 (d, J=9.8 Hz, 1H), 7.41 (d, J=8.5 Hz, 1H), 7.16 (d, J=8.6 Hz, 1H), 7.05 (d, J=9.7 Hz, 1H), 4.62 (s, 2H), 4.27 (t, J=6.9 Hz, 2H), 4.03 (td, J=11.6, 3.3 Hz, 1H), 3.74 (td, J=11.1, 3.3 Hz, 1H), 2.86-2.80 (m, 2H), 2.79-2.71 (m, 2H), 2.44-2.37 (m, 1H), 2.13 (br. s, 1H) 1.95-1.92 (m, 1H), 1.43 (q, J=11.2 Hz, 1H), 1.36-1.26 (m, 1H), 1.24-1.13 (m, 1H).

Example 56:—1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-2-oxo-1,2-dihydroquinoline-7-carbonitrile

56

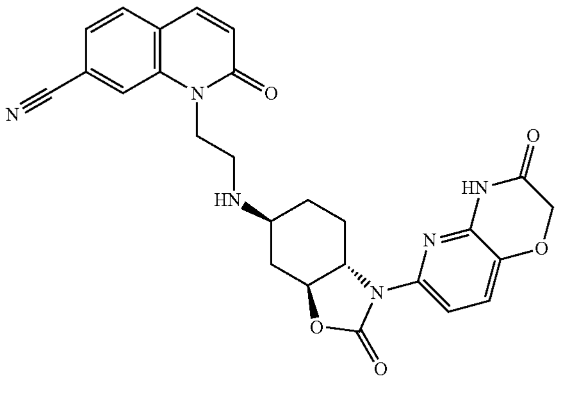

a) 1-(2-{[(3aS,6S,7aS)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-2-oxo-1,2-dihydroquinoline-7-carbonitrile 56a A solution of (3aS,6S,7aS)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 29c (120 mg, 0.28 mmol) and 2-oxo-1-(2-oxoethyl)quinolone-7-carbonitrile (J. Med. Chem (2014) 57 (11), 4889-4905) (60 mg, 0.28 mmol) in DCM (15 mL) was stirred at room temperature for 2 h. $NaBH(OAc)_3$ (300 mg, 1.41 mmol) was added and stirred for 5 h. The reaction was basified to pH 8 with saturated aqueous $NaHCO_3$ passed through an SPE phase separator. The organic portion was concentrated under reduced pressure and purified via silica gel chromatography using 0-20% MeOH in DCM to give 1-(2-{[(3aS,6S,7aS)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl]amino}ethyl)-2-oxo-1,2-dihydroquinoline-7-carbonitrile 56a (79 mg, 45%). LC-MS (Method A) 621.2 $[M+H]^+$; RT 2.70 min.

b) 1-(2-{[(3aS,6S,7aS)-2-oxo-3-{3-oxo-2H,3H,4H-pyrido[3,2-b][1,4]oxazin-6-yl}-octahydro-1, 3-benzoxazol-6-yl]amino}ethyl)-2-oxo-1,2-dihydroquinoline-7-carbonitrile 56

To a stirring solution of 1-(2-{[(3aS,6S,7aS)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl]amino}ethyl)-2-oxo-1,2-dihydroquinoline-7-carbonitrile 56a (79 mg, 0.13 mmol) in DCM (15 mL) was added TFA (0.34 mL) followed by $CF_3SO_3H$ (0.01 mL). The reaction was stirred at room temperature for 1 h then diluted with MeOH (5 mL) and DCM (15 mL), basified to pH 8~9 with saturated aqueous $Na_2CO_3$ and passed through an SPE phase separator. The organic portion was concentrated under reduced pressure and the residue purified via silica gel chromatography using 0-20% MeOH in DCM to give 1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-2-oxo-1,2-dihydroquinoline-7-carbonitrile 56 (17 mg, 28%). LC-MS (Method B) 501.2 $[M+H]^+$; RT 5.36 min. $^1H$ NMR (Method C) (DMSO-d6): δ ppm 11.23 (s, 1H), 8.19 (d, J=1.3 Hz, 1H), 8.01 (d, J=9.5 Hz, 1H), 7.92 (d, J=8.0 Hz, 1H), 7.66 (dd, J=8.1, 1.3 Hz, 1H), 7.42 (d, J=8.5 Hz, 1H), 7.17 (d, J=8.5 Hz, 1H), 6.80 (d, J=9.5 Hz, 1H), 4.62 (s, 2H), 4.29 (t, J=7.2 Hz, 2H), 4.04 (td, J=11.8, 3.3 Hz, 1H), 3.75 (td, J=11.2, 3.4 Hz, 1H), 2.85-2.74 (m, 4H), 2.45-2.42 (m, 1H), 2.19 (br. s, 1H), 1.99-1.96 (m, 1H), 1.46 (q, J=11.2 Hz, 1H), 1.33 (m, 1H), 1.28-1.16 (m, 1H).

Example 57:—6-[3-({[(3aS,6S,7aS)-2-oxo-3-{3-oxo-2H,3H,4H-pyrido[3,2-b][1,4]oxazin-6-yl}-octahydro-1,3-benzoxazol-6-yl]amino}methyl)phenyl]pyridine-2-carbonitrile

57

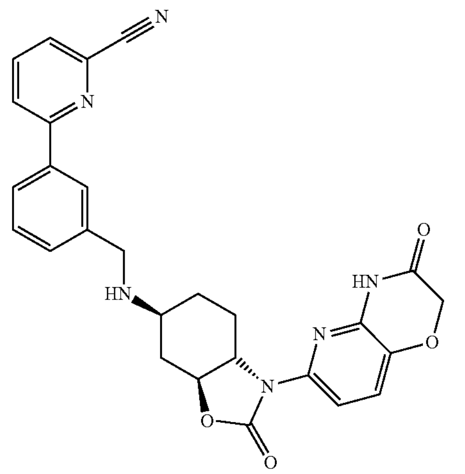

a) (3aS,6S,7aS)-6-amino-3-{3-oxo-2H,3H,4H-pyrido[3,2-b][1,4]oxazin-6-yl}-octahydro-1,3-benzoxazol-2-one 57a To a solution of tert-butylN-[(3aS,6S,7aS)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]carbamate 29b (615 mg, 1.17 mmol) in DCM (50 mL) was added TFA (1.35 mL, 17.59 mmol) followed by $CF_3SO_3H$ (519 μL, 5.86 mmol) and the mixture was stirred at room temperature for 15 min. The reaction was quenched with MeOH (6 mL), adjusted to pH 8~9 with saturated aqueous $Na_2CO_3$ and extracted with EtOAc (5×100 mL). The combined organic extracts were washed with brine, dried ($MgSO_4$), filtered and concentrated under reduced pressure to give (3aS,6S,7aS)-6-amino-3-{3-oxo-2H,3H,4H-pyrido[3,2-b][1,4]oxazin-6-yl}-octahydro-1,3-benzoxazol-2-one 57a (273.3 mg, 76%) as a white solid. LC-MS (Method A) 305.1 $[M+H]^+$; RT 1.65 min.

b) 6-[3-({[(3aS,6S,7aS)-2-oxo-3-{3-oxo-2H,3H,4H-pyrido[3,2-b][1,4]oxazin-6-yl}-octahydro-1,3-benzoxazol-6-yl]amino}methyl)phenyl]pyridine-2-carbonitrile 57

(3aS,6S,7aS)-6-amino-3-{3-oxo-2H,3H,4H-pyrido[3,2-b][1,4]oxazin-6-yl}-octahydro-1,3-benzoxazol-2-one 57a (100 mg, 0.33 mmol) and 6-(3-formylphenyl)pyridine-2-carbonitrile (68 mg, 0.33 mmol) in DCM (15 mL) were stirred for 4 h over molecular sieves (4 Å). $NaBH(OAc)_3$ (208.9 mg, 0.99 mmol) was added and the mixture stirred at ambient temperature for 72 h. The mixture was filtered and the filtrate concentrated down under reduced pressure. The residue was purified by silica chromatography using 0-10% IPA in DCM to give 6-[3-({[(3aS,6S,7aS)-2-oxo-3-{3-oxo-2H,3H,4H-pyrido[3,2-b][1,4]oxazin-6-yl}-octahydro-1,3-benzoxazol-6-yl]amino}methyl)phenyl]pyridine-2-carbonitrile 57 (49 mg, 28.5%). LC-MS (Method A) 497.1 $[M+H]^+$;

RT 2.37 min. $^1$H NMR (Method C) ($CDCl_3$): δ ppm 8.05 (d, J=1.7 Hz, 1H), 7.97 (dd, J=8.2, 1.0 Hz, 1H), 7.93-7.87 (m, 2H), 7.64 (dd, J=7.5, 1.0 Hz, 1H), 7.51-7.44 (m, 2H), 7.35-7.28 (m, 2H), 4.63 (s, 2H), 4.02-3.92 (m, 3H), 3.83 (td, J=11.1, 3.3 Hz, 1H), 2.91 (td, J=10.8, 5.2 Hz, 1H), 2.77-2.71 (m, 1H), 2.71-2.64 (m, 1H), 2.20 (dt, J=14.7, 5.0 Hz, 1H), 1.69 (q, J=11.4 Hz, 1H), 1.51 (qd, J=12.6, 12.0, 3.9 Hz, 1H), 1.40 (qd, J=12.2, 3.4 Hz, 1H).

Example 58:—1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl](2-aminoethyl)amino}ethyl)-2-oxo-1,2-dihydroquinoline-7-carbonitrile

58

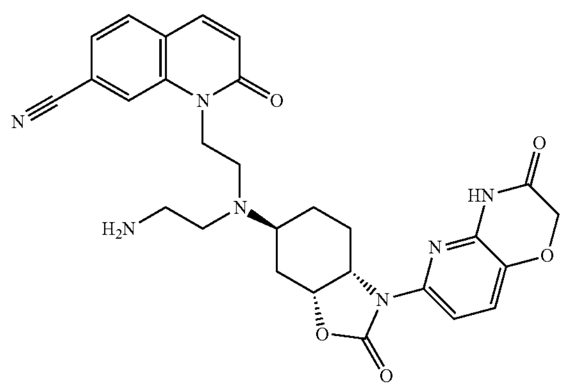

a) 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-2-oxo-1,2-dihydroquinoline-7-carbonitrile 58a A solution of (3aS,6S,7aR)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 4c (200 mg, 0.47 mmol) and 2-oxo-1-(2-oxoethyl)-1,2-dihydroquinoline-7-carbonitrile (100 mg, 0.47 mmol) (J. Med. Chem (2014) 57 (11), 4889-4905) in DCM (20 mL) was stirred, at room temperature, over molecular sieves (3 Å) for 2 h. NaBH$(OAc)_3$ (499 mg, 2.36 mmol) was added and stirred at room temperature for 90 min. The reaction was basified to pH 8 with saturated $NaHCO_3$ and the resulting mixture was passed through an SPE phase separator. The organic portion was collected and concentrated under reduced pressure to give 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-2-oxo-1,2-dihydroquinoline-7-carbonitrile 58a (270 mg, 92%) which was used without further purification. LC- MS (Method A) 621.3 $[M+H]^+$; RT 2.30 min.

b) tert-butyl N-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl][2-(7-cyano-2-oxo-1,2-dihydroquinolin-1-yl)ethyl]amino}ethyl)carbamate 58b A solution of 1-(2-{[(3aS,6S,7aR)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl]amino}ethyl)-2-oxo-1,2-dihydroquinoline-7-carbonitrile 58a (50 mg, 0.08 mmol) and tert-butyl N-(2-oxoethyl)carbamate (25.6 mg, 0.16 mmol) in DCM (5 mL) was stirred, at room temperature, over molecular sieves (3 Å) for 2 h. NaBH$(OAc)_3$ (85.4 mg, 0.4 mmol) was added and stirred for 17 h. Another portion of tert-butyl N-(2-oxoethyl)carbamate (12.8 mg, 0.08 mmol) was added and stirred for 1 h. The reaction was quenched with MeOH (1 mL), basified to pH 8 with saturated $NaHCO_3$ and the resulting mixture was passed through an SPE phase separator. The aqueous portion was extracted with DCM:IPA (4:1, 20 mL), the organics combined and concentrated under reduced pressure to give tert-butyl N-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl][2-(7-cyano-2-oxo-1,2-dihydroquinolin-1-yl)ethyl]amino}ethyl)carbamate 58b (82 mg, 133%) which was used without further purification. LC-MS (Method A) 764.3 $[M+H]^+$; RT 3.39 min.

c) 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl](2-aminoethyl)amino}ethyl)-2-oxo-1,2-dihydroquinoline-7-carbonitrile 58

To a stirring solution of tert-butyl N-(2-{[(3aS,6S,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl][2-(7-cyano-2-oxo-1,2-dihydroquinolin-1-yl)ethyl]amino}ethyl)carbamate 58b (82 mg, 0.11 mmol) in DCM (5 mL) was added TFA (0.1 mL) followed by $CF_3SO_3H$ (0.04 mL). The reaction was stirred for 1 h then quenched with MeOH (1 mL) and basified with saturated $Na_2CO_3$ to pH 8~9. The mixture was diluted with DCM:IPA (4:1, 10 mL), passed through an SPE phase separator and the organic portion concentrated under reduced pressure. The residue was purified via silica gel chromatography using 0-20% MeOH in DCM to give 1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl](2-aminoethyl)amino}ethyl)-2-oxo-1,2-dihydroquinoline-7-carbonitrile 58 (5.6 mg, 10%). LC-MS (Method B) 544.1 $[M+H]^+$; RT 5.84 min. $^1$H NMR (Method C) (DMSO-d6): δ ppm 8.07 (s, 1H), 8.05 (d, J=9.6 Hz, 1H), 7.96 (d, J=8.1 Hz, 1H), 7.70 (dd, J=8.0, 1.2 Hz, 1H), 7.49 (d, J=8.6 Hz, 1H), 7.39 (d, J=8.7 Hz, 1H), 6.83 (d, J=9.5 Hz, 1H), 4.74 (m, 1H), 4.60 (s, 3H), 4.42-4.30 (m, 4H), 2.84-2.79 (m, 2H), 2.79-2.69 (m, 6H), 2.09-2.03 (m, 1H), 1.65 (m, 1H), 1.48 (d, J=13.0 Hz, 1H), 1.25-1.21 (m, 1H), 1.09-1.06 (m, 1H).

Example 59:—1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-2-oxo-1,2-dihydroquinoline-7-carbonitrile

59

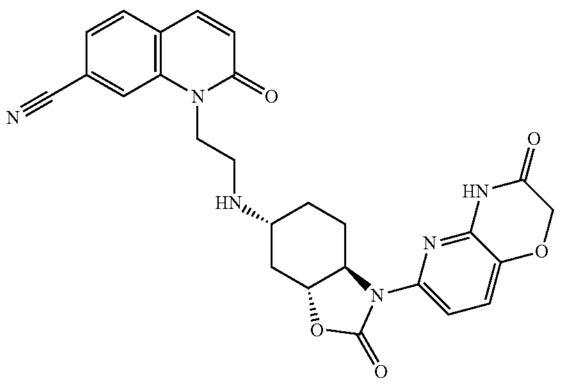

a) 1-(2-{[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]amino}ethyl)-2-oxo-1,2-dihydroquinoline-7-carbonitrile 59a A solution of (3aR,6R,7aR)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 1c (80 mg, 0.19 mmol) and 2-oxo-1-(2-oxoethyl)-1,2-dihydroquinoline-7-carbonitrile (J. Med. Chem (2014) 57 (11), 4889-4905) (40 mg, 0.19 mmol) in DCM (5 mL) was stirred, at room temperature, over molecular sieves (3 Å) for 2 h. NaBH$(OAc)_3$ (200 mg, 0.94 mmol) was added and stirred at room temperature for 2 h. The reaction was basified to pH 8 with saturated aqueous $NaHCO_3$ and the resulting mixture was passed through an SPE phase separator. The organic portion was concentrated under reduced pressure and the residue purified via silica gel chromatography using 0-20% MeOH in DCM to give 1-(2-{[(3aR,6R,7aR)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl]amino}ethyl)-2-oxo-1,2-dihydroquinoline-7-carbonitrile 59a (75 mg, 64%). LC-MS (Method A) 621.1 $[M+H]^+$; RT 2.49 min.

b) 1-(2-{[(3aR,6R,7aR)-2-oxo-3-{3-oxo-2H,3H,4H-pyrido[3,2-b][1,4]oxazin-6-yl}-octahydro-1, 3-benzoxazol-6-yl]amino}ethyl)-2-oxo-1,2-dihydroquinoline-7-carbonitrile 59

To a stirring solution of 1-(2-{[(3aR,6R,7aR)-3-{4-[(4-methoxyphenyl)methyl]-3-oxo-2H,3H,4H-pyrido[3,2-b][1,4]oxazin-6-yl}-2-oxo- octahydro-1,3-benzoxazol-6-yl]amino}ethyl)-2-oxo-1,2-dihydroquinoline-7-carbonitrile 59a (75 mg, 0.12 mmol) in DCM (15 mL) was added TFA (0.2 mL) followed by $CF_3SO_3H$ (0.05 mL). The reaction was stirred at room temperature for 30 min then quenched with MeOH (5 mL) and basified with saturated aqueous $Na_2CO_3$ to pH 8~9. The resulting mixture was diluted with DCM (15 mL), passed through an SPE phase separator and the organic portion concentrated under reduced pressure. The residue was purified via silica gel chromatography using 0-20% MeOH in DCM to give 1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-2-oxo-1,2-dihydroquinoline-7-carbonitrile 59 (20.6 mg, 32%). LC-MS (Method B) 501.1 $[M+H]^+$; RT 5.50 min. $^1H$ NMR (Method C) (DMSO-d6): δ ppm 11.21 (s, 1H), 8.18 (s, 1H), 8.01 (d, J=9.5 Hz, 1H), 7.92 (d, J=8.1 Hz, 1H), 7.66 (dd, J=7.9, 1.3 Hz, 1H), 7.41 (d, J=8.5 Hz, 1H), 7.17 (d, J=8.5 Hz, 1H), 6.79 (d, J=9.5 Hz, 1H), 4.62 (s, 2H), 4.29 (t, J=7.2 Hz, 2H), 4.07-4.00 (m, 1H), 3.75 (td, J=11.2, 3.4 Hz, 1H), 2.85-2.72 (m, 4H), 2.43 (m, 1H), 2.08 (m, 1H), 1.97 (m, 1H), 1.45 (q, J=11.1 Hz, 1H), 1.37-1.27 (m, 1H), 1.25-1.19 (m, 1H).

Example 60:—1-(3-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}propyl)-2-oxo-1,2-dihydroquinoline-7-carbonitrile

60

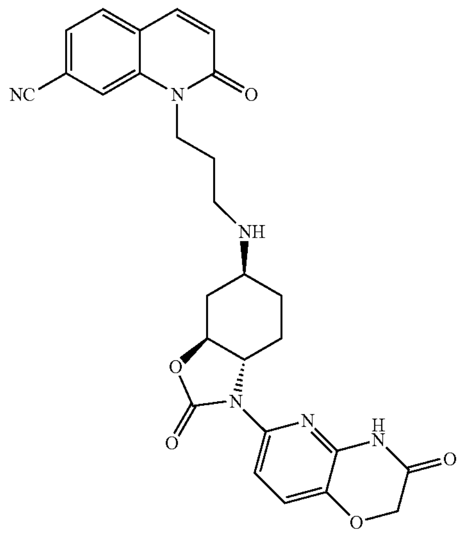

a) 7-bromo-1-(3,3-dimethoxypropyl)-1,2-dihydroquinolin-2-one 60a

A solution of 7-bromo-1,2-dihydroquinolin-2-one (1.5 g, 6.68 mmol), 3-bromo-1,1-dimethoxypropane (0.96 mL, 7.03 mmol) and cesium carbonate (6.54 g, 20.03 mmol) in DMF (100 mL) was heated overnight at 100° C. $H_2O$ (250 mL) was added, extracted with EtOAc (3×100 mL), dried with $MgSO_4$ and concentrated under reduced pressure. The residue was purified via silica gel chromatography eluting with (0-100% EtOAc in petroleum ether) to give a colourless solid as 7-bromo-1-(3,3-dimethoxypropyl)-1,2-dihydroquinolin-2-one 60a (740 mg, 34%). LC-MS (Method A) 296.0 $[M-OMe]^+$; RT 2.78 min.

b) 1-(3,3-dimethoxypropyl)-2-oxo-1,2-dihydroquinoline-7-carbonitrile 60b

A solution of 7-bromo-1-(3,3-dimethoxypropyl)-1,2-dihydroquinolin-2-one 60a (740 mg, 2.27 mmol), Palladium tetrakis (131 mg, 0.11 mmol) and zinc cyanide (159 mg, 1.4 mmol) in DMF (3 mL) was sealed in a microwave vial and irradiated at 150° C. for 90 min. $H_2O$ (50 mL) was added, extracted with EtOAc (3×30 mL), dried over $MgSO_4$ and concentrated under reduced pressure to give a yellow solid. Purification via silica gel chromatography eluting with (0-100% EtOAc in petroleum ether) gave 1-(3,3-dimethoxypropyl)-2-oxo-1,2-dihydroquinoline-7-carbonitrile 60b (340 mg, 51%). LC-MS (Method A) 241.1 [M−OMe]$^+$; RT 2.32 min.

c) 2-oxo-1-(3-oxopropyl)-1,2-dihydroquinoline-7-carbonitrile 60c

A solution of 1-(3,3-dimethoxypropyl)-2-oxo-1,2-dihydroquinoline-7-carbonitrile 60b in HCl (2M solution in THF, 5 mL) was stirred at room temperature for 2 h. $H_2O$ (20 mL) was added, extracted with EtOAc (3×30 mL), dried over $MgSO_4$ and concentrated under reduced pressure to give an off white solid 2-oxo-1-(3-oxopropyl)-1,2-dihydroquinoline-7-Carbonitrile 60c (210 mg, 82%). LC-MS (Method A) 227.5 [M+H]$^+$; RT 1.47 min.

d) (3aS,6S,7aS)-2-oxo-3-{3-oxo-2H,3H,4H-pyrido[3,2-b][1,4]oxazin-6-yl}-octahydro-1,3-benzoxazol-6-aminium trifluoroacetate 60d To a solution of tert-butyl N-[(3aS,6S,7aS)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]carbamate 29b (6.26 g, 11.93 mmol) in DCM (60 mL) under nitrogen, was added TFA (9.14 mL, 119.34 mmol) followed by $CF_3SO_3H$ (3.59 mL, 40.57 mmol) and the reaction was stirred for 4 h at room temperature. The reaction was quenched with MeOH (5 mL) and solvent removed in vacuo to afford a brown/white solid. To this was added MeOH (40 mL) and DCM (10 mL) and the mixture was sonicated for 20 min and filtered. The solid was suspended in DCM (40 mL), stirred for 20 min and filtered to give (3aS,6S,7aS)-2-oxo-3-{3-oxo-2H,3H,4H-pyrido[3,2-b][1,4]oxazin-6-yl}-octahydro-1,3-benzoxazol-6-aminium trifluoroacetate 60d (4.32 g, 10.33 mmol, 86%) as a white solid. LC-MS (Method A) 305.1 [M+H]$^+$; RT 1.68 min.

e) 1-(3-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}propyl)-2-oxo-1,2-dihydroquinoline-7-carbonitrile 60

(3aS,6S,7aS)-2-oxo-3-{3-oxo-2H,3H,4H-pyrido[3,2-b][1,4]oxazin-6-yl}-octahydro-1,3-benzoxazol-6-aminium trifluoroacetate 60d (130 mg, 0.43 mmol) and 2-oxo-1-(3-oxopropyl)-1,2-dihydroquinoline-7-Carbonitrile 60c (97 mg, 0.42 mmol) in DCM (5 mL) and triethylamine (0.17 mL and 1.28 mmol) were stirred for 2 h over molecular sieves (4 Å). $NaBH(OAc)_3$ (271 mg, 1.28 mmol) was added and the mixture stirred at room temperature for 2 h. Sat. aqueous $Na_2CO_3$ (20 mL) was added and the mixture extracted with DCM (3×20 mL), dried over $MgSO_4$ and concentrated under reduced pressure. The residue was purified by silica chromatography eluting with 0-10% MeOH in DCM to give 1-(3-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}propyl)-2-oxo-1,2-dihydroquinoline-7-carbonitrile 60 (16 mg, 8%) as a white solid. LC-MS (Method A) 515.3 [M+H]$^+$, RT 2.41 min. $^1$H NMR (Method C) ($CDCl_3$): δ ppm 8.00 (bs, 1H) 7.91 (d, J=1.5 Hz, 1H), 7.71 (d, J=9.5 Hz, 1H), 7.67 (d, J=8.0 Hz, 1H), 7.49 (d, J=8.0, 1H), 7.35-7.29 (m, 2H), 6.84 (d, J=9.5 Hz, 1H), 4.64 (s, 2H), 4.47-4.38 (m, 2H), 3.98 (td, J=11.8, 3.3 Hz, 1H), 3.86 (td, J=11.8, 3.3 Hz, 1H), 2.88-2.61 (m, 5H), 2.22 (d, J=12.7 Hz, 1H), 2.01-1.93 (m, 2H), 1.70-1.43 (m, 4H).

Example 61:—1-(2-{[(3aS,6S,7aS)-2-oxo-3-{3-oxo-2H,3H,4H-pyrido[3,2-b][1,4]thiazin-6-yl}-octahydro-1,3-benzoxazol-6-yl]amino}ethyl)-7-methoxy-1,2-dihydro-1,8-naphthyridin-2-one

61

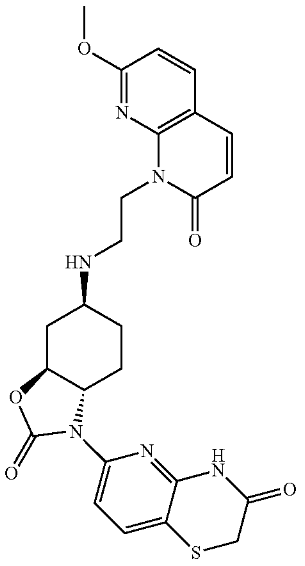

a) tert-butyl N-[(3aS,6S,7aS)-2-oxo-3-{3-oxo-2H,3H,4H-pyrido[3,2-b][1,4]thiazin-6-yl}-octahydro-1,3-benzoxazol-6-yl]carbamate 61a A solution of tert-butyl N-[(3aS,6S,7aS)-2-oxo-octahydro-1,3-benzoxazol-6-yl]carbamate 29a (1 g, 3.01 mmol), 6-chloro-2H,3H,4H-pyrido[3,2-b][1,4]thiazin-3-one (WO201408832 A1), $K_3PO_4$ (1.66 g, 7.8 mmol) and XPhos Pd G2 (306 mg, 0.39 mmol) in DMA (5 mL) was subjected to microwave irradiation at 150° C. for 90 min under nitrogen. On cooling $H_2O$ (20 mL) was added and the mixture extracted with EtOAc (3×20 mL), dried over $MgSO_4$ and concentrated under reduced pressure. The residue was purified by flash column chromatography eluting with 0-100% EtOAc in petroleum ether to give tert-butyl N-[(3aS,6S,7aS)-2-oxo-3-{3-oxo-2H,3H,4H-pyrido[3,2-b][1,4]thiazin-6-yl}-octahydro-1,3-benzoxazol-6-yl]carbamate 61a (800 mg, 48%) as a yellow oil. LC-MS (Method A) 421.4 [M+H]$^+$, RT 2.84 min.

b) (3aS,6S,7aS)-2-oxo-3-{3-oxo-2H,3H,4H-pyrido[3,2-b][1,4]thiazin-6-yl}-octahydro-1,3-benzoxazol-6-aminium chloride 61b A solution of tert-butyl N-[(3aS,6S,7aS)-2-oxo-3-{3-oxo-2H,3H,4H-pyrido[3,2-b][1,4]thiazin-6-yl}-octahydro-1,3-benzoxazol-6-yl]carbamate 61a (700 mg, 1.66 mmol) and HCl in MeOH (4M, 20 mL) in DCM (100 mL) was stirred at room temperature for 17 h. The reaction was concentrated in vacuo to give (3aS,6S,7aS)-2-oxo-3-{3-oxo-2H,3H,4H-pyrido[3,2-b][1,4]thiazin-6-yl}-octahydro-1,3-benzoxazol- 6-aminium chloride 61 b (600 mg, 100%) as a brown solid. LC-MS (Method A) 321.1 $[M+H]^+$, RT 2.05 min.

c) 1-(2-{[(3aS,6S,7aS)-2-oxo-3-{3-oxo-2H,3H,4H-pyrido[3,2-b][1,4]thiazin-6-yl}-octahydro-1,3-benzoxazol-6-yl]amino}ethyl)-7-methoxy-1,2-dihydro-1,8-naphthyridin-2-one 61

Prepared as described in example 60e using 2-(7-methoxy-2-oxo-1,2-dihydro-1,8-naphthyridin-1-yl)acetaldehyde (prepared as described in WO2008009700)(36.0 mg, 0.17 mmol) and (3aS,6S,7aS)-2-oxo-3-{3-oxo-2H,3H,4H-pyrido[3,2-b][1,4]thiazin-6-yl}-octahydro-1,3-benzoxazol-6-aminium chloride 61b (73.5 mg, 0.21 mmol) to afford 1-(2-{[(3aS,6S,7aS)-2-oxo-3-{3-oxo-2H,3H,4H-pyrido[3,2-b][1,4]thiazin-6-yl}-octahydro-1,3-benzoxazol-6-yl]amino}ethyl)-7-methoxy-1,2-dihydro-1,8-naphthyridin-2-one 61 (56.4 mg, 52.4%) as a colourless solid. LC-MS (Method A) 523.3 $[M+H]^+$, RT 2.60 min. $^1$H NMR (Method C) (DMSO-d6): δ ppm 10.97 (s, 1H), 8.06 (d, J=8.5, 1H), 7.87 (d, J=9.5, 1H), 7.79 (d, J=8.5, 1H), 7.29 (d, J=8.5, 1H), 6.74 (d, J=8.5, 1H), 6.50 (d, J=9.5, 1H), 4.43 (m, 2H), 4.05 (m, 1H), 4.00 (s, 3H), 3.74 (m, 1H), 3.57 (d, J=15, 1H), 3.51 (d, J=15, 1H), 2.95 (m, 1H), 2.88 (m, 2H), 2.80 (m, 1H), 1.46 (m, 1H), 1.30-1.21 (m, 4H)

Example 62:—1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydro-1,6-naphthyridin-2-one

62

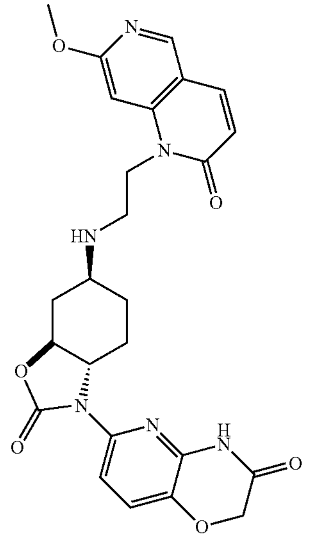

a) butyl (2E)-3-(4-amino-6-methoxypyridin-3-yl)prop-2-enoate 62a

Butyl prop-2-enoate (3.6 mL, 24.6 mmol) and triethylamine (10.3 mL, 73.9 mmol) were added to a sealed microwave vial under nitrogen containing 5-bromo-2-methoxypyridin-4-amine (500 mg, 2.46 mmol) and tetrakis (triphenylphosphine)palladium(0)(142.3 mg, 0.12 mmol). The reaction mixture was irradiated at 150° C. in a Biotage Initiator for 1.3 h, allowed to cool to room temperature and then vented. The reaction mixture was filtered to remove solid side-product which was washed with DCM (3×20 mL). The filtrate was collected and concentrated under reduced pressure to afford a residue which was taken up in H2O (20 mL) and EtOAc (20 mL) and the resulting layers separated. The aqueous layer was further extracted with EtOAc (2×20 mL) and the extracts combined with the original organic layer, dried ($MgSO_4$), filtered and concentrated under reduced pressure. The resulting crude product was purified via silica gel chromatography using a gradient of 0-50% EtOAc/DCM. Clean product fractions were collected and concentrated under reduced pressure to afford butyl (2E)-3-(4-amino-6-methoxypyridin-3-yl)prop-2-enoate 62a as a yellow solid (310 mg, 50%). LC-MS (Method A): 251.1 $[M+H]^+$, RT: 2.84 min.

b) 7-methoxy-1,2-dihydro-1,6-naphthyridin-2-one 62b

A solution of butyl (2E)-3-(4-amino-6-methoxypyridin-3-yl)prop-2-enoate 62a (310 mg, 1.24 mmol) in EtOH (40 mL) with 3 Å molecular sieves was stirred for 10 min under an atmosphere of nitrogen. Sodium hydride (60% dispersed in mineral oil, 49.5 mg, 1.24 mmol) was added to the reaction mixture and heated at 60° C. for 3 h under nitrogen. The reaction mixture was allowed to cool to room temperature, filtered and the filtrate quenched with saturated aqueous $NH_4Cl$ (10 mL). The resulting solid was filtered under vacuum to afford ethyl (2E)-3-(4-amino-6-methoxypyridin-3-yl)prop-2-enoate which was immediately taken up in EtOH (20 mL) and allowed to stand at room temperature in the presence of 3 Å molecular sieves under a nitrogen atmosphere for 17 h. Sodium hydride (60% dispersed in mineral oil, 134.9 mg, 3.37 mmol) was added to the reaction mixture and heated at 80° C. for 1 h under nitrogen. The reaction mixture was allowed to cool to room temperature, filtered and washed with EtOH (20 mL). The collected filtrate was quenched with sat. $NH_4Cl$ (20 mL) and $H_2O$ (20 mL) and then concentrated under reduced pressure until the precipitation of a white solid was observed. The solid was filtered, washed with $Et_2O$ (20 mL) and dried under vacuum to afford 7-methoxy-1,2-dihydro-1,6-naphthyridin-2-one 62b as a white solid (153 mg, 70%). LC-MS (Method A): 177.0 $[M+H]^+$, RT: 1.10 min.

c) 1-(2,2-dimethoxyethyl)-7-methoxy-1,2-dihydro-1,6-naphthyridin-2-one 62c 2-bromo-1,1-dimethoxyethane (0.15 mL, 1.25 mmol) was added to a saturated solution of 7-methoxy-1,2-dihydro-1,6-naphthyridin-2-one 62b (170 mg, 0.97 mmol) and cesium carbonate (408 mg, 1.25 mmol) in DMF (5 mL) and heated at 80° C. under nitrogen for 17 h. The reaction mixture was allowed to cool to room temperature, quenched with $H_2O$ (20 mL) and extracted with $Et_2O$ (4×40 mL). The combined organic extracts were dried ($MgSO_4$), filtered and concentrated under reduced pressure. The resulting crude product was purified via silica gel chromatography using a gradient of 0-100% EtOAc/DCM. Clean product fractions were collected and concentrated under reduced pressure to afford 1-(2,2-dimethoxyethyl)-7-methoxy-1,2-dihydro-1,6-naphthyridin-2-one 62c as a white solid (31 mg, 12%). LC-MS (Method A): 265.0 $[M+H]^+$, RT: 1.76 min.

d) 2-(7-methoxy-2-oxo-1,2-dihydro-1,6-naphthyridin-1-yl)acetaldehyde 62d

Aq. HCl (3M, 5 mL, 15 mmol) was added to a solution of 1-(2,2-dimethoxyethyl)-7-methoxy-1,2-dihydro-1,6-naphthyridin-2-one 62c (31 mg, 0.12 mmol) in THF (1 mL) and stirred at room temperature for 17 h. The reaction mixture was quenched with solid $NaHCO_3$ to pH 8 and diluted with $H_2O$ (20 mL). Volatile organic solvent was removed under reduced pressure and the resulting aqueous extracted with EtOAc (3×20 mL). The organic extracts were combined, dried ($MgSO_4$), filtered and concentrated under reduced pressure to afford an impure sample of 2-(7-methoxy-2-oxo-1,2-dihydro-1,6-naphthyridin-1-yl)acetaldehyde 62d as a white solid (30 mg, 117%). LC-MS (Method A): 219.0 $[M+H]^+$, RT: 1.47 min.

e) 1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydro-1,6-naphthyridin-2-one 62

Prepared as described in example 60e using 2-(7-methoxy-2-oxo-1,2-dihydro-1,6-naphthyridin-1-yl)acetaldehyde 62d (30 mg, 0.38 mmol) and (3aS,6S,7aS)-2-oxo-3-{3-oxo-2H,3H,4H-pyrido[3,2-b][1,4]oxazin-6-yl}-octahydro-1,3-benzoxazol-6-aminium trifluoroacetate 60d (63 mg, 0.15 mmol) to afford 1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydro-1,6-naphthyridin-2-one 62 as a white solid (10.9 mg, 16%). LC-MS (Method A): 507.1 $[M+H]^+$, RT: 2.18 min. $^1$H NMR (Method C) (DMSO-d6): δ ppm 11.2 (br. s, 1H), 8.56 (s, 1H), 7.92 (d, J=9.5 Hz, 1H), 7.42 (d, J=8.7 Hz, 1H), 7.18 (d, J=8.7 Hz, 1H), 6.90 (s, 1H), 6.48 (d, J=9.5 Hz, 1H), 4.63 (s, 2H), 4.16 (t, J=7.4 Hz, 2H), 4.05 (td, J=11.7, 3.3 Hz, 1H), 3.95 (s, 3H), 3.75 (td, J=11.1, 3.3 Hz, 1H), 3.81-2.74 (m, 3H), 2.59-2.53 (m, 1H), 2.00-1.95 (m, 2H), 1.38-1.25 (m, 3H).

Example 63:—(3aS,6S,7aS)-6-[(2-{3-methoxy-6-oxo-5H,6H-pyrido[2,3-b]pyrazin-5-yl}ethyl)amino]-3-{3-oxo-2H,3H,4H-pyrido[3,2-b][1,4]oxazin-6-yl}-octahydro-1,3-benzoxazol-2-one

63

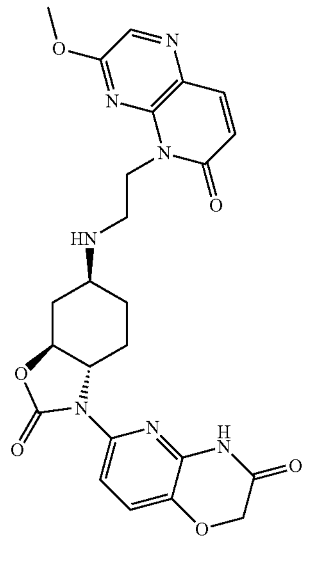

Prepared as described in Example 60e using 2-{3-methoxy-6-oxo-5H,6H-pyrido[2,3-b]pyrazin-5-yl}acetaldehyde (PCT Int. Appl., 2008009700)(48.2 mg, 0.22 mmol) and (3aS,6S,7aS)-2-oxo-3-{3-oxo-2H,3H,4H-pyrido[3,2-b][1,4]oxazin-6-yl}-octahydro-1,3-benzoxazol-6-aminium trifluoroacetate 60d (92 mg, 0.22 mmol) to afford (3aS,6S,7aS)-6-[(2-{3-methoxy-6-oxo-5H,6H-pyrido[2,3-b]pyrazin-5-yl}ethyl)amino]-3-{3-oxo-2H,3H,4H-pyrido[3,2-b][1,4]oxazin-6-yl}-octahydro-1,3-benzoxazol-2-one 63 (45 mg, 40.3%). LC-MS (Method A) 508.3 $[M+H]^+$; RT 2.15 min. $^1$H NMR (Method C) (DMSO-d6): δ ppm 11.24 (s, 1H), 8.23 (s, 1H), 7.96 (d, J=9.5 Hz, 1H), 7.41 (d, J=8.5 Hz, 1H), 7.18 (d, J=8.5 Hz, 1H), 6.74 (d, J=9.5 Hz, 1H), 4.62 (s, 2H), 4.39 (t, J=7.2 Hz, 2H), 4.11-4.01 (m, 4H), 3.75 (td, J=11.2, 3.4 Hz, 1H), 2.91-2.72 (m, 4H), 2.45-2.42 (m, 1H), 2.06 (br. s, 1H), 1.99-1.96 (m, 1H), 1.46 (q, J=11.2 Hz, 1H), 1.33 (m, 1H), 1.28-1.16 (m, 1H).

Example 64:—4-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-3,4-dihydroquinoxaline-6-carbonitrile

64

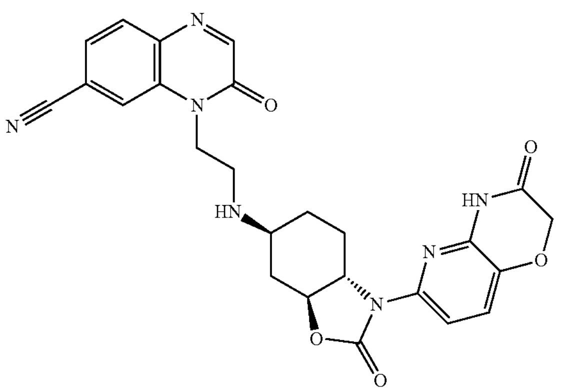

Prepared as described in example 60e using (3aS,6S,7aS)-2-oxo-3-{3-oxo-2H,3H,4H-pyrido[3,2-b][1,4]oxazin-6-yl}-octahydro-1,3-benzoxazol-6-aminium trifluoroacetate 60d (313 mg, 0.75 mmol) and 3-oxo-4-(2-oxoethyl)-3,4-dihydroquinoxaline-6-carbonitrile (prepared as described in WO2006137485) (143.6 mg, 0.67 mmol) to afford 4-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-3-oxo-3,4-dihydroquinoxaline-6-carbonitrile 64 (245 mg, 65%) as a pale orange solid. LC-MS (Method B) 502.1 $[M+H]^+$; RT 6.24 min. $^1$H NMR (Method C) ($CDCl_3$): δ ppm 8.40 (s, 1H), 8.00 (d, J=8.2 Hz, 1H), 7.75 (d, J=1.6 Hz, 1H), 7.61 (dd, J=8.2, 1.6 Hz, 1H), 7.34-7.30 (m, 2H), 4.63 (s, 2H), 4.35 (t, J=6.8 Hz, 2H), 3.95 (td, J=11.8, 3.4 Hz, 1H), 3.79 (td, J=11.0, 3.4 Hz, 1H), 3.14-3.04 (m, 2H), 2.88-2.81 (m, 1H), 2.71-2.66 (m, 1H), 2.60-2.56 (m, 1H), 2.14-2.08 (m, 1H), 1.56-1.48 (m, 1H), 1.41-1.31 (m, 2H).

Example 65:—1-(2-{[(3aS,6S,7aR)-2-oxo-3-{7-oxo-6H,7H,8H-pyrimido[5,4-b][1,4]oxazin-2-yl}-octahydro-1,3-benzoxazol-6-yl]amino}ethyl)-6,7-difluoro-1,2-dihydroquinoxalin-2-one

65

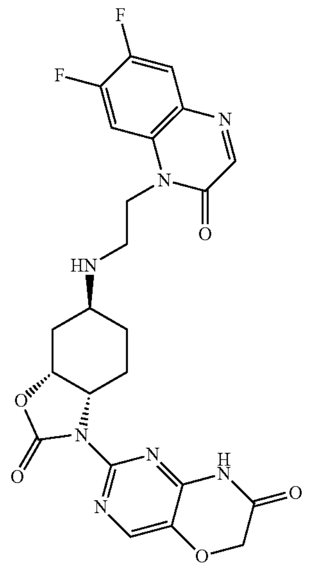

a) 1-(2-{[(3aS,6S,7aR)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]amino}ethyl)-6,7-difluoro-1,2-dihydroquinoxalin-2-one 65a Prepared as in the method described in example 16d using (3aS,6S,7aR)-6-amino-3-{8-[(4-methoxyphenyl)methyl]-7-oxo-6H,7H,8H-pyrimido[5,4-b][1,4]oxazin-2-yl}-octahydro-1,3-benzoxazol-2-one 16c (113.9 mg, 0.27 mmol) and 2-(6,7-difluoro-2-oxo-1,2-dihydroquinoxalin-1-yl)acetaldehyde (60.0 mg, 0.27 mmol) (prepared as described in WO2008009700) to afford 1-(2-{[(3aS,6S,7aR)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]amino}ethyl)-6,7-difluoro-1,2-dihydroquinoxalin-2-one 65a (195 mg, 115%)—used without purification. LC-MS (Method A) 634.1 $[M+H]^+$; RT 2.53 min.

b) 1-(2-{[(3aS,6S,7aR)-2-oxo-3-{7-oxo-6H,7H,8H-pyrimido[5,4-b][1,4]oxazin-2-yl}-octahydro-1,3-benzoxazol-6-yl]amino}ethyl)-6,7-difluoro-1,2-dihydroquinoxalin-2-one 65

Prepared as in the method described in Example 16e using 1-(2-{[(3aS,6S,7aR)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]amino}ethyl)-6,7-difluoro-1,2-dihydroquinoxalin-2-one 65a (195.0 mg, 0.31 mmol). The crude material was purified via silica gel chromatography using 0-20% MeOH/DCM followed by prep. HPLC (Method B) 0.1% $NH_3$ in $MeCN/H_2O$ to afford 1-(2-{[(3aS,6S,7aR)-2-oxo-3-{7-oxo-6H,7H,8H-pyrimido[5,4-b][1,4]oxazin-2-yl}-octahydro-1,3-benzoxazol-6-yl]amino}ethyl)-6,7-difluoro-1,2-dihydroquinoxalin-2-one 65 (4.8 mg, 3%). LC-MS (Method A) 514.2 $[M+H]^+$; RT 1.79 min. $^1H$ NMR (Method C) (DMSO-d6): δ ppm 8.26 (s, 1H), 8.19 (s, 1H), 8.05-7.74 (m, 2H), 4.74-4.67 (m, 3H), 4.43-4.35 (m, 1H), 4.28-4.17 (m, 2H), 2.87-2.78 (m, 2H), 2.73-2.61 (m, 1H), 2.47-2.37 (m, 1H), 2.20-2.13 (m, 1H), 1.82-1.67 (m, 1H), 1.54-1.45 (m, 1H), 1.41-1.26 (m, 1H), 1.08-0.92 (m, 1H).

Example 66:—1-(2-{[(3aS,6S,7aS)-2-oxo-3-{7-oxo-6H,7H,8H-pyrimido[5,4-b][1,4]oxazin-2-yl}-octahydro-1,3-benzoxazol-6-yl]amino}ethyl)-6,7-difluoro-1,2-dihydroquinoxalin-2-one

66

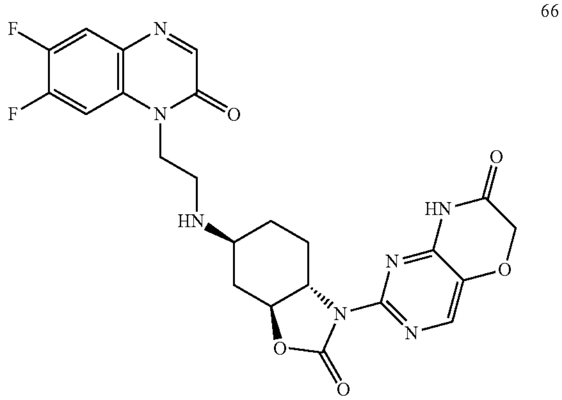 [SMILES: O=C1COc2cnc(N3C(=O)O[C@H]4C[C@@H](NCCn5c(=O)cnc6cc(F)c(F)cc65)CC[C@@H]43)nc2N1]

a) tert-butyl N-[(3aS,6S,7aS)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]carbamate 66a A solution of a 2:1 mixture of 2-bromo-8-[(4-methoxyphenyl)methyl]-6H,7H,8H-pyrimido[5,4-b][1,4]oxazin-7-one and 2-chloro-8-[(4-methoxyphenyl)methyl]-6H,7H,8H-pyrimido[5,4-b][1,4]oxazin-7-one 16a (1.37 g, 3.9 mmol), tert-butyl N-[(3aS,6S,7aS)-2-oxo-octahydro-1,3-benzoxazol-6-yl]carbamate 29a (1.00 g, 3.9 mmol), trans-1,2-diaminocyclohexane (89.1 mg, 0.78 mmol), CuI (148.6 mg, 0.78 mmol) and $K_2CO_3$ (1.08 g, 7.8 mmol) in 1,4-Dioxane (35 mL) was stirred at 110° C. for 17 h. CuI (148.6 mg, 0.78 mmol) and trans-1,2-diaminocyclhexane (89.1 mg, 0.78 mmol) were added and the mixture stirred at 110° C. for a further 17 h. The reaction was allowed to cool to room temperature and the remaining solid was filtered, washed with EtOAc and the filtrate concentrated under reduced pressure. The resulting residue was purified via silica gel chromatography using 0-100% EtOAc in DCM to afford tert-butyl N-[(3aS,6S,7aS)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]carbamate 66a (514.0 mg, 25%) as a white solid. LC-MS (Method A) 526.3 $[M+H]^+$; RT 2.94 min.

b) (3aS,6S,7aS)-6-amino-3-{8-[(4-methoxyphenyl)methyl]-7-oxo-6H,7H,8H-pyrimido[5,4-b][1,4]oxazin-2-yl}-octahydro-1,3-benzoxazol-2-one 66b TFA (4.8 mL, 62.7 mmol) was added to a solution of tert-butyl N-[(3aS,6S,7aS)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]carbamate 66a (514 mg, 0.98 mmol) in DCM (15 mL) and stirred at room temperature for 1 h. The reaction mixture was concentrated under reduced pressure and the resulting residue dissolved in DCM (10 mL), washed with sat. aq. $NaHCO_3$, brine (1 mL) and passed through a SPE phase separator. The aqueous phase was further extracted with a mixture of DCM:MeOH (4:1, 25 mL) and passed through a SPE phase separator. The organic filtrates were combined and concentrated under reduced pressure to afford. (3aS,6S,7aS)-6-amino-3-{8-[(4-methoxyphenyl)methyl]-7-oxo-6H,7H,8H-pyrimido[5,4-b][1,4]oxazin-2-yl}-octahydro-1,3-benzoxazol-2-one 66b (214 mg, 51%). $^1H$ NMR (Method C) (DMSO-d6): δ ppm 8.32 (s, 1H), 7.48-7.26 (m, 2H), 6.97-6.74 (m, 2H), 5.14-5.04 (m, 2H), 4.97-4.88 (m, 2H), 4.13-4.00 (m, 1H), 3.80-3.72 (m, 1H), 3.72 (s, 3H), 2.87-2.79 (m, 1H), 2.32-2.26 (m, 1H), 2.14-2.06 (m, 1H), 2.09-1.94 (m, 2H), 1.81-1.74 (m, 1H), 1.56-1.46 (m, 1H), 1.28-1.15 (m, 2H).

c) 1-(2-{[(3aS,6S,7aS)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]amino}ethyl)-6,7-difluoro-1,2-dihydroquinoxalin-2-one 66c A solution of 2-(6,7-difluoro-2-oxo-1,2-dihydroquinoxalin-1-yl)acetaldehyde (50.0 mg, 0.22 mmol) and (3aS,6S,7aS)-6-amino-3-{8-[(4-methoxyphenyl)methyl]-7-oxo-6H,7H,8H-pyrimido[5,4-b][1,4]oxazin-2-yl}-octahydro-1,3-benzoxazol-2-one 66b (94.9 mg, 0.22 mmol) in DCM (15 mL) was stirred at room temperature over molecular sieves (3 Å) for 2 h. $NaBH(OAc)_3$ (189.1 mg, 0.89 mmol) was added and the reaction stirred at room temperature for a further 3 h. The reaction was adjusted to pH 8 with saturated aqueous $NaHCO_3$ and passed through a SPE phase separator. The organic filtrate was concentrated under reduced pressure to afford 1-(2-{[(3aS,6S,7aS)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]amino}ethyl)-6,7-difluoro-1,2-dihydroquinoxalin-2-one 66c which used without purification. (assumed quantitative). LC-MS (Method A) 634.3 $[M+H]^+$; RT 2.65 min.

d) 1-(2-{[(3aS,6S,7aS)-2-oxo-3-{7-oxo-6H,7H,8H-pyrimido[5,4-b][1,4]oxazin-2-yl}-octahydro-1,3-benzoxazol-6-yl]amino}ethyl)-6,7-difluoro-1,2-dihydroquinoxalin-2-one 66

TFA (1.01 mL, 13.2 mmol) and $CF_3SO_3H$ (0.23 mL, 2.63 mmol) were added to a solution of 1-(2-{[(3aS,6S,7aS)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]amino}ethyl)-6,7-difluoro-1,2-dihydroquinoxalin-2-one 66c (238. mg, 0.38 mmol) in DCM (15 mL) and the reaction stirred at room temperature for 140 h. The reaction was quenched with MeOH (5 mL), neutralised with saturated aqueous $NaHCO_3$, diluted with DCM (30 mL) and passed through an SPE phase separator. The organic filtrate was concentrated under reduced pressure and the resulting residue purified via silica gel chromatography using 0-20% MeOH in DCM. Clean product fractions were collected and concentrated under reduced pressure to afford an off white residue. The residue was dissolved in a minimum volume of DCM and $Et_2O$ added until a precipitate crashed out. Solvent was removed under reduced pressure to afford 1-(2-{[(3aS,6S,7aS)-2-oxo-3-{7-oxo-6H,7H,8H-pyrimido[5,4-b][1,4]oxazin-2-yl}-octahydro-1,3-benzoxazol-6-yl]amino}ethyl)-6,7-difluoro-1,2-dihydroquinoxalin-2-one 66 (11.9 mg, 6%) as an off white solid. LC-MS (Method A) 514.2 $[M+H]^+$; RT 1.77 min. $^1H$ NMR (Method C) (DMSO-d6): δ ppm 8.26 (s, 1H), 8.25 (s, 1H), 7.99-7.88 (m, 2H), 4.79-4.67 (m, 2H), 4.27-4.17 (m, 2H), 4.10-3.99 (m, 1H), 3.84-3.74 (m, 1H), 2.90-2.74 (m, 3H), 2.44-2.36 (m, 2H), 1.99-1.90 (m, 1H), 1.52-1.40 (m, 1H), 1.38-1.03 (m, 2H).

Example 67:—1-(2-{[(3aS,6S,7aS)-2-oxo-3-{7-oxo-6H,7H,8H-pyrimido[5,4-b][1,4]oxazin-2-yl}-octahydro-1,3-benzoxazol-6-yl]amino}ethyl)-7-methoxy-1,2-dihydro-1,8-naphthyridin-2-one

67

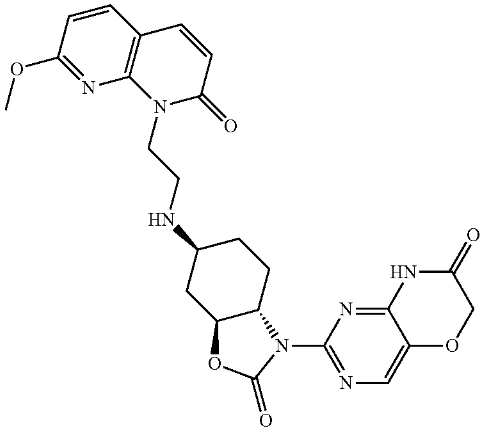

a) 1-(2-{[(3aS,6S,7aS)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]amino}ethyl)-7-methoxy-1,2-dihydro-1,8-naphthyridin-2-one 67a Prepared as described in example 66c using (3aS,6S,7aS)-6-amino-3-{8-[(4-methoxyphenyl)methyl]-7-oxo-6H,7H,8H-pyrimido[5,4-b][1,4]oxazin-2-yl}-octahydro-1,3-benzoxazol-2-one 66b (97.5 mg, 0.23 mmol) and 2-(7-methoxy-2-oxo-1,2-dihydro-1,8-naphthyridin-1-yl)acetaldehyde (50 mg, 0.23 mmol) (prepared as described in WO2008009700). The crude material was purified via silica gel chromatography using 0-20% MeOH in DCM to afford 1-(2-{[(3aS,6S,7aS)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]amino}ethyl)-7-methoxy-1,2-dihydro-1,8-naphthyridin-2-one 67a (130 mg, 90%). LC-MS (Method A) 628.3 $[M+H]^+$; RT 2.31 min b) 1-(2-{[(3aS,6S,7aS)-2-oxo-3-{7-oxo-6H,7H,8H-pyrimido[5,4-b][1,4]oxazin-2-yl}-octahydro-1,3-benzoxazol-6-yl]amino}ethyl)-7-methoxy-1,2-dihydro-1,8-naphthyridin-2-one 67

Prepared as described in example 66d using 1-(2-{[(3aS,6S,7aS)-3-{8-[(4-methoxyphenyl)methyl]-7-oxo-6H,7H,8H-pyrimido[5,4-b][1,4]oxazin-2-yl}-2-oxo-octahydro-1,3-benzoxazol-6-yl]amino}ethyl)-7-methoxy-1,2-dihydro-1,8-naphthyridin-2-one 67a (130.2 mg, 0.21 mmol). The crude material was purified via silica gel chromatography using 0-20% MeOH/DCM to afford 1-(2-{[(3aS,6S,7aS)-2-oxo-3-{7-oxo-6H,7H,8H-pyrimido[5,4-b][1,4]oxazin-2-yl}-octahydro-1,3-benzoxazol-6-yl]amino}ethyl)-7-methoxy-1,2- dihydro-1,8-naphthyridin-2-one 67 (33.8 mg, 32%) as an off white solid. LC-MS (Method B) 508.2 [M+H]$^+$; RT 4.54 min. $^1$H NMR (Method C) (DMSO-d6): δ ppm 8.25 (s, 1H), 8.06 (d, J=8.5 Hz, 1H), 7.87 (d, J=9.4 Hz, 1H), 6.74 (d, J=8.5 Hz, 1H), 6.51 (d, J=9.4 Hz, 1H), 4.79-4.67 (m, 2H), 4.48-4.38 (m, 2H), 4.09-4.02 (m, 1H), 4.00 (s, 3H), 3.83-3.76 (m, 1H), 2.95-2.85 (m, 2H), 2.85-2.76 (m, 1H), 2.47-2.39 (m, 2H), 2.03-1.94 (m, 1H), 1.52-1.43 (m, 1H), 1.40-1.16 (m, 2H).

Example 68:—4-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-3-oxo-3,4-dihydroquinoxaline-6-carbonitrile

68

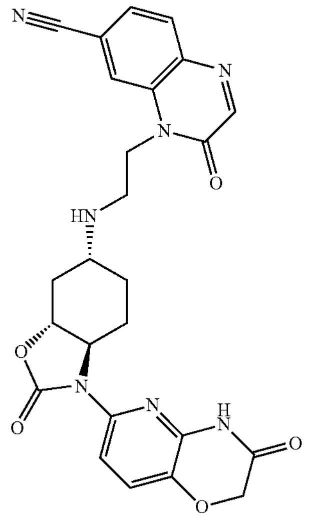

Prepared as described in the method in Example 60e using 3-oxo-4-(2-oxoethyl)-3,4-dihydroquinoxaline-6-carbonitrile (WO 2006137485 A1 (95 mg, 0.45 mmol) and (3aR,6R,7aR)-2-oxo-3-{3-oxo-2H,3H,4H-pyrido[3,2-b][1,4]oxazin-6-yl}-octahydro-1,3-benzoxazol-6-aminium trifluoroacetate 74a (205 mg, 0.49 mmol) to afford 4-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-3-oxo-3,4-dihydroquinoxaline-6-carbonitrile 68 (91 mg, 39%). LC-MS (Method A) 502.2 [M+H]$^+$; RT 2.31 min. $^1$H NMR (Method C) (DMSO-d6): δ ppm 11.25 (s, 1H), 8.39 (s, 1H), 8.29 (s, 1H), 7.98 (d, J=7.8 Hz, 1H), 7.78 (d, J=7.8 Hz, 1H), 7.41 (d, J=8.3 Hz, 1H), 7.18 (d, J=8.3 Hz, 1H), 4.62 (s, 2H), 4.27 (t, J=6.8 Hz, 2H), 4.05 (td, J=11.2, 3.4 Hz, 1H), 3.76 (td, J=11.2, 3.4 Hz, 1H), 2.92-2.85 (m, 2H), 2.81-2.74 (m, 2H), 2.44-2.39 (m, 1H), 2.14-2.07 (m, 1H), 1.97-1.91 (m, 1H), 1.45 (q, J=11.1 Hz, 1H), 1.33 (q, J=11.1 Hz, 1H), 1.20 (q, J=11.1 Hz, 1H).

Example 69:—1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydro-1,5-naphthyridin-2-one

69

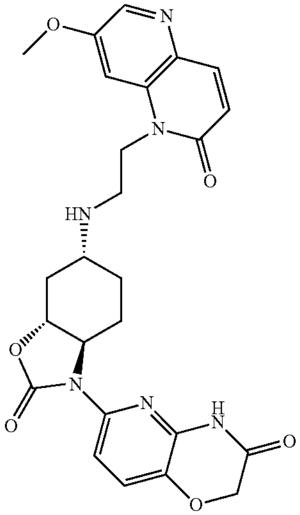

Prepared as described in Example 60e using 2-(7-methoxy-2-oxo-1,5-naphthyridin-1-yl)acetaldehyde (77 mg, 0.35 mmol) (prepared as described in WO2011148962A1) and (3aR,6R,7aR)-2-oxo-3-{3-oxo-2H,3H,4H-pyrido[3,2-b][1,4]oxazin-6-yl}-octahydro-1,3-benzoxazol-6-aminium trifluoroacetate 74a (53.2 mg, 0.24 mmol) and (102 mg, 0.24 mmol) to afford 1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydro-1,5-naphthyridin-2-one 69 (20 mg, 16%) as a colourless solid. LC-MS (Method D) 507.2 [M+H]$^+$, RT 1.81 min. $^1$H NMR (Method E) (DMSO-d6): δ ppm 11.21 (s, 1H), 8.29 (d, J=2.5, 1H), 7.87 (d, J=9.5, 1H), 7.50 (d, J=8.5, 1H), 7.41 (d, J=8.5, 1H), 7.16 (d, J=8.5, 1H), 6.67 (d, J=9.5, 1H), 4.61 (s, 2H), 4.28 (t, J=7.0, 2H), 4.03 (m, 1H), 3.99 (s, 3H), 3.74 (m, 1H), 3.17 (d, J=5.0, 1H), 2.85-2.74 (m, 4H), 2.12 (m, 1H), 1.97 (m, 1H), 1.45 (q, J=11.0, 1H), 1.31 (m, 1H), 1.22 (m, 1H)

Example 70:—1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-6,7-difluoro-1,2-dihydroquinoxalin-2-one

70

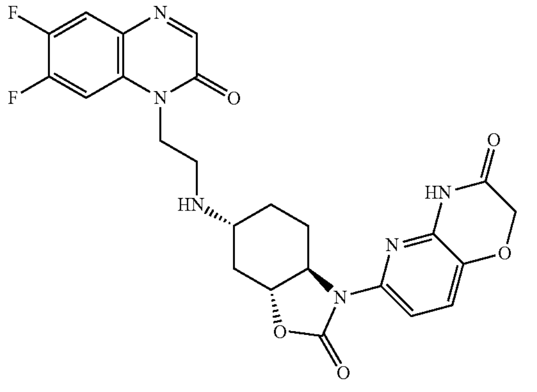

Prepared as described in example 60e using (3aR,6R,7aR)-2-oxo-3-{3-oxo-2H,3H,4H-pyrido[3,2-b][1,4]oxazin-6-yl}-octahydro-1,3-benzoxazol-6-aminium trifluoroacetate 74a (200.0 mg, 0.48 mmol) and 2-(6,7-difluoro-2-oxo-1,2-dihydroquinoxalin-1-yl)acetaldehyde (prepared as described in WO2008009700) (96.5 mg, 0.43 mmol) to afford 1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-6,7-difluoro-1,2-dihydroquinoxalin-2-one 70 (132.5 mg, 54%) as an orange solid. LC-MS (Method B) 513.2 $[M+H]^+$; RT 6.52 min. $^1H$ NMR (Method C) (DMSO-d6): δ ppm 11.20 (br s, 1H), 8.27 (s, 1H), 8.00-7.89 (m, 2H), 7.42 (d, J=8.6 Hz, 1H), 7.17 (d, J=8.6, 1H), 4.62 (s, 2H), 4.22 (t, J=6.9 Hz, 2H), 4.04 (td, J=11.8, 3.3 Hz, 1H), 3.74 (td, J=11.1, 3.3 Hz, 1H), 2.88-2.82 (m, 2H), 2.81-2.71 (m, 2H), 2.43-2.38 (m, 1H), 2.09 (br s, 1H), 1.99-1.91 (m, 1H), 1.44 (q, J=11.1 Hz, 1H), 1.37-1.27 (m, 1H), 1.24-1.14 (m, 1H).

Example 71:—6-[3-({[(3aS,6S,7aS)-2-oxo-3-{3-oxo-2H,3H,4H-pyrido[3,2-b][1,4]oxazin-6-yl}-octahydro-1,3-benzoxazol-6-yl]amino}methyl)phenyl]pyridine-3-carbonitrile

71

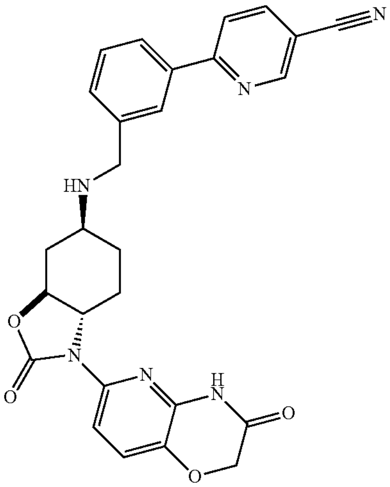

Prepared as in the method described in example 60e using 6-(3-formylphenyl)pyridine-3-carbonitrile (WO2014170821) (140.0 mg, 0.67 mmol) and (3aS,6S,7aS)-2-oxo-3-{3-oxo-2H,3H,4H-pyrido[3,2-b][1,4]oxazin-6-yl}-octahydro-1,3-benzoxazol-6-aminium trifluoroacetate 60d (305.5 mg, 0.67 mmol) to afford 6-[3-({[(3aS,6S,7aS)-2-oxo-3-{3-oxo-2H,3H,4H-pyrido[3,2-b][1,4]oxazin-6-yl}-octahydro-1,3-benzoxazol-6-yl]amino}methyl)phenyl]pyridine-3-carbonitrile 71 (31.4 mg, 9%) LC-MS (Method A) 497.8 [M+H]*; RT 2.07 min. $^1H$ NMR (Method C) ($CDCl_3$): δ ppm 8.96 (dd, J=2.2, 0.9 Hz, 1H), 8.06 (s, 1H), 8.03 (dd, J=8.3, 2.2 Hz, 1H), 7.95-7.90 (m, 1H), 7.88 (dd, J=8.4, 0.9 Hz, 1H), 7.81 (s, 1H), 7.52-7.46 (m, 2H), 7.36-7.29 (m, 2H), 4.64 (s, 2H), 4.01-3.91 (m, 3H), 3.82 (td, J=11.0, 3.2 Hz, 1H), 2.88 (td, J=10.9, 5.3 Hz, 1H), 2.75-2.64 (m, 2H), 2.19 (d, J=12.2 Hz, 1H), 1.69-1.18 (m, 3H).

Example 72:—(3aR,6R,7aR)-6-({[2-hydroxy-3-(5-methoxypyridazin-3-yl)phenyl]methyl}amino)-3-{3-oxo-2H,3H,4H-pyrido[3,2-b][1,4]oxazin-6-yl}-octahydro-1,3-benzoxazol-2-one

72

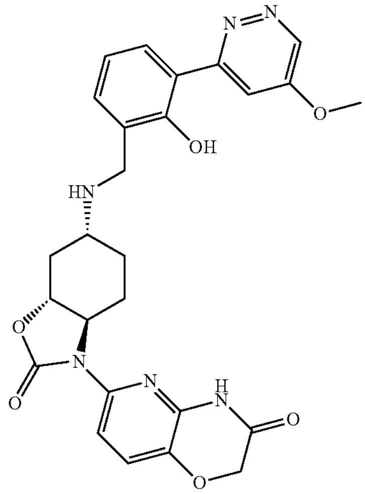

a) 2-(benzyloxy)-3-(5-methoxypyridazin-3-yl)benzaldehyde 72a

A mixture of 2-(benzyloxy)-3-(4,4,5,5-tetramethyl-1,3-dioxolan-2-yl)benzaldehyde (250 mg, 0.74 mmol)(prepared as in the method described for the intermediate in example 18b starting from 18a), 3-chloro-5-methoxypyridazine (0.09 mL, 0.74 mmol), (XPhos)(35.24 mg, 0.07 mmol), XPhos Pd G2 (58.3 mg, 0.07 mmol) and $CsCO_3$ (722 mg, 2.22 mmol) in a mixture of monoglyme (2.4 mL) and $H_2O$ (0.4 mL) (deoxygenated by bubbling N2 through) was stirred at 60° C. for 24 h. The mixture was allowed to cool, diluted with EtOAc (10 mL) and washed with $H_2O$ (4 mL). The organic phase was dried ($MgSO_4$) and the resultant material purified by silica gel chromatography using 40-100% EtOAc in petroleum ether to afford 2-benzyloxy-3-(5-methoxy-pyridazin-3-yl)benzaldehyde (134 mg, 56.6%). LC-MS (Method A) 321.0 [M+H]*; RT 2.51 min. $^1H$ NMR (Method C) ($CDCl_3$): δ ppm 10.37 (d, J=0.8 Hz, 1H), 8.90 (d, J=3.0 Hz, 1H), 8.21 (dd, J=7.6, 1.9 Hz, 1H), 7.98 (dd, J=7.7, 1.9 Hz, 1H), 7.50-7.39 (m, 2H), 7.34-7.27 (m, 3H), 7.16-7.10 (m, 2H), 4.75 (s, 2H), 3.73 (s, 3H).

b) (3aR,6R,7aR)-6-({[2-(benzyloxy)-3-(5-methoxy-pyridazin-3-yl)phenyl]methyl}amino)-3-{4-[(4-methoxyphenyl)methyl]-3-oxo-2H,3H,4H-pyrido[3,2-b][1,4]oxazin-6-yl}-octahydro-1,3-benzoxazol-2-one 72b Prepared as in the method described in example 1d using (3aR,6R,7aR)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one 1c (160. mg, 0.3800 mmol) and 2-(benzyloxy)-3-(5-methoxypyridazin-3-yl)benzaldehyde 72a (126.19 mg, 0.3900 mmol) to afford (3aR,6R,7aR)-6-({[2-(benzyloxy)-3-(5-methoxypyridazin-3-yl)phenyl]methyl}amino)-3-{4-[(4-methoxyphenyl)methyl]-3-oxo-2H,3H,4H-pyrido[3,2-b][1,4]oxazin-6-yl}-octahydro- 1,3-benzoxazol-2-one 72b (59 mg, 22%). $^1$H NMR (Method C) ($CDCl_3$): δ ppm 8.87 (d, J=3.0, 1.5 Hz, 1H), 7.84 (dd, J=7.7, 1.7 Hz, 1H), 7.47 (dd, J=7.6, 1.8 Hz, 1H), 7.44 (d, J=2.9, 1.9 Hz, 1H), 7.34-7.26 (m, 6H), 7.21-7.13 (m, 4H), 6.85-6.77 (m, 2H), 5.19 (s, 2H), 4.71 (s, 2H), 4.66-4.59 (m, 2H), 3.95-3.82 (m, 3H), 3.79-3.69 (m, 7H), 2.76 (dq, J=10.4, 5.1, 4.3 Hz, 1H), 2.64-2.55 (m, 1H), 2.33-2.25 (m, 1H), 1.98 (d, J=11.7 Hz, 1H), 1.56 (q, J=11.3 Hz, 1H), 1.36-1.19 (m, 2H).

c) (3aR,6R,7aR)-6-({[2-hydroxy-3-(5-methoxy-pyridazin-3-yl)phenyl]methyl}amino)-3-{3-oxo-2H,3H,4H-pyrido[3,2-b][1,4]oxazin-6-yl}-octahydro-1,3-benzoxazol-2-one 72

Prepared as in the method described in Example 1d using (3aR,6R,7aR)-6-({[2-(benzyloxy)-3-(5-methoxypyridazin-3-yl)phenyl]methyl}amino)-3-{4-[(4-methoxyphenyl)methyl]-3-oxo-2H,3H,4H-pyrido[3,2-b][1,4]oxazin-6-yl}-octahydro-1,3-benzoxazol-2-one 72b (50.1 mg, 0.07 mmol) to afford (3aR,6R,7aR)-6-({[2-hydroxy-3-(5-methoxy-pyridazin-3-yl)phenyl]methyl}amino)-3-{3-oxo-2H,3H,4H-pyrido[3,2-b][1,4]oxazin-6-yl}-octahydro-1,3-benzoxazol-2-one 72 (10 mg, 28% yield). LC-MS (Method A) 519.2 $[M+H]^+$; RT 2.51 min. $^1$H NMR (Method C) ($CDCl_3$): δ ppm 8.77 (d, J=2.8 Hz, 1H), 7.69 (d, J=8.1 Hz, 1H), 7.44-7.38 (m, 2H), 7.33-7.26 (m, 2H), 6.95 (t, J=7.7 Hz, 1H), 4.62 (d, J=1.2 Hz, 2H), 4.27-3.70 (m, 7H), 3.09-2.98 (m, 1H), 2.80-2.66 (m, 2H), 2.30-2.20 (m, 1H), 1.85-1.75 (m, 1H), 1.69-1.56 (m, 1H), 1.46-1.34 (m, 1H).

Example 73:—(3aS,6S,7aS)-6-({[3-(6-methoxypyridin-2-yl)phenyl]methyl}amino)-3-{3-oxo-2H,3H,4H-pyrido[3,2-b][1,4]oxazin-6-yl}-octahydro-1,3-benzoxazol-2-one

73

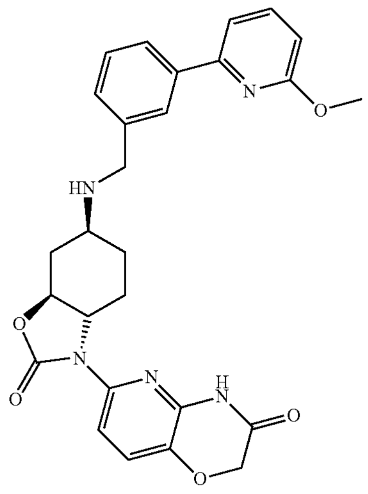

a) (3aS,6S,7aS)-3-{4-[(4-methoxyphenyl)methyl]-3-oxo-2H,3H,4H-pyrido[3,2-b][1,4]oxazin-6-yl}-6-({[3-(6-methoxypyridin-2-yl)phenyl]methyl}amino)-octahydro-1,3-benzoxazol-2-one 73a Prepared as in the method described in example 29d using (3aS,6S,7aS)-6-amino-3-{4-[(4-methoxyphenyl)methyl]-3-oxo-2H,3H,4H-pyrido[3,2-b][1,4]oxazin-6-yl}-octahydro-1,3-benzoxazol-2-one (188.0 mg, 0.44 mmol) 29c and 3-(6-methoxypyridin-2-yl)benzaldehyde (103.9 mg, 0.49 mmol) (prepared according to WO 2014170821) to afford (3aS,6S,7aS)-3-{4-[(4-methoxyphenyl)methyl]-3-oxo-2H,3H,4H-pyrido[3,2-b][1,4]oxazin-6-yl}-6-({[3-(6-methoxypyridin-2-yl)phenyl]methyl}amino)-octahydro-1,3-benzoxazol-2-one 73a (137.0 mg, 50% yield). LC-MS (Method A) 622.3 $[M+H]^+$; RT 3.33 min. $^1$H NMR (Method C) ($CDCl_3$): δ ppm 7.99 (d, J=1.8 Hz, 1H), 7.95 (dt, J=7.8, 1.5 Hz, 1H), 7.64 (dd, J=8.2, 7.4 Hz, 1H), 7.44 (t, J=7.6 Hz, 1H), 7.39-7.34 (m, 2H), 7.32-7.26 (m, 2H), 7.22-7.16 (m, 2H), 6.85-6.79 (m, 2H), 6.71 (dd, J=8.2, 0.7 Hz, 1H), 5.19 (s, 2H), 4.71 (s, 2H), 4.05 (s, 3H), 3.98-3.88 (m, 3H), 3.76 (s, 4H), 2.84 (td, J=10.7, 5.2 Hz, 1H), 2.67 (d, J=11.2 Hz, 1H), 2.28 (dd, J=11.9, 3.3 Hz, 1H), 2.01 (s, 1H), 1.63 (q, J=11.3 Hz, 1H), 1.38-1.26 (m, 2H).

b) (3aS,6S,7aS)-6-({[3-(6-methoxypyridin-2-yl)phenyl]methyl}amino)-3-{3-oxo-2H,3H,4H-pyrido[3,2-b][1,4]oxazin-6-yl}-octahydro-1,3-benzoxazol-2-one 73

Prepared as in the method described in example 1e using (3aS,6S,7aS)-3-{4-[(4-methoxyphenyl)methyl]-3-oxo-2H,3H,4H-pyrido[3,2-b][1,4]oxazin-6-yl}-6-({[3-(6-methoxy-pyridin-2-yl)phenyl]methyl}amino)-octahydro-1,3-benzoxazol-2-one 73a (165.0 mg, 0.27 mmol) to afford (3aS,6S,7aS)-6-({[3-(6-methoxypyridin-2-yl)phenyl]methyl}amino)-3-{3-oxo-2H,3H,4H-pyrido[3,2-b][1,4]oxazin-6-yl}-octahydro-1,3-benzoxazol-2-one 73 (21.8 mg, 15%). LC-MS (Method B) 502.2 $[M+H]^+$; RT 6.54 min. $^1$H NMR (Method C) ($CDCl_3$): δ ppm 8.01 (s, 1H), 7.96 (d, J=7.6 Hz, 1H), 7.64 (dd, J=8.2, 7.4 Hz, 1H), 7.44 (t, J=7.6 Hz, 1H), 7.40-7.28 (m, 4H), 6.70 (dd, J=8.2, 0.7 Hz, 1H), 4.63 (d, J=0.8 Hz, 2H), 4.04 (s, 3H), 4.03-3.91 (m, 3H), 3.86-3.72 (m, 1H), 2.91 (d, J=11.1 Hz, 1H), 2.77-2.66 (m, 2H), 2.19 (d, J=13.5 Hz, 1H), 1.74-1.46 (m, 2H), 1.44-1.34 (m, 1H).

Example 74:—1-(3-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}propyl)-2-oxo-1,2-dihydroquinoline-7-carbonitrile

74

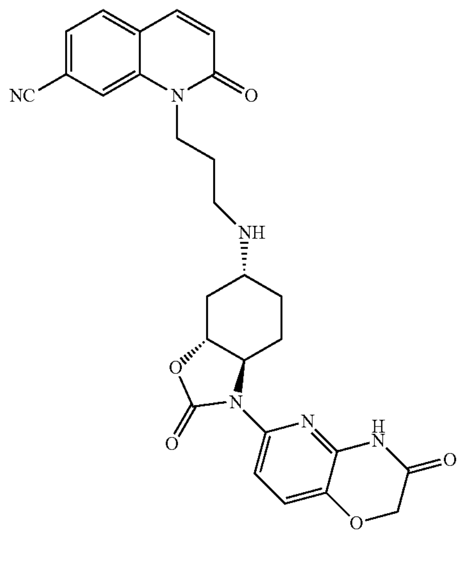

(3aR,6R,7aR)-2-oxo-3-{3-oxo-2H,3H,4H-pyrido[3,2-b][1,4]oxazin-6-yl}-octahydro-1,3-benzoxazol-6-aminium trifluoroacetate 74a (175 mg, 0.42 mmol)(prepared using the method described in example 60d starting with tert-butyl N-[(3aR,6R,7aR)-3-{4-[(4-methoxyphenyl)methyl]-3-oxo-2H,3H,4H-pyrido[3,2-b][1,4]oxazin-6-yl}-2-oxo-octahydro-1,3-benzoxazol-6-yl]carbamate 1b) and 2-oxo-1-(3-oxopropyl)-1,2-dihydroquinoline-7-carbonitrile 60c (95 mg, 0.419 mmol) in DCM (5 mL) and triethylamine (0.17 mL, 1.26 mmol) were stirred for 2 h over molecular sieves (4 Å). $NaBH(OAc)_3$ (271 mg, 1.25 mmol) was added and the mixture stirred at room temperature for 2 h. Sat. aqueous $Na_2CO_3$ (20 mL) was added and the mixture extracted with DCM (50 mL), dried over $MgSO_4$ and concentrated under reduced pressure. The residue was purified by silica chromatography using 0-10% MeOH in EtOAc to give 1-(3-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}propyl)-2-oxo-1,2-dihydroquinoline-7-carbonitrile 74 (20 mg, 10%) as a white solid. LC-MS (Method A) 515.3 $[M+H]^+$, RT 2.43 min. $^1H$ NMR (Method C) ($CDCl_3$): δ ppm 7.99 (br s, 1H), 7.90 (s, 1H), 7.71 (d, J=9.5 Hz, 1H), 7.67 (d, J=8.0 Hz, 1H), 7.48 (dd, J=8, 0, 1.3 Hz, 1H), 7.38-7.28 (m, 2H), 6.84 (d, J=9.5 Hz, 1H), 4.64 (s, 2H), 4.47-4.38 (m, 2H), 3.98 (td, J=10.9, 3.3 Hz, 1H), 3.86 (td, J=10.9, 3.3 Hz, 1H), 2.87-2.61 (m, 5H), 2.21 (d, J=12.4 Hz, 1H), 2.01-1.92 (m, 2H), 1.70-1.43 (m, 4H).

Example 75:—(3aS,6S,7aS)—N-{2-[7-(2-azaniumylethoxy)-2-oxo-1,2-dihydroquinolin-1-yl]ethyl}-2-oxo-3-{3-oxo-2H,3H,4H-pyrido[3,2-b][1,4]oxazin-6-yl}-octahydro-1,3-benzoxazol-6-aminium dichloride

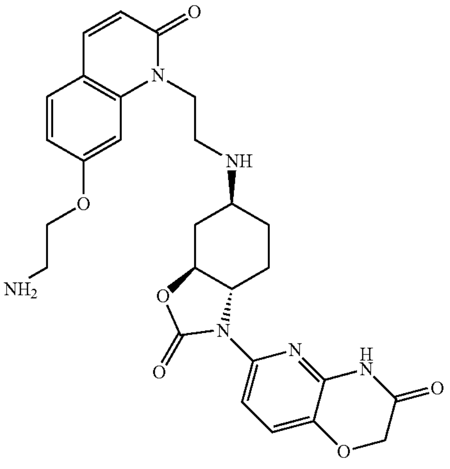

75 a) tert-butyl N-(2-{[1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-2-oxo-1,2-dihydroquinolin-7-yl]oxy}ethyl)carbamate 75a Prepared using the method described in example 60e using tert-butyl N-(2-{[2-oxo-1-(2-oxoethyl)-1,2-dihydroquinolin-7-yl]oxy}ethyl)carbamate 9f (166.7 mg, 0.43 mmol) and (3aS,6S,7aS)-2-oxo-3-{3-oxo-2H,3H,4H-pyrido[3,2-b][1,4]oxazin-6-yl}-octahydro-1,3-benzoxazol-6-aminium trifluoroacetate 60d (418.3 mg, 0.43 mmol) to afford tert-butyl N-(2-{[1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-2-oxo-1,2-dihydroquinolin-7-yl]oxy}ethyl)carbamate 75a (215 mg, 78%)—isolated without purification. LC-MS (Method A) 635.3 $[M+H]^+$, RT 2.87 min.

b) (3aS,6S,7aS)—N-{2-[7-(2-azaniumylethoxy)-2-oxo-1,2-dihydroquinolin-1-yl]ethyl}-2-oxo-3-{3-oxo-2H,3H,4H-pyrido[3,2-b][1,4]oxazin-6-yl}-octahydro-1,3-benzoxazol-6-aminium dichloride 75

TFA (0.3 mL, 3.92 mmol) was added to a solution of tert-butyl N-(2-{[1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-2-oxo-1,2-dihydroquinolin-7-yl]oxy}ethyl)carbamate 75a (100 mg, 0.16 mmol) in DCM (3 mL) and stirred for 90 min. $NH_3$ in MeOH (7N) was added to adjust the pH of the reaction mixture to 8. The crude product was pre absorbed onto silica using MeOH then purified using silica gel chromatography with 0-20% MeOH/DCM followed by 0-20% $NH_3$ in MeOH/DCM. Clean product fractions were collected and concentrated (with Et2O azetroping) under reduced pressure. The resulting white solid was dissolved in a minimum volume of MeOH/DCM and HCl (1M in $Et_2O$, 2 mL). The solution was concentrated under reduced pressure and the resulting brown solid was dried under house vacuum to afford (3aS,6S,7aS)—N-{2-[7-(2-azaniumylethoxy)-2-oxo-1,2-dihydroquinolin-1-yl]ethyl}-2-oxo-3-{3-oxo-2H,3H,4H-pyrido[3,2-b][1,4]oxazin-6-yl}-octahydro-1,3-benzoxazol-6-aminium dichloride 75 (7.7 mg, 8.2%). LC-MS (Method B) 535.4 $[M+H]^+$, RT 4.84 min. $^1H$ NMR (Method C) (DMSO-d6): δ ppm 11.29 (s, 1H), 9.92 (br. s, 2H), 8.24-8.19 (m, 3H), 7.92 (d, J=9.5 Hz, 1H), 7.72 (d, J=8.8 Hz, 1H), 7.44 (d, J=8.5 Hz, 1H), 7.40-7.33 (m, 1H), 7.18 (d, J=8.5 Hz, 1H), 7.00-6.97 (m, 1H), 6.51 (d, J=9.5 Hz, 1H), 4.73-4.59 (m, 1H), 4.64 (s, 3H), 4.57-4.48 (m, 2H), 4.19-4.04 (m, 1H), 3.88-3.77 (m, 1H), 3.57-3.47 (m, 1H), 3.31-3.23 (m, 2H), 3.23-3.12 (m, 2H), 2.93-2.83 (m, 1H), 2.77-2.69 (m, 1H), 2.32-2.24 (m, 1H), 2.07-1.96 (m, 1H), 1.81-1.66 (m, 1H), 1.50-1.38 (m, 1H).

Example 76:—1-(3-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}propyl)-7-methoxy-1,2-dihydro-1,8-naphthyridin-2-one

76

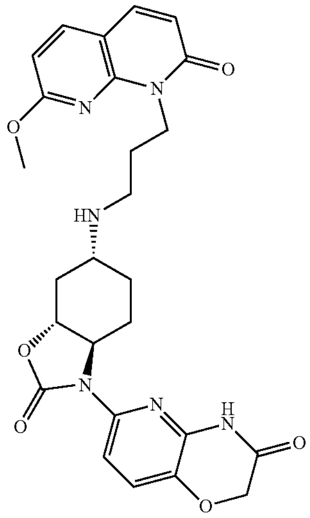

Prepared as in the method described in example 60e using (3aR,6R,7aR)-2-oxo-3-{3-oxo-2H,3H,4H-pyrido[3,2-b][1,4]oxazin-6-yl}-octahydro-1,3-benzoxazol-6-aminium trifluoroacetate 74a (205 mg, 0.49 mmol) and 3-(7-methoxy-2-oxo-1,2-dihydro-1,8-naphthyridin-1-yl)propanal 85b (104 mg, 0.45 mmol) to afford 1-(3-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}propyl)-7-methoxy-1,2-dihydro-1,8-naphthyridin-2-one 76 (106 mg, 43%). LC-MS (Method A) 521.3 [M+H]*; RT 2.52 min. $^1$H NMR (Method C) (DMSO-d6): δ ppm 11.23 (br. s, 1H), 8.07 (d, J=8.4 Hz, 1H), 7.88 (d, J=9.4 Hz, 1H), 7.42 (d, J=8.5 Hz, 1H), 7.18 (d, J=8.5 Hz, 1H), 6.75 (d, J=8.4 Hz, 1H), 6.52 (d, J=9.4 Hz, 1H), 4.64 (s, 2H), 4.44 (dd, J=8.1, 6.3 Hz, 2H), 4.09-3.97 (m, 4H), 3.75 (td, J=11.1, 3.3 Hz, 1H), 2.82-2.71 (m, 2H), 2.71-2.59 (m, 2H), 2.43 (dd, J=8.4, 4.3 Hz, 1H), 2.06-1.93 (m, 1H), 1.93-1.78 (m, 2H), 1.48 (q, J=11.2 Hz, 1H), 1.40-1.16 (m, 2H).

Example 77:—5-(2-{[(3aS,6S,7aS)-2-oxo-3-{3-oxo-2H,3H,4H-pyrido[3,2-b][1,4]thiazin-6-yl}-octahydro-1,3-benzoxazol-6-yl]amino}ethyl)-6-oxo-5,6-dihydro-1,5-naphthyridine-3-carbonitrile

77

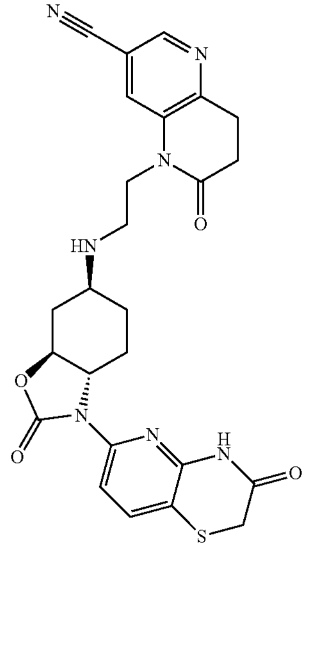

Prepared as in the method described in example 60e using 6-oxo-5-(2-oxoethyl)-5,6-dihydro-1,5-naphthyridine-3-carbonitrile (prepared as described in WO2008009700A1) (15.7 mg, 0.074 mmol) and (3aS,6S,7aS)-2-oxo-3-{3-oxo-2H,3H,4H-pyrido[3,2-b][1,4]thiazin-6-yl}-octahydro-1,3-benzoxazol-6-aminium chloride 61 b (32.8 mg, 0.092 mmol) to afford 5-(2-{[(3aS,6S,7aS)-2-oxo-3-{3-oxo-2H,3H,4H-pyrido[3,2-b][1,4]thiazin-6-yl}-octahydro-1,3-benzoxazol-6-yl]amino}ethyl)-6-oxo-5,6-dihydro-1,5-naphthyridine-3-carbonitrile 77 (20.1 mg, 42%) as a colourless solid. LC-MS (Method A) 518.2 [M+H]$^+$, RT 2.22 min. $^1$H NMR (Method C) (DMSO-d6): δ ppm 10.95 (s, 1H), 8.89 (s, 1H), 8.71 (s, 1H), 8.02 (d, J=9.5, 1H), 7.78 (d, J=8.5, 1H), 7.29 (d, J=9.67, 1H), 7.05 (d, J=9.5, 1H), 4.34-4.22 (m, 2H), 4.04 (m, 1H), 3.74 (td, J=11.0, 3.5, 1H), 3.60-3.49 (m, 2H), 2.95 (m, 1H), 2.89-2.83 (m, 2H), 2.79 (m, 1H), 2.44-2.40 (m, 2H), 1.93 (m, 1H), 1.44 (m, 1H), 1.15-1.10 (m, 1H), 0.91-0.82 (m, 1H).

Example 78:—{[(3aS,6S,7aS)-2-oxo-3-{3-oxo-2H,3H,4H-pyrido[3,2-b][1,4]oxazin-6-yl}-octahydro-1,3-benzoxazol-6-yl][2-(7-methoxy-2-oxo-1,2-dihydro-1,8-naphthyridin-1-yl)ethyl]carbamoyl}methanaminium chloride

78

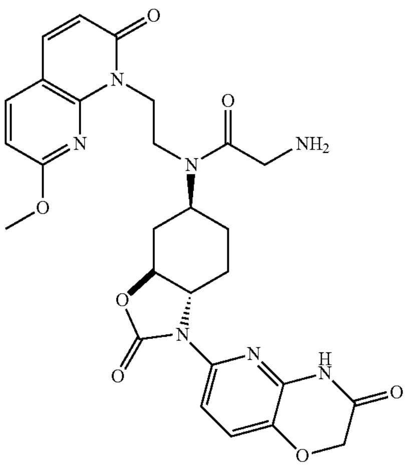

a) tert-butyl N-({[(3aS,6S,7aS)-2-oxo-3-{3-oxo-2H,3H,4H-pyrido[3,2-b][1,4]oxazin-6-yl}-octahydro-1,3-benzoxazol-6-yl][2-(7-methoxy-2-oxo-1,2-dihydro-1,8-naphthyridin-1-yl)ethyl]carbamoyl}methyl)carbamate 78a N-Boc-glycine (0.03 mL, 0.17 mmol), 1-Hydroxybenzotriazole hydrate (29.5 mg, 0.22 mmol), EDCl (48.3 mg, 0.25 mmol) and triethylamine (0.1 mL, 0.72 mmol) were added to a solution of 1-(2-{[(3aS,6S,7aS)-2-oxo-3-{3-oxo-2H, 3H,4H-pyrido[3,2-b][1,4]oxazin-6-yl}-octahydro-1,3-benzoxazol-6-yl]amino}ethyl)-7-methoxy-1,2-dihydro-1,8-naphthyridin-2-one 29 (85 mg, 0.17 mmol) in THF (3 mL) and DMF (0.3 mL) and the reaction mixture stirred at room temperature for 17 h under nitrogen. Further DMF (0.70 mL), EDCl (48.3 mg, 0.25 mmol) and triethylamine (0.1 mL, 0.72 mmol) were added and the reaction mixture stirred for a further 17 h at room temperature under nitrogen. DCM (40 mL) and $H_2O$ (5 mL) were added and the resulting organic layer separated through a SPE phase separator. The organic filtrate was collected and concentrated under reduced pressure with toluene and $Et_2O$ azeotroping to afford a white solid/gum. Crude product was purified via silica gel chromatography using a gradient of 0-100% petroleum ether/EtOAc followed by 0-20% MeOH/EtOAc. Product fractions were collected and concentrated under reduced pressure to afford tert-butyl N-({[(3aS,6S,7aS)-2-oxo-3-{3-oxo-2H,3H,4H-pyrido[3,2-b][1,4]oxazin-6-yl}-octahydro-1,3-benzoxazol-6-yl][2-(7-methoxy-2-oxo-1,2-dihydro-1,8-naphthyridin-1-yl)ethyl]carbamoyl}methyl)carbamate 78a (19 mg, 17.1%). LC-MS (Method A) 664.4 $[M+H]^+$, RT 2.88 min.

b) {[(3aS,6S,7aS)-2-oxo-3-{3-oxo-2H,3H,4H-pyrido[3,2-b][1,4]oxazin-6-yl}-octahydro-1,3-benzoxazol-6-yl][2-(7-methoxy-2-oxo-1,2-dihydro-1,8-naphthyridin-1-yl)ethyl]carbamoyl}methanaminium chloride 78

HCl (4M in Dioxane, 2 mL, 2.69 mmol) was added to a solution of tert-butyl N-({[(3aS,6S,7aS)-2-oxo-3-{3-oxo-2H,3H,4H-pyrido[3,2-b][1,4]oxazin-6-yl}-octahydro-1,3-benzoxazol-6-yl][2-(7-methoxy-2-oxo-1,2-dihydro-1,8-naphthyridin-1-yl)ethyl]carbamoyl}methyl)carbamate 78a (20.0 mg, 0.03 mmol) in MeOH (20 mL). The reaction mixture was stirred at room temperature for 6 h then concentrated under reduced pressure with $Et_2O$ azeotroping to afford a yellow solid. The crude product was purified via prep. HPLC (Method B) using 0.1% $NH_3$ in $MeCN/H_2O$. Clean fractions were collected and concentrated under reduced pressure with $Et_2O$ azeotroping to afford a white solid which was dissolved in MeOH and HCl (1M in $Et_2O$, 0.1 mL). The mixture was concentrated under reduced pressure with $Et_2O$ azeotroping to afford {[(3aS,6S,7aS)-2-oxo-3-{3-oxo-2H,3H,4H-pyrido[3,2-b][1,4]oxazin-6-yl}-octahydro-1,3-benzoxazol-6-yl][2-(7-methoxy-2-oxo-1,2-dihydro-1,8-naphthyridin-1-yl)ethyl]carbamoyl}methanaminium chloride 78 (7.8 mg, 43%) as a white solid. LC-MS (Method B) 564.3 $[M+H]^+$, RT 6.20 min. $^1H$ NMR (rotamers)(Method C) (DMSO-d6): δ ppm 11.31-11.21 (m, 1H), 8.19-8.04 (m, 4H), 8.00-7.88 (m, 1H), 7.48-7.42 (m, 1H), 7.24-7.20 (m, 1H), 6.83-6.75 (m, 1H), 6.61-6.50 (m, 1H), 4.66-4.62 (m, 2H), 4.61-4.54 (m, 1H), 4.55-4.40 (m, 1H), 4.28-4.13 (m, 2H), 4.13-4.06 (m, 3H), 4.02-3.75 (m, 2H), 3.72-3.45 (m, 2H), 2.95-2.82 (m, 1H), 2.38-2.24 (m, 2H), 2.03-1.78 (m, 3H), 1.55-1.44 (m, 1H).

Example 79:—1-(3-{[(3aR,6R,7aR)-2-oxo-3-{7-oxo-6H,7H,8H-pyrimido[5,4-b][1,4]oxazin-2-yl}-octahydro-1,3-benzoxazol-6-yl]amino}propyl)-7-methoxy-1,2-dihydro-1,8-naphthyridin-2-one

79

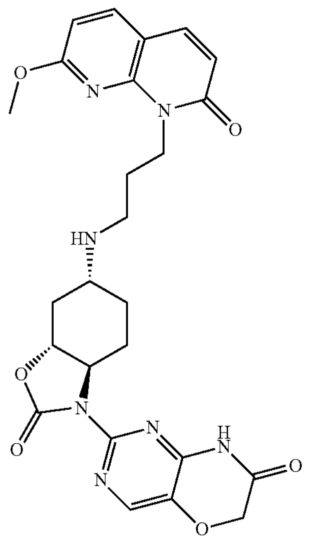

Prepared as in the method described in example 60e using (3aR,6R,7aR)-6-amino-3-{7-oxo-6H,7H,8H-pyrimido[5,4-b][1,4]oxazin-2-yl}-octahydro-1,3-benzoxazol-6-aminium trifluoroacetate (prepared from example 33a using the method described in example 60d) (246 mg, 0.49 mmol) and 3-(7-methoxy-2-oxo-1,2-dihydro-1,8-naphthyridin-1-yl) propanal 85b (104 mg, 0.45 mmol) to afford 1-(3-{[(3aR,6R,7aR)-2-oxo-3-{7-oxo-6H,7H,8H-pyrimido[5,4-b][1,4]oxazin-2-yl}-octahydro-1, 3-benzoxazol-6-yl]amino}propyl)-7-methoxy-1,2-dihydro-1,8-naphthyridin-2-one 79 (50 mg, 19%). LC-MS (Method A) 522.3 $[M+H]^+$; RT 1.74 min. $^1H$ NMR (Method C) (DMSO-d6): δ ppm 8.25 (s, 1H), 8.07 (d, J=9.2 Hz, 1H), 7.87 (d, J=8.3 Hz, 1H), 6.74 (d, J=8.3 Hz, 1H), 6.50 (d, J=9.2 Hz, 1H), 4.72 (s, 2H), 4.75-4.38 (m, 3H), 4.06 (td, J=11.2, 3.4 Hz, 1H), (4.00 s, 3H), 3.79 (td, J=11.2, 3.4 Hz, 1H), 2.76-2.58 (m, 3H), 2.46-2.37 (m, 2H), 2.03-1.94 (m, 1H), 1.89-1.79 (m, 2H), 1.47 (q, J=11.1 Hz, 1H), 1.38-1.17 (m, 2H).

Example 80:—(3aR,6R,7aR)-6-({[3-(6-methoxy-pyridin-2-yl)phenyl]methyl}amino)-3-{3-oxo-2H,3H,4H-pyrido[3,2-b][1,4]oxazin-6-yl}-octahydro-1,3-benzoxazol-2-one

80

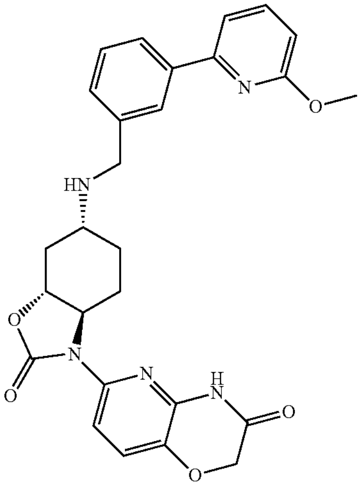

Prepared as in the method described in example 74 using 3-(6-methoxypyridin-2-yl)benzaldehyde (104 mg, 0.49 mmol) (WO 2014170821A1) (128. mg, 0.60 mmol) and (3aR,6R,7aR)-2-oxo-3-{3-oxo-2H,3H,4H-pyrido[3,2-b][1,4]oxazin-6-yl}-octahydro-1,3-benzoxazol-6-aminium trifluoroacetate 74a (233.1 mg, 0.56 mmol) to afford (3aR,6R,7aR)-6-({[3-(6-methoxypyridin-2-yl)phenyl]methyl}amino)-3-{3-oxo-2H,3H,4H-pyrido[3,2-b][1,4]oxazin-6-yl}-octahydro-1,3-benzoxazol-2-one 80 (34 mg, 11.%). LC-MS (Method B) 502.3 $[M+H]^+$; RT 6.24 min. $^1H$ NMR (Method C) ($CDCl_3$): δ ppm 8.01-7.98 (m, 1H), 7.97-7.92 (m, 1H), 7.64 (dd, J=8.2, 7.4 Hz, 1H), 7.44 (t, J=7.6 Hz, 1H), 7.39-7.28 (m, 4H), 6.70 (dd, J=8.2, 0.7 Hz, 1H), 4.63 (s, 2H), 4.05 (s, 3H), 4.03-3.90 (m, 3H), 3.82 (td, J=11.1, 3.3 Hz, 1H), 2.94-2.84 (m, 1H), 2.73-2.65 (m, 2H), 2.17 (dd, J=12.2, 4.3 Hz, 1H), 1.64 (q, J=11.4 Hz, 1H), 1.51-1.34 (m, 2H).

Example 81:—1-(2-{[(3aS,6S,7aS)-2-oxo-3-{3-oxo-2H,3H,4H-pyrido[3,2-b][1,4]thiazin-6-yl}-octahydro-1,3-benzoxazol-6-yl]amino}ethyl)-7-methoxy-1,2-dihydro-1,5-naphthyridin-2-one

81

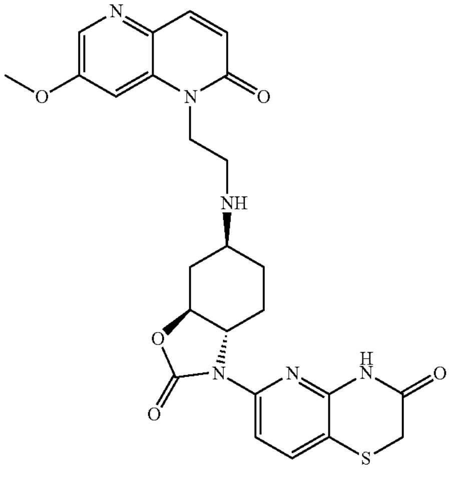

Prepared as described in example 60e using 2-(7-methoxy-2-oxo-1,2-dihydro-1,5-naphthyridin-1-yl)acetaldehyde (prepared as described in WO2011148962A1) (17.0 mg, 0.08 mmol) and (3aS,6S,7aS)-2-oxo-3-{3-oxo-2H,3H,4H-pyrido[3,2-b][1,4]thiazin-6-yl}-octahydro-1,3-benzoxazol-6-aminium chloride 61 b (34.7 mg, 0.10 mmol) to afford 1-(2-{[(3aS,6S,7aS)-2-oxo-3-{3-oxo-2H,3H,4H-pyrido[3,2-b][1,4]thiazin-6-yl}-octahydro-1,3-benzoxazol-6-yl]amino}ethyl)-7-methoxy-1,2-dihydro-1,5-naphthyridin-2-one 81 (18.5 mg, 36%) as a colourless solid. LC-MS (Method A) 523.2 $[M+H]^+$, RT 2.27 min. $^1H$ NMR (Method C) (DMSO-d6): δ ppm 10.96 (s, 1H), 8.29 (d, J=2.5, 1H), 7.87 (d, J=8.5, 1H), 7.79 (d, J=8.5, 1H), 7.51 (d, J=2.5, 1H), 7.28 (d, J=8.5, 1H), 6.67 (d, J=9.5, 1H), 4.32-4.29 (m, 2H), 4.06 (m, 1H), 3.99 (s, 3H), 3.74 (td, J=11.0, 3.5, 1H), 3.57 (d, J=15.0, 1H), 3.51 (d, J=15.0), 2.97 (m, 1H), 2.89-2.80 (m, 3H), 2.45 (m, 1H), 1.98 (m, 1H), 1.48 (m, 1H), 1.31-1.21 (m, 4H).

Example 82:—5-(3-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}propyl)-6-oxo-5,6-dihydro-1,5-naphthyridine-3-carbonitrile

82

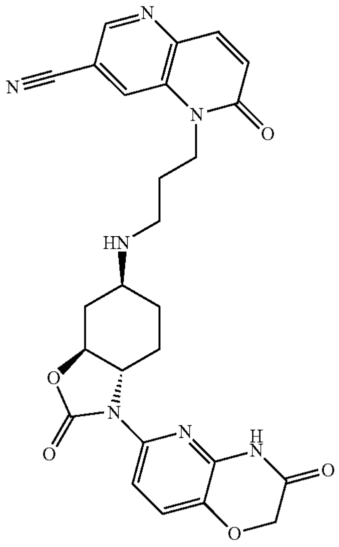

a) 7-bromo-1-(3,3-dimethoxypropyl)-1,2-dihydro-1,5-naphthyridin-2-one 82a 7-bromo-1,2-dihydro-1,5-naphthyridin-2-one (3.77 g, 16.70 mmol) (prepared according to WO2013078441), $Cs_2CO_3$ (1.60 g, 4.91 mmol) and 3-bromo-1,1-dimethoxypropane (2.97 mL, 21.78 mmol) were added to DMF (50 mL) and heated at 60° C. for 17 h. The reaction was quenched with $H_2O$ (100 mL) and extracted with $Et_2O$ (2×100 mL). The combined organic extracts were dried ($MgSO_4$), filtered and concentrated under reduced pressure to afford an orange gum. Purification via column chromatography using a gradient of 50-100% EtOAc in heptane afforded 7-bromo-1-(3,3-dimethoxypropyl)-1,2-dihydro-1,5-naphthyridin-2-one 82a (1.72 g, 31%) as a yellow solid. LC-MS (Method A) 328.9 $[M+H]^+$; RT 0.53 min.

b) 5-(3,3-dimethoxypropyl)-6-oxo-5,6-dihydro-1,5-naphthyridine-3-carbonitrile 82b 7-bromo-1-(3,3-dimethoxypropyl)-1,2-dihydro-1,5-naphthyridin-2-one 82a (1.7 g, 5.20 mmol), XPhos Pd G2 (204 mg, 0.26 mmol) and zinc cyanide (0.92 g, 7.79 mmol) were heated in DMF (50 mL) at 100° C. for 1 h. The reaction was diluted with $Et_2O$ (100 mL), filtered, and the filtrate concentrated under reduced pressure to afford a viscous yellow gum. The crude product was purified via column chromatography using a gradient of 50-100% EtOAc in petroleum ether to afford 5-(3,3-dimethoxypropyl)-6-oxo-5,6-dihydro-1,5-naphthyridine-3-carbonitrile 82b (1.42 g, 99%) as a yellow gum which solidified on standing. LC-MS (Method A) 274.0 $[M+H]^+$; RT 1.40 min. $^1H$ NMR (Method C): ($CDCl_3$) δ ppm 8.73 (d, J=1.6 Hz, 1H), 8.11 (d, J=1.6 Hz, 1H), 7.94 (d, J=9.8 Hz, 1H), 7.05 (d, J=9.8 Hz, 1H), 4.49 (t, J=5.0 Hz, 1H), 4.38-4.27 (m, 2H), 3.40 (s, 6H), 2.04 (td, J=7.7, 5.0 Hz, 2H).

c) 6-oxo-5-(3-oxopropyl)-5,6-dihydro-1,5-naphthyridine-3-carbonitrile 82c 5-(3,3-dimethoxypropyl)-6-oxo-5,6-dihydro-1,5-naphthyridine-3-carbonitrile 82b (1.42 g, 5.2 mmol) was added to aq. HCl (3 M, 10 mL, 51.9 mmol) and THF (10 mL) and the mixture stirred at room temperature for 2 h The reaction mixture was quenched with $H_2O$ (30 mL), basified with solid $K_2CO_3$ and extracted with $Et_2O$/EtOAc (1:1) (2×75 ml). The extracts were combined, dried ($MgSO_4$), filtered and concentrated under reduced pressure to afford an off white solid. Crude product was triturated with $Et_2O$ and the resulting solid was filtered and dried under vacuum to afford 6-oxo-5-(3-oxopropyl)-5,6-dihydro-1,5-naphthyridine-3-carbonitrile 82c (450 mg, 38%) as a white solid. $^1H$ NMR (Method C) ($CDCl_3$) δ ppm 9.86 (s, 1H), 8.75 (d, J=1.9 Hz, 1H), 8.09 (d, J=1.9 Hz, 1H), 7.96 (dd, J=9.8, 0.9 Hz, 1H), 7.04 (d, J=9.8 Hz, 1H), 4.53 (t, J=6.9 Hz, 2H), 3.01 (td, J=6.9, 0.9 Hz, 2H).

d) 5-(3-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}propyl)-6-oxo-5,6-dihydro-1,5-naphthyridine-3-carbonitrile 82

Prepared as described in example 60e using (3aS,6S,7aS)-2-oxo-3-{3-oxo-2H,3H,4H-pyrido[3,2-b][1,4]oxazin-6-yl}-octahydro-1,3-benzoxazol-6-aminium trifluoroacetate 60d (150 mg, 0.36 mmol) and 6-oxo-5-(3-oxopropyl)-5,6-dihydro-1,5-naphthyridine-3-carbonitrile 82c (81 mg, 0.36 mmol) to afford 5-(3-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}propyl)-6-oxo-5,6-dihydro-1,5-naphthyridine-3-carbonitrile 82 (63 mg, 34%). LC-MS (Method A) 516.1 $[M+H]^+$; RT 1.75 min. $^1H$ NMR (Method C) (DMSO-d6): δ ppm 11.24 (s, 1H), 8.92 (d, J=1.6 Hz, 1H), 8.76 (d, J=1.6 Hz, 1H), 8.04 (d, J=9.8 Hz, 1H), 7.43 (d, J=8.6 Hz, 1H), 7.18 (d, J=8.6 Hz, 1H), 7.06 (d, J=9.8 Hz, 1H), 4.63 (s, 2H), 4.30 (t, J=7.3 Hz, 2H), 4.07 (td, J=11.7, 3.4 Hz, 1H), 3.77 (td, J=11.0, 3.4 Hz, 1H), 3.40-3.30 (m, 1H), 2.89-2.60 (m, 4H), 2.06 (d, J=11.4 Hz, 1H), 1.90-1.73 (m, 2H), 1.56 (m, 1H), 1.36 (dd, J=16.1, 7.2 Hz, 2H).

Example 83:—1-(3-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}propyl)-7-methoxy-1,2-dihydro-1,8-naphthyridin-2-one

83

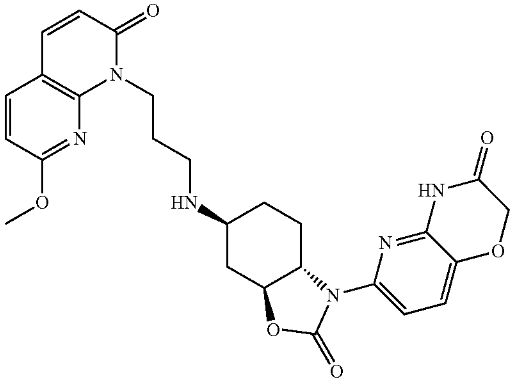

Prepared following the method described in example 60e using (3aS,6S,7aS)-2-oxo-3-{3-oxo-2H,3H,4H-pyrido[3,2-b][1,4]oxazin-6-yl}-octahydro-1,3-benzoxazol-6-aminium trifluoroacetate 60d (550.0 mg, 1.32 mmol) and 3-(7-methoxy-2-oxo-1,2-dihydro-1,8-naphthyridin-1-yl)propanal 85b (290.1 mg, 1.25 mmol) to afford 1-(3-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}propyl)-7-methoxy-1,2-dihydro-1,8-naphthyridin-2-one 83 (296.3 mg, 43%) as a white solid. LC-MS (Method B) 521.2 $[M+H]^+$; RT 6.87 min. $^1H$ NMR (Method C) (DMSO-d6): δ ppm 11.23 (br s, 1H), 8.07 (d, J=8.5 Hz, 1H), 7.88 (d, J=9.4 Hz, 1H), 7.42 (d, J=8.5 Hz, 1H), 7.18 (d, J=8.5 Hz, 1H), 6.75 (d, J=8.5 Hz, 1H), 6.52 (d, J=9.4 Hz, 1H), 4.63 (s, 2H), 4.43 (t, J=7.3, 2H), 4.05 (td, J=11.8, 3.3 Hz, 1H), 4.01 (s, 3H), 3.74 (td, J=11.2, 3.3 Hz, 1H), 2.79-2.68 (m, 2H), 2.67-6.59 (m, 2H), 2.45-2.40 (m, 1H), 2.01-1.95 (m, 1H), 1.88-1.80 (m, 2H), 1.46 (q, J=11.2 Hz, 1H), 1.37-1.28 (m, 1H), 1.28-1.18 (m, 1H).

Example 84:—1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-fluoro-1,2-dihydroquinoxalin-2-one

84

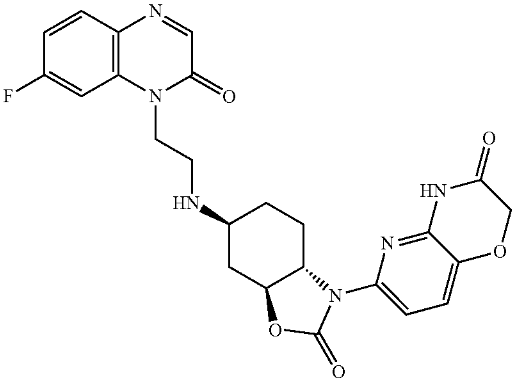

Prepared as in the method described in example 60e using (3aS,6S,7aS)-2-oxo-3-{3-oxo-2H,3H,4H-pyrido[3,2-b][1,4]oxazin-6-yl}-octahydro-1,3-benzoxazol-6-aminium trifluoroacetate 60d (225 mg, 0.54 mmol) and 2-(7-fluoro-2-oxo-1,2-dihydroquinoxalin-1-yl)acetaldehyde (prepared as described in WO 2008009700) (105.4 mg, 0.51 mmol) to afford 1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-fluoro-1,2-dihydroquinoxalin-2-one 84 (116.3 mg, 44%) as a pale yellow solid. LC-MS (Method B) 495.3 $[M+H]^+$; RT 6.48 min. $^1H$ NMR (Method C) (DMSO-d6): δ ppm 11.21 (brs, 1H), 8.21 (s, 1H), 7.89 (dd, J=8.6, 6.1 Hz, 1H), 7.63 (dd, J=11.1, 2.6 Hz, 1H), 7.42 (d, J=8.6 Hz, 1H), 7.26 (td, J=8.6, 2.6 Hz, 1H), 7.17 (d, J=8.6 Hz, 1H), 4.62 (s, 2H), 4.23 (t, J=7.0 Hz, 2H), 4.04 (td, J=11.8, 3.3 Hz, 1H), 3.74 (td, J=11.1, 3.3 Hz, 1H), 2.89-2.82 (m, 2H), 2.79-2.73 (m, 2H), 2.44-2.38 (m, 1H), 2.11 (br s, 1H), 1.99-1.92 (m, 1H), 1.44 (q, J=11.1 Hz, 1H), 1.37-1.28 (m, 1H), 1.25-1.24 (m, 1H).

Example 85:—1-(3-{[(3aS,6S,7aS)-2-oxo-3-{3-oxo-2H,3H,4H-pyrido[3,2-b][1,4]thiazin-6-yl}-octahydro-1,3-benzoxazol-6-yl]amino}propyl)-7-methoxy-1,2-dihydro-1,8-naphthyridin-2-one

85

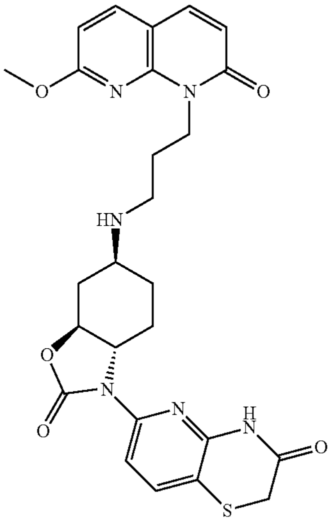

a) 1-(3,3-dimethoxypropyl)-7-methoxy-1,2-dihydro-1,8-naphthyridin-2-one 85a 7-methoxy-1,2-dihydro-1,8-naphthyridin-2-one (0.9 g, 5.11 mmol), $CsCO_3$ (1.6 g, 4.91 mmol) and 3-bromo-1,1-dimethoxypropane (0.91 mL, 6.64 mmol) were suspended in DMF (50 mL) and heated to 90° C. for 1 h. $H_2O$ (100 mL) was added and the mixture extracted with $Et_2O$ (2×100 mL). Organics were combined, dried ($MgSO_4$) and solvent evaporated to afford an orange gum. Purification via column chromatography eluting with 50-100% $Et_2O$ in heptane yielded 1-(3,3-dimethoxypropyl)-7-methoxy-1,2-dihydro-1,8-naphthyridin-2-one 85a (0.87 g, 2.97 mmol, 58%) as a yellow solid. LC-MS (Method A) 301.2 $[M+Na]^+$; RT 2.45 min.

b) 3-(7-methoxy-2-oxo-1,2-dihydro-1,8-naphthyridin-1-yl)propanal 85b 1-(3,3-dimethoxypropyl)-7-methoxy-1,2-dihydro-1,8-naphthyridin-2-one 85a (0.64 g, 2.3 mmol) was added to THF (15 mL) and HCl (3M, 10 mL, 2.3 mmol) and the mixture was stirred at 60° C. for 27 h. The mixture was allowed to cool and sat. aqueous $Na_2CO_3$ (100 mL) was added then extracted with DCM (2×100 mL), dried ($MgSO_4$) and solvent evaporated under reduced pressure to afford 3-(7-methoxy-2-oxo-1,2-dihydro-1,8-naphthyridin-1-yl)propanal 85b (320 mg, 1.24 mmol, 53.9% yield) as a yellow gum which solidified. $^1H$ NMR (Method C)$^1H$-NMR ($CDCl_3$) δ: 9.78 (s 1H), 8.05 (d, J=8.3 Hz, 1H), 7.88 (d, J=9.5 Hz, 1H), 6.72 (d, J=8.3 Hz, 1H), 6.50 (d, J=9.5 Hz, 1H), 4.65 (t, J=7.3 Hz, 2H), 3.95 (s, 3H), 2.82 (t, J=7.3 Hz, 2H).

c) 1-(3-{[(3aS,6S,7aS)-2-oxo-3-{3-oxo-2H,3H,4H-pyrido[3,2-b][1,4]thiazin-6-yl}-octahydro-1,3-benzoxazol-6-yl]amino}propyl)-7-methoxy-1,2-dihydro-1,8-naphthyridin-2-one 85

A solution of (3aS,6S,7aS)-2-oxo-3-{3-oxo-2H,3H,4H-pyrido[3,2-b][1,4]thiazin-6-yl}-octahydro-1,3-benzoxazol-6-aminium chloride 61b (200 mg, 0.56 mmol) in DCM (10 mL) and triethylamine (0.23 mL, 1.68 mmol) was stirred over molecular sieves (4 Å) for 2 h. 3-(7-methoxy-2-oxo-1,2-dihydro-1,8-naphthyridin-1-yl)propanal 85b (117 mg, 0.56 mmol) was added and stirred for 17 h then $NaBH(OAc)_3$ (356 mg, 1.17 mmol) added and stirring continued for a further 17 h. Sat. aqueous $NaHCO_3$ (20 mL) was added and the mixture extracted with DCM (3×20 mL), dried over $MgSO_4$ and concentrated under reduced pressure. The residue was purified by silica gel chromatography using 0-10% MeOH in EtOAc to give 1-(3-{[(3aS,6S,7aS)-2-oxo-3-{3-oxo-2H,3H,4H-pyrido[3,2-b][1,4]thiazin-6-yl}-octahydro-1,3-benzoxazol-6-yl]amino}propyl)-7-methoxy-1,2-dihydro-1,8-naphthyridin-2-one 85 (3 mg, 4%)—as a white solid. LC-MS (Method A) 537.3 $[M+H]^+$, RT 2.76 min. $^1H$ NMR (Method C) ($CDCl_3$): δ ppm 8.40 (s, 1H), 7.78 (d, J=8.4 Hz, 1H), 7.68-7.58 (m, 2H), 7.43 (d, J=8.4 Hz, 1H), 6.67-6.60 (m, 2H), 4.67-4.57 (m, 2H), 4.03 (s, 3H), 3.99-3.79 (m, 2H), 3.48 (s, 2H), 3.00-2.95 (m, 1H), 2.89-2.82 (m, 1H), 2.79-2.77 (m, 2H), 2.67-2.65 (m, 1H), 2.25-2.22 (m, 3H), 1.85-1.72 (m, 1H), 1.63 (d, J=12.8 Hz, 1H), 1.49-1.34 (m, 1H).

Example 86:—1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-fluoro-1,2-dihydroquinoxalin-2-one

86

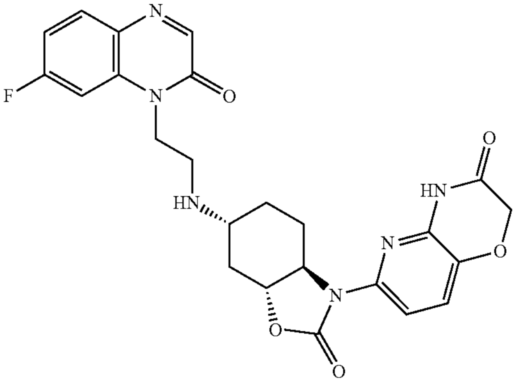

Prepared as in the method described in example 60e using (3aR,6R,7aR)-2-oxo-3-{3-oxo-2H,3H,4H-pyrido[3,2-b][1,4]oxazin-6-yl}-octahydro-1,3-benzoxazol-6-aminium trifluoroacetate 74a (200.0 mg, 0.48 mmol) and 2-(7-fluoro-2-oxo-1,2-dihydroquinoxalin-1-yl)acetaldehyde (prepared as described in WO 2008009700) (93.6 mg, 0.45 mmol) to afford 1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-fluoro-1,2-dihydroquinoxalin-2-one 86 (93.9 mg, 40%) as a pale yellow solid. LC-MS (Method B) 495.3 $[M+H]^+$; RT 6.46 min. $^1$H NMR (Method C) (DMSO-d6): δ ppm 11.23 (brs, 1H), 8.21 (s, 1H), 7.89 (dd, J=8.6, 6.1 Hz, 1H), 7.64 (dd, J=11.1, 2.6 Hz, 1H), 7.42 (d, J=8.6 Hz, 1H), 7.26 (td, J=8.6, 2.6 Hz, 1H), 7.17 (d, J=8.6 Hz, 1H), 4.62 (s, 2H), 4.23 (t, J=7.0 Hz, 2H), 4.04 (td, J=11.8, 3.3 Hz, 1H), 3.74 (td, J=11.1, 3.3 Hz, 1H), 3.14-2.92 (m, 1H) 2.88-2.83 (m, 2H), 2.79-2.72 (m, 2H), 2.44-2.38 (m, 1H), 1.98-1.92 (m, 1H), 1.45 (q, J=11.1 Hz, 1H), 1.37-1.27 (m, 1H), 1.26-1.14 (m, 1H).

Example 87:—(3aR,6R,7aR)-6-[(2-{3-methoxy-6-oxo-5H,6H-pyrido[2,3-b]pyrazin-5-yl}ethyl)amino]-3-{3-oxo-2H,3H,4H-pyrido[3,2-b][1,4]oxazin-6-yl}-octahydro-1,3-benzoxazol-2-one

87

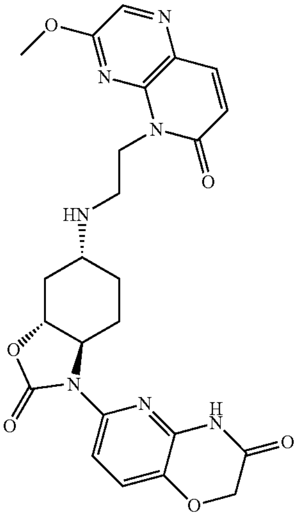

Prepared as in the method described in Example 60e using 2-{3-methoxy-6-oxo-5H,6H-pyrido[2,3-b]pyrazin-5-yl}acetaldehyde (55 mg, 0.25 mmol)(WO2008009700) and (3aR,6R,7aR)-2-oxo-3-{3-oxo-2H,3H,4H-pyrido[3,2-b][1,4]oxazin-6-yl}-octahydro-1,3-benzoxazol-6-aminium trifluoroacetate 74a (105 mg, 0.25 mmol) to afford (3aR,6R,7aR)-6-[(2-{3-methoxy-6-oxo-5H,6H-pyrido[2,3-b]pyrazin-5-yl}ethyl)amino]-3-{3-oxo-2H,3H,4H-pyrido[3,2-b][1,4]oxazin-6-yl}-octahydro-1,3-benzoxazol-2-one 87 (19 mg, 15%). LC-MS (Method A) 508.3 $[M+H]^+$; RT 2.31 min. $^1$H NMR (Method C) (DMSO-d6): δ ppm 11.24 (s, 1H), 8.23 (s, 1H), 7.96 (d, J=9.5 Hz, 1H), 7.42 (d, J=8.5 Hz, 1H), 7.18 (d, J=8.5 Hz, 1H), 6.74 (d, J=9.5 Hz, 1H), 4.62 (s, 2H), 4.39 (t, J=7.2 Hz, 2H), 4.11-4.01 (m, 4H), 3.75 (td, J=11.2, 3.4 Hz, 1H), 2.91-2.72 (m, 4H), 2.45-2.42 (m, 1H), 2.06 (br. s, 1H), 1.99-1.96 (m, 1H), 1.46 (q, J=11.2 Hz, 1H), 1.37-1.29 (m, 1H), 1.28-1.16 (m, 1H).

Example 88:—1-(3-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}propyl)-6,7-difluoro-1,2-dihydroquinoxalin-2-one

88

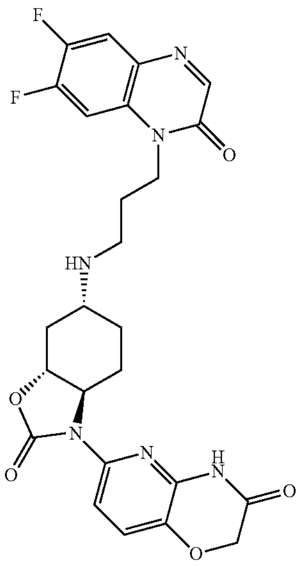

Prepared as in the method described in Example 60e using 3-(6,7-difluoro-2-oxo-1,2-dihydroquinoxalin-1-yl)propanal (114 mg, 0.48 mmol) (WO 2012108376) and (3aR,6R,7aR)-2-oxo-3-{3-oxo-2H,3H,4H-pyrido[3,2-b][1,4]oxazin-6-yl}-octahydro-1,3-benzoxazol-6-aminium trifluoroacetate 74a (200 mg, 0.48 mmol) to afford 1-(3-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}propyl)-6,7-difluoro-1,2-dihydroquinoxalin-2-one 88 (111 mg, 44%). LC-MS (Method A) 527.3 $[M+H]^+$; RT 2.61 min. $^1$H NMR (Method C) (DMSO-d6): δ ppm 11.25 (br. s, 1H), 8.27 (s, 1H), 8.10-7.94 (m, 2H), 7.42 (d, J=8.3 Hz, 1H), 7.18 (d, J=8.3 Hz, 1H), 4.62 (s, 2H), 4.22 (t, J=7.4 Hz, 1H), 4.06 (td, J=11.2, 3.4 Hz, 1H), 3.75 (td, J=11.2, 3.4 Hz, 1H), 2.80-2.74 (m, 1H), 2.71-2.54 (m, 4H), 2.53-2.42 (m, 2H), 2.06-1.94 (m, 1H), 1.80-1.70 (m, 2H), 1.52-1.20 (m, 3H).

Example 89:—1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-(prop-2-en-1-yloxy)-1,2-dihydroquinolin-2-one

89

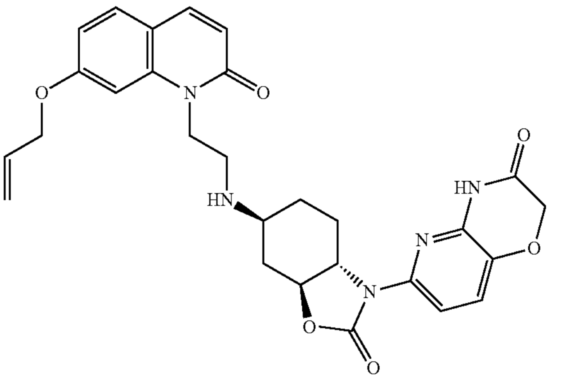

(3aS,6S,7aS)-2-oxo-3-{3-oxo-2H,3H,4H-pyrido[3,2-b][1,4]oxazin-6-yl}-octahydro-1,3-benzoxazol-6-aminium trifluoroacetate 60d (250 mg, 0.60 mmol) was added to DCM (30 mL) to afford a pink insoluble mixture. Trimethylamine (0.41 mL, 2.96 mmol) (reaction decolourised) was added and all the solid dissolved after 5 min. To this was added 2-[2-oxo-7-(prop-2-en-1-yloxy)-1,2-dihydroquinolin-1-yl] acetaldehyde 9b (145 mg, 0.60 mmol) and 3 Å molecular sieves and the mixture stirred for 17 h. $NaBH(OAc)_3$ (380 mg, 1.79) was added and the mixture stirred for a further 72 h. The reaction was quenched with sat. aq. $K_2CO_3$ (50 mL), extracted with DCM (1×50 mL), dried over $MgSO_4$ and solvent evaporated to afford an orange foam. Purification via column chromatography eluting with DCM and then 5% MeOH/DCM gave a white solid. This was triturated with $Et_2O$ (50 mL) and the solid was filtered and air dried to give 1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-(prop-2-en-1-yloxy)-1,2-dihydroquinolin-2-one 89 (268 mg, 83% yield) as a white solid. LC-MS (Method A) 532.3 $[M+H]^+$; RT 2.58 min. $^1H$ NMR (Method C) (DMSO-d6): δ ppm 11.23 (s, 1H), 7.82 (d, J=9.4 Hz, 1H), 7.65 (d, J=8.7 Hz, 1H), 7.42 (d, J=8.5 Hz, 1H), 7.18 (d, J=8.5 Hz, 1H), 7.06 (d, J=2.3 Hz, 1H), 6.93 (dd, J=8.7 Hz, 2.3 Hz, 1H), 6.43 (d, J=9.4 Hz, 1H), 6.14-6.04 (m, 1H), 5.47 (d, J=17.3 Hz, 1H), 5.31 (d, J=10.5 Hz, 1H), 4.77-4.73 (m, 2H), 4.63 (s, 2H), 4.26 (t, J=7.4 Hz, 2H), 4.08 (t, J=11.7 Hz, 1H), 3.76 (td, J=11.2, 3.4 Hz, 1H), 2.96-2.67 (m, 4H), 2.45-2.42 (m, 2H), 2.06-1.94 (m, 1H), 1.49 (q, J=11.2 Hz, 1H), 1.35-1.21 (m, 2H).

Example 90:—1-(3-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}propyl)-6,7-difluoro-1,2-dihydroquinoxalin-2-one

90

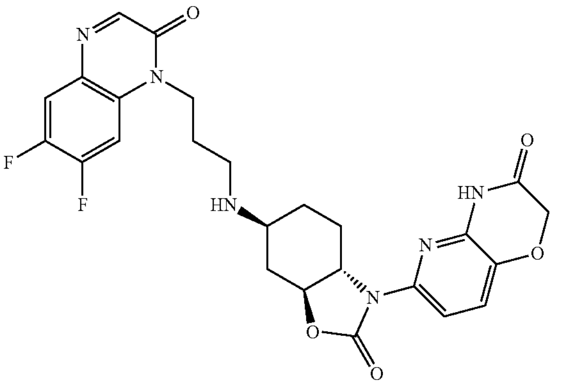

Prepared as described in example 60e using (3aS,6S,7aS)-2-oxo-3-{3-oxo-2H,3H,4H-pyrido[3,2-b][1,4]oxazin-6-yl}-octahydro-1,3-benzoxazol-6-aminium trifluoroacetate 60d (108.0 mg, 0.26 mmol) and 3-oxo-4-(2-oxoethyl)-3,4-dihydroquinoxaline-6-carbonitrile (prepared as described in WO 2012108376) (58.6 mg, 0.25 mmol) to afford 1-(3-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}propyl)-6,7-difluoro-1,2-dihydroquinoxalin-2-one 90 (21.0 mg, 15%) as a yellow solid. LC-MS (Method B) 527.3 $[M+H]^+$; RT 6.53 min. $^1H$ NMR (Method C) (DMSO-d6): δ ppm 11.23 (br s, 1H), 8.26 (s, 1H), 8.01-7.93 (m, 2H), 7.42 (d, J=8.5 Hz, 1H), 7.18 (d, J=8.5 Hz, 1H), 4.63 (s, 2H), 4.23 (t, J=7.2 Hz, 2H), 4.06 (td, J=11.8, 3.3 Hz, 1H), 3.75 (td, J=11.1, 3.3 Hz, 1H), 2.81-2.74 (m, 1H), 2.72-2.57 (m, 3H), 2.48-2.42 (m, 1H), 2.05-1.97 (m, 1H), 1.82-1.73 (m, 2H), 1.48 (q, J=11.1 Hz, 1H), 1.38-1.21 (m, 2H).

Example 91:—1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-propoxy-1,2-dihydroquinolin-2-one

91

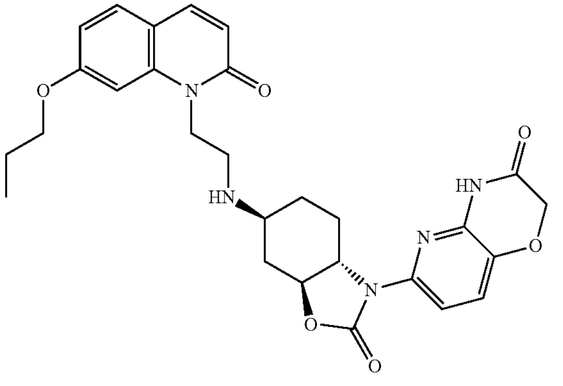

1-(2-{[(3aS,6S,7aS)-2-oxo-3-{3-oxo-2H,3H,4H-pyrido[3,2-b][1,4]oxazin-6-yl}-octahydro-1,3benzoxazol-6-yl]amino}ethyl)-7-(prop-2-en-1-yloxy)-1,2-dihydroquinolin-2-one 89 (168 mg, 0.32 mmol) was dissolved in THF (10 mL)/EtOH (30 mL) and to this was added Palladium, 10 wt. % on carbon powder (dry) (16.8 mg, 0.16 mmol). The mixture was stirred under an atmosphere of $H_2$ for 48 h. The reaction was filtered, evaporated and the concentrated residue purified via column chromatography eluting with 0 to 5% MeOH in DCM to afford 1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-propoxy-1,2-dihydroquinolin-2-one 91 (6 mg, 3.38%) as a white solid. LC-MS (Method A) 534.3 $[M+H]^+$; RT 2.68 min. $^1H$ NMR (Method C) (DMSO-d6): δ ppm 11.23 (s, 1H), 7.82 (d, J=9.4 Hz, 1H), 7.65 (d, J=8.7 Hz, 1H), 7.42 (d, J=8.5 Hz, 1H), 7.18 (d, J=8.5 Hz, 1H), 7.06 (d, J=2.3 Hz, 1H), 6.93 (dd, J=8.7 Hz, 2.3 Hz, 1H), 6.43 (d, J=9.4 Hz, 1H), 4.63 (s, 2H), 4.27 (t, J=7.4 Hz, 2H), 4.11-4.02 (m, 3H), 3.76 (td, J=11.2, 3.4 Hz, 1H), 2.96-2.67 (m, 4H), 2.45-2.42 (m, 2H), 2.06-1.94 (m, 1H), 1.80 (sextet, J=7.3 Hz, 2H), 1.49 (q, J=11.2 Hz, 1H), 1.35-1.21 (m, 2H), 1.04 (t, J=7.3 Hz, 3H).

Example 92:—1-(3-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}propyl)-7-fluoro-1,2-dihydroquinoxalin-2-one

92

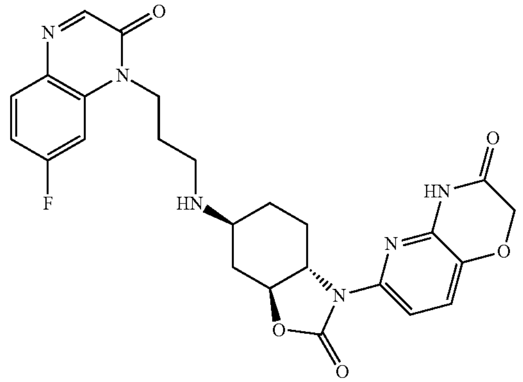

Prepared as described in example 60e using (3aS,6S,7aS)-2-oxo-3-{3-oxo-2H,3H,4H-pyrido[3,2-b][1,4]oxazin-6-yl}-octahydro-1,3-benzoxazol-6-aminium trifluoroacetate 60d (100.0 mg, 0.24 mmol) and 3-(6-fluoro-2-oxo-1,2-dihydroquinoxalin-1-yl)propanal (prepared as described in WO 2012108376) (50.0 mg, 0.23 mmol) to afford 1-(3-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}propyl)-7-fluoro-1,2-dihydroquinoxalin-2-one 92 (66.4 mg, 55%) as a yellow solid. LC-MS (Method B) 509.2 $[M+H]^+$; RT 6.28 min. $^1H$ NMR (Method C) (DMSO-d6): δ ppm 11.24 (br s, 1H), 8.20 (s, 1H), 7.90 (dd, J=8.5, 6.2 Hz, 1H), 7.68 (dd, J=11.1, 2.6 Hz, 1H), 7.42 (d, J=8.5 Hz, 1H), 7.26 (td, J=8.5, 2.6 Hz, 1H), 7.17 (d, J=8.5 Hz, 1H), 4.62 (s, 2H), 4.23 (dd, J=8.5, 6.2 Hz, 2H), 4.05 (td, J=11.8, 3.3 Hz, 1H), 3.75 (td, J=11.1, 3.3 Hz, 1H), 2.80-2.74 (m, 1H), 2.71-2.57 (m, 3H), 2.49-2.40 (m, 1H), 2.05-1.98 (m, 1H), 1.81-1.73 (m, 2H), 1.48 (q, J=11.1 Hz, 1H), 1.39-1.26 (m, 1H), 1.28-1.20 (m, 1H).

Example 93:—1-(3-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}propyl)-7-(difluoromethoxy)-1,2-dihydro-1,5-naphthyridin-2-one

93

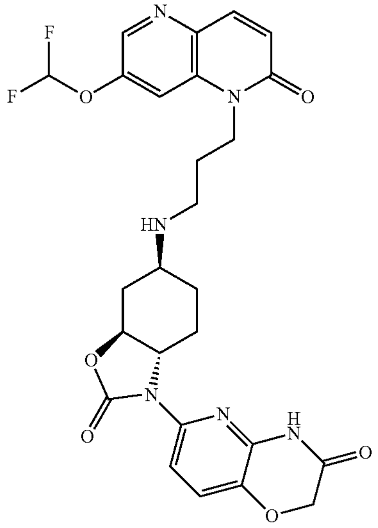

a) 7-(difluoromethoxy)-2-methoxy-1,5-naphthyridine 93a

Sodium chlorodifluoroacetate (1.3 g, 8.5 mmol) was added to a stirred solution of 6-methoxy-1,5-naphthyridin-3-ol (prepared as described in WO2010084152) (500 mg, 2.8 mmol) and $Cs_2CO_3$ (2.78 g, 8.5 mmol) in DMF (5.7 mL) and heated to 100° C. for 17 h under nitrogen. The reaction mixture was allowed to cool to room temperature and diluted with a 10% MeOH/DCM solution (20 mL). The reaction mixture was filtered through a pad of celite and washed with 10% MeOH/DCM (40 mL). The filtrate was collected and concentrated under reduced pressure and the resulting crude product purified by chromatography using a gradient of 0-5% MeOH/DCM. Clean product fractions were collected and concentrated under reduced pressure to afford 7-(difluoromethoxy)-2-methoxy-1,5-naphthyridine 93a (196 mg, 31%) as a white solid. LC-MS (Method A): 227.1 $[M+H]^+$, RT: 2.80 min.

b) 7-(difluoromethoxy)-1,2-dihydro-1,5-naphthyridin-2-one 93b

HCl (6M in isopropanol) (2.0 mL, 12 mmol) was added to a stirred solution of 7-(difluoromethoxy)-2-methoxy-1,5-naphthyridine 93a (196 mg, 0.87 mmol) in IPA (10 mL) and heated to 100° C. for 2 h. The reaction mixture was allowed to cool to room temperature and quenched with 2M NaOH solution to pH 8-9. Volatile organic solvent was removed under reduced pressure and the resulting saturated aqueous solution filtered under reduced pressure to afford 7-(difluoromethoxy)-1,2-dihydro-1,5-naphthyridin-2-one 93b (139 mg, 76%) as a white solid. LC-MS (Method A): 213.0 $[M+H]^+$, RT: 1.38 min.

c) 7-(difluoromethoxy)-1-(3,3-dimethoxypropyl)-1,2-dihydro-1,5-naphthyridin-2-one 93c 3-Bromo-1,1-dimethoxypropane (0.15 mL, 1.1 mmol) was added to a stirred solution of 7-(difluoromethoxy)-1,2-dihydro-1,5-naphthyridin-2-one 93b (140 mg, 0.66 mmol) and $Cs_2CO_3$ (280 mg, 0.86 mmol) in DMF (2.5 mL) and heated to 60° C. for 17 h. The reaction mixture was allowed to cool to room temperature and quenched with $H_2O$ (20 mL) and extracted with $Et_2O$ (3×40 mL). Organic extracts were combined, dried ($MgSO_4$) and concentrated under reduced pressure to afford crude product. The crude product was purified by chromatography using a gradient of 0-100% EtOAc/DCM. Clean product fractions were collected and concentrated under reduced pressure to afford 7-(difluoromethoxy)-1-(3,3-dimethoxypropyl)-1,2-dihydro-1,5-naphthyridin-2-one 93c (61.9 mg, 30%) as a white solid. LCMS (Method A): 315.1 $[M+H]^+$, RT: 2.28 min.

d) 3-[7-(difluoromethoxy)-2-oxo-1,2-dihydro-1,5-naphthyridin-1-yl]propanal 93d

HCl (3M, 0.33 mL, 0.98 mmol) was added to a solution of 7-(difluoromethoxy)-1-(3,3-dimethoxypropyl)-1,2-dihydro-1,5-naphthyridin-2-one 93c (61.9 mg, 0.2 mmol) in THF (2 mL) and heated to 60° C. for 2 h. The reaction mixture was allowed to cool to room temperature and quenched with solid $NaHCO_3$ to pH 8 and diluted with $H_2O$ (20 mL). Volatile organic solvent was removed under reduced pressure and the resulting aqueous extracted with EtOAc (3×20 mL). The organic extracts were combined, dried ($MgSO_4$) and concentrated under reduced pressure to afford 3-[7-(difluoromethoxy)-2-oxo-1,2-dihydro-1,5-naphthyridin-1-yl]propanal 93d (47.8 mg, 91%) as a white solid. LC-MS (Method A): 269.0 $[M+H]^+$, RT: 1.37 min.

e) 1-(3-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}propyl)-7-(difluoromethoxy)-1,2-dihydro-1,5-naphthyridin-2-one 93

Prepared as described in example 60e using 3-[7-(difluoromethoxy)-2-oxo-1,2-dihydro-1,5-naphthyridin-1-yl]propanal 93d (41 mg, 0.15 mmol) and (3aS,6S,7aS)-2-oxo-3-{3-oxo-2H,3H,4H-pyrido[3,2-b][1,4]oxazin-6-yl}-octahydro-1,3-benzoxazol-6-aminium trifluoroacetate 60d (70.3 mg, 0.17 mmol) to afford 1-(3-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}propyl)-7-(difluoromethoxy)-1,2-dihydro-1,5-naphthyridin-2-one 93 (40.1 mg, 47%) as a white solid. LC-MS (Method A): 557.2 $[M+H]^+$, RT: 2.38 min. $^1H$ NMR (Method C) (DMSO-d6): δ ppm 11.26 (s, 1H), 8.48 (d, 1.9 Hz, 1H), 7.97 (d, 1.9 Hz, 1H), 7.96 (d, 9.9 Hz, 1H), 7.53 (t, 73.2 Hz, 1H), 7.43 (d, 8.6 Hz, 1H), 7.17 (d, 8.6 Hz, 1H), 6.86 (d, 9.9 Hz, 1H), 4.63 (s, 2H), 4.27 (t, 7.2 Hz, 2H), 4.05 (td, 11.9, 3.2 Hz, 1H), 3.75 (td, 11.2, 3.2 Hz, 1H), 2.78-2.75 (m, 1H), 2.68-2.58 (m, 3H), 2.02 (d, 1.3 Hz, 1H), 1.74 (t, 7.2 Hz, 2H), 1.51-1.44 (m, 1H), 1.37-1.23 (m, 3H).

Example 94:—1-[(2S)-3-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}-2-hydroxypropyl]-7-fluoro-1,2-dihydroquinoxalin-2-one & 1-[(2R)-3-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}-2-hydroxypropyl]-7-fluoro-1,2-dihydroquinoxalin-2-one

94

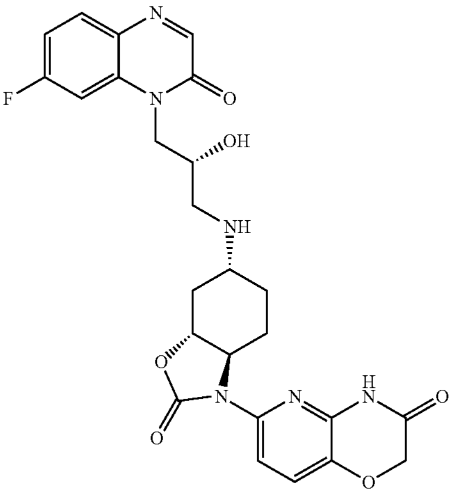

+

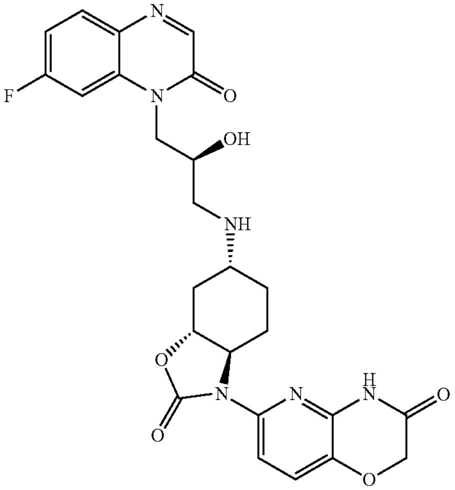

a) rac-7-fluoro-1-(oxiran-2-ylmethyl)-1,2-dihydroquinoxalin-2-one 94a 7-fluoro-1,2-dihydroquinoxalin-2-one (1.0 g, 6.09 mmol), $CsCO_3$ (1.6 g, 4.91 mmol) and 2-(bromomethyl)oxirane (0.68 mL, 7.92 mmol) were mixed with DMF (50 mL) and stirred for 17 h. The mixture was quenched with sat. $NH_4Cl$ (50 mL), extracted with $Et_2O$ (2×75 ml), dried ($MgSO_4$), and evaporated to afford a yellow liquid. The crude was purified via silica gel chromatography eluting with $Et_2O$ to afford rac-7-fluoro-1-(oxiran-2-ylmethyl)-1,2-dihydroquinoxalin-2-one 94a (420 mg, 31% yield) as a white solid.

b) 1-[(2S)-3-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}-2-hydroxypropyl]-7-fluoro-1,2-dihydroquinoxalin-2-one & 1-[(2R)-3-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}-2-hydroxypropyl]-7-fluoro-1,2-dihydroquinoxalin-2-one 94

(3aR,6R,7aR)-2-oxo-3-{3-oxo-2H,3H,4H-pyrido[3,2-b][1,4]oxazin-6-yl}-octahydro-1,3-benzoxazol-6-aminium trifluoroacetate 74a (247 mg, 0.59 mmol), 7-fluoro-1-(oxiran-2-ylmethyl)-1,2-dihydroquinoxalin-2-one 94a (130 mg, 0.59 mmol) and triethylamine (0.33 mL, 2.36 mmol) were added to EtOH (30 mL) and heated at 69° C. for 10 h. The reaction was evaporated and purified via silica gel chromatography, eluting with 0-10% MeOH in EtOAc to afford a solid. This solid was dissolved in DCM and $Et_2O$ added to afford a precipitate which was filtered and air dried to give 1-[(2S)-3-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}-2-hydroxypropyl]-7-fluoro-1,2-dihydroquinoxalin-2-one & 1-[(2R)-3-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}-2-hydroxypropyl]-7-fluoro-1,2-dihydroquinoxalin-2-one 94 (53.6 mg, 17%) as a white solid. LC-MS (Method A) 525.2 $[M+H]^+$; RT 2.22 min. $^1H$ NMR (Method C) (DMSO-d6): δ ppm 11.28 (s, 1H), 8.22 (s, 1H), 7.89 (dd, J=7.4 Hz, J=5.2 Hz 1H), 7.68 (d, J=7.4 Hz, 1H), 7.43 (t, J=8.3 Hz, 1H), 7.24 (dd J=7.4 Hz, J=7.4 Hz, 1H), 7.17 (d, J=8.3 Hz, 1H), 5.06 (brs, 1H), 4.63 (s, 2H), 4.28-4.17 (m, 2H), 4.06 (td, J=11.2, 3.4 Hz, 1H), 3.97-3.81 (m, 1H), 3.76 (td, J=11.2, 3.4 Hz, 1H), 2.82-2.62 (m, 4H), 2.08-1.81 (m, 3H), 1.59-1.46 (m, 1H), 1.40-1.21 (m, 2H).

Example 95:—1-[(2S)-3-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}-2-hydroxypropyl]-7-fluoro-1,2-dihydroquinoxalin-2-one & 1-[(2R)-3-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}-2-hydroxypropyl]-7-fluoro-1,2-dihydroquinoxalin-2-one

95

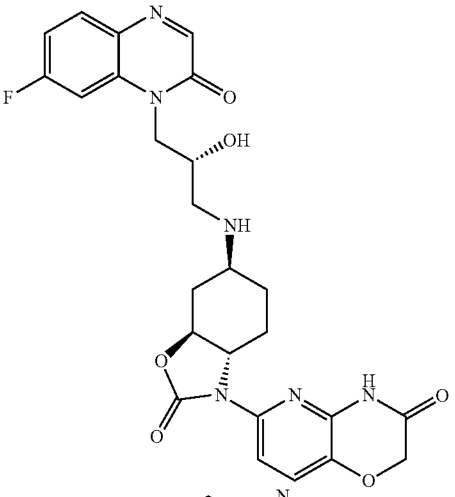

+

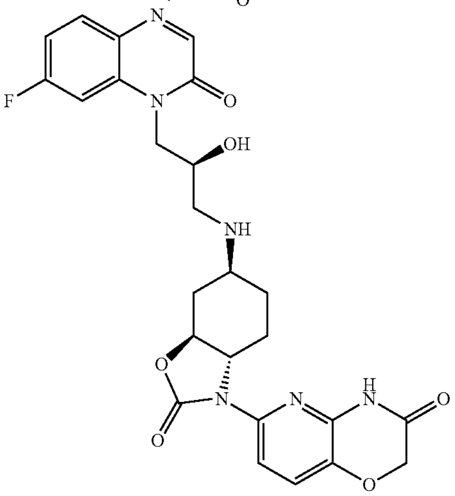

(3aS,6S,7aS)-2-oxo-3-{3-oxo-2H,3H,4H-pyrido[3,2-b][1,4]oxazin-6-yl}-octahydro-1,3-benzoxazol-6-aminium trifluoroacetate 60d (247 mg, 0.59 mmol), rac-7-fluoro-1-(oxiran-2-ylmethyl)quinoxalin-2-one 94a (130 mg, 0.59 mmol) and triethylamine (0.33 mL, 2.36 mmol) were added to EtOH (30 mL) and heated at 69° C. for 10 h. The reaction was evaporated and purified via silica gel column chromatography eluting with 0-10% MeOH in EtOAc to afford a solid which was dissolved in DCM. $Et_2O$ was added to afford a precipitate which was filtered and air dried to give 1-[(2S)-3-{[(3aS,6S,7aS)-2-oxo-3-{3-oxo-2H,3H,4H-pyrido[3,2-b][1,4]oxazin-6-yl}-octahydro-1,3-benzoxazol- 6-yl]amino}-2-hydroxypropyl]-7-fluoro-1,2-dihydroquinoxalin-2-one & 1-[(2R)-3-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}-2-hydroxypropyl]-7-fluoro-1,2-dihydroquinoxalin-2-one 95 (45 mg, 14% yield) as a white solid. LC-MS (Method A) 525.2 [M+H]$^+$; RT 2.20 min. $^1$H NMR (Method C) (DMSO-d6): δ ppm 11.28 (s, 1H), 8.22 (s, 1H), 7.89 (dd, J=7.4 Hz, J=5.2 Hz 1H), 7.68 (d, J=7.4 Hz, 1H), 7.43 (t, J=8.3 Hz, 1H), 7.24 (dd J=7.4 Hz, J=7.4 Hz, 1H), 7.17 (d, J=8.3 Hz, 1H), 5.06 (brs, 1H), 4.63 (s, 2H), 4.28-4.17 (m, 2H), 4.06 (td, J=11.2, 3.4 Hz, 1H), 3.97-3.81 (m, 1H), 3.76 (td, J=11.2, 3.4 Hz, 1H), 2.82-2.62 (m, 4H), 2.08-1.81 (m, 3H), 1.59-1.46 (m, 1H), 1.40-1.21 (m, 2H).

Example 96: 1-(3-{[(3aS,6S,7aS)-2-oxo-3-{3-oxo-2H,3H,4H-pyrido[3,2-b][1,4]thiazin-6-yl}-octahydro-1,3-benzoxazol-6-yl]amino}propyl)-7-methoxy-1,2-dihydro-1,5-naphthyridin-2-one

96

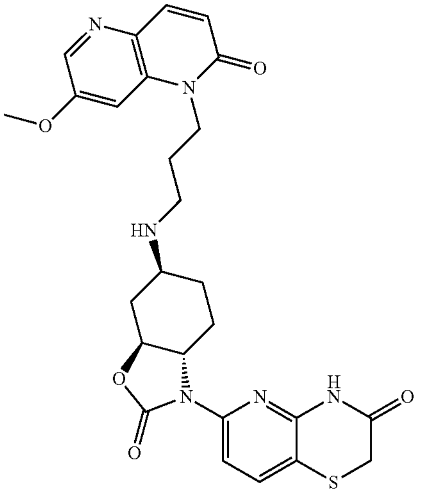

Prepared as described in example 60e using 3-(7-methoxy-2-oxo-1,2-dihydro-1,5-naphthyridin-1-yl)propanal (prepared according to WO2011148962) (63.2 mg, 0.15 mmol) and (3aS,6S,7aS)-2-oxo-3-{3-oxo-2H,3H,4H-pyrido[3,2-b][1,4]thiazin-6-yl}-octahydro-1,3-benzoxazol-6-aminium chloride 61b (144.6 mg, 0.35 mmol) to afford 1-(3-{[(3aS,6S,7aS)-2-oxo-3-{3-oxo-2H,3H,4H-pyrido[3,2-b][1,4]thiazin-6-yl}-octahydro-1,3-benzoxazol-6-yl]amino}propyl)-7-methoxy-1,2-dihydro-1,5-naphthyridin-2-one 96 as a white solid (10 mg, 10%). LC-MS (Method A): 537.2 [M+H]$^+$, RT: 2.44 min. $^1$H NMR (Method C) ($CDCl_3$): δ ppm 10.98 (s, 1H), 8.31 (d, J=2.2 Hz, 1H), 7.88 (d, J=9.7 Hz, 1H), 7.79, d, J=8.3 Hz, 1H), 7.53 (d, J=2.2 Hz, 1H), 7.29, d, J=8.3 Hz, 1H), 6.68 (d, J=9.7 Hz, 1H), 4.31 (t, J=7.2 Hz, 2H), 4.08 (td, J=11.8, 3.3 Hz, 1H), 4.00 (s, 3H), 3.79-3.73 (m, 1H), 3.57 (d, J=14.9 Hz, 1H), 3.53 (d, J=14.9 Hz, 1H), 3.00-2.94 (m, 1H), 2.59-2.53 (m, 1H), 2.04-1.99 (m, 2H), 1.82-1.71 (m, 2H), 1.54-1.42 (m, 2H), 1.33-1.24 (m, 3H).

Example 97:—1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-[2-(morpholin-4-yl)ethoxy]-1,2-dihydroquinolin-2-one

97

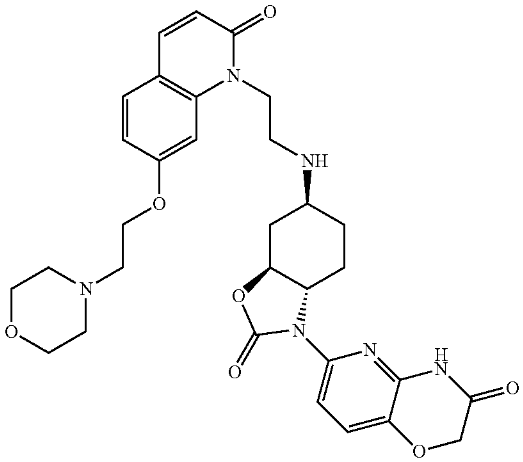

a) 1-(2,2-diethoxyethyl)-7-[2-(morpholin-4-yl)ethoxy]-1,2-dihydroquinolin-2-one 97a $K_2CO_3$ (450 mg, 3.25 mmol) was added to a solution of 1-(2,2-diethoxyethyl)-7-hydroxy-1,2-dihydroquinolin-2-one 9d (300 mg, 1.08 mmol) and 4-(2-bromoethyl)morpholine (800 mg, 4.12 mmol) in NMP (3 mL) and heated at 90° C. under nitrogen for 17 h. Water and EtOAc were added and the resulting layers separated. The aqueous phase was further extracted with EtOAc and 20% MeOH/DCM. Organic extracts were combined with the original organic layer and concentrated under reduced pressure to afford a brown residue. The crude product was purified via silica gel chromatography using a gradient of 0-100% EtOAc/petroleum ether followed by 0-15% MeOH/EtOAc. Clean product fractions were collected and concentrated under reduced pressure to afford 1-(2,2-diethoxyethyl)-7-[2-(morpholin-4-yl)ethoxy]-1,2-dihydroquinolin-2-one 97a (269 mg, 63%) as a clear oil. LC-MS (Method A) 391.2 [M+H]$^+$; RT 1.71 min.

b) 2-{7-[2-(morpholin-4-yl)ethoxy]-2-oxo-1,2-dihydroquinolin-1-yl}acetaldehyde 97b Aqueous HCl (1M, 10 mL, 10 mmol) was added to a solution of 1-(2,2-diethoxyethyl)-7-[2-(morpholin-4-yl)ethoxy]-1,2-dihydroquinolin-2-one 97a (260 mg, 0.67 mmol) in THF (10 mL) and stirred at room temperature for 7 h. The reaction mixture was adjusted to pH 7-8 using saturated aqueous $Na_2CO_3$ and concentrated under reduced pressure to afford a yellow residue. This residue was diluted with EtOAc (100 mL), stirred for 1 h at room temperature and the resulting solid filtered. The filtrate was collected and concentrated under reduced pressure to afford 2-{7-[2-(morpholin-4-yl)ethoxy]-2-oxo-1,2-dihydroquinolin-1-yl}acetaldehyde 97b (109 mg, 41%, 80% purity) as a light brown gum and used without further purification. LC-MS (Method A) 317.2 [M+H]$^+$; RT 1.36 min.

c) 1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-[2-(morpholin-4-yl)ethoxy]-1,2-dihydroquinolin-2-one 97

Prepared as described in example 60e using 2-{7-[2-(morpholin-4-yl)ethoxy]-2-oxo-1,2-dihydroquinolin-1-yl}acetaldehyde 97b (105.0 mg, 0.27 mmol) and (3aS,6S,7aS)-2-oxo-3-{3-oxo-2H,3H,4H-pyrido[3,2-b][1,4]oxazin-6-yl}-octahydro-1,3-benzoxazol-6-aminium trifluoroacetate 60d (111.1 mg, 0.27 mmol). The reaction mixture was quenched with sat. aq. $Na_2CO_3$ (5 mL) and mixed with 20% MeOH in DCM (100 mL) before passing through a SPE phase separator. The organic filtrate was concentrated under reduced pressure and the resulting residue purified via silica gel chromatography using 0-100% EtOAC/DCM, 0-20% MeOH/EtOAc and then 0-20% $NH_3$ in MeOH/EtOAc. Clean product fractions were concentrated under reduced pressure with ether azeotroping to afford 1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-[2-(morpholin-4-yl)ethoxy]-1,2-dihydroquinolin-2-one 97 (9.4 mg, 5%) as an off white solid. LC-MS (Method A) 605.3 $[M+H]^+$, RT 1.66 min. $^1H$ NMR (Method C) (DMSO-d6): δ ppm 7.82 (d, J=9.3 Hz, 1H), 7.64 (d, J=8.7 Hz, 1H), 7.42 (d, J=8.4, 1H), 7.16 (d, J=8.6, 1H), 7.06-7.02 (m, 1H), 6.91 (dd, J=8.7, 2.2 Hz, 1H), 6.42 (d, J=9.3 Hz, 1H), 4.62 (s, 2H), 4.20-4.31 (m, 3H), 4.09-3.98 (m, 2H), 3.80-3.70 (m, 1H), 3.65-3.52 (m, 3H), 3.43-3.24 (m, 4H), 2.85-2.76 (m, 3H), 2.76-2.72 (m, 2H), 2.46-2.36 (m, 2H), 2.04-1.96 (m, 1H), 1.56-1.40 (m, 1H), 1.39-1.28 (m, 1H), 1.24-1.20 (m, 2H).

Example 98: 1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-(difluoromethoxy)-1,2-dihydro-1,5-naphthyridin-2-one

98

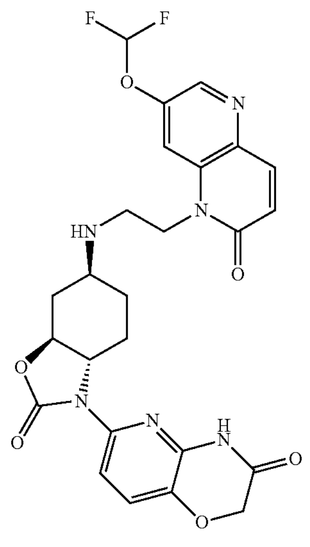

a) 7-(difluoromethoxy)-1-(2,2-dimethoxyethyl)-1,2-dihydro-1,5-naphthyridin-2-one 98a 2-Bromo-1,1-dimethoxypropane (0.08 mL, 0.7 mmol) was added to a stirred solution of 7-(difluoromethoxy)-1,2-dihydro-1,5-naphthyridin-2-one 93b (115 mg, 0.54 mmol) and $Cs_2CO_3$ (230 mg, 0.70 mmol) in DMF (3 mL) and heated to 80° C. for 17 h. The reaction mixture was allowed to cool to room temperature and quenched with $H_2O$ (20 mL) and extracted with $Et_2O$ (3×40 mL). Organic extracts were combined, dried ($MgSO_4$) and concentrated under reduced pressure to afford crude product. Crude product was purified by chromatography using a gradient of 0-60% EtOAc/DCM. Clean product fractions were collected and concentrated under reduced pressure to afford 7-(difluoromethoxy)-1-(2,2-dimethoxyethyl)-1,2-dihydro-1,5-naphthyridin-2-one 98a as a white solid (74.2 mg, 46%). LCMS (Method A): 301.1 $[M+H]^+$, RT: 2.26 min.

b) 2-[7-(difluoromethoxy)-2-oxo-1,2-dihydro-1,5-naphthyridin-1-yl]acetaldehyde 98b 3M HCl (0.57 mL, 1.71 mmol) was added to a solution of 7-(difluoromethoxy)-1-(2,2-dimethoxyethyl)-1,2-dihydro-1,5-naphthyridin-2-one 98a (74.2 mg, 0.25 mmol) in THF (5 mL) and heated to 60° C. for 2 h under nitrogen. The reaction mixture was allowed to cool to room temperature and quenched with solid $NaHCO_3$ to pH 8 and diluted with $H_2O$ (20 mL). Volatile organic solvent was removed under reduced pressure and the resulting aqueous extracted with EtOAc (3×20 mL). The organic extracts were combined, dried ($MgSO_4$) and concentrated under reduced pressure to afford 2-[7-(difluoromethoxy)-2-oxo-1,2-dihydro-1,5-naphthyridin-1-yl]acetaldehyde 98b as a white solid (53.9 mg, 86%). LC-MS (Method A): 255.0 $[M+H]^+$, RT: 1.60 min.

c) 1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-(difluoromethoxy)-1,2-dihydro-1,5-naphthyridin-2-one 98

Prepared as described in Example 60e using 2-[7-(difluoromethoxy)-2-oxo-1,2-dihydro-1,5-naphthyridin-1-yl]acetaldehyde 98b (53.9 mg, 0.21 mmol) and (3aS,6S,7aS)-2-oxo-3-{3-oxo-2H,3H,4H-pyrido[3,2-b][1,4]oxazin-6-yl}-octahydro-1,3-benzoxazol-6-aminium trifluoroacetate 60d (97.6 mg, 0.23 mmol) to afford 1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-(difluoromethoxy)-1,2-dihydro-1,5-naphthyridin-2-one 98 as a white solid (84.3 mg, 73%). LC-MS (Method A): 543.2 $[M+H]^+$, RT: 2.23 min. $^1H$ NMR (Method C) (DMSO-d6):

δ ppm 11.23 (s, 1H), 8.46 (d, 2.2 Hz, 1H), 7.96 (d, 9.7 Hz, 1H), 7.94 (d, 2.3 Hz, 1H), 7.52 (t, 73.2 Hz, 1H), 7.41 (d, 8.3 Hz, 1H), 7.16 (d, 8.7 Hz, 1H), 6.85 (9.83 Hz, d, 1H), 4.62 (s, 2H), 4.25 (t, 6.9 Hz, 2H), 4.02 (td, 11.9, 3.3 Hz, 1H), 3.73 (d, 11.5, 3.3 Hz, 1H), 2.85-2.78 (m, 2H), 2.77-2.71 (m, 2H), 2.42-2.38 (m, 1H), 2.13 (br. S, 1H), 1.96-1.92 (m, 1H), 1.42 (q, 11.3 Hz, 1H), 1.35-1.26 (m, 1H), 1.23-1.13 (m, 1H).

Example 99: 1-(3-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}propyl)-7-methoxy-1,2-dihydro-1,5-naphthyridin-2-one

99

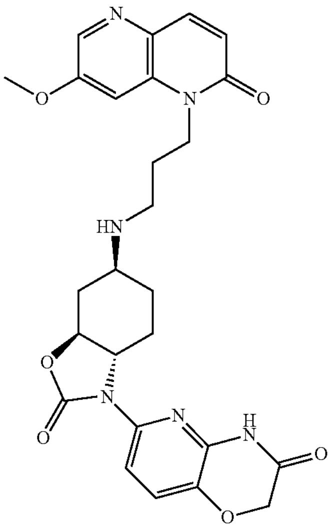

Prepared as described in example 60e using 3-(7-methoxy-2-oxo-1,2-dihydro-1,5-naphthyridin-1-yl)propanal (prepared according to WO2011148962) (73 mg, 0.31 mmol) and (3aS,6S,7aS)-2-oxo-3-{3-oxo-2H,3H,4H-pyrido[3,2-b][1,4]oxazin-6-yl}-octahydro-1,3-benzoxazol-6-aminium trifluoroacetate 60d (144.6 mg, 0.35 mmol) to afford 1-(3-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}propyl)-7-methoxy-1,2-dihydro-1,5-naphthyridin-2-one 99 as a white solid (10.6 mg, 6%). LC-MS (Method A): 521.2 $[M+H]^+$, RT: 2.10 min. $^1H$ NMR (Method C) ($CDCl_3$): δ ppm 8.31 (d, 2.31 Hz, 1H), 7.88 (d, 9.8 Hz, 1H), 7.34-7.30 (m, 2H), 7.20 (d, 2.3 Hz, 1H), 6.77 (d, 9.8 Hz, 1H), 4.64 (s, 2H), 4.41-4.31 (m, 2H), 3.99 (s, 3H), 3.96 (td, 11.2, 3.2 Hz, 1H), 3.82 (td, 11.2, 3.3 Hz, 1H), 2.82-2.77 (m, 1H), 2.73-2.66 (m, 3H), 2.64-2.60 (m, 1H), 2.18-2.14 (m, 1H), 1.99-1.94 (m, 2H), 1.58 (q, 11.2 Hz, 2H), 1.41-1.37 (m, 1H).

Example 100:—(3aS,6S,7aS)-3-{3-oxo-2H,3H,4H-pyrido[3,2-b][1,4]oxazin-6-yl}-6-[(2-{6-oxo-5H,6H-pyrido[2,3-b]pyrazin-5-yl}ethyl)amino]-octahydro-1,3-benzoxazol-2-one

100

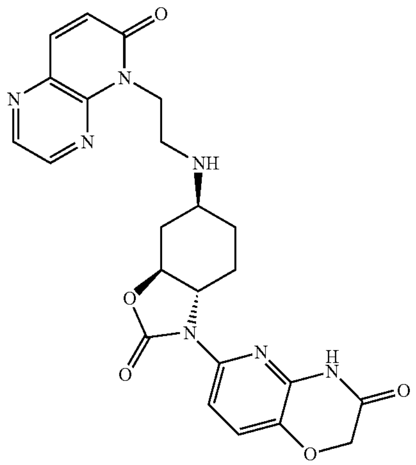

a) 3-chloro-N-(2,2-dimethoxyethyl)pyrazin-2-amine 110a

A solution of 2,3-dichloropyrazine (2.5 g, 16.78 mmol), 2,2-dimethoxyethan-1-amine (2.34 mL, 17.78 mmol) and $K_2CO_3$ (4.64 g, 33.56 mmol) in DMF (50 mL) was heated to 60° C. for 24 h. 2,2-dimethoxyethan-1-amine (2.34 mL, 17.78 mmol) was added and heating continued for a further 24 h. After cooling, $H_2O$ (50 mL) was added and the mixture extracted with diethyl ether (3×20 mL), dried over $MgSO_4$ and concentrated under reduced pressure. The residue was purified by silica gel chromatography using 0-20% EtOAc in pet ether to give 3-chloro-N-(2,2-dimethoxyethyl)pyrazin-2-amine 100a (1.46 g, 40%) as a colourless oil. LC-MS (Method A) 186.0 $[M-OMe]^+$; RT 2.13 min.

b) Butyl (2E)-3-{3-[(2,2-dimethoxyethyl)amino]pyrazin-2-yl}prop-2-enoate 100b

A solution of 3-chloro-N-(2,2-dimethoxyethyl)pyrazin-2-amine 100a (1.3 g, 5.97 mmol), $Pd(OAc)_2$ (134 mg, 0.60 mmol), di-tert-butyl(3-phenylphenyl)phosphane (267 mg, 0.90 mmol), butyl prop-2-enoate (4.7 mL, 33.10 mmol) in triethylamine (18 mL) in a microwave vial was irradiated in the microwave at 150° C. for 90 m. After cooling the reaction was concentrated under reduced pressure and purified by silica gel chromatography using 0-20% EtOAc in pet ether to give butyl (2E)-3-{3-[(2,2-dimethoxyethyl)amino]pyrazin-2-yl}prop-2-enoate 100b (910 mg, 49%) as a yellow solid. LC-MS (Method A) 310.0 $[M+H]^+$, RT 3.15 min.

c) 5-(2,2-dimethoxyethyl)-5H,6H-pyrido[2,3-b]pyrazin-6-one 100c

A solution of butyl (2E)-3-{3-[(2,2-dimethoxyethyl)amino]pyrazin-2-yl}prop-2-enoate 100b (910 mg, 2.94 mmol) followed by sodium hydride (60% in mineral oil) (71 mg, 1.47 mmol) in dry ethanol (50 mL) and heated to 80° C. for 1 h. After this time the reaction was complete, quenched with ammonium chloride and extracted with EtOAc to give a yellow solid as 5-(2,2-dimethoxyethyl)-5H,6H-pyrido[2,3-b]pyrazin-6-one 100c (691 mg, 100%). LC-MS (Method C) 204.0 $[M+H]^+$, RT 1.70 min.

d) 2-{6-oxo-5H,6H-pyrido[2,3-b]pyrazin-5-yl}acetaldehyde 100d

A solution of 5-(2,2-dimethoxyethyl)-5H,6H-pyrido[2,3-b]pyrazin-6-one 100c (240 mg, 1.02 mmol) and HCl in MeOH (4M, 5 mL) in THF (5 mL) was stirred at room temperature for 2 h. $H_2O$ (20 mL) was added and the mixture extracted with EtOAc (3×20 mL), dried over $MgSO_4$ and concentrated under reduced pressure to give 2-{6-oxo-5H,6H-pyrido[2,3-b]pyrazin-5-yl}acetaldehyde 100d (110 mg, 57%) as a white solid. $^1$H NMR (Method C) ($CDCl_3$): δ ppm 9.75 (s, 1H), 8.53 (d, J=2.4 Hz, 1H), 8.45 (d, J=2.4 Hz, 1H), 7.98 (d, J=9.8 Hz, 1H), 7.04 (d, J=9.8 Hz, 1H), 5.35 (s, 2H).

e) (3aS,6S,7aS)-3-{3-oxo-2H,3H,4H-pyrido[3,2-b][1,4]oxazin-6-yl}-6-[(2-{6-oxo-5H,6H-pyrido[2,3-b]pyrazin-5-yl}ethyl)amino]-octahydro-1,3-benzoxazol-2-one 100

Prepared as described in Example 60e from 2-{6-oxo-5H,6H-pyrido[2,3-b]pyrazin-5-yl}acetaldehyde 100d (50 mg, 0.26 mmol) and (3aS,6S,7aS)-2-oxo-3-{3-oxo-2H,3H,4H-pyrido[3,2-b][1,4]oxazin-6-yl}-octahydro-1,3-benzoxazol-6-aminium trifluoroacetate 60d (121 mg, 0.26 mmol). Purified by silica gel chromatography using 0-20% MeOH in EtOAc. The isolated residue was then dissolved in DCM (1 mL) and triturated with diethyl ether (3 mL) to give (3aS,6S,7aS)-3-{3-oxo-2H,3H,4H-pyrido[3,2-b][1,4]oxazin-6-yl}-6-[(2-{6-oxo-5H,6H-pyrido[2,3-b]pyrazin-5-yl}ethyl)amino]-octahydro-1,3-benzoxazol-2-one 100 (12 mg, 10%) as a white solid. LC-MS (Method A) 478.2 $[M+H]^+$, RT 1.94 min. $^1$H NMR (Method C) (DMSO-d6): δ ppm 11.24 (s, 1H), 8.71 (s, 1H), 8.63-8.58 (m, 1H), 8.03 (d, J=9.7 Hz, 1H), 7.43 (d, J=8.5 Hz, 1H), 7.17 (d, J=8.5 Hz, 1H), 7.01 (d, J=9.7 Hz, 1H), 4.62 (s, 2H), 4.43 (s, 2H), 4.06 (t, J=11.3 Hz, 1H), 3.74 (m, 1H), 2.90-2.60 (m, 4H), 2.59-2.45 (m, 1H), 1.99 (m, 1H), 1.46 (m, 1H), 1.33 (m, 1H), 1.24 (m, 1H).

Example 101:—1-(2-{[(3aS,6S,7aS)-2-oxo-3-{3-oxo-2H,3H,4H-pyrido[3,2-b][1,4]oxazin-6 yl}-octahydro-1,3-benzoxazol-6-yl]amino}ethyl)-7-(difluoromethoxy)-1,2-dihydro quinolin-2-one

101

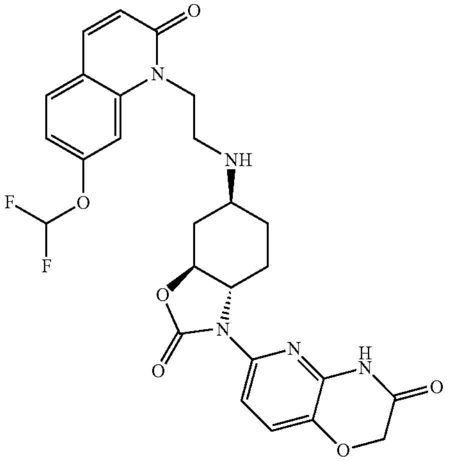

a) 1-(2,2-diethoxyethyl)-7-(difluoromethoxy)-1,2-dihydroquinolin-2-one 101a 1-(2,2-diethoxyethyl)-7-hydroxy-1,2-dihydroquinolin-2-one 9d (1.1 g, 3.97 mmol), sodium chlorodifluoroacetate (1.21 g, 7.93 mmol) and $K_2CO_3$ (0.66 g, 4.76 mmol) were added to DMF (25 mL)/$H_2O$ (2.5 mL) and the mixture heated at 100° C. for 7 h. A further sodium chlorodifluoroacetate (1.21 g, 7.93 mmol) and potassium carbonate (0.66 g, 4.76 mmol) were added and the mixture further heated at 100° C. for 17 h. The mixture was quenched with $H_2O$ (100 mL), extracted with $Et_2O$ (2×100 mL), dried over $MgSO_4$ and evaporated to afford a yellow liquid. Purification via silica gel chromatography using 60% $Et_2O$ in petroleum ether gave 1-(2,2-diethoxyethyl)-7-(difluoromethoxy)-1,2-dihydroquinolin-2-one 101a (618 mg, 48% yield) as a clear liquid. $^1$H NMR (Method C) ($CDCl_3$): δ ppm 7.67 (d, J=9.3 Hz, 1H), 7.54-7.48 (m, 2H), 6.99 (dd, J=8.5, 2.2 Hz, 1H), 6.66 (d, J=9.3 Hz, 1H), 6.59 (t, J=73.2 Hz, 1H), 4.80 (t, J=5.3 Hz, 1H), 4.36 (d, J=5.3 Hz, 2H), 3.81-3.74 (m, 2H), 3.57-3.48 (m, 2H), 1.12 (t, J=7.0 Hz, 6H).

b) 2-[7-(difluoromethoxy)-2-oxo-1,2-dihydroquinolin-1-yl]acetaldehyde 101b 1-(2,2-diethoxyethyl)-7-(difluoromethoxy)-1,2-dihydroquinolin-2-one 101a (0.6 g, 1.83 mmol) was added to THF (5 mL) and HCl (3.0 N, 5 mL, 1.83 mmol) and the mixture was stirred at 60° C. for 1 h. The mixture was quenched with $H_2O$ (50 mL), extracted with $Et_2O$ (2×50 mL), dried ($MgSO_4$) and solvent evaporated to afford a white solid. DCM and petroleum ether were added and the DCM evaporated to afford a white precipitate which was filtered and dried to give 2-[7-(difluoromethoxy)-2-oxo-1,2-dihydroquinolin-1-yl]acetaldehyde 101b (370 mg, 80% yield) as a white solid. LC-MS (Method A) 254.0 $[M+H]^+$; RT 2.04 min. $^1$H NMR (Method C) ($CDCl_3$): δ ppm 9.74 (s, 1H), 7.74 (d, J=9.3 Hz, 1H), 7.60 (d, J=8.5 Hz, 1H), 7.04 (dd, J=8.5, 2.1 Hz, 1H), 6.74-6.66 (m, 2H), 6.57 (t, J=73.0 Hz, 1H), 5.14 (s, 2H).

c) 1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-(difluoromethoxy)-1,2-dihydro quinolin-2-one 101

Prepared as described in example 60e using 2-[7-(difluoromethoxy)-2-oxo-1,2-dihydroquinolin-1-yl]acetaldehyde 101b (91 mg, 0.36 mmol) and (3aS,6S,7aS)-2-oxo-3-{3-oxo-2H,3H,4H-pyrido[3,2-b][1,4]oxazin-6-yl}-octahydro-1,3-benzoxazol-6-aminiumtrifluoroacetate 60d (150 mg, 0.36 mmol) to afford 1-(2-{[(3aS,6S,7aS)-2-oxo-3-{3-oxo-2H,3H,4H-pyrido[3,2-b][1,4]oxazin-6yl}-octahydro-1,3-benzoxazol-6-yl]amino}ethyl)-7-(difluoromethoxy)-1,2-dihydro quinolin-2-one 101 (95 mg, 49%). LC-MS (Method A) 542.2 $[M+H]^+$; RT 2.52 min. $^1$H NMR (Method C) (DMSO-d6): δ ppm 11.26 (s, 1H), 7.92 (d, J=9.2 Hz, 1H), 7.80 (d, J=8.7 Hz, 1H), 7.45 (t, J=62 Hz, 1H), 7.45-7.39 (m, 2H), 7.17 (d, J=8.5 Hz, 1H), 7.10 (d, J=2.3 Hz, 1H), 6.59 (d, J=9.4 Hz, 1H), 4.62 (s, 2H), 4.32-4.24 (m, 2H), 4.06 (td, J=11.2, 3.4 Hz, 1H), 3.76 (td, J=11.2, 3.4 Hz, 1H), 2.91-2.75 (m, 4H), 2.45-2.42 (m, 2H), 2.06-1.94 (m, 1H), 1.40-1.21 (m, 3H).

Example 102:—1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydroquinolin-2-one

102

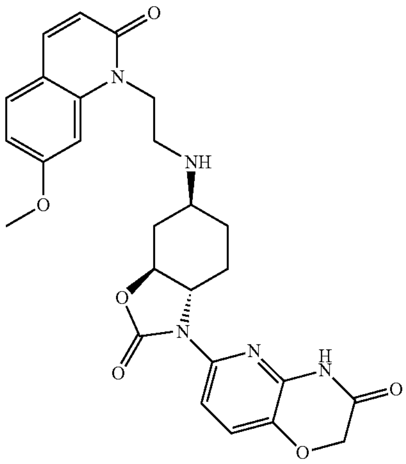

Prepared as described in example 60e using 2-(7-methoxy-2-oxo-1,2-dihydroquinolin-1-yl)acetaldehyde (WO2008009700)(78 mg, 0.36 mmol) and (3aS,6S,7aS)-2-oxo-3-{3-oxo-2H,3H,4H-pyrido[3,2-b][1,4]oxazin-6-yl}-octahydro-1,3-benzoxazol-6-aminiumtrifluoroacetate 60d (150 mg, 0.36 mmol) to afford 1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydroquinolin-2-one 102 (97 mg, 51%). LC-MS (Method A) 506.1 $[M+H]^+$; RT 2.21 min. $^1H$ NMR (Method C) (DMSO-d6): δ ppm 11.23 (s, 1H), 7.82 (d, J=9.4 Hz, 1H), 7.66 (d, J=8.7 Hz, 1H), 7.42 (d, J=8.5 Hz, 1H), 7.18 (d, J=8.5 Hz, 1H), 7.06 (d, J=2.3 Hz, 1H), 6.92 (dd, J=8.7 Hz, 2.3 Hz, 1H), 6.43 (d, J=9.4 Hz, 1H), 4.62 (s, 2H), 4.32-4.24 (m, 2H), 4.06 (td, J=11.2, 3.4 Hz, 1H), 3.91 (s, 3H), 3.76 (td, J=11.2, 3.4 Hz, 1H), 2.91-2.76 (m, 4H), 2.45-2.42 (m, 2H), 2.06-1.94 (m, 1H), 1.40-1.21 (m, 3H).

Example 103:—1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-(azetidin-3-yloxy)-1,2-dihydroquinolin-2-one

103

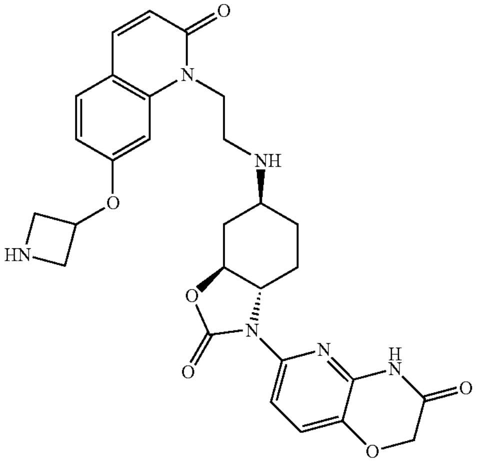

tert-butyl 3-{[1-(2,2-diethoxyethyl)-2-oxo-1,2-dihydroquinolin-7-yl]oxy}azetidine-1-carboxylate 103a a) 1-(2,2-diethoxyethyl)-7-hydroxy-1,2-dihydroquinolin-2-one 9d (0.20 g, 0.72 mmol), tert-butyl 3-bromoazetidine-1-carboxylate (0.34 g, 1.44 mmol) and $K_2CO_3$ (0.30 g, 2.16 mmol) were mixed with NMP (3 mL) and heated to 90° C. for 17 h under nitrogen. The reaction mixture was allowed to cool to room temperature, partitioned between EtOAc (50 mL) and $H_2O$ (50 mL) and the organic phase separated. The aqueous phase was further extracted with EtOAc (2×50 mL) and the extracts combined with the original organic layer and concentrated under reduced pressure to give a residue. The residue was partitioned between $Et_2O$ (30 mL) and $H_2O$ (30 mL) and the layers separated. The organic layer was further washed with $H_2O$ (2×30 mL), brine (30 mL) and concentrated under reduced pressure. The residue was dissolved in DCM and $H_2O$ and passed through a SPE phase separator. The DCM filtrate was collected and concentrated under reduced pressure to give a clear oil. Purification via silica gel chromatography using 0-100% EtOAc/pet ether gave tert-butyl 3-{[1-(2,2-diethoxyethyl)-2-oxo-1,2-dihydroquinolin-7-yl]oxy}azetidine-1-carboxylate 103a (210.0 mg, 67%) as a white gum. LC-MS (Method A) 387.2 $[M-OEt]^+$, RT 3.32 min b) tert-butyl 3-{[2-oxo-1-(2-oxoethyl)-1,2-dihydroquinolin-7-yl]oxy}azetidine-1-carboxylate 103b HCl (1 M in $H_2O$, 1.5 mL, 0.49 mmol) was added to a solution of tert-butyl 3-{[1-(2,2-diethoxyethyl)-2-oxo-1,2-dihydroquinolin-7-yl]oxy}azetidine-1-carboxylate 103a (210 mg, 0.49 mmol) in THF (4.5 mL) and. and stirred at room temperature for 2 h then left standing with no stirring for 90 h. The pH of the reaction mixture was adjusted to 8 using sat. aqueous $NaHCO_3$ and then the reaction mixture was extracted with EtOAc (2×50 mL). Organic extracts were combined, washed with brine and concentrated under reduced pressure. The resulting residue was purified via silica gel chromatography using 0-100% EtOAc/petroleum ether. Clean fractions were combined and concentrated under reduced pressure with ether azeotroping to afford tert-butyl 3-{[2-oxo-1-(2-oxoethyl)-1,2-dihydroquinolin-7-yl]oxy}azetidine-1-carboxylate 103b (86 mg, 49%) as a white solid. LC-MS (Method A) 359.2 $[M+H]^+$, RT 2.63 min. $^1H$ NMR (Method C) (DMSO-d6): δ ppm 9.69 (s, 1H), 7.92 (d, J=9.4 Hz, 1H), 7.70 (d, J=8.6 Hz, 1H), 6.81 (dd, J=8.6, 2.3 Hz, 1H), 6.72 (d, J=2.3 Hz, 1H), 6.49 (d, J=9.4 Hz, 1H), 5.26 (s, 2H), 5.16-5.11 (m, 1H), 4.40-4.27 (m, 2H), 3.85-3.72 (m, 2H), 1.39 (s, 9H).

c) tert-butyl 3-{[1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-2-oxo-1,2-dihydroquinolin-7-yl]oxy}azetidine-1-carboxylate 103c Triethylamine (0.19 mL, 1.35 mmol) was added to a solution of tert-butyl 3-{[2-oxo-1-(2-oxoethyl)-1,2-dihydroquinolin-7-yl]oxy}azetidine-1-carboxylate 103b (80 mg, 0.20 mmol) and (3aS,6S,7aS)-2-oxo-3-{3-oxo-2H,3H,4H-pyrido[3,2-b][1,4]oxazin-6-yl}-octahydro-1,3-benzoxazol-6-aminium trifluoroacetate 60d (132.1 mg, 0.22 mmol) in DCM (10 mL) in the presence of. 3 Å molecular sieves and stirred at room temperature for 10 min under nitrogen.

NaBH(OAc)$_3$ (280. mg, 1.32 mmol) was added to the reaction mixture and stirred for a further 17 h. The reaction mixture was diluted with DCM (20 mL) and MeOH (1 mL). Sat. aq. NaHCO$_3$ was added adjusting the pH to 8, then the mixture passed through a SPE phase separator. The aqueous phase was further extracted with DCM (20 mL) and the extracts passed through a SPE phase separator. The combined organic filtrates were concentrated under reduced pressure to give a crude residue (175 mg). The residue was purified via silica gel chromatography using 0-100% EtOAc/pet ether and 0-20% MeOH/EtOAc. The clean fractions were collected and concentrated under reduced pressure with Et$_2$O azeotroping to afford tert-butyl 3-{[1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-2-oxo-1,2-dihydroquinolin-7-yl]oxy}azetidine-1-carboxylate 103c (105.0 mg, 80%) as a white solid. LC-MS (Method A) 647.4 [M+H]$^+$, RT 2.95 min.

d) 1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-(azetidin-3-yloxy)-1,2-dihydroquinolin-2-one 103

TFA (0.33 mL, 4.25 mmol) was added to a solution of tert-butyl 3-{[1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-2-oxo-1,2-dihydroquinolin-7-yl]oxy}azetidine-1-carboxylate 103c (58.9 mg, 0.09 mmol) in DCM (5 mL) and the reaction mixture stirred at room temperature for 3.5 h and allowed to stand for 17 h. The reaction mixture was concentrated under reduced pressure and the resulting residue dissolved in DCM (75 mL) and MeOH (1 mL). The pH was adjusted to 8 using sat. aq. NaHCO$_3$ and the organic layer passed through a SPE phase separator. The aqueous phase was further extracted with DCM (75 mL) and MeOH (1 mL) and the separated organic filtrates were combined and concentrated under reduced pressure to afford a white solid. Product remained in the aqueous phase so product was further extracted with 20% MeOH/DCM (3×50 mL) and passed through a SPE phase separator. All organic filtrates were combined with the isolated white solid and concentrated under reduced pressure. The crude material was purified via silica gel chromatography using 0-20% MeOH/DCM, NH$_3$ in 0-20% MeOH/DCM and then via prep. HPLC (Method B) 0.1% NH$_3$ in MeCN/H$_2$O to afford 1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-(azetidin-3-yloxy)-1,2-dihydroquinolin-2-one 103 (5.0 mg, 10%). LC-MS (Method B) 547.2 [M+H]$^+$, RT 6.33 min. $^1$H NMR (Method C) (DMSO-d6): δ ppm 7.82 (d, J=9.5 Hz, 1H), 7.64 (d, J=8.6 Hz, 1H), 7.42 (d, J=8.5 Hz, 1H), 7.17 (d, J=8.6 Hz, 1H), 6.90-6.83 (m, 1H), 6.80-6.74 (d, J=8.5 Hz, 1H), 6.43 (d, J=9.5 Hz, 1H), 5.21-5.12 (m, 1H), 4.62 (s, 2H), 4.24 (t, J=7.5 Hz, 2H), 4.09-4.01 (m, 1H), 3.88-3.79 (m, 2H), 3.79-3.70 (m, 1H), 3.59-3.52 (m, 2H), 2.86-2.68 (m, 5H), 2.05-1.94 (m, 1H), 1.48 (d, J=11.3 Hz, 1H), 1.38-1.17 (m, 3H).

Example 104:—1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-(1-methyl-1H-pyrazol-3-yl)-1,2-dihydroquinolin-2-one

104

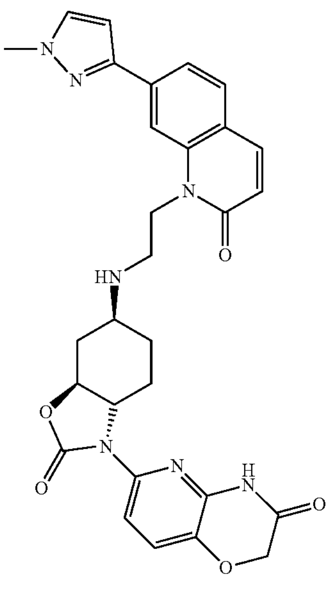

a) 1-(2,2-diethoxyethyl)-2-oxo-1,2-dihydroquinolin-7-yl trifluoromethanesulfonate 104a 1-(2,2-diethoxyethyl)-7-hydroxy-1,2-dihydroquinolin-2-one 9d (1.5 g, 5.41 mmol) was dissolved in DCM (80 mL) and N-phenyl bis-trifluoromethane sulfonimide (1.9 g, 5.41 mmol) and triethylamine (0.98 mL, 7.03 mmol) added. The mixture was stirred for 17 h and then evaporated to 80% of the initial volume. This was quenched with H$_2$O (100 mL), extracted with petroleum ether (2×50 mL), dried (MgSO$_4$) and the solvent evaporated to afford a clear gum. This was purified by silica gel chromatography, eluting with Et$_2$O and then 50% Et$_2$O:50% EtOAc to afford a yellow gum. To this was added Et$_2$O and the mixture rapidly stirred, filtered and dried to give 1-(2,2-diethoxyethyl)-2-oxo-1,2-dihydroquinolin-7-yl trifluoromethanesulfonate 104a (1.5 g, 68%) as a white solid. $^1$H NMR (Method C) (CDCl$_3$): δ ppm 7.71 (d, J=9.3 Hz, 1H), 7.68 (d, J=2.2 Hz, 1H), 7.60 (d, J=8.5 Hz, 1H), 7.13 (dd, J=8.5, 2.2 Hz, 1H), 6.74 (d, J=9.3 Hz, 1H), 4.80 (t, J=5.3 Hz, 1H), 4.35 (d, J=5.3 Hz, 2H), 3.81-3.75 (m, 2H), 3.56-3.49 (m, 2H), 1.12 (t, J=7.0 Hz, 6H).

b) 1-(2,2-diethoxyethyl)-7-(1-methyl-1H-pyrazol-3-yl)-1,2-dihydroquinolin-2-one 104b 1-(2,2-diethoxyethyl)-2-oxo-1,2-dihydroquinolin-7-yl trifluoromethanesulfonate 104a (500 mg, 1.22 mmol) was dissolved in THF (30 mL)/water (7 mL) and to this was added 1-methyl-3-(tetramethyl-1,3,2-dioxaborolan-2-yl)-1H-pyrazole (305 mg, 1.47 mmol), XPhos Pd G2 (48 mg, 0.06 mmol) and K$_3$PO$_4$ (518 mg, 2.44 mmol) The mixture was stirred at 40° C. for 1 h then at room temperature over 72 h. The reaction was quenched with H$_2$O (50 mL), extracted with Et$_2$O (2×50 mL), dried (MgSO$_4$) and the solvent evaporated to afford a yellow gum. This was purified via column chromatography, eluting with $Et_2O$ and then EtOAc to afford 1-(2,2-diethoxyethyl)-7-(1-methyl-1H-pyrazol-3-yl)-1,2-dihydroquinolin-2-one 104b (280 mg, 64%) as a yellow gum which solidified on standing. LC-MS (Method A) 342.2 $[M+H]^+$; RT 2.44 min; $^1H$ NMR (Method C) ($CDCl_3$): δ ppm 7.86 (s, 2H), 7.76 (s, 1H), 7.68 (d, J=9.2 Hz, 1H), 7.50 (d, J=8.4 Hz, 1H), 7.32 (d, J=8.4 Hz, 1H), 6.63 (d, J=9.2 Hz, 1H), 4.82 (t, J=5.3 Hz, 1H), 4.45 (d, J=5.3 Hz, 2H), 3.98 (s, 3H), 3.83-3.76 (m, 2H), 3.58-3.50 (m, 2H), 1.12 (t, J=7.0 Hz, 6H).

c) 2-[7-(1-methyl-1H-pyrazol-3-yl)-2-oxo-1,2-dihydroquinolin-1-yl]acetaldehyde 104c 1-(2,2-diethoxyethyl)-7-(1-methyl-1H-pyrazol-3-yl)-1,2-dihydroquinolin-2-one 104b (280 mg, 0.82 mmol) was stirred with aq.HCl (3N, 5.0 mL) in THF (5 mL) at room temperature for 2 h. The reaction was quenched with $H_2O$ (50 mL), extracted with EtOAc (2×50 mL), dried ($MgSO_4$) and concentrated to give 2-[7-(1-methyl-1H-pyrazol-3-yl)-2-oxo-1,2-dihydroquinolin-1-yl]acetaldehyde 104c (100 mg, 45%) as a white solid which was used with no further purification. LC-MS (Method A) 268.0 $[M+H]^+$; RT 1.77 min; $^1H$ NMR (Method C) ($CDCl_3$): δ ppm 9.71 (s, 1H), 7.79 (s, 1H), 7.74 (d, J=9.2 Hz, 1H), 7.68 (s, 1H), 7.59 (d, J=8.5 Hz, 1H), 7.36 (d, J=8.5, 1H), 7.06 (s, 1H), 6.71 (d, J=9.2 Hz, 1H), 5.18 (s, 2H), 3.97 (s, 3H).

d) 1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-(1-methyl-1H-pyrazol-3-yl)-1,2-dihydroquinolin-2-one 104

Prepared as described in example 60e using (3aS,6S,7aS)-2-oxo-3-{3-oxo-2H,3H,4H-pyrido[3,2-b][1,4]oxazin-6-yl}-octahydro-1,3-benzoxazol-6-aminium trifluoroacetate 60d (150 mg, 0.36 mmol) and 2-[7-(1-methyl-1H-pyrazol-3-yl)-2-oxo-1,2-dihydroquinolin-1-yl]acetaldehyde 104c (96 mg, 0.36 mmol) to give 1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-(1-methyl-1H-pyrazol-3-yl)-1,2-dihydroquinolin-2-one 104 (10 mg, 5%). LC-MS (Method A) 556.2 $[M+H]^+$; RT 2.16 min. $^1H$ NMR (Method C) (DMSO-d6): δ ppm 11.24 (s, 1H), 8.35 (s, 1H), 8.09 (s, 1H), 7.86 (d, J=9.3 Hz, 1H), 7.72-7.67 (m, 2H), 7.48 (d, J=8.1 Hz, 1H), 7.42 (d, J=8.7 Hz, 1H), 7.17 (d, J=8.7 Hz, 1H), 6.53 (d, J=9.3 Hz, 1H), 4.62 (s, 2H), 4.35 (s, 2H), 4.07 (d, J=12.4 Hz, 1H), 3.90 (s, 3H), 3.76 (s, 1H), 3.40 (m, 1H), 2.80 (d, J=43.8 Hz, 4H), 1.99 (s, 1H), 1.47 (s, 1H), 1.28 (d, J=43.4 Hz, 2H), 1.04 (d, J=6.0 Hz, 1H).

Example 105:—3-[6-({[(3aS,6S,7aS)-2-oxo-3-{3-oxo-2H,3H,4H-pyrido[3,2-b][1,4]oxazin-6-yl}-octahydro-1,3-benzoxazol-6-yl]amino}methyl)pyridin-2-yl]benzonitrile

105

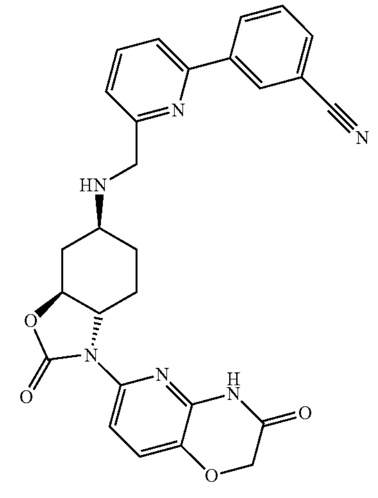

Prepared as described in example 60e using 3-(6-formylpyridin-2-yl)benzonitrile (121.63 mg, 0.58 mmol) and (3aS,6S,7aS)-2-oxo-3-{3-oxo-2H,3H,4H-pyrido[3,2-b][1,4]oxazin-6-yl}-octahydro-1,3-benzoxazol-6-aminium trifluoroacetate 60d (244.4 mg, 0.58 mmol) to afford 3-[6-({[(3aS,6S,7aS)-2-oxo-3-{3-oxo-2H,3H,4H-pyrido[3,2-b][1,4]oxazin-6-yl}-octahydro-1,3-benzoxazol-6-yl]amino}methyl)pyridin-2-yl]benzonitrile 105 (28 mg, 10% yield). LC-MS (Method A) 497.1 [M+H]*; RT 2.59 min. $^1H$ NMR (Method C) (DMSO-d6): δ ppm δ 11.26 (s, 1H), 8.79-8.71 (m, 1H), 8.57 (dt, J=8.0, 1.5 Hz, 1H), 8.17 (d, J=7.9 Hz, 1H), 8.07 (t, J=7.8 Hz, 1H), 7.98 (dt, J=7.7, 1.4 Hz, 1H), 7.78 (t, J=7.8 Hz, 1H), 7.55 (d, J=7.6 Hz, 1H), 7.45 (d, J=8.6 Hz, 1H), 7.22 (d, J=8.6 Hz, 1H), 4.65 (s, 2H), 4.63-4.49 (m, 2H), 4.17 (td, J=11.8, 3.4 Hz, 1H), 3.86 (td, J=11.3, 3.3 Hz, 1H), 3.61-3.48 (m, 1H), 3.00-2.90 (m, 1H), 2.84-2.73 (m, 1H), 2.38-2.27 (m, 1H), 2.12-1.88 (m, 1H), 1.69 (q, J=12.9, 12.3 Hz, 1H), 1.54-1.39 (m, 1H).

Example 106:—. 1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-2-oxo-1,2-dihydroquinoline-6-carbonitrile

106

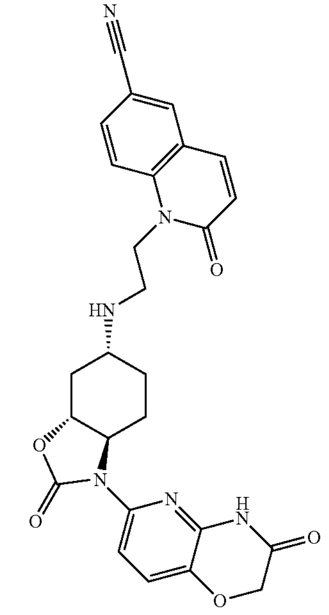

Prepared as described in example 60e using (3aR,6R,7aR)-2-oxo-3-{3-oxo-2H,3H,4H-pyrido[3,2-b][1,4]oxazin-6-yl}-octahydro-1,3-benzoxazol-6-aminium trifluoroacetate 74a (121 mg, 0.39 mmol) and 2-oxo-1-(2-oxoethyl)-1,2-dihydroquinoline-6-carbonitrile 107c (80 mg, 0.38 mmol) to give 1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-2-oxo-1,2-dihydroquinoline-6-carbonitrile 106 (40 mg, 21%). LC-MS (Method A) 501.1 $[M+H]^+$; RT 2.30 min. $^1H$ NMR (Method C) (DMSO-d6): δ ppm 11.22 (s, 1H), 8.31 (d, J=2.2 Hz, 1H), 8.02 (dd, J=8.9, 2.2 Hz, 1H), 7.97 (d, J=9.5 Hz, 1H), 7.80 (d, J=8.9 Hz, 1H), 7.42 (d, J=8.7 Hz, 1H), 7.17 (d, J=8.7 Hz, 1H), 6.76 (d, J=9.5 Hz, 1H), 4.63 (s, 2H), 4.30 (t, J=7.3 Hz, 2H), 4.04 (td, J=11.8, 3.3 Hz, 1H), 3.83-3.66 (m, 1H), 2.88-2.69 (m, 4H), 2.45-2.31 (m, 1H), 2.03-1.85 (m, 1H), 1.46 (q, J=11.1 Hz, 1H), 1.39-1.12 (m, 3H).

Example 107: 1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-2-oxo-1,2-dihydroquinoline-6-carbonitrile

107

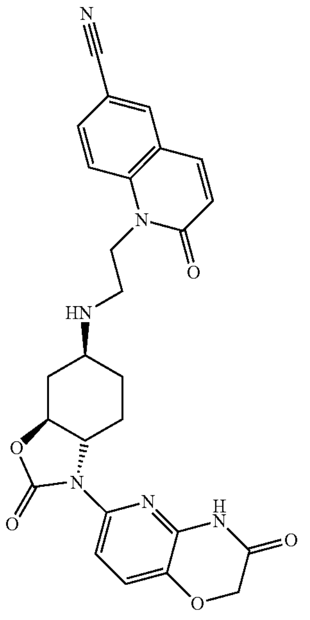

a) 6-bromo-1-(2,2-diethoxyethyl)-1,2-dihydroquinolin-2-one 107a

6-Bromo-1,2-dihydroquinolin-2-one (1.0 g, 4.46 mmol), $Cs_2CO_3$ (1.8, 5.89 mmol) and bromoacetaldehyde diethyl acetal (0.74 mL, 4.79 mmol) were dissolved in DMF (10 mL) and heated in the microwave at 100° C. for 3 h. The reaction was quenched with $H_2O$ (50 mL) and extracted with $Et_2O$ (2×50 mL). The organic extracts were combined, dried ($MgSO_4$), filtered and concentrated under reduced pressure to afford a yellow gum. This was purified via column chromatography eluting with 40-100% EtOAc in petroleum ether to afford 6-bromo-1-(2,2-diethoxyethyl)-1,2-dihydroquinolin-2-one as yellow oil (850 mg, 56%). LC-MS (Method A) 295.9 $[M-OEt]^+$; RT 2.78 min.

b) 1-(2,2-diethoxyethyl)-2-oxo-1,2-dihydroquinoline-6-carbonitrile 107b

A solution of 6-bromo-1-(2,2-diethoxyethyl)-1,2-dihydroquinolin-2-one 107a (886 mg, 2.61 mmol), zinc cyanide (183 mg, 1.56 mmol) and tetrakis(triphenylphosphine)palladium(0) (150 mg, 0.13 mmol) in DMF (4 mL) was heated in a microwave reactor at 100° C. for 90 min. The reaction was diluted with $H_2O$ (30 mL) and extracted with EtOAc (2×50 mL). Combined organic extracts were dried ($MgSO_4$), filtered and concentrated under reduced pressure to afford crude product as an oil which solidified on standing. Crude product was purified via column chromatography using 60% petroleum ether in EtOAc to afford 1-(2,2-diethoxyethyl)-2-oxo-1,2-dihydroquinoline-6-carbonitrile 107b (210 mg, 28%) as a white solid. Product was used directly without further purification.

c) 2-oxo-1-(2-oxoethyl)-1,2-dihydroquinoline-6-carbonitrile 107c

Aqueous HCl (3N, 7.7 mL, 30.7 mmol) was added to a solution of 1-(2,2-diethoxyethyl)-2-oxo-1,2-dihydroquinoline-6-carbonitrile 107c (500 mg, 1.75 mmol) in THF (5 mL) and stirred at room temperature for 2 h. The reaction was quenched with water (50 mL) and extracted with EtOAc (2×50 ml). The organic extracts were combined, dried ($MgSO_4$), filtered and concentrated under reduced pressure to afford 2-oxo-1-(2-oxoethyl)-1,2-dihydroquinoline-6-carbonitrile 107c (290 mg, 78%) as a white solid. LC-MS (Method A) 213.2 $[M+H]^+$; RT 0.75 min. $^1H$ NMR (Method C) ($CDCl_3$): δ 9.76 (s, 1H), 7.93 (s, 1H), 7.78-7.72 (m, 2H), 7.09 (d, J=8.5 Hz, 1H), 6.86 (d, J=9.3 Hz, 1H), 5.22 (s, 2H).

d) 1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-2-oxo-1,2-dihydroquinoline-6-carbonitrile 107

Prepared as described in example 60e using (3aS,6S,7aS)-2-oxo-3-{3-oxo-2H,3H,4H-pyrido[3,2-b][1,4]oxazin-6-yl}-octahydro-1,3-benzoxazol-6-aminium trifluoroacetate 60d (228 mg, 0.54 mmol) and 2-oxo-1-(2-oxoethyl)-1,2-dihydroquinoline-6-carbonitrile 107c (110 mg, 0.52 mmol) to afford 1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-2-oxo-1,2-dihydroquinoline-6-carbonitrile 107 (100 mg, 38%). LC-MS (Method A) 501.1 $[M+H]^+$; RT 2.29 min. $^1H$ NMR (Method C) (DMSO-d6): δ ppm 11.22 (s, 1H), 8.31 (d, J=2.2 Hz, 1H), 8.02 (dd, J=8.9, 2.2 Hz, 1H), 7.97 (d, J=9.5 Hz, 1H), 7.80 (d, J=8.9 Hz, 1H), 7.42 (d, J=8.7 Hz, 1H), 7.17 (d, J=8.7 Hz, 1H), 6.76 (d, J=9.5 Hz, 1H), 4.63 (s, 2H), 4.30 (t, J=7.3 Hz, 2H), 4.04 (td, J=11.8, 3.3 Hz, 1H), 3.83-3.66 (m, 1H), 2.88-2.69 (m, 4H), 2.45-2.31 (m, 1H), 2.03-1.85 (m, 1H), 1.46 (q, J=11.1 Hz, 1H), 1.39-1.12 (m, 3H).

Example 108—Antibacterial Susceptibility Testing

Minimum Inhibitory Concentrations (MICs) versus planktonic bacteria are determined by the broth microdilution procedure according to the guidelines of the Clinical and Laboratory Standards Institute (Clinical and Laboratory Standards Institute. *Methods for Dilution Antimicrobial Susceptibility Tests for Bacteria That Grow Aerobically; Approved Standard—Ninth Edition*. CLSI document M07-A10, 2015). The broth dilution method involves a two-fold serial dilution of compounds in 96-well microtitre plates, giving a typical final concentration range of 0.25-128 μg/mL and a maximum final concentration of 1% DMSO. The bacterial strains tested include the Gram-positive strains *Staphylococcus aureus* ATCC 29213, *Streptococcus pneumoniae* ATCC 49619, *Enterococcus faecalis* ATCC 29212, *Enterococcus faecium* ATCC 19434, the fluoroquinolone-resistant *Enterococcus faecium* ATCC 700221 and the Gram negative strains *Acinetobacter baumannii* NCTC 13420, *Acinetobacter baumannii* ATCC 19606, *Enterobacter cloacae* NCTC 13406, *Escherichia coli* ATCC 25922, *E. coli* ATCC BAA-2452, *E. coli* NCTC 13476, *E. coli* MG1655 and the gyrase A mutants *E. coli* MG1655 S83L and *E. coli* MG1655 D87G derived from the isogenic parent strain *E. coli* MG1655, *Haemophilus influenzae* ATCC 49247, *Klebsiella pneumoniae* ATCC 700603, *Klebsiella pneumoniae* NCTC 13443, *Mycobacterium smegmatis* ATCC 19420 (a recognised fast-growing and non-pathogenic surrogate for *M. tuberculosis* (Tuberculosis, 2010, 90:333), *Neisseria meningitidis* ATCC 13090, *Pseudomonas aeruginosa* ATCC 27853.

Strains are grown in cation-adjusted Müller-Hinton broth at 37° C. in an ambient atmosphere. The MIC is determined as the lowest concentration of compound that inhibits growth following a 16-20 h incubation period. The data reported correspond to the modes of three independent experiments and is reported in Table 1.

All compounds tested show activity against both Gram-negative and Gram-positive bacteria. Compounds 1 and 76 in particular, exhibited excellent activity against both Gram-negative and Gram-positive bacteria. Compounds 1-4, 7, 12, 14-16, 18, 22, 24-31, 33-38, 41-52, 53-57, 59-70, 74, 76-79, 81-95, 99-102, 104 and 106 showed excellent activity against the Gram-positive strains *S. aureus* and *S. pneumoniae*. Compounds 4, 21, 22, 34, 45, 55, 56, 68, 69, 77, 80, 81, 85, 88, 90, 101, 102 and 105 exhibited excellent activity against all strains of *A. baumannii* and *E. coli* tested, including those which are resistant to fluoroquinolone antibiotics and other antibiotics. Compounds 14, 21, 24, 35, 40, 43, 59-61, 63, 74, 76, 87, 92 and 93 exhibited excellent activity against all strains of *A. baumannii, E. coli, E. cloacae, P. aeruginosa* and *H. influenzae* strains tested.

TABLE 1

MIC values of reference compound and test compounds 1-107 against Gram-negative and Gram-positive bacterial strains

| Strains | Ab NCTC 13420 | Ab ATCC 19606 | Ecl NCTC 13406 | Ec ATCC 25922 | Ec ATCC BAA 2452 | Ec NCTC 13476 | Ec MG1655 WT | Hi ATCC 49247 | Kp ATCC 700603 |
|---|---|---|---|---|---|---|---|---|---|
| CIP | C | A | A | A | A | C | A | A | A |
| 1 | A | A | A | A | A | A | A | A | A |
| 2 | A | A | A | A | A | B | A | A | B |
| 3 | C | D | C | B | | | | C | C |
| 4 | A | A | A | A | A | A | A | B | B |
| 5 | D | | D | C | | | | D | D |
| 6 | C | | C | B | | | | B | C |
| 7 | A | B | B | A | B | B | A | B | C |
| 8 | C | | C | B | | | | A | D |
| 9 | D | | D | B | | | | C | D |
| 10 | D | | D | B | | | | C | D |
| 11 | A | B | B | A | | | A | B | C |
| 12 | B | B | B | A | | | A | B | C |
| 13 | C | | C | B | | B | | C | C |
| 14 | A | A | A | A | A | A | A | A | B |
| 15 | B | B | B | A | B | B | B | B | C |
| 16 | B | | B | A | | | | A | C |
| 17 | C | | C | B | | | | C | D |
| 18 | A | A | A | A | B | B | A | B | B |
| 19 | C | | D | C | | | | C | D |
| 20 | C | | B | A | | | | A | C |
| 21 | A | A | A | A | A | A | A | A | B |
| 22 | A | A | A | A | A | A | A | A | B |
| 23 | C | | D | A | B | C | B | D | D |
| 24 | A | A | A | A | A | A | A | A | B |
| 25 | A | | A | A | | | | A | B |
| 26 | A | | B | A | | | | A | B |
| 27 | B | | B | A | | | | B | B |
| 28 | B | | B | A | | | | B | B |
| 29 | A | A | A | A | A | | A | A | B |
| 30 | A | B | B | A | A | A | A | A | B |
| 31 | A | A | A | A | A | B | A | A | B |
| 32 | D | | C | B | | | | C | D |
| 33 | C | | B | A | | | | B | C |
| 34 | A | A | A | A | A | A | A | A | B |
| 35 | A | A | A | A | A | A | A | A | B |
| 36 | A | A | A | A | | | | A | B |
| 37 | B | B | A | A | | | | A | B |
| 38 | B | B | A | A | B | B | A | A | B |
| 39 | C | D | C | B | | | | C | D |
| 40 | A | A | A | A | A | A | A | A | B |
| 41 | C | | B | A | | | | | C |
| 42 | A | B | A | A | | | A | A | B |
| 43 | A | A | A | A | A | A | A | A | B |
| 44 | A | A | A | A | A | B | A | A | B |

TABLE 1-continued

MIC values of reference compound and test compounds 1-107 against Gram-negative and Gram-positive bacterial strains

| | | | | | | | | | |
|---|---|---|---|---|---|---|---|---|---|
| 45 | A | A | A | A | A | A | A | A | B |
| 46 | B | B | A | A | B | B | A | A | B |
| 47 | A | A | A | A | A | B | A | A | B |
| 48 | A | | C | B | | | | B | C |
| 49 | C | | D | C | | | | C | D |
| 50 | B | | B | A | | | | A | B |
| 51 | B | | B | B | | | | A | C |
| 52 | B | | B | A | | | | A | C |
| 53 | B | | C | B | | | | B | C |
| 54 | B | | B | A | | | | B | C |
| 55 | A | A | A | A | A | A | A | A | B |
| 56 | A | A | A | A | A | A | A | A | B |
| 57 | A | A | B | A | B | B | A | A | B |
| 58 | D | | D | C | | | | D | D |
| 59 | A | A | A | A | A | A | A | A | B |
| 60 | A | A | A | A | A | A | A | A | B |
| 61 | A | A | A | A | A | A | A | A | B |
| 62 | A | B | | A | B | B | B | B | C |
| 63 | A | A | A | A | A | A | A | A | B |
| 64 | A | B | A | A | A | B | A | A | C |
| 65 | C | | B | B | | | | B | C |
| 66 | B | | C | B | | | | B | C |
| 67 | A | B | B | A | B | B | A | A | C |
| 68 | A | A | A | A | A | A | A | A | B |
| 69 | A | A | A | A | A | A | A | A | B |
| 70 | A | | A | A | A | A | A | A | B |
| 71 | B | | B | A | | | | B | D |
| 72 | A | A | B | A | A | B | A | A | B |
| 73 | B | | B | A | | | | B | D |
| 74 | A | A | A | A | A | A | A | A | B |
| 75 | D | | B | A | | | | C | D |
| 76 | A | A | A | A | A | A | A | A | |
| 77 | A | A | A | A | A | A | A | A | C |
| 78 | C | | D | B | | | | C | D |
| 79 | A | B | B | A | | | | A | B |
| 80 | A | A | B | A | A | A | A | A | B |
| 81 | A | A | A | A | A | A | A | A | B |
| 82 | B | B | B | A | B | | A | A | B |
| 83 | A | A | A | A | A | A | | A | B |
| 84 | | A | A | A | A | A | A | A | B |
| 85 | A | A | A | A | A | A | A | A | B |
| 86 | A | A | A | A | A | A | | A | B |
| 87 | A | A | A | A | A | A | A | A | B |
| 88 | A | A | A | A | A | A | A | A | B |
| 89 | A | A | B | A | A | B | | B | C |
| 90 | A | A | A | A | A | A | A | A | B |
| 91 | A | A | B | A | A | B | A | A | C |
| 92 | A | A | A | A | A | A | A | A | B |
| 93 | A | A | B | A | A | A | A | A | B |
| 94 | B | B | B | A | A | A | A | A | B |
| 95 | A | B | B | A | A | A | A | A | C |
| 96 | A | | A | | | | | A | B |
| 97 | B | | C | B | | | | B | D |
| 98 | A | A | B | A | A | B | A | A | C |
| 99 | A | B | B | A | A | A | A | A | B |
| 100 | A | B | B | A | B | B | A | A | C |
| 101 | A | A | B | A | A | A | A | | B |
| 102 | A | A | A | A | A | A | A | | B |
| 103 | C | | | B | | | | | |
| 104 | A | | B | B | | | | A | D |
| 105 | A | A | B | A | A | B | A | A | C |
| 106 | B | | B | A | | | A | | C |
| 107 | B | | C | B | | | | B | D |

| Strains | Kp NCTC 13443 | Ms ATCC 19420 | Nm ATCC 13090 | Pa ATCC 27853 | Sa ATCC 29213 | Ef ATCC 29212 | Efm ATCC 19434 | Efm ATCC 700221 | Sp ATCC 49619 |
|---|---|---|---|---|---|---|---|---|---|
| CIP | D | A | A | A | A | A | B | C | A |
| 1 | A | A | A | A | A | A | A | A | A |
| 2 | B | A | A | B | A | | | | A |
| 3 | | | | B | A | A | | | |
| 4 | B | A | A | B | A | | | | A |
| 5 | | B | | B | B | | | | C |
| 6 | | A | | B | B | | | | A |
| 7 | C | | | B | A | | | | A |
| 8 | | A | | C | A | | | | B |

TABLE 1-continued

MIC values of reference compound and test compounds 1-107 against Gram-negative and Gram-positive bacterial strains

| | | | | | | | | | |
|---|---|---|---|---|---|---|---|---|---|
| 9 | | D | | B | B | | | | C |
| 10 | | D | | B | C | | | | C |
| 11 | | | | B | A | | | | B |
| 12 | | | | B | A | | | | A |
| 13 | | | | B | A | | | | B |
| 14 | B | | | A | A | | | | A |
| 15 | C | | | B | A | | | | A |
| 16 | | | | B | A | | | | A |
| 17 | | | | C | B | | | | C |
| 18 | B | | A | B | A | | | | A |
| 19 | | | | C | A | | | | D |
| 20 | | | | B | A | | | | C |
| 21 | B | | | A | A | | | | B |
| 22 | B | | | B | A | | | | A |
| 23 | | | | B | A | | | | B |
| 24 | | | | A | A | | | | A |
| 25 | | | | B | A | | | | A |
| 26 | | | | B | A | | | | A |
| 27 | | | | B | A | | | | A |
| 28 | | | | B | A | | | | A |
| 29 | A | | | A | A | A | A | A | A |
| 30 | B | | | A | A | | | | A |
| 31 | B | | | B | A | | | | A |
| 32 | | | | B | B | | | | B |
| 33 | | | | C | A | | | | A |
| 34 | | | | B | A | A | A | A | A |
| 35 | B | | | A | A | | | | A |
| 36 | | | | B | A | | | | A |
| 37 | | | | B | A | | | | A |
| 38 | C | | | B | A | | | | A |
| 39 | | | | B | B | | | | B |
| 40 | B | | | A | A | A | A | A | B |
| 41 | | | | B | A | | | | A |
| 42 | | | | B | A | | | | A |
| 43 | A | | | A | A | A | A | A | A |
| 44 | C | | | B | A | | | | A |
| 45 | B | | | B | A | | | | A |
| 46 | C | | | B | A | | | | A |
| 47 | B | | | A | A | | | | A |
| 48 | | | | C | A | | | | A |
| 49 | | | | C | A | | | | A |
| 50 | | | | A | A | | | | A |
| 51 | | | | B | A | | | | A |
| 52 | | | | C | A | | | | A |
| 53 | | | | C | A | | | | B |
| 54 | | | | B | A | | | | A |
| 55 | C | | | | A | | | | A |
| 56 | B | | | | A | | | | A |
| 57 | C | | | | A | | | | A |
| 58 | | B | | B | A | | | | D |
| 59 | B | | | A | A | A | A | A | A |
| 60 | B | | | A | A | A | | | A |
| 61 | A | | | A | A | A | A | A | A |
| 62 | | | | C | A | | | | A |
| 63 | B | | | A | A | A | | | A |
| 64 | B | | | B | A | | | | A |
| 65 | | | | C | A | | | | A |
| 66 | | | | D | A | | | | A |
| 67 | | | | B | A | | | | A |
| 68 | B | | | B | A | | | | A |
| 69 | B | | | B | A | | | | A |
| 70 | B | | | A | A | | | | A |
| 71 | | | | C | A | | | | B |
| 72 | C | | | B | A | | | | B |
| 73 | | | | C | A | | | | B |
| 74 | B | | | A | A | | | | A |
| 75 | | | | B | B | | | | A |
| 76 | A | | | A | A | A | A | A | A |
| 77 | | | | B | A | | A | | A |
| 78 | | | | B | A | | | | A |
| 79 | | | | B | A | | | | A |
| 80 | | | | B | A | A | B | B | B |
| 81 | | | | B | A | A | A | A | A |
| 82 | | | | B | A | | | | A |
| 83 | | | | B | A | | | | A |
| 84 | B | | | B | A | | | | A |
| 85 | B | | | B | A | | | | A |

TABLE 1-continued

MIC values of reference compound and test compounds 1-107 against Gram-negative and Gram-positive bacterial strains

| | | | | | | | |
|---|---|---|---|---|---|---|---|
| 86 | | B | A | | | | A |
| 87 | B | A | A | A | B | | A |
| 88 | B | B | A | | | | A |
| 89 | | B | A | | | | A |
| 90 | B | B | A | | | | A |
| 91 | | C | A | B | B | B | A |
| 92 | B | A | A | | | | A |
| 93 | B | A | A | | | | A |
| 94 | | B | A | | | | A |
| 95 | | B | A | | | | A |
| 96 | | B | A | | | | |
| 97 | | C | A | | | | B |
| 98 | | B | A | | | | |
| 99 | B | B | A | | | | A |
| 100 | | C | A | | | | A |
| 101 | | B | A | | | | A |
| 102 | | B | A | A | A | A | A |
| 103 | | B | | | | | B |
| 104 | | C | A | | | | A |
| 105 | | B | A | | | | |
| 106 | | | A | | | | A |
| 107 | | D | B | | | | B |

CIP = ciprofloxacin;
Ab = *Acinetobacter baumannii*;
Ecl = *Enterobacter cloacae*;
Ec = *Escherichia coli*;
Hi = *Haemophilus influenzae*;
Kp = *Klebsiella pneumoniae*;
Ms = *Mycobacterium smegmatis*;
Nm = *Neisseria meningitidis*;
Pa = *Pseudomonas aeruginosa*;
Sa = *Staphylococcus aureus*;
Ef = *Enterococcus faecalis*;
Efm = *Enterococcus faecium*;
Sp = *Streptococcus pneumoniae*

In Table 1, an MIC (in μg/mL) of less or equal to 1 is assigned the letter A; a MIC of from 1 to 10 is assigned the letter B; a MIC of from 10 to 100 is assigned the letter C; and a MIC of over 100 is assigned the letter D.

TABLE 2

Fold increase in MIC against fluoroquinolone-resistant single point mutant *Escherichia coli* strains (MG1655 S83L and MG1655 D87G) compared to the isogenic parent strain *E. coli* MG1655.

| Compound | *E. coli* MG1655 S83L[1] | *E. coli* MG1655 D87G[2] |
|---|---|---|
| CIP | 16 | 8 |
| LEV | 8 | 8 |
| 1 | 1 | 1 |
| 2 | 1 | 1 |
| 4 | 1 | 1 |
| 7 | 1 | 1 |
| 11 | 2 | 1 |
| 12 | 1 | 1 |
| 14 | 2 | 2 |
| 15 | 1 | 1 |
| 18 | 2 | 1 |
| 21 | 1 | 2 |
| 22 | 2 | 2 |
| 23 | 0.5 | 0.5 |
| 24 | 2 | 2 |
| 29 | 1 | 2 |
| 30 | 2 | 2 |
| 31 | 1 | 2 |
| 34 | 1 | 2 |
| 35 | 1 | 2 |
| 38 | 2 | ND |
| 40 | 1 | 1 |
| 42 | 1 | 2 |

TABLE 2-continued

Fold increase in MIC against fluoroquinolone-resistant single point mutant *Escherichia coli* strains (MG1655 S83L and MG1655 D87G) compared to the isogenic parent strain *E. coli* MG1655.

| Compound | *E. coli* MG1655 S83L[1] | *E. coli* MG1655 D87G[2] |
|---|---|---|
| 43 | 1 | 0.5 |
| 44 | 2 | 2 |
| 45 | 2 | 1 |
| 46 | 2 | 1 |
| 47 | 2 | 1 |
| 55 | 1 | 1 |
| 56 | 1 | 2 |
| 57 | 1 | 1 |
| 59 | 1 | 1 |
| 60 | 4 | 2 |
| 61 | 1 | 1 |
| 62 | 1 | 0.5 |
| 63 | 1 | 1 |
| 64 | 0.5 | 1 |
| 67 | 1 | 1 |
| 68 | 1 | 1 |
| 69 | 1 | 1 |
| 70 | 2 | 4 |
| 72 | 0.5 | 0.5 |
| 74 | 1 | 1 |
| 76 | 2 | 2 |
| 77 | 1 | 1 |
| 80 | 1 | 1 |
| 81 | 1 | 1 |
| 82 | 0.5 | 1 |
| 84 | 1 | 1 |
| 85 | 1 | 1 |
| 87 | 2 | 2 |
| 88 | 2 | 1 |

TABLE 2-continued

Fold increase in MIC against fluoroquinolone-resistant single point mutant *Escherichia coli* strains (MG1655 S83L and MG1655 D87G) compared to the isogenic parent strain *E. coli* MG1655.

| Compound | *E. coli* MG1655 S83L[1] | *E. coli* MG1655 D87G[2] |
|---|---|---|
| 90 | 2 | 4 |
| 91 | 0.5 | 1 |
| 92 | 1 | 1 |
| 93 | 1 | 1 |
| 94 | 1 | 2 |
| 95 | 0.5 | 1 |
| 98 | 1 | 1 |
| 99 | 0.5 | 1 |
| 100 | 1 | 1 |
| 101 | 1 | 1 |
| 102 | 2 | 2 |
| 105 | 1 | 1 |

CIP = ciprofloxacin;
LEV = levofloxacin
[1]S83L mutation on DNA gyrase subunit GyrA
[2]D87G mutation on DNA gyrase subunit GyrA Compounds 1-59, 61-69, 72-88, and 91-105 showed no significant (lower than or equal to 2-fold change) loss of activity against the *E. coli* MG1655 fluoroquinolone-mutant strains.

Thus all compounds tested were less susceptible to the gyrase S83L and D87G mutations than the fluoroquinolone antibiotics ciprofloxacin and levofloxacin.

Example 109 Antibacterial Susceptibility Testing of Biodefence Microorganisms MICs against strains of *Bacillus anthracis, Burkholderia mallei, Burkholderia pseudomallei, Francisella tularensis* and *Yersinia pestis* were measured using the broth microdilution procedure according to the guidelines of the Clinical and Laboratory Standards Institute (Clinical and Laboratory Standards Institute. *Methods for Dilution Antimicrobial Susceptibility Tests for Bacteria That Grow Aerobically; Approved Standard—Tenth Edition*. CLSI document M07-A10, 2015). Two-fold serial dilutions of compounds were tested in triplicate over the concentration range 0.03 to 64 μg/mL. Doxycycline was included as a control antibiotic. Assay medium was CA-MHB (supplemented with 2% IsoVitalex in the case of *F. tularensis*). Cultures were incubated in the presence of compound for up to 24 hours, up to 38 hours (*F. tularensis*) or 24-48 hours (*Y. pestis*). The MIC is reported as the lowest concentration of compound that visually inhibited growth of the test organism.

In Table 3 a MIC (in μg/mL) of less than 1 is assigned the letter A; a MIC equal to or greater than 1 but less than or equal to 4 is assigned the letter B; a MIC greater than 4 but less than or equal to 16 is assigned the letter C; a MIC greater than 16 but less than or equal to 64 is assigned the letter D; and a MIC greater than 64 is assigned the letter E.

TABLE 3

MICs against biodefence microorganisms

| Species and strain | DOX | 2 |
|---|---|---|
| *Bacillus anthracis* Ames | A | A |
| *Burkholderia mallei* China 7 | A | B |
| *Burkholderia pseudomallei* DD503 | B | B |
| *Burkholderia pseudomallei* K96243 | B | B |
| *Burkholderia pseudomallei* 1026b | B | B |
| *Francisella tularensis* SCHU S4 | A | B |
| *Yersinia pestis* CO92 | B | A |

DOX—doxycycline

The compound of the invention tested proved to be active against all of the Gram-negative and Gram-positive biodefence pathogens evaluated.

Example 110—Antibacterial Susceptibility Testing of Anaerobes

Antibacterial susceptibility of anaerobes to compounds of the invention was determined by measuring the minimum inhibitory concentration (MIC) using the agar dilution method according to the guidelines of the CLSI (Clinical and Laboratory Standards Institute. Methods for Antimicrobial Susceptibility Testing of Anaerobic Bacteria; Approved Standard—Eighth Edition. CLSI document M11-A8, 2012). Reference organisms were *Clostridium difficile* ATCC 700057, *Bacteroides fragilis* ATCC 25285 and *Bacteroides thetaiotaomicron* ATCC 29741. Strains of anaerobic bacteria were contemporary clinical isolates from diverse infection types and geographic locations. Stock solutions of vancomycin and ciprofloxacin were made in water at 5,120 μg/mL. Stock solution of metronidazole was made in DMSO at 5,120 μg/mL. Stock solutions of compounds were made in DMSO at 12,800 μg/mL. Compounds were diluted to 100-fold the test range concentrations in DMSO and 400 μL of the 100× solutions were added to 39.6 mL of *Brucella* blood agar supplemented with haemin and vitamin K1. Isolates were sub-cultured twice on *Brucella* blood agar plates at 35° C. for 48 h in an anaerobic cabinet. Colonies were re-suspended in *Brucella* broth to a turbidity of 0.5 McFarland and 100 μL of the suspension was transferred to a 96-well plate. The antibacterial agent containing plates were inoculated with 1 μL of bacterial suspension using a Masturi® Dot inoculator. Plates were incubated at 35° C. for 48 h in anaerobic conditions and MICs were read visually following CLSI guidelines. The MIC was defined as the lowest concentration of compound that inhibited visible growth.

In Tables 4 to 14 a MIC (in μg/mL) of less than 1 is assigned the letter A; a MIC equal to or greater than 1 but less than or equal to 4 is assigned the letter B; a MIC greater than 4 but less than or equal to 16 is assigned the letter C; a MIC greater than 16 but less than or equal to 64 is assigned the letter D; and a MIC greater than 64 is assigned the letter E.

TABLE 4

MICs against reference strains of anaerobic bacteria

| Strain | MTZ | VAN | CIP | 21 | 27 |
|---|---|---|---|---|---|
| *C. difficile* ATCC 700057 | A | B | C | A | B |
| *B. fragilis* ATCC 25285 | A | D | B | A | C |
| *B. thetaiotaomicron* ATCC | B | D | C | A | B |

MTZ, metronidazole;
VAN, vancomycin;
CIP, ciprofloxacin

Compounds tested proved to be active against the exemplary obligate anaerobic reference bacterial strains of *C. difficile, B. fragilis* and *B. thetaiotaomicron*.

TABLE 5

| MICs against strains of *Clostridium perfringens* | | | | | |
|---|---|---|---|---|---|
| Strain | MTZ | VAN | CIP | 21 | 27 |
| 1 | B | A | A | A | A |
| 2 | A | A | A | A | A |
| 3 | A | A | A | A | A |
| 4 | A | A | A | A | A |
| 5 | A | A | A | A | A |
| 6 | B | A | A | A | A |
| 7 | A | A | A | A | A |
| 8 | A | A | A | A | B |
| 9 | A | A | A | A | A |
| 10 | A | A | A | A | A |
| 11 | B | A | A | A | A |

MTZ, metronidazole;
VAN, vancomycin;
CIP, ciprofloxacin

The compounds tested showed activity against the clinical isolates of *C. perfringens*, an exemplary obligate anaerobic bacterium.

TABLE 6

| MICs against strains of *Finegoldia magna* | | | | | |
|---|---|---|---|---|---|
| Strain | MTZ | VAN | CIP | 21 | 27 |
| 1 | A | A | D | A | B |
| 2 | A | A | A | A | D |
| 3 | B | A | D | A | B |
| 4 | A | A | A | A | D |
| 5 | B | A | A | A | D |
| 6 | B | A | A | A | D |
| 7 | B | A | C | A | E |
| 8 | B | A | D | A | B |
| 9 | B | A | A | A | E |
| 10 | B | A | D | A | C |
| 11 | B | A | A | A | D |
| 12 | A | A | A | A | D |

MTZ, metronidazole;
VAN, vancomycin;
CIP, ciprofloxacin

The compounds tested showed activity against the clinical isolates of *F. magna*, an exemplary obligate anaerobic bacterium.

TABLE 7

| MICs against strains of *Parvimonas micra* | | | | | |
|---|---|---|---|---|---|
| Strain | MTZ | VAN | CIP | 21 | 27 |
| 1 | B | A | B | A | E |
| 2 | A | A | A | A | D |
| 3 | A | A | A | A | E |
| 4 | A | B | C | B | E |
| 5 | A | B | C | A | E |
| 6 | A | A | A | A | B |
| 7 | A | B | A | A | D |
| 8 | A | A | A | A | D |
| 9 | A | A | C | A | D |
| 10 | B | A | A | A | D |
| 11 | A | A | A | A | D |
| 12 | A | A | A | A | D |

MTZ, metronidazole;
VAN, vancomycin;
CIP, ciprofloxacin

The compounds tested showed activity against the clinical isolates of *P. micra*, an exemplary obligate anaerobic bacterium.

TABLE 8

| MICs against strains of *Peptoniphilus harei* | | | | | |
|---|---|---|---|---|---|
| Strain | MTZ | VAN | CIP | 21 | 27 |
| 1 | B | A | B | A | A |
| 2 | A | A | B | A | A |
| 3 | A | A | C | A | A |
| 4 | B | A | B | A | A |
| 5 | A | A | B | A | A |
| 6 | A | A | B | A | A |
| 7 | A | A | B | A | A |
| 8 | A | A | B | A | A |
| 9 | B | A | B | A | A |
| 10 | A | A | B | A | A |
| 11 | A | A | B | A | A |
| 12 | B | A | B | A | A |

MTZ, metronidazole;
VAN, vancomycin;
CIP, ciprofloxacin

The compounds tested showed activity against the clinical isolates of *P. harei*, an exemplary obligate anaerobic bacterium.

TABLE 9

| MICs against strains of *Peptostreptococcus anaerobius* | | | | | |
|---|---|---|---|---|---|
| Strain | MTZ | VAN | CIP | 21 | 27 |
| 1 | A | A | A | A | A |
| 2 | A | A | B | A | A |
| 3 | A | A | A | A | A |
| 4 | A | E | C | A | C |
| 5 | A | A | C | A | A |
| 6 | A | A | A | A | A |
| 7 | A | A | C | A | A |
| 8 | A | A | B | A | A |
| 9 | A | A | C | A | A |
| 10 | A | A | A | A | A |

MTZ, metronidazole;
VAN, vancomycin;
CIP, ciprofloxacin

The compounds tested showed activity against the clinical isolates of *P. anaerobius*, an exemplary obligate anaerobic bacterium.

TABLE 10

| MICs against strains of *Propionibacterium acnes* | | | | | |
|---|---|---|---|---|---|
| Strain | MTZ | VAN | CIP | 21 | 27 |
| 1 | D | A | B | A | B |
| 2 | D | A | B | A | A |
| 3 | D | A | B | A | A |
| 4 | D | A | A | A | A |
| 5 | D | A | B | A | B |
| 6 | D | A | B | A | B |
| 7 | D | A | B | A | B |
| 8 | D | A | B | A | B |
| 9 | D | A | B | A | B |
| 10 | D | A | B | A | B |
| 11 | D | A | B | A | A |
| 12 | D | C | B | A | B |

MTZ, metronidazole;
VAN, vancomycin;
CIP, ciprofloxacin

The compounds tested showed activity against the clinical isolates of *P. acnes*, an exemplary obligate anaerobic bacterium.

TABLE 11

| MICs against strains of *Bacteroides fragilis* | | | | | |
|---|---|---|---|---|---|
| Strain | MTZ | VAN | CIP | 21 | 27 |
| 1 | A | D | B | B | D |
| 2 | A | D | B | A | B |
| 3 | A | C | B | A | B |
| 4 | A | D | D | A | B |
| 5 | A | D | B | A | B |
| 6 | A | C | B | A | B |
| 7 | A | C | C | A | C |
| 8 | A | D | B | A | B |
| 9 | A | C | B | A | B |
| 10 | A | D | C | A | B |
| 11 | A | D | B | A | B |
| 12 | A | D | B | A | B |

MTZ, metronidazole;
VAN, vancomycin;
CIP, ciprofloxacin

The compounds tested showed activity against the clinical isolates of *B. fragilis*, an exemplary obligate anaerobic bacterium.

TABLE 12

| MICs against strains of *Bacteroides thetaiotaomicron* | | | | | |
|---|---|---|---|---|---|
| Strain | MTZ | VAN | CIP | 21 | 27 |
| 1 | A | D | D | A | C |
| 2 | A | D | D | A | B |
| 3 | B | D | C | A | C |
| 4 | B | D | C | A | C |
| 5 | B | D | C | A | B |
| 6 | B | D | D | A | C |
| 7 | A | D | D | A | C |
| 8 | B | D | C | A | B |
| 9 | A | A | A | A | A |
| 10 | B | D | C | A | B |
| 11 | B | D | D | B | C |

MTZ, metronidazole;
VAN, vancomycin;
CIP, ciprofloxacin

The compounds tested showed activity against the clinical isolates of *B. thetaiotaomicron*, an exemplary obligate anaerobic bacterium.

TABLE 13

| MICs against strains of *Prevotella bivia* | | | | | |
|---|---|---|---|---|---|
| Strain | MTZ | VAN | CIP | 21 | 27 |
| 1 | B | E | C | A | A |
| 2 | B | E | D | A | A |
| 3 | B | D | C | A | B |
| 4 | B | E | D | A | B |
| 5 | B | E | D | A | A |
| 6 | B | E | D | A | B |
| 7 | B | E | D | A | B |
| 8 | B | D | C | A | A |
| 9 | B | E | C | A | A |
| 10 | B | D | C | A | A |

MTZ, metronidazole;
VAN, vancomycin;
CIP, ciprofloxacin

The compounds tested showed activity against the clinical isolates of *P. bivia*, an exemplary obligate anaerobic bacterium.

TABLE 14

| MICs against strains of *Prevotella melaninogenica* | | | | | |
|---|---|---|---|---|---|
| Strain | MTZ | VAN | CIP | 21 | 27 |
| 1 | A | E | B | A | B |
| 2 | A | C | B | A | A |
| 3 | A | E | B | A | A |
| 4 | A | E | B | A | A |
| 5 | A | D | B | A | A |
| 6 | A | E | B | A | A |
| 7 | A | D | B | A | A |
| 8 | A | C | C | A | A |
| 9 | A | C | A | A | A |
| 10 | A | E | B | A | B |
| 11 | A | E | B | A | A |

MTZ, metronidazole;
VAN, vancomycin;
CIP, ciprofloxacin

The compounds tested showed activity against the clinical isolates of *P. melaninogenica*, an exemplary obligate anaerobic bacterium.

Example 111—Human Cell Viability Assay

Compounds are assessed for potential non-specific cytotoxic effects against a human hepatic cell line (HepG2 ATCC HB-8065). HepG2 cells are seeded at 20,000 cells/well in 96-well microtitre plates in minimal essential medium (MEM) supplemented with a final concentration of 10% FBS and 1 mM sodium pyruvate. After 24 h compound dilutions are prepared in Dulbecco's minimum essential media (DMEM) supplemented with final concentrations of 0.001% FBS, 0.3% bovine albumin and 0.02% HEPES and added to cells. Compounds are tested in two-fold serial dilutions over a final concentration range of 1-128 μg/mL in a final DMSO concentration of 1% vol/vol. Chlorpromazine is used as a positive control. Cells are incubated with compound at 37° C. and 5% $CO_2$ for a further 24 h, after which time the CellTiter-Glo reagent (Promega) is added. Luminescence is measured on a BMG Omega plate reader. Data are analysed using GraphPad Prism software to determine the concentration of compound that inhibits cell viability by fifty percent ($IC_{50}$). The results are provided in Table 14.

In Table 14, an $IC_{50}$ (in μg/mL) of less than 1 is assigned the letter D; an $IC_{50}$ of from 1 to 10 is assigned the letter C; an $IC_{50}$ of from 10 to 100 is assigned the letter B; and an $IC_{50}$ of over 100 is assigned the letter A.

TABLE 14

| $IC_{50}$ values against HepG2 cell line | |
|---|---|
| Compound | $IC_{50}$ (μg/mL) HepG2 |
| 1 | A |
| 2 | A |
| 3 | A |
| 4 | B |
| 5 | A |
| 6 | A |
| 7 | A |
| 8 | B |
| 9 | A |
| 10 | A |
| 11 | B |
| 12 | A |
| 13 | A |

TABLE 14-continued

| IC$_{50}$ values against HepG2 cell line | |
|---|---|
| Compound | IC$_{50}$ (μg/mL) HepG2 |
| 14 | A |
| 15 | B |
| 16 | A |
| 17 | B |
| 18 | C |
| 19 | A |
| 20 | A |
| 21 | A |
| 23 | A |
| 24 | A |
| 25 | B |
| 26 | A |
| 27 | A |
| 28 | A |
| 29 | B |
| 30 | A |
| 31 | A |
| 32 | A |
| 35 | A |
| 36 | B |
| 37 | A |
| 38 | B |
| 39 | A |
| 40 | B |
| 42 | A |
| 43 | A |
| 44 | A |
| 45 | B |
| 46 | A |
| 47 | B |
| 48 | A |
| 49 | A |
| 50 | A |
| 51 | A |
| 53 | A |
| 54 | A |
| 55 | A |
| 56 | B |
| 58 | A |
| 59 | B |
| 60 | B |
| 61 | B |
| 63 | A |
| 64 | B |
| 65 | A |
| 66 | A |
| 67 | A |
| 68 | B |
| 69 | A |
| 70 | B |
| 71 | B |
| 72 | B |
| 74 | B |
| 75 | A |
| 76 | B |
| 77 | A |
| 78 | A |
| 79 | B |
| 80 | B |
| 81 | B |
| 83 | B |
| 84 | B |
| 85 | B |
| 86 | B |
| 87 | B |
| 88 | B |
| 89 | B |
| 90 | B |
| 91 | B |
| 92 | A |
| 93 | A |
| 94 | A |
| 95 | A |
| 98 | A |
| 99 | B |
| 100 | A |
| 101 | B |
| 102 | B |
| 104 | B |
| 105 | B |

Compounds 1-17, 19-103 show low toxicities against HepG2 human hepatic cell line. In particular, compounds 1-3, 5-7, 9-10, 12-14, 16, 19-24, 37, 39, 42-44, 46, 48-53, 54-55, 58, 63, 65-67, 69, 75, 77, 78, 92-98 and 100 showed no detectable toxicity against the tested human hepatic cell line. These compounds therefore show an excellent therapeutic benefit relative to their hepatic toxicities. Compounds 4, 8, 11, 15, 17, 25, 29, 36, 38, 40, 45, 47, 56, 59-61, 64, 68, 70-74, 76, 79-91, 99, and 101-105 also demonstrate an acceptable level of hepatic toxicity relative to therapeutic activity. This indicates that these compounds have the potential to have an excellent therapeutic benefit relative to their hepatic toxicity.

The invention claimed is:

1. A compound of formula (I), or a pharmaceutically acceptable salt or N-oxide thereof:

(I)

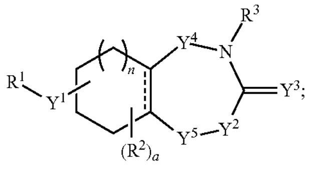

wherein ------ is a double bond or a single bond;

$Y^1$ is independently selected from the group consisting of $NR^4$, O and S;

$Y^2$ is independently selected from the group consisting of O and S;

$Y^3$ is independently selected from the group consisting of O and S;

$Y^4$ is $(CH_2)_m$;

$Y^5$ is $(CH_2)_p$;

$R^1$ is independently selected from the group consisting of $-L^1-Ar^1-Ar^2$ and

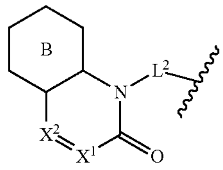

;

$Ar^1$ and $Ar^2$ are each independently a phenyl or monocyclic heteroaryl group;

$-L^1-$ is $-C_1-C_3$-alkylene-;

$X^1$ is independently selected from the group consisting of N and $CR^5$; and $X^2$ is independently selected from the group consisting of N and $CR^6$; or $X^1$ and $X^2$ together form a 5-membered heteroaryl ring;

-$L^2$- is —$C_2$-$C_3$-alkylene-;

Ring B is independently selected from the group consisting of phenyl, monocyclic 6-membered heteroaryl and pyridinone, optionally substituted with a single —$Y^6$—$R^7$ group; wherein $Y^6$ is absent or is independently selected from the group consisting of $NR^8$, O and S; where Ring B is a pyridinone ring, the nitrogen of the Ring B pyridinone may be attached to the proximal end of a —$C_1$-$C_3$-alkylene- group that is attached at its distal end to the group -$L^2$-;

$R^2$ is independently at each occurrence selected from the group consisting of halo, nitro, cyano, $NR^9R^{10}$, $NR^9S(O)_2R^9$, $NR^9CONR^9R^9$, $NR^9C(O)R^9$, $NR^9CO_2R^9$, $OR^9$, $SR^9$, $SOR^9$, $SO_3R^9$, $SO_2R^9$, $SO_2NR^9R^9$, $CO_2R^9$, $C(O)R^9$, $CONR^9R^9$, $C_1$-$C_4$-alkyl, $C_2$-$C_4$-alkenyl, $C_2$-$C_4$-alkynyl, $C_1$-$C_4$-haloalkyl and O—$C_1$-$C_4$-haloalkyl;

$R^3$ is a bicyclic carbocyclic or a bicyclic heterocyclic ring system in which at least one of the two rings is aryl or heteroaryl;

or $R^3$ is -$L^3$-phenyl; wherein -$L^3$- is selected from the group consisting of —$CR^{11}$═$CR^{11}$— and —$C_4$-cycloalkyl-;

$R^4$ is independently selected from the group consisting of H, $C_1$-$C_4$-alkyl, C(O)—$C_1$-$C_4$-alkyl and $C_1$-$C_3$-alkylene-$R^{12}$; wherein $R^{12}$ is independently phenyl or monocyclic heteroaryl;

or wherein $R^4$ and either -$L^1$- or -$L^2$- and the nitrogen to which they are attached together form a 4- to 7-membered heterocycloalkyl ring;

$R^5$ and $R^6$ are each independently selected from the group consisting of H, halo, cyano, $C_1$-$C_4$-alkyl and O—$C_1$-$C_4$-alkyl;

$R^7$ is independently selected from the group consisting of H, $C_1$-$C_4$-alkyl, $C_2$-$C_4$-alkenyl, $C_2$-$C_4$-alkynyl, $C_1$-$C_4$-haloalkyl, $C_3$-$C_8$-cycloalkyl, 4-7-heterocycloalkyl, phenyl, monocyclic heteroaryl and $C_1$-$C_3$-alkylene-$R^{7a}$; wherein $R^{7a}$ is independently selected from the group consisting of $C_3$-$C_8$-cycloalkyl, $_{4-7}$-heterocycloalkyl, phenyl and monocyclic heteroaryl;

$R^8$ is independently selected from the group consisting of H and $C_1$-$C_4$-alkyl;

or $R^7$ and $R^8$ together with the nitrogen to which they are attached form a 4- to 7-membered heterocycloalkyl ring;

$R^9$ is independently at each occurrence selected from the group consisting of H and $C_1$-$C_4$-alkyl;

$R^{10}$ is independently selected from the group consisting of H, $C_1$-$C_4$-alkyl, $C_1$-$C_4$-haloalkyl, $S(O)_2$—$C_1$-$C_4$-alkyl and C(O)—$C_1$-$C_4$-alkyl;

$R^{11}$ is independently at each occurrence selected from the group consisting of H and $C_1$-$C_4$-alkyl;

a is an integer from 0 to 4;

n is an integer selected from the group consisting of 0, 1 and 2;

m and p are each an integer selected from the group consisting of 0 and 1;

wherein any of the aforementioned alkyl, alkylene, alkenyl, alkynyl, haloalkyl, cycloalkyl, carbocyclic, heterocyclic, heterocycloalkyl, aryl, phenyl and heteroaryl groups is optionally substituted, where chemically possible, by 1 to 5 substituents which are each independently at each occurrence selected from the group consisting of oxo, $=NR^a$, $=NOR^a$, halo, nitro, cyano, $NR^aR^a$, $NR^aS(O)_2R^a$, $NR^aC(O)R^a$, $NR^aCONR^aR^a$, $NR^aCO_2R^a$, $OR^a$, $SR^a$, $SOR^a$, $SO_3R^a$, $SO_2R^a$, $SO_2NR^aR^a$, $CO_2R^a$, $C(O)R^a$, $CONR^aR^a$, $CR^aR^aNR^aR^a$, $CR^aR^aOR^a$, $C_1$-$C_4$-alkyl, $C_2$-$C_4$-alkenyl, $C_2$-$C_4$ alkynyl, $C_1$-$C_4$-haloalkyl and O—$C_1$-$C_4$-haloalkyl; and wherein $R^a$ is independently at each occurrence selected from the group consisting of H and $C_1$-$C_4$-alkyl.

2. The compound of claim 1, where the compound is represented by formula (X):

(X)

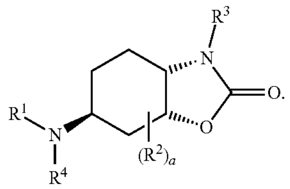

3. The compound of claim 1, wherein the compound is represented by formula (XI):

(XI)

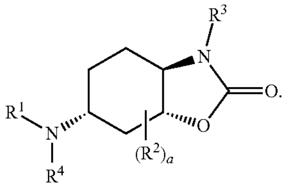

4. The compound of claim 1, wherein the compound is represented by formula (XII):

(XII)

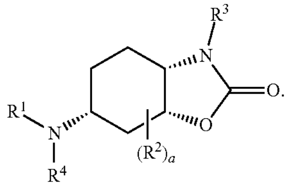

5. The compound of claim 1, wherein the compound is represented by formula (XIII):

(XIII)

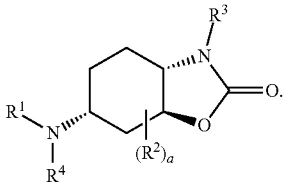

6. The compound of claim 1, wherein $R^1$ is:

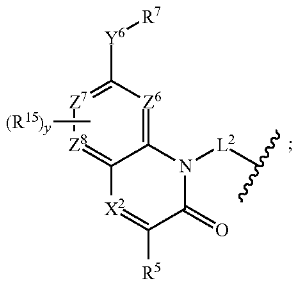

wherein y is an integer from 0 to 2; $Z^6$, $Z^7$ and $Z^8$ are each independently carbon or nitrogen; provided that no more than 2 of $Z^6$, $Z^7$ and $Z^8$ are nitrogen; and $R^{15}$ is independently selected from the group consisting of halo, nitro, cyano, $NR^aR^a$, $NR^aS(O)_2R^a$, $NR^aC(O)R^a$, $NR^aCONR^aR^a$, $NR^aCO_2R^a$, $OR^a$, $SR^a$, $SOR^a$, $SO_3R^a$, $SO_2R^a$, $SO_2NR^aR^a$, $CO_2R^a$, $C(O)R^a$, $CONR^aR^a$, $CR^aR^aNR^aR^a$, $CR^aR^aOR^a$, $C_1$-$C_4$-alkyl, $C_2$-$C_4$-alkenyl, $C_2$-$C_4$-alkynyl and $C_1$-$C_4$-haloalkyl.

7. The compound of claim 6, wherein $Y^6$ is O; and $R^7$ is independently selected from the group consisting of $C_1$-$C_4$-alkyl, $C_2$-$C_4$-alkenyl, $C_2$-$C_4$-alkynyl, $C_1$-$C_4$-haloalkyl, $C_3$-$C_8$-cycloalkyl, $_{4-7}$-heterocycloalkyl, phenyl, monocyclic heteroaryl and $C_1$-$C_3$-alkylene-$R^{7a}$.

8. The A compound of claim 6, wherein $R^5$ and $R^6$, together with the carbons to which they are attached, form a 5-membered heteroaryl ring, and the heteroaryl ring is selected from the group consisting of oxazole, thiazole, isoxazole and isothiazole.

9. The compound of claim 1, wherein $R^1$ is -$L^1$-$Ar^1$—$Ar^2$; wherein $Ar^1$ and $Ar^2$ are each independently a phenyl or monocyclic heteroaryl group.

10. The compound of claim 9, wherein $Ar^1$ is a phenyl group; and $Ar^2$ is a 6-membered heteroaryl group.

11. The compound of claim 9, wherein $Ar^1$ is a 6-membered heteroaryl group; and $Ar^2$ is a phenyl group.

12. The A compound of claim 1, wherein $R^3$ is:

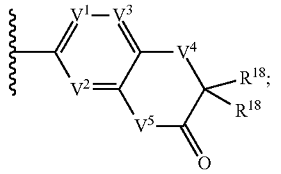

wherein $V^1$, $V^2$ and $V^3$ are each independently selected from the group consisting of N and $CR^{13}$;

with the proviso that no more than two of $V^1$, $V^2$ and $V^3$ are N; $V^4$ and $V^5$ are each independently selected from the group consisting of O, S and $NR^a$; wherein $R^{13}$ is independently at each occurrence selected from the group consisting of H, halo, nitro, cyano, $NR^aR^a$, $NR^aS(O)_2R^a$, $NR^aC(O)R^a$, $NR^aCONR^aR^a$, $NR^aCO_2R^a$, $OR^a$, $SR^a$, $SOR^a$, $SO_3R^a$, $SO_2R^a$, $SO_2NR^aR^a$, $CO_2R^a$, $C(O)R^a$, $CONR^aR^a$, $CR^aR^a NR^aR^a$, $CR^aR^aOR^a$, $C_1$-$C_4$-alkyl, $C_2$-$C_4$-alkenyl, $C_2$-$C_4$-alkynyl and $C_1$-$C_4$-haloalkyl; and $R^{18}$ is independently at each occurrence selected from the group consisting of H, fluoro, cyano, $CO_2R^a$, $C(O)R^a$, $CONR^aR^a$, $C_1$-$C_4$-alkyl, $C_2$-$C_4$-alkenyl, $C_2$-$C_4$-alkynyl and $C_1$-$C_4$-haloalkyl.

13. The compound of claim 1, wherein the compound of formula (I) is selected from the group consisting of:

1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydro-1,8-naphthyridin-2-one;

(3aR,6R,7aR)-6-[(2-{2-methoxy-7-oxo-7H,8H-pyrido[2,3-d]pyrimidin-8-yl}ethyl)amino]-3-(3-oxo-2H,3H,4H-pyrido[3,2-b][1,4]oxazin-6-yl}-octahydro-1,3-benzoxazol-2-one;

1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-(3-aminopropoxy)-1,2-dihydroquinolin-2-one;

1-(2-{[(3aS,6S,7aR)-2-oxo-2H,3H,4H-pyrido[3,2-b][1,4]oxazin-6-yl}-octahydro-1,3-benzoxazol-6-yl]amino}ethyl)-7-methoxy-1,2-dihydro-1,8-naphthyridin-2-one;

1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-(3-aminopropoxy)-1,2-dihydro-1,8-naphthyridin-2-one;

1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-(2-hydroxyethoxy)-1,2-dihydro-1,8-naphthyridin-2-one;

1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl](2-hydroxyethyl)amino}ethyl)-7-methoxy-1,2-dihydro-1,8-naphthyridin-2-one;

4-{[8-(2-{[(3aR,6R,7aR)-2-oxo-3-{3-oxo-2H,3H,4H-pyrido[3,2-b][1,4]oxazin-6-yl-octahydro-1,3-benzoxazol-6-yl]amino}ethyl)-7-oxo-7,8-dihydro-1,8-naphthyridin-2-yl]oxy}benzene-1-sulphonamide;

1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-(2-aminoethoxy)-1,2-dihydroquinolin-2-one;

1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-(2-aminoethoxy)-1,2-dihydro-1,8-naphthyridin-2-one;

(3aS,6S,7aR)-6-[(2-{7-methoxy-4-oxo-4H,5H-[1,2]oxazolo[3,4-c]quinolin-5-yl}ethyl)amino]-3-3-oxo-2H,3H,4H-pyrido[3,2-b][1,4]oxazin-6-yl}-octahydro-1,3-benzoxazol-2-one;

1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-(pyridin-3-yloxy)-1,2-dihydro-1,8-naphthyridin-2-one;

1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl](2-aminoethyl)amino}ethyl)-7-(methoxy)-1,2-dihydro-1,8-naphthyridin-2-one;

1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-2-oxo-1,2-dihydroquinoline-7-carbonitrile;

8-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-oxo-7,8-dihydro-1,8-naphthyridine-2-carbonitrile;

1-(2-{[(3aS,6S,7aR)-2-oxo-3-{7-oxo-6H,7H,8H-pyrimido[5,4-b][1,4]oxazin-6-yl}-octahydro-1,3-benzoxazol-6-yl]amino}ethyl)-7-methoxy-1,2-dihydro-1,8-naphthyridin-2-one;

(3aS,6S,7aR)-6-[(2-{2-methoxy-7-oxo-7H,8H-pyrido[2,3-d]pyrimidin-8-yl}ethyl)amino]-3-{3-oxo-2H,3H,4H-pyrido[3,2-b][1,4]oxazin-6-yl}-octahydro-1,3-benzoxazol-2-one;

6-[3-({[(3aS,6S,7aR)-2-oxo-3-{3-oxo-2H,3H,4H-pyrido[3,2-b][1,4]oxazin-6-yl}-octahydro-1,3-benzoxazol-6-yl]amino}methyl)-2-hydroxyphenyl]pyridine-2-carbonitrile;

1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl](2-aminoethyl)amino}ethyl)-2-oxo-1,2-dihydroquinoline-7-carbonitrile;

1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-hydroxy-1,2-dihydroquinolin-2-one;

1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydroquinoxalin-2-one;

1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-6,7-difluoro-1,2-dihydroquinoxalin-2-one;

1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-(2-aminoethoxy)-1,2-dihydroquinolin-2-one;

1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydroquinoxalin-2-one;

1-(2-{[(3aR,6R,7aS)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydro-1,8-naphthyridin-2-one;

1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-fluoro-1,2-dihydroquinoxalin-2-one;

1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-methyl-1,2-dihydroquinoxalin-2-one;

1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-fluoro-1,2-dihydro-1,5-naphthyridin-2-one;

1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydro-1,8-naphthyridin-2-one;

1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydro-1,5-naphthyridin-2-one;

4-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-3-oxo-3,4-dihydroquinoxaline-6-carbonitrile;

1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-[2-(dimethylamino)ethoxy]-1,2-dihydroquinolin-2-one;

(3aR,6R,7aR)-6-[(2-{2-methoxy-7-oxo-7H,8H-pyrido[2,3-d]pyrimidin-8-yl}ethyl)amino]-3-{7-oxo-6H,7H,8H-pyrimido[5,4-b][1,4]oxazin-2-yl}-octahydro-1,3-benzoxazol-2-one;

1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-6,7-difluoro-1,2-dihydroquinoxalin-2-one;

(3aS,6S,7aR)-6-[(2-{6-methoxy-3-oxo-3H,4H-pyrido[2,3-b]pyrazin-4-yl}ethyl)amino]-3-{3-oxo-2H,3H,4H-pyrido[3,2-b][1,4]oxazin-6-yl}-octahydro-1,3-benzoxazol-2-one;

methyl 1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-2-oxo-1,2-dihydroquinoline-7-carboxylate;

1-(2-{[(3aR,6R,7aR)-2-oxo-3-{7-oxo-6H,7H,8H-pyrimido[5,4-b][1,4]oxazin-2-yl}-octahydro-1,3-benzoxazol-6-yl]amino}ethyl)-2-oxo-1,2-dihydroquinoline-7-carbonitrile;

1-(2-{[(3aR,6R,7aR)-2-oxo-3-{7-oxo-6H,7H,8H-pyrimido[5,4-b][1,4]oxazin-2-yl}-octahydro-1,3-benzoxazol-6-yl]amino}ethyl)-6,7-difluoro-1,2-dihydroquinoxalin-2-one;

(3 aR,6R,7aR)—N-(2-{7-[2-(methylazaniumyl)ethoxy]-2-oxo-1,2-dihydroquinolin-1-yl}ethyl)-2-oxo-3-{3-oxo-2H,3H,4H-pyrido[3,2-b][1,4]oxazin-6-yl}-octahydro-1,3-benzoxazol-6-amine;

6-[3-({[(3aR,6R,7aR)-2-oxo-3-{3-oxo-2H,3H,4H-pyrido[3,2-b][1,4]oxazin-6-yl}-octahydro-1,3-benzoxazol-6-yl]amino}methyl)-2-hydroxyphenyl]pyridine-2-carbonitrile;

1-(2-{[(3aR,6R,7aR)-2-oxo-3-{7-oxo-6H,7H,8H-pyrimido[5,4-b][1,4]oxazin-2-yl}-octahydro-1,3-benzoxazol-6-yl]amino}ethyl)-7-methoxy-1,2-dihydro-1,5-naphthyridin-2-one;

7-methoxy-1-{2-[(2-oxo-3-{3-oxo-2H,3H,4H-pyrido[3,2-b][1,4]oxazin-6-yl}-octahydro-1,3-benzoxazol-6-yl)amino]ethyl}-1,2-dihydro-1,5-naphthyridin-2-one;

(3aR,6R,7aR)-6-[(2-{6-methoxy-3-oxo-3H,4H-pyrido[2,3-b]pyrazin-4-yl}ethyl)amino]-3-{3-oxo-2H,3H,4H-pyrido[3,2-b][1,4]oxazin-6-yl}-octahydro-1,3-benzoxazol-2-one;

1-(2-{[(3aR,6R,7aR)-2-oxo-3-{7-oxo-6H,7H,8H-pyrimido[5,4-b][1,4]oxazin-2-yl}-octahydro-1,3-benzoxazol-6-yl]amino}ethyl)-7-methoxy-1,2-dihydro-1,8-naphthyridin-2-one;

(3aS,6S,7aS)-6-[(2-{6-methoxy-3-oxo-3H,4H-pyrido[2,3-b]pyrazin-4-yl}ethyl)amino]-3-{3-oxo-2H,3H,4H-pyrido[3,2-b][1,4]oxazin-6-yl}-octahydro-1,3-benzoxazol-2-one;

5-(2-{[(3aS,6S,7aR)-2-oxo-3-{3-oxo-2H,3H,4H-pyrido[3,2-b][1,4]oxazin-6-yl}-octahydro-1,3-benzoxazol-6-yl]amino}ethyl)-6-oxo-5,6-dihydro-1,5-naphthyridine-3-carbonitrile;

1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl](methyl)amino}ethyl)-2-oxo-1,2-dihydroquinoline-7-carbonitrile;

1-(2-{[(3aS,6S,7aS)-3-{2,2-dimethyl-3-oxo-2H,3H,4H-pyrido[3,2-b][1,4]oxazin-6-yl}-2-oxo-octahydro-1,3-benzoxazol-6-yl]amino}ethyl)-7-methoxy-1,2-dihydro-1,8-naphthyridin-2-one;

1-(2-{[(3aR,6R,7aR)-3-{6H,7H-[1,4]dioxino[2,3-c]pyridazin-3-yl}-2-oxo-octahydro-1,3-benzoxazol-6-yl]amino}ethyl)-7-methoxy-1,2-dihydro-1,8-naphthyridin-2-one;

5-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-6-oxo-5,6-dihydro-1,5-naphthyridine-3-carbonitrile;

1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl](methyl)amino}ethyl)-7-methoxy-1,2-dihydro-1,5-naphthyridin-2-one;

(3aS,6S,7aS)-6-[(2-{2-methoxy-7-oxo-7H,8H-pyrido[2,3-d]pyrimidin-8-yl}ethyl)amino]-3-{3-oxo-2H,3H,4H-pyrido[3,2-b][1,4]oxazin-6-yl}-octahydro-1,3-benzoxazol-2-one;

(3aS,6S,7aR)-6-({2-[2-(methylsulfanyl)-7-oxo-7H,8H-pyrido[2,3-d]pyrimidin-8-yl]ethyl}amino)-3-13-oxo-2H,3H,4H-pyrido[3,2-b][1,4]oxazin-6-yl}-octahydro-1,3-benzoxazol-2-one;

(3aR,6R,7aR)-6-[({2-hydroxy-3-[6-(morpholin-4-yl)pyridin-2-yl]phenyl}methyl)amino]-3-{4-[(4-methoxyphenyl)methyl]-3-oxo-2H,3H,4H-pyrido[3,2-b][1,4]oxazin-6-yl}-octahydro-1,3-benzoxazol-2-one;

(3 aR,5S,7aR)—N-{2-[7-(2-azaniumylethoxy)-2-oxo-1,2-dihydroquinolin-1-yl]ethyl}-N-methyl-2-oxo-3-{3-oxo-2H,3H,4H-pyrido[3,2-b][1,4]oxazin-6-yl}-octahydro-1,3-benzoxazol-5-amine;

5-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-6-oxo-5,6-dihydro-1,5-naphthyridine-3-carbonitrile;

1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-2-oxo-1,2-dihydroquinoline-7-carbonitrile;

6-[3-({[(3aS,6S,7aS)-2-oxo-3-{3-oxo-2H,3H,4H-pyrido[3,2-b][1,4]oxazin-6-yl}-octahydro-1,3-benzoxazol-6-yl]amino}methyl)phenyl]pyridine-2-carbonitrile;

1-(2-{[(3aS,6S,7aR)-2-oxo-3-{3-oxo-2H,3H,4H-pyrido[3,2-b][1,4]oxazin-6-yl}-octahydro-1,3-benzoxazol-6-yl](2-aminoethyl)amino}ethyl)-2-oxo-1,2-dihydroquinoline-7-carbonitrile;

1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-2-oxo-1,2-dihydroquinoline-7-carbonitrile;

1-(3-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}propyl)-2-oxo-1,2-dihydroquinoline-7-carbonitrile;

1-(2-{[(3aS,6S,7aS)-2-oxo-3-{3-oxo-2H,3H,4H-pyrido[3,2-b][1,4]thiazin-6-yl}-octahydro-1,3-benzoxazol-6-yl]amino}ethyl)-7-methoxy-1,2-dihydro-1,8-naphthyridin-2-one;

(3aS,6S,7aS)-6-[(2-{3-methoxy-6-oxo-5H,6H-pyrido[2,3-b]pyrazin-5-yl}ethyl)amino]-3-{3-oxo-2H,3H,4H-pyrido[3,2-b][1,4]oxazin-6-yl}-octahydro-1,3-benzoxazol-2-one;

4-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-3-oxo-3,4-dihydroquinoxaline-6-carbonitrile;

1-(2-{[(3aS,6S,7aR)-2-oxo-3-{7-oxo-6H,7H,8H-pyrimido[5,4-b][1,4]oxazin-2-yl}-octahydro-1,3-benzoxazol-6-yl]amino}ethyl)-6,7-difluoro-1,2-dihydroquinoxalin-2-one;

1-(2-{[(3aS,6S,7aS)-2-oxo-3-{7-oxo-6H,7H,8H-pyrimido[5,4-b][1,4]oxazin-2-yl}-octahydro-1,3-benzoxazol-6-yl]amino}ethyl)-6,7-difluoro-1,2-dihydroquinoxalin-2-one;

1-(2-{[(3aS,6S,7aS)-2-oxo-3-{7-oxo-6H,7H,8H-pyrimido[5,4-b][1,4]oxazin-2-yl}-octahydro-1,3-benzoxazol-6-yl]amino}ethyl)-7-methoxy-1,2-dihydro-1,8-naphthyridin-2-one;

4-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-3-oxo-3,4-dihydroquinoxaline-6-carbonitrile;

1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydro-1,5-naphthyridin-2-one;

1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-6,7-difluoro-1,2-dihydroquinoxalin-2-one;

6-[3-({[(3aS,6S,7aS)-2-oxo-3-{3-oxo-2H,3H,4H-pyrido[3,2-b][1,4]oxazin-6-yl}-octahydro-1,3-benzoxazol-6-yl]amino}methyl)phenyl]pyridine-3-carbonitrile;

(3aR,6R,7aR)-6-({[2-hydroxy-3-(5-methoxypyridazin-3-yl)phenyl]methyl}amino)-3-{3-oxo-2H,3H,4H-pyrido[3,2-b][1,4]oxazin-6-yl}-octahydro-1,3-benzoxazol-2-one;

(3aS,6S,7aS)-6-({[3-(6-methoxypyridin-2-yl)phenyl]methyl}amino)-3-{3-oxo-2H,3H,4H-pyrido[3,2-b][1,4]oxazin-6-yl}-octahydro-1,3-benzoxazol-2-one;

1-(3-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}propyl)-2-oxo-1,2-dihydroquinoline-7-carbonitrile;

1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-(2-aminoethoxy)-1,2-dihydroquinolin-2-one 1-(3-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}propyl)-7-methoxy-1,2-dihydro-1,8-naphthyridin-2-one;

5-(2-{[(3aS,6S,7aS)-2-oxo-3-{3-oxo-2H,3H,4H-pyrido[3,2-b][1,4]thiazin-6-yl}-octahydro-1,3-benzoxazol-6-yl]amino}ethyl)-6-oxo-5,6-dihydro-1,5-naphthyridine-3-carbonitrile;

N-[(3aS,6S,7aS)-2-oxo-3-{3-oxo-2H,3H,4H-pyrido[3,2-b][1,4]oxazin-6-yl}-octahydro-1,3-benzoxazol-6-yl]-2-amino-N-[2-(7-methoxy-2-oxo-1,2-dihydro-1,8-naphthyridin-1-yl)ethyl]acetamide 1-(3-{[(3aR,6R,7aR)-2-oxo-3-{7-oxo-6H,7H,8H-pyrimido[5,4-b][1,4]oxazin-2-yl}-octahydro-1,3-benzoxazol-6-yl]amino}propyl)-7-methoxy-1,2-dihydro-1,8-naphthyridin-2-one;

(3aR,6R,7aR)-6-({[3-(6-methoxypyridin-2-yl)phenyl]methyl}amino)-3-{3-oxo-2H,3H,4H-pyrido[3,2-b][1,4]oxazin-6-yl}-octahydro-1,3-benzoxazol-2-one;

1-(2-{[(3aS,6S,7aS)-2-oxo-3-{3-oxo-2H,3H,4H-pyrido[3,2-b][1,4]thiazin-6-yl}-octahydro-1,3-benzoxazol-6-yl]amino}ethyl)-7-methoxy-1,2-dihydro-1,5-naphthyridin-2-one;

5-(3-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}propyl)-6-oxo-5,6-dihydro-1,5-naphthyridine-3-carbonitrile;

1-(3-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}propyl)-7-methoxy-1,2-dihydro-1,8-naphthyridin-2-one;

1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-fluoro-1,2-dihydroquinoxalin-2-one;

1-(3-{[(3aS,6S,7aS)-2-oxo-3-{3-oxo-2H,3H,4H-pyrido[3,2-b][1,4]thiazin-6-yl}-octahydro-1,3-benzoxazol-6-yl]amino}propyl)-7-methoxy-1,2-dihydro-1,8-naphthyridin-2-one;

1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-7-fluoro-1,2-dihydroquinoxalin-2-one;

(3aR,6R,7aR)-6-[(2-3-methoxy-6-oxo-5H,6H-pyrido[2,3-b]pyrazin-5-yl}ethyl)amino]-3-{3-oxo-2H,3H,4H-pyrido[3,2-b][1,4]oxazin-6-yl}-octahydro-1,3-benzoxazol-2-one;

1-(3-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}propyl)-6,7-difluoro-1,2-dihydroquinoxalin-2-one;

1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-(prop-2-en-1-yloxy)-1,2-dihydroquinolin-2-one;

1-(3-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}propyl)-6,7-difluoro-1,2-dihydroquinoxalin-2-one;

1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-propoxy-1,2-dihydroquinolin-2-one;

1-(3-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}propyl)-7-fluoro-1,2-dihydroquinoxalin-2-one;

1-(3-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}propyl)-7-(difluoromethoxy)-1,2-dihydro-1,5-naphthyridin-2-one;

1-[(2S)-3-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}-2-hydroxypropyl]-7-fluoro-1,2-dihydroquinoxalin-2-one;

1-[(2R)-3-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}-2-hydroxypropyl]-7-fluoro-1,2-dihydroquinoxalin-2-one;

1-[(2S)-3-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}-2-hydroxypropyl]-7-fluoro-1,2-dihydroquinoxalin-2-one;

1-[(2R)-3-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}-2-hydroxypropyl]-7-fluoro-1,2-dihydroquinoxalin-2-one;

1-(3-{[(3aS,6S,7aS)-2-oxo-3-{3-oxo-2H,3H,4H-pyrido[3,2-b][1,4]thiazin-6-yl}-octahydro-1,3-benzoxazol-6-yl]amino}propyl)-7-methoxy-1,2-dihydro-1,5-naphthyridin-2-one;

1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-[2-(morpholin-4-yl)ethoxy]-1,2-dihydroquinolin-2-one;

1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-(difluoromethoxy)-1,2-dihydro-1,5-naphthyridin-2-one;

1-(3-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}propyl)-7-methoxy-1,2-dihydro-1,5-naphthyridin-2-one;

(3aS,6S,7aS)-3-{3-oxo-2H,3H,4H-pyrido[3,2-b][1,4]oxazin-6-yl}-6-[(2-{6-oxo-5H,6H-pyrido[2,3-b]pyrazin-5-yl}ethyl)amino]-octahydro-1,3-benzoxazol-2-one;

1-(2-{[(3aS,6S,7aS)-2-oxo-3-{3-oxo-2H,3H,4H-pyrido[3,2-b][1,4]oxazin-6 yl}-octahydro-1,3-benzoxazol-6-yl]amino}ethyl)-7-(difluoromethoxy)-1,2-dihydro quinolin-2-one;

1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-methoxy-1,2-dihydroquinolin-2-one;

1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-(azetidin-3-yloxy)-1,2-dihydroquinolin-2-one;

1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-7-(1-methyl-1H-pyrazol-3-yl)-1,2-dihydroquinolin-2-one;

3-[6-({[(3aS,6S,7aS)-2-oxo-3-{3-oxo-2H,3H,4H-pyrido[3,2-b][1,4]oxazin-6-yl}-octahydro-1,3-benzoxazol-6-yl]amino}methyl)pyridin-2-yl]benzonitrile;

1-(2-{[(3aR,6R,7aR)-2-oxo-3-{3-oxo-2H,3H,4H-pyrido[3,2-b][1,4]oxazin-6-yl}-octahydro-1,3-benzoxazol-6-yl]amino}ethyl)-2-oxo-1,2-dihydroquinoline-6-carbonitrile; and 1-(2-{[(3aS,6S,7aS)-2-oxo-3-{3-oxo-2H,3H,4H-pyrido[3,2-b][1,4]oxazin-6-yl}-octahydro-1,3-benzoxazol-6-yl]amino}ethyl)-2-oxo-1,2-dihydroquinoline-6-carbonitrile.

14. A pharmaceutical composition comprising a compound of claim 1; and at least one pharmaceutically acceptable excipient.

15. A method of treating a bacterial infection or a mycobacterial infection, comprising administering to a patient in need thereof a therapeutic amount of a compound of formula (I), or a pharmaceutically acceptable salt or N-oxide thereof:

(I)

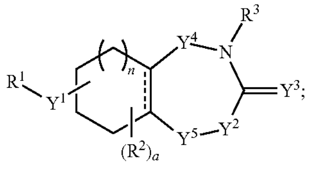

wherein ------ is a double bond or a single bond;

$Y^1$ is independently selected from the group consisting of $NR^4$, O and S;

$Y^2$ is independently selected from the group consisting of O and S;

$Y^3$ is independently selected from the group consisting of O and S;

$Y^4$ is $(CH_2)_m$;

$Y^5$ is $(CH_2)_p$;

$R^1$ is independently selected from the group consisting of $-L^1-Ar^1—Ar^2$ and

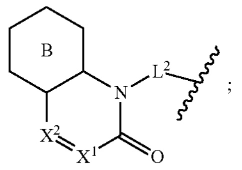

Ar$^1$ and Ar$^2$ are each independently a phenyl or monocyclic heteroaryl group;

-L$^1$- is —$C_1$-$C_3$-alkylene-;

X$^1$ is independently selected from the group consisting of N and CR$^5$; and X$^2$ is independently selected from the group consisting of N and CR$^6$; or X$^1$ and X$^2$ together form a 5-membered heteroaryl ring;

-L$^2$- is —$C_2$-$C_3$-alkylene-;

Ring B is independently selected from the group consisting of phenyl, monocyclic 6-membered heteroaryl and pyridinone, optionally substituted with a single —Y$^6$—R$^7$ group; wherein Y$^6$ is absent or is independently selected from the group consisting of NR$^8$, O and S; where Ring B is a pyridinone ring, the nitrogen of the Ring B pyridinone may be attached to the proximal end of a —$C_1$-$C_3$-alkylene- group that is attached at its distal end to the group -L$^2$-;

R$^2$ is independently at each occurrence selected from the group consisting of halo, nitro, cyano, NR$^9$R$^{10}$, NR$^9$S(O)$_2$R$^9$, NR$^9$CONR$^9$R$^9$, NR$^9$C(O)R$^9$, NR$^9$CO$_2$R$^9$, OR$^9$, SR$^9$, SOR$^9$, SO$_3$R$^9$, SO$_2$R$^9$, SO$_2$NR$^9$R$^9$, CO$_2$R$^9$, C(O)R$^9$, CONR$^9$R$^9$, $C_1$-$C_4$-alkyl, $C_2$-$C_4$-alkenyl, $C_2$-$C_4$-alkynyl, $C_1$-$C_4$-haloalkyl and O—$C_1$-$C_4$-haloalkyl;

R$^3$ is a bicyclic carbocyclic or a bicyclic heterocyclic ring system in which at least one of the two rings is aryl or heteroaryl;

or R$^3$ is -L$^3$-phenyl; wherein -L$^3$- is selected from the group consisting of —CR$^{11}$═CR$^{11}$— and —$C_4$-cycloalkyl-;

R$^4$ is independently selected from the group consisting of H, $C_1$-$C_4$-alkyl, C(O)—$C_1$-$C_4$-alkyl and $C_1$-$C_3$-alkylene-R$^{12}$; wherein R$^{12}$ is independently phenyl or monocyclic heteroaryl;

or wherein R$^4$ and either -L$^1$- or -L$^2$- and the nitrogen to which they are attached together form a 4- to 7-membered heterocycloalkyl ring;

R$^5$ and R$^6$ are each independently selected from the group consisting of H, halo, cyano, $C_1$-$C_4$-alkyl and O—$C_1$-$C_4$-alkyl;

R$^7$ is independently selected from the group consisting of H, $C_1$-$C_4$-alkyl, $C_2$-$C_4$-alkenyl, $C_2$-$C_4$-alkynyl, $C_1$-$C_4$-haloalkyl, $C_3$-$C_8$-cycloalkyl, $_{4-7}$-heterocycloalkyl, phenyl, monocyclic heteroaryl and $C_1$-$C_3$-alkylene-R$^{7a}$; wherein R$^{7a}$ is independently selected from the group consisting of $C_3$-$C_8$-cycloalkyl, $_{4-7}$-heterocycloalkyl, phenyl and monocyclic heteroaryl;

R$^8$ is independently selected from the group consisting of H and $C_1$-$C_4$-alkyl;

or R$^7$ and R$^8$ together with the nitrogen to which they are attached form a 4- to 7-membered heterocycloalkyl ring;

R$^9$ is independently at each occurrence selected from the group consisting of H and $C_1$-$C_4$-alkyl;

R$^{10}$ is independently selected from the group consisting of H, $C_1$-$C_4$-alkyl, $C_1$-$C_4$-haloalkyl, S(O)$_2$—$C_1$-$C_4$-alkyl and C(O)—$C_1$-$C_4$-alkyl;

R$^{11}$ is independently at each occurrence selected from the group consisting of H and $C_1$-$C_4$-alkyl;

a is an integer from 0 to 4;

n is an integer selected from the group consisting of 0, 1 and 2;

m and p are each an integer selected from the group consisting of 0 and 1;

wherein any of the aforementioned alkyl, alkylene, alkenyl, alkynyl, haloalkyl, cycloalkyl, carbocyclic, heterocyclic, heterocycloalkyl, aryl, phenyl and heteroaryl groups is optionally substituted, where chemically possible, by 1 to 5 substituents which are each independently at each occurrence selected from the group consisting of oxo, ═NR$^a$, ═NOR$^a$, halo, nitro, cyano, NR$^a$R$^a$, NR$^a$S(O)$_2$R$^a$, NR$^a$C(O)R$^a$, NR$^a$CONR$^a$R$^a$, NR$^a$CO$_2$R$^a$, OR$^a$, SR$^a$, SOR$^a$, SO$_3$R$^a$, SO$_2$R$^a$, SO$_2$NR$^a$R$^a$, CO$_2$R$^a$, C(O)R$^a$, CONR$^a$R$^a$, CR$^a$R$^a$NR$^a$R$^a$, CR$^a$R$^a$OR$^a$, $C_1$-$C_4$-alkyl, $C_2$-$C_4$-alkenyl, $C_2$-$C_4$-alkynyl, $C_1$-$C_4$-haloalkyl and O—$C_1$-$C_4$-haloalkyl; and wherein R$^a$ is independently at each occurrence selected from the group consisting of H and $C_1$-$C_4$-alkyl.

16. The method of claim 15, wherein the bacterial infection is caused by a Gram-positive bacteria.

17. The method of claim 15, wherein the bacterial infection is caused by a Gram-negative bacteria.

18. The method of claim 15, wherein the bacterial infection is caused by a bacterial strain that is resistant to at least one approved antibacterial drug.

19. The method of claim 15, wherein the mycobacterial infection is caused by mycobacteria.

20. The method of claim 15, wherein the mycobacterial infection is caused by a mycobacterial strain that is resistant to at least one approved antimycobacterial drug.

* * * * *